(12) United States Patent
Shendure et al.

(10) Patent No.: US 11,352,670 B2
(45) Date of Patent: Jun. 7, 2022

(54) METHODS OF DETERMINING TISSUES AND/OR CELL TYPES GIVING RISE TO CELL-FREE DNA, AND METHODS OF IDENTIFYING A DISEASE OR DISORDER USING SAME

(71) Applicant: UNIVERSITY OF WASHINGTON, Seattle, WA (US)

(72) Inventors: Jay Shendure, Seattle, WA (US); Matthew Snyder, Seattle, WA (US); Martin Kircher, Seattle, WA (US)

(73) Assignee: UNIVERSITY OF WASHINGTON, Seattle, WA (US)

(*) Notice: Subject to any disclaimer, the term of this patent is extended or adjusted under 35 U.S.C. 154(b) by 0 days.

(21) Appl. No.: 16/880,884

(22) Filed: May 21, 2020

(65) Prior Publication Data

US 2021/0010081 A1    Jan. 14, 2021

Related U.S. Application Data

(63) Continuation of application No. 16/160,330, filed on Oct. 15, 2018, now abandoned, which is a
(Continued)

(51) Int. Cl.
*C12Q 1/6881* (2018.01)
*G16H 50/20* (2018.01)
(Continued)

(52) U.S. Cl.
CPC ......... *C12Q 1/6881* (2013.01); *C12Q 1/6883* (2013.01); *G16B 20/00* (2019.02);
(Continued)

(58) Field of Classification Search
CPC ............ C12Q 1/6869; C12Q 2600/156; C12Q 1/6886; C12Q 1/6883; C12Q 1/6827;
(Continued)

(56) References Cited

U.S. PATENT DOCUMENTS 7,842,482 B2    11/2010  Lo et al.
8,124,383 B2    2/2012   Lo et al.
(Continued)

FOREIGN PATENT DOCUMENTS

CN        1452665 A    10/2003
CN      102369299 A     3/2012
(Continued)

OTHER PUBLICATIONS

Bronkhorst, A.J. et al., "Towards systematic nomenclature for cell-free DNA" Human Genetics, Published Online Oct. 29, 2020, 14 pages.
(Continued)

*Primary Examiner* — Mary K Zeman
(74) *Attorney, Agent, or Firm* — Perkins Coie LLP

(57) ABSTRACT

The present disclosure provides methods of determining one or more tissues and/or cell-types contributing to cell-free DNA ("cfDNA") in a biological sample of a subject. In some embodiments, the present disclosure provides a method of identifying a disease or disorder in a subject as a function of one or more determined more tissues and/or cell-types contributing to cfDNA in a biological sample from the subject.

10 Claims, 74 Drawing Sheets
(64 of 74 Drawing Sheet(s) Filed in Color)

Specification includes a Sequence Listing.

Related U.S. Application Data continuation of application No. 15/329,228, filed as application No. PCT/US2015/042310 on Jul. 27, 2015, now abandoned.

(60) Provisional application No. 62/087,619, filed on Dec. 4, 2014, provisional application No. 62/029,178, filed on Jul. 25, 2014.

(51) Int. Cl.
    *G16B 20/00*     (2019.01)
    *G16B 40/00*     (2019.01)
    *G16B 45/00*     (2019.01)
    *G16B 20/30*     (2019.01)
    *G16B 30/00*     (2019.01)
    *G16B 20/10*     (2019.01)
    *G16B 20/20*     (2019.01)
    *G16B 40/10*     (2019.01)
    *C12Q 1/6883*     (2018.01)
    *C12Q 1/6869*     (2018.01)

(52) U.S. Cl.
    CPC .............. *G16B 20/10* (2019.02); *G16B 20/20* (2019.02); *G16B 20/30* (2019.02); *G16B 30/00* (2019.02); *G16B 40/00* (2019.02); *G16B 40/10* (2019.02); *G16B 45/00* (2019.02); *G16H 50/20* (2018.01); *C12Q 1/6869* (2013.01)

(58) Field of Classification Search
    CPC ........ C12Q 2535/122; C12Q 2600/112; C12Q 2537/165; C12Q 2600/118; G16B 30/00; G16B 20/00; G16B 20/20; G16B 30/10; G16B 20/10; G16B 40/00; G16B 40/20; G16B 25/00; G16B 20/40; G16B 30/20; G16B 40/30; G16B 25/20; G16B 5/00; G16B 50/00; G16B 45/00; G16B 5/20; G16B 50/30; G16B 20/30; G16B 50/10; G16H 50/20; G16H 50/30; G16H 10/40; G16H 50/70; G16H 50/50; G16H 10/60; G16H 15/00; G16H 70/60; G16H 10/00; G16H 70/00; G16H 70/20; G16H 40/60; G01N 33/574; G01N 33/5091; G01N 2800/56; G01N 2800/7028; G01N 2800/60; G01N 33/543; C40B 40/06; G06N 7/005; G06N 20/00; G06N 3/08; G06N 5/003; G06N 3/082; G06N 5/02; G06N 5/022; G06N 7/00; G06N 7/023; G06F 17/18; G06F 19/00; G06F 17/10; G06F 17/11; G06F 17/153; G06F 16/22; G06F 30/27; G06F 7/00; G06F 16/2465; G06F 19/34; G06F 2216/03; G06K 9/6267; G06K 9/00147; G06K 9/6231; G06K 9/00523; G06K 9/0055; G06K 9/6277; G06K 9/00; G06K 9/00228

See application file for complete search history.

(56) References Cited

U.S. PATENT DOCUMENTS

| | | | |
|---|---|---|---|
| 8,620,593 | B2 | 12/2013 | Lo et al. |
| 8,741,811 | B2 | 6/2014 | Lo et al. |
| 8,748,100 | B2 | 6/2014 | Lo et al. |
| 9,121,069 | B2 | 9/2015 | Lo et al. |
| 9,218,449 | B2 | 12/2015 | Lo et al. |
| 9,371,566 | B2 | 6/2016 | Lo et al. |
| 2005/0164241 | A1 | 7/2005 | Hahn |
| 2007/0122823 | A1 | 5/2007 | Bianchi |
| 2007/0202525 | A1 | 8/2007 | Quake |
| 2009/0029377 | A1 | 1/2009 | Lo |
| 2009/0170102 | A1 | 7/2009 | Lo et al. |
| 2010/0041048 | A1 | 2/2010 | Diehl et al. |
| 2011/0105353 | A1 | 5/2011 | Lo et al. |
| 2011/0171741 | A1 | 7/2011 | Wang et al. |
| 2011/0246083 | A1 | 10/2011 | Fan et al. |
| 2013/0029852 | A1 | 1/2013 | Rava et al. |
| 2013/0040824 | A1 | 2/2013 | Lo et al. |
| 2013/0230858 | A1* | 9/2013 | Cantor ................. C12Q 1/6804 435/6.12 |
| 2013/0237431 | A1 | 9/2013 | Lo et al. |
| 2013/0252835 | A1 | 9/2013 | Koh et al. |
| 2013/0288244 | A1 | 10/2013 | Deciu et al. |
| 2014/0051583 | A1 | 2/2014 | Fan et al. |
| 2014/0080715 | A1 | 3/2014 | Lo et al. |
| 2014/0100121 | A1* | 4/2014 | Lo .......................... G16B 30/00 506/2 |
| 2014/0227699 | A1 | 8/2014 | Lo et al. |
| 2016/0017419 | A1 | 1/2016 | Chiu et al. |
| 2016/0019338 | A1* | 1/2016 | Chudova ................ G16B 30/00 702/20 |
| 2016/0333416 | A1 | 11/2016 | Babiarz et al. |
| 2017/0107576 | A1* | 4/2017 | Babiarz .................. G16B 25/00 |
| 2017/0235877 | A1 | 8/2017 | Lo |
| 2017/0326238 | A1 | 11/2017 | Chang et al. |
| 2019/0127794 | A1 | 5/2019 | Shendure |

FOREIGN PATENT DOCUMENTS

| | | | | |
|---|---|---|---|---|
| CN | 102648292 | A | 8/2012 | |
| CN | 103370456 | A | 10/2013 | |
| EP | 2426217 | A1 | 3/2012 | |
| JP | 2002272497 | A | 9/2002 | |
| WO | 2004/078999 | A1 | 9/2004 | |
| WO | 2007/028155 | A2 | 3/2007 | |
| WO | 2007/100911 | A2 | 9/2007 | |
| WO | 2009/013492 | A1 | 1/2009 | |
| WO | 2009/019455 | A2 | 2/2009 | |
| WO | 2009/051842 | A2 | 4/2009 | |
| WO | 2010/112316 | A1 | 10/2010 | |
| WO | 2011/053790 | A2 | 5/2011 | |
| WO | 2011/054936 | A1 | 5/2011 | |
| WO | 2011/090556 | A1 | 7/2011 | |
| WO | 2011/103236 | A2 | 8/2011 | |
| WO | 2012/071621 | A1 | 6/2012 | |
| WO | 2013/043922 | A1 | 3/2013 | |
| WO | 2013/060762 | A1 | 5/2013 | |
| WO | 2013/132305 | A1 | 9/2013 | |
| WO | 2013/177086 | A1 | 11/2013 | |
| WO | 2013/177581 | A2 | 11/2013 | |
| WO | WO-2013177581 | A2 * | 11/2013 | ........... C12Q 1/6874 |
| WO | 2014/039556 | A1 | 3/2014 | |
| WO | 2014/043763 | A1 | 3/2014 | |
| WO | 2014/190286 | A2 | 11/2014 | |
| WO | 2014/194113 | A2 | 12/2014 | |
| WO | 2016/112850 | A1 | 7/2016 | |
| WO | 2016/112851 | A1 | 7/2016 | |
| WO | 2016/116033 | A1 | 7/2016 | |
| WO | 2016/127944 | A1 | 8/2016 | |
| WO | 2017/012592 | A1 | 1/2017 | |

OTHER PUBLICATIONS

FDA, "FDA Approves First Liquid Biopsy Next-Generation Sequencing Companion" Aug. 7, 2020. Retrieved from https://www.fda.gov/news-events/press-announcements/fda-approves-first-liquid-biopsy-next-generation-sequencing-companion-diagnostic-test Nov. 18, 2020. 2 pages.

FDA, "FDA Approves Liquid Biopsy Next-Generation Sequencing Companion Diagnostic Test" Aug. 26, 2020. Retrieved from https://www.fda.gov/drugs/drug-approvals-and-databases/fda-approves-liquid-biopsy-next-generation-sequencing-companion-diagnostic-test Nov. 18, 2020. 2 pages.

Snyder, M. et al. "Cell-free DNA Comprises an In Vivo Nucleosome Footprint that Informs Its Tissues-Of-Origin" Cell, 2016, vol. 164, pp. 57-68.

(56) References Cited

OTHER PUBLICATIONS

EPO, Examination Report for European Patent Application No. 15824425.1, dated Jun. 3, 2020. 8 pages.
JPO, Final Notice of Refusal for Japanese Patent Application No. 2017-525327, dated Jun. 8, 2020. 5 pages with English translation.
SIPO, First Office Action for Chinese Patent Application No. 201580052170.7, dated Nov. 10, 2020. 10 pages with English translation.
Adler, J. et al. "Quantifying Colocalization by Correlation: The Pearson Correlation Coefficient is Superior to the Mandler's Overlap Coefficient" Cytometry Part A: 77A: 773-742.
Agarwal, A. et al. "Commercial landscape of noninvasive prenatal testing in the United States" Prenatal Diagnosis; 2013; vol. 33, No. 6; pp. 521-531.
Bettegowda, C. et al. "Detection of Circulating Tumor DNA in Early-and Late-Stage Human Malignancies" Sci Transl Med. Feb. 19, 2014; vol. 6, Issue 224, pp. 224ra24.
Bianchi, D. et al., "Large Amounts of Cell-Free DNA are Present in Amniotic Fluid" 2001, Clinical Chemistry, vol. 47, No. 10, pp. 1867-1869.
Breitbach, S. et al. "Direction Quantification of Cell-Free, Circulating DNA from Unpurified Plasma" PLoS ONE, Mar. 2014, vol. 9, Issue 3, 11 pages.
Bronkhorst, A.J. et al., The emerging role of cell-free DNA as a molecular marker for cancer management, Biomol. Detect. Quant., vol. 17, 100087, pp. 1-23 (Year: 2019).
Chan, K.C. et al. "Persistent Aberrations in Circulating DNA Integrity after RadiotherapyAre Associated with Poor Prognosis in Nasopharyngeal Carcinoma Patients" Clinical Cancer Research, 2008, VOI. 14, No. 13, pp. 4141-4145.
Chan, K.C. et al., "Molecular Characterization of Circulating EBV DNA in the Plasma of Nasopharyngeal Carcinoma and Lymphoma Patients" Cancer Research, May 1, 2003, vol. 63, pp. 2028-2032.
Chan, K.C. et al., Size Distributions of Maternal and Fetal DNA in Maternal Plasma, Clinical Chemistry, 2004, 5 pages.
Chan, K.C. et al.; "Cancer Genome Scanning in Plasma: Detection of Tumor-Associated Copy Number Aberrations, Single-Nucleotide Variants, and Tumoral Heterogeneity by Massively Parallel Sequencing"; Clinical Chemistry; 2013 (Epub Oct. 11, 2012 ); vol. 59, No. 1; pp. 211-224.
Chan, K.C. et al.; "Hypermethylated RASSF1A in Maternal Plasma: A Universal Fetal DNA Marker that Improves the Reliability of Noninvasive Prenatal Diagnosis"; Clinical Chemistry 2006; 52:12; pp. 2211-2218.
Chandrananda, D. et al. "High-resolution characterization of sequence signatures due to non-random cleavage of cell-free DNA," BMC Medical Genomics, 8:29 (2015).
Chim, S. et al.; "Detection of the placental epigenetic signature of the maspin gene in maternal plasma"; PNAS; 2005; vol. 102, No. 41; pp. 14753-14758.
Chiu, R. et al., "Non-Invasive Prenatal Diagnosis by Single Molecule Counting Technologies" Jul. 1, 2009, Trends in Genetics, vol. 25, No. 7, pp. 324-331.
Chiu, R. et al., "Noninvasive Prenatal Diagnosis of Fetal Chromosomal Aneuploidy by Massively Parallel Genomic Sequencing of DNA in Maternal Plasma" Dec. 23, 2008, Proceedings of the National Academy of Sciences of the United States of America, vol. 105, No. 51, pp. 20458-20463.
Chiu, R. et al.; "Non-invasive prenatal assessment of trisomy 21 by multiplexed maternal plasma DNA sequencing: large scale validity study"; BMJ; 2011; ;342:c7401; 9 pages.
De Vlaminck, I. et al. "Circulating cell-free DNA enables noninvasive diagnosis of heart transplant rejection" Sci Transl Med. Jun. 18, 2014; vol. 6, Issue 241, pp. 241ra77.
Devonshire, A. et al. "Towards standardisation of cell-free DNA measurement in plasma controls for extraction efficiency, fragment size bias and quantification" Anal Bioanal Chem; 2014; vol. 406; pp. 6499-6512.
Diaz, L. et al., "Liquid Biopsies: Genotyping Circulating Tumor DNA", Journal Of Clinical Oncology, vol. 32, No. 6, Feb. 20, 2014, pp. 579-586.
Diehl, F. et al., "Detection and quantification of mutations in the plasma of patients with colorectal tumors"PNAS, Nov. 8, 2005, vol. 102, No. 45, pp. 16368-16373.
Ding, C., et al. "MS Analysis of Single-Nucleotide Differences in Circulating Nucleic Acids Application to Noninvasive Prenatal Diagnosis" Jul. 20, 2004, Proceedings of the National Academy of Sciences of the United States of America, vol. 101, No. 29, pp. 10762-10767.
Ellinger, J., et al., "Cell-free circulating DNA: diagnostic value in patients with testicular germ cell cancer," Journal of Urology, Jan. 1, 2009, vol. 181, No. 1, pp. 363-371.
Elshimali, Y. et al. "The Clinical Utilization of Circulating Cell Free DNA (CCFDNA) in Blood of Cancer Patients" Int. J. Mol. Sci; Sep. 2013; vol. 14, No. 9; pp. 18925-18958.
EPO, Extended European Search Report dated Feb. 26, 2018, European Application No. 15824425.1, Applicant: University of Washington, 11 pages.
Fan, H. et al. "Detection of Aneuploidy with Digital Polymerase Chain Reaction" Analytical Chemistry, 2007, 4 pages.
Fan, H. et al. "Noninvasive diagnosis of fetal aneuploidy by shotgun sequencing DNA from maternal blood" PNAS; Oct. 2008; vol. 105, No. 42; pp. 16266-16271.
Fan, H. et al.; "Analysis of the Size Distributions of Fetal and Maternal Cell-Free DNA by Paired-End Sequencing"; Clinical Chemistry; 2010; pp. 1279-1286; vol. 56, No. 8; American Association for Clinical Chemistry.
Fan, H. et al.; "Sensitivity of Noninvasive Prenatal Detection of Fetal Aneuploidy from Maternal Plasma Using Shotgun Sequencing Is Limited Only by Counting Statistics"; PLoS ONE; 2010; vol. 5, Issue 5; e10439; 7 pages.
Forshew et al., "Noninvasive Identification and Monitoring of Cancer Mutations by Targeted Deep Sequencing of Plasma DNA," Science Translational Medicine, vol. 4, No. 136, May 30, 2012, 14 pages.
Gaffney, D. et al. "Controls of Nucleosome Positioning in the Human Genome" PLOS Genetics; Nov. 2012; vol. 8, Issue 11; e1003036; 13 pages.
Gang, F. et al. "Prediction of Clear Cell Renal Cell Carcinoma by Integrity of Cell-free DNA in Serum" Urology, Feb. 2010; vol. 75, Issue 2; pp. 262-265.—Abstract Only.
Handstad, et al., "A ChiP-Seq benchmark shows that sequence conservation mainly improves detection of strong transcription factor binding sites", PLoS One, 6 1-9 (2011).
Intellectual Property India, Examination Report for Indian Patent Application No. 201747006075, dated Jan. 16, 2020. 9 pages.
Jahr, Sabine, et al., "DNA Fragments in the Blood Plasma of Cancer Patients: Quantitations and Evidence fortheir Origin from Apoptotic and Necrotic Cells" Cancer Research, Feb. 15, 2001, vol. 61, pp. 1659-1665.
JPO, Office Action for Japanese Patent Application No. 2017-525327, dated Jun. 17, 2019. 7 pages with English Translation.
Jiang, P. et al. "Lengthening and shortening of plasma DNA in hepatocellular carcinoma patients" PNAS, Mar. 2015, vol. 112, No. 11, 9 pages.
Jiang, Wei-Wen, et al., "Increased plasma DNA integrity index in head and neck cancer patients" Int. J. Cancer, 2006, vol. 119, pp. 2673-2676.
Katoh, et al., "MAFFT: a novel method for rapid multiple sequence alignment based on fast Fourier transform", Nucleic Acids Res 30 3059-66 (2002).
Kitzman, J. et al. "Noninvasive whole-genome sequencing of a human fetus" Sci Transl Med. Jun. 6, 2012; vol. 4, Issue 137 pp. 137ra76.
Korbel, Jan. 0. et al.; "Paired-End Mapping Reveals Extensive Structural Variation in the Human Genome"; Science; Oct. 19, 2007; vol. 318; pp. 420-426.
Langmead et al. "Ultrafast and memory-efficient alignment of short DNA sequences to the human genome" Genome Biology 2009, 10: R25. 10 pages.

(56) References Cited

OTHER PUBLICATIONS

Lapaire, O. et al., "Array-CGH Analysis of Cell-Free Fetal DNA in 10 ml of Amniotic Fluid Supernatant" Prenatal Diagnosis, May 2007, vol. 27, pp. 616-621.
Lapaire, O. et al., "Cell-Free Fetal DNA in Amniotic Fluid: Unique Fragmentation Signatures in Euploid and Aneuploid Fetuses" 2007, Clinical Chemistry, vol. 53, No. 3, pp. 405-411.
Lapaire, O. et al., "Larger Columns and Change of Lysis Buffer Increase the Yield of Cell-Free DNA Extracted from Amniotic Fluid" 2006, Letters to the Editor, Clinical Chemistry, vol. 52, No. 1, pp. 156-157.
Larrabee, Paige, B., et al., "Microarray Analysis of Cell-Free Fetal DNA in Amniotic Fluid: A Prenatal Molecular Karyotype" Sep. 1, 2004, American Journal of Human Genetics, vol. 75, No. 3, pp. 485-491.
Leary, R. et al. "Detection of Chromosomal Alterations in the Circulation of Cancer Patients with Whole-Genome Sequencing"; Science Translational Medicine; Nov. 28, 2012; vol. 4, Issue 162; 162ra154; 13 pages.
Leary, R. et al. "Development of Personalized Tumor Biomarkers Using Massively Parallel Sequencing", Science Translational Medicine, vol. 2, Issue 20, Feb. 24, 2010, 8 pages.
Lecoeur, Herve, "Nuclear Apoptosis Detection by Flow Cytometry: Influence of Endogenous Endonucleases" 2002, Experimental Cell Research, vol. 277, pp. 1-14.
Li et al. "Fast and accurate short read alignment with Burrows-Wheeler transform" Bioinformatics, 2009; vol. 25, pp. 1754-1760.
Li et al. "SOAP: Short Oligonucleotide Alignment Program" Bioinformatics, 2008, vol. 24. pp. 713-714.
Li et al. "The Sequence Alignment Map format and SAMtools" vol. 25, pp. 2078-2079.
Li, Ying, et al., "Size Separation of Circulatory DNA in Maternal Plasma Permits Ready Detection of Fetal DNA Polymorphisms" Jun. 1, 2004, Clinical Chemistry, American Association for Clinical Chemistry, vol. 50, No. 6, pp. 1002-1011.
Liu, Kevin J. et al.; "Decoding Circulation Nucleic Acids in Human Serum Using Microfluidic Single Molecule Spectroscopy"; Journal of the American Chemical Society; 2010; 132(16); pp. 5793-5798.
Lo, Y. et al.; "Presence of fetal DNA in maternal plasma and serum"; The Lancet; 1997; 350; pp. 485-487.
Lo, Y. M. Dennis et al.; "Quantitative Analysis of Fetal DNA in Maternal Plasma and Serum: Implications for Noninvasive Prenatal Diagnosis"; Am. J. Hum. Genet.; 1998; 62; pp. 768-775.
Lo, Y. M. Dennis, et al., "Digital PCR for the Molecular Detection of Fetal Chromosomal Aneuploidy" Aug. 2007, Proceedings of the National Academy of Sciences of the United States of America, vol. 104, No. 32, pp. 13116-13121.
Lo, Y.M. Dennis, et al., "Maternal Plasma DNA Sequencing Reveals the Genome-Wide Genetic and Mutational Profile of the Fetus" Dec. 8, 2010, Science Translational Medicine, vol. 2, Issue 61, 15 pages.
Lun, Fiona M. F. et al.; "Microfluidics Digital PCR Reveals a Higher than Expected Fraction of Fetal DNA in Maternal Plasma"; Clinical Chemistry; 2008; 54:10; pp. 1664-1672.
Lun, Fiona, M.F., et al., "Noninvasive Prenatal Diagnosis of Monogenic Diseases by Digital Size Selection and Relative Mutation Dosage on DNA in Maternal Plasma" Dec. 16, 2008, Proceedings of the National Academy of Sciences of the United States of America, vol. 105, No. 50, pp. 19920-19925.
Maron, J. et al. "Prenatal diagnosis using cell-free nucleic acids in maternal body fluids: a decade of progress" Am J Med Genet C Semin Med Genet. Feb. 15, 2007;145C(1):5-17.
Maurano, M. et al. "Systematic Localization of Common Disease-Associated Variation in Regulatory DNA" Science, Sep. 2012, vol. 337, pp. 1190-1195.
Metz et al., "Ultradeep sequencing detects GNAQ and GNAII mutations in cell-free DNA from plasma of patients with uveal melanoma," Cancer Medicine, vol. 2, No. 2, Feb. 14, 2013, pp. 208-215.
Mouliere, F. et al. "The importance of examining the proportion of circulating DNA originating from tumor, microenvironment and normal cells in colorectal cancer patients" Expert Opinion on Biological Therapy; 2012; vol. 12, Supp. 1, pp. S209-S215 (8 pages).
Mouliere, F., et al., "High fragmentation characterizes tumour-derived circulating DNA" PLOS One, Sep. 6, 2011, vol. 6, No. 9, 10 pages.
Newman, A. et al. "An ultrasensitive method for quantitating circulating tumor DNA with broad patient coverage" Nature Medicine, May 2014, vol. 20, No. 5, pp. 548-556.
Nygren, Anders O.H. et al.; "Quantification of Fetal DNA by Use of Methylation-Based DNA Discrimination"; Clinical Chemistry; 2010; 56:10; pp. 1627-1635.
Palomaki, Glenn E. et al.; "DNA sequencing of maternal plasma to detect Down syndrome: An international clinical validation study"; Genetics in Medicine; 2011; vol. 13, No. 11; pp. 913-920.
Papageorgiou, Elisavet A. et al.; "Fetal-specific DNA methylation ratio permits noninvasive prenatal diagnosis of trisomy 21"; Nature Medicine; 2011; 17; pp. 510-513.
Pedersen, J.S. et al. "Genome-wide nucleosome map and cytosine methylation levels of an ancient human genome" Genome Research; Mar. 2014; vol. 24, Issue 3; pp. 454-466.
Peter, Inga, PhD., et al., "Cell-Free DNA Fragmentation Patterns in Amniotic Fluid Identify Genetic Abnormalities and Changes due to Storage," Sep. 2008, Diagn. Mol. Pathol., vol. 17, No. 3, pp. 185-190.
Reed, W, et al., "Non-Invasive Determination of the Paternal HLA Haplotype of a Fetus Using Kinetic PCR to Detect Fetal Microchimerism in Maternal Plasma" Mar. 2, 2002, Bone Marrow Transplantation, vol. 29, No. 6, pp. 527-529.
Schep, A. et al. "Structured nucleosome fingerprints enable high-resolution mapping of chromatin architecture within regulatory regions" Genome Research, Nov. 2015, vol. 25, Issue 11; pp. 1757-1770.
Schwarzenbach, H. et al. "Cell-free nucleic acids as biomarkers in cancer patients" Nat Rev Cancer. Jun. 2011;11(6):426-37.
Sonnenberg, A. et al. "Dielectrophoretic isolation and detection of cancer-related circulating cell-free DNA biomarkers from blood and plasma" Electrophoresis, Jul. 2014, vol. 35, pp. 1828-1836. NIH Author Manuscript. 16 pages.
Sparks, Andrew B. et al.; "Noninvasive prenatal detection and selective analysis of cell-free DNA obtained from maternal blood: evaluation for trisomy 21 and trisomy 18"; American Journal of Obstetrics & Gynecology; 2012; vol. 206, Issue 4; pp. 319.e1-319.e9.
Tsui, N. et al. "High Resolution Size Analysis of Fetal DNA in the Urine of Pregnant Women by Paired-End Massively Parallel Sequencing" PLOS ONE; Oct. 2012; vol. 7, No. 10; 7 pages.
Tsui, N. et al.; "Noninvasive prenatal diagnosis of hemophilia by microfluidics digital PCR analysis of maternal plasma DNA"; Blood; 2011; 117; pp. 3684-3691.
USPTO, International Search Report and Written Opinion for PCT/US2015/042310, dated Jan. 12, 2016. 17 pages.
Volik, S. et al., Cell-free DNA (cfDNA): Clinical Significance and Utility in Cancer Shaped by Emerging Technologies, Mol. Cancer Res., vol. 14, pp. 898-908 (Year: 2016).
Wang, B. et al. "Increased Plasma DNA Integrity in Cancer Patients" Cancer Research; Jul. 2003; vol. 63, No. 14; pp. 3966-3968.
Wang, L. et al. "BRAF Mutations in Colon Cancer Are Not Likely Attributable to Defective DNA Mismatch Repair" Cancer Research, Sep. 2003, vol. 63, pp. 5209-5212.
Yu, Stephanie, C. Y., et al., "Size-based molecular diagnosis using plasma DNA for noninvasive prenatal testing," PNAS, Jun. 10, 2014, vol. 111, No. 23, pp. 8583-8588.
Zheng, Yama WL., et al., "Nonhematopoietically Derived DNA is Shorter than Hematopoietically Derived DNA in Plasma: A Transplantation Model" Clinical Chemistry, 2012, vol. 58, pp. 549-558.
Cristiano, S. et al., Genome-wide cell-free DNA fragmentation in patients with cancer, Nature, vol. 570, pp. 385-389, plus Methods, pp. 1-2 plus Extended Data, pp. 1-13 (Year: 2019).
IP Office Australia, Examiner's First Report for Australian Patent Application No. 2015292311, dated Jan. 20, 2021.
USPTO, Nonfinal Office Action for U.S. Appl. No. 16/160,990, dated Mar. 22, 2021.

(56) References Cited

OTHER PUBLICATIONS

IP Office India, Refusal Order for Indian Patent Application No. 201747006075, dated Jun. 24, 2021. 9 pages.
IP Office Canada, Office Action for Canadian Patent Application No. 2956208, dated Jul. 16, 2021.
IP Office China, Second Office Action for Chinese Patent Application No. 201580052170.7, dated Jul. 23, 2021. 6 pages with English summary.
IO Office Korea, Office Action for Korean Patent Application No. 10-2017-7004904, with English translation, Sep. 15, 2021.
Ulz, P. et al., "Inference of transcription factor binding from cellfree DNA enables tumor subtype prediction and early detection," Nature Comm., vol. 10:4666, pp. 1-11 (Year: 2019).
IP Office China, Office Action for Chinese Patent Application No. 201580052170.7, with English translation, dated Feb. 14, 2022.
IP Office Japan, Office Action for Japanese Patent Application No. 2020-203304. dated Feb. 14, 2022.

\* cited by examiner

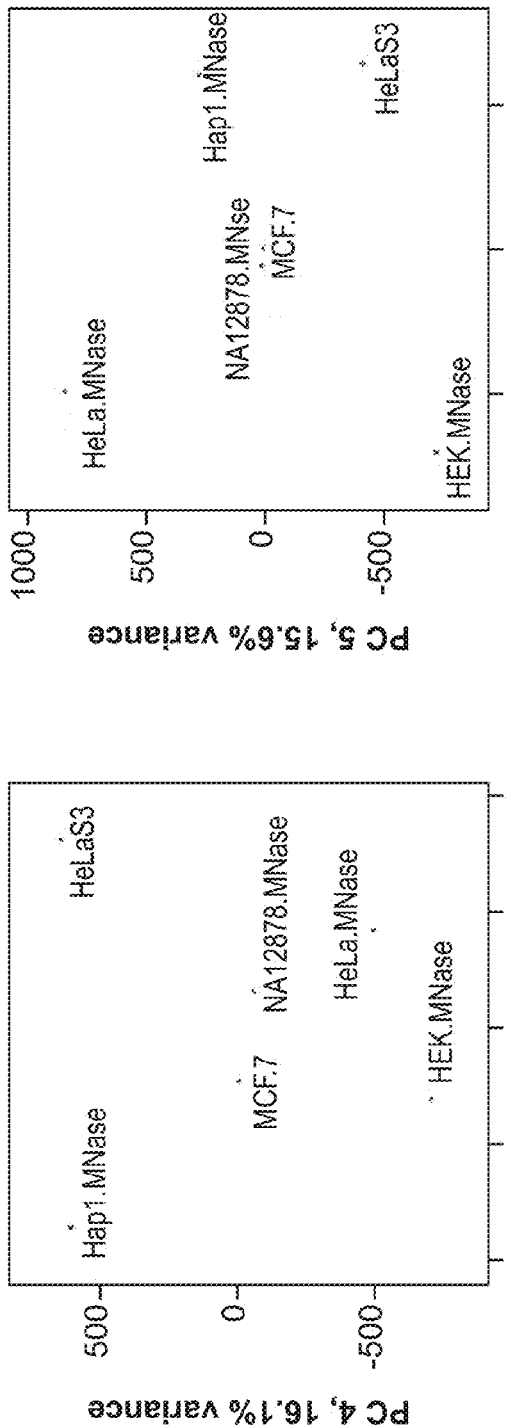
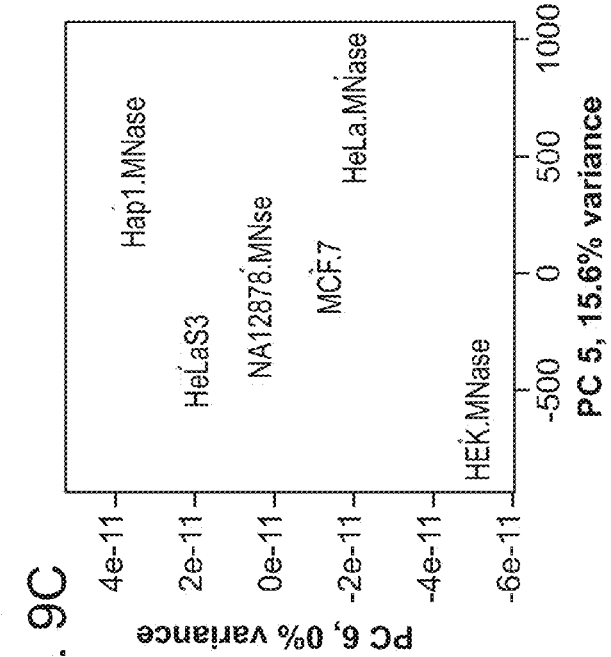
FIG. 9C
FIG. 9D
FIG. 9E

SEQUENCE LISTING

<160> NUMBER OF SEQ ID NOS: 4

<210> SEQ ID NO 1
<211> LENGTH: 34
<212> TYPE: DNA
<213> ORGANISM: Artificial Sequence
<220> FEATURE:
<223> OTHER INFORMATION: Synthetic oligonucleotide: CL9

<400> SEQUENCE: 1
gtgactggag ttcagacgtg tgctcttccg atct                                   34

<210> SEQ ID NO 2
<211> LENGTH: 16
<212> TYPE: DNA
<213> ORGANISM: Artificial Sequence
<220> FEATURE:
<223> OTHER INFORMATION: Synthetic oligonucleotide: Adapter 2.1
<220> FEATURE:
<221> NAME/KEY: misc_feature
<222> LOCATION: (16)..(16)
<223> OTHER INFORMATION: ddT at 3' end

<400> SEQUENCE: 2
cgacgctctt ccgatc                                                       16

<210> SEQ ID NO 3
<211> LENGTH: 34
<212> TYPE: DNA
<213> ORGANISM: Artificial Sequence
<220> FEATURE:
<223> OTHER INFORMATION: Synthetic oligonucleotide: Adapter 2.2
<220> FEATURE:
<221> NAME/KEY: misc_feature
<222> LOCATION: (1)..(1)
<223> OTHER INFORMATION: 5Phos at 5' end
<220> FEATURE:
<221> NAME/KEY: misc_feature
<222> LOCATION: (30)..(31)
<223> OTHER INFORMATION: Phosphorothioate bond
<220> FEATURE:
<221> NAME/KEY: misc_feature
<222> LOCATION: (31)..(32)
<223> OTHER INFORMATION: Phosphorothioate bond
<220> FEATURE:
<221> NAME/KEY: misc_feature
<222> LOCATION: (32)..(33)
<223> OTHER INFORMATION: Phosphorothioate bond
<220> FEATURE:
<221> NAME/KEY: misc_feature
<222> LOCATION: (33)..(34)
<223> OTHER INFORMATION: Phosphorothioate bond

<400> SEQUENCE: 3
agatcggaag agcgtcgtgt agggaaagag tgta                                   34

<210> SEQ ID NO 4
<211> LENGTH: 10
<212> TYPE: DNA
<213> ORGANISM: Artificial Sequence
<220> FEATURE:
<223> OTHER INFORMATION: Synthetic oligonucleotide: CL78
<220> FEATURE:
<221> NAME/KEY: misc_feature
<222> LOCATION: (1)..(1)
<223> OTHER INFORMATION: 5Phos at 5' end

```
<220> FEATURE:
<221> NAME/KEY: misc_feature
<222> LOCATION: (10)..(10)
<223> OTHER INFORMATION: (iSpC3)10 and 3BioTEG at 3' end

<400> SEQUENCE: 4
agatcggaag                                                                          10
```

US 11,352,670 B2

METHODS OF DETERMINING TISSUES AND/OR CELL TYPES GIVING RISE TO CELL-FREE DNA, AND METHODS OF IDENTIFYING A DISEASE OR DISORDER USING SAME

PRIORITY CLAIM

This application is a continuation of U.S. patent application Ser. No. 16/160,990, filed on Oct. 15, 2018, which is a continuation of U.S. patent application Ser. No. 15/329,228, filed on Jan. 25, 2017, which is a 371 national phase application of International Application No. PCT/US2015/042310, filed on Jul. 27, 2015, which claims the benefit of U.S. Provisional Application No. 62/029,178, filed on Jul. 25, 2014 and U.S. Provisional Application No. 62/087,619 filed on Dec. 4, 2014. The contents of the aforementioned applications are incorporated herein by reference.

STATEMENT OF GOVERNMENT INTEREST

This invention was made with government support under Grant Nos. 1DP1HG007811 awarded by the National Institutes of Health (NIH). The government has certain rights in the invention.

SEQUENCE LISTING

This application contains a Sequence Listing, which is submitted in ASCII format via USPTO EFS-Web, and is hereby incorporated by reference in its entirety. The ASCII copy, created on May 21, 2020, is named Sequence_Listing_ST25_072227-8115US02 and is 2 kilobytes in size.

TECHNICAL FIELD

The present disclosure relates to methods of determining one or more tissues and/or cell-types giving rise to cell-free DNA. In some embodiments, the present disclosure provides a method of identifying a disease or disorder in a subject as a function of one or more determined tissues and/or cell-types associated with cell-free DNA in a biological sample from the subject.

BACKGROUND

Cell-free DNA ("cfDNA") is present in the circulating plasma, urine, and other bodily fluids of humans. The cfDNA comprises double-stranded DNA fragments that are relatively short (overwhelmingly less than 200 base-pairs) and are normally at a low concentration (e.g. 1-100 ng/mL in plasma). In the circulating plasma of healthy individuals, cfDNA is believed to primarily derive from apoptosis of blood cells (i.e., normal cells of the hematopoietic lineage). However, in specific situations, other tissues can contribute substantially to the composition of cfDNA in bodily fluids such as circulating plasma.

While cfDNA has been used in certain specialties (e.g., reproductive medicine, cancer diagnostics, and transplant medicine), existing tests based on cfDNA rely on differences in genotypes (e.g., primary sequence or copy number representation of a particular sequence) between two or more cell populations (e.g., maternal genome vs. fetal genome; normal genome vs. cancer genome; transplant recipient genome vs. donor genome, etc.). Unfortunately, because the overwhelming majority of cfDNA fragments found in any given biological sample derive from regions of the genome that are identical in sequence between the contributing cell populations, existing cfDNA-based tests are extremely limited in their scope of application. In addition, many diseases and disorders are accompanied by changes in the tissues and/or cell-types giving rise to cfDNA, for example from tissue damage or inflammatory processes associated with the disease or disorder. Existing cfDNA-based diagnostic tests relying on differences in primary sequence or copy number representation of particular sequences between two genomes cannot detect such changes. Thus, while the potential for cfDNA to provide powerful biopsy-free diagnostic methods is enormous, there still remains a need for cfDNA-based diagnostic methodologies that can be applied to diagnose a wide variety of diseases and disorders.

SUMMARY

The present disclosure provides methods of determining one or more tissues and/or cell-types giving rise to cell-free DNA ("cfDNA") in a biological sample of a subject. In some embodiments, the present disclosure provides a method of identifying a disease or disorder in a subject as a function of one or more determined tissues and/or cell-types associated with cfDNA in a biological sample from the subject.

In some embodiments, the present disclosure provides a method of determining tissues and/or cell types giving rise to cell-free DNA (cfDNA) in a subject, the method comprising isolating cfDNA from a biological sample from the subject, the isolated cfDNA comprising a plurality of cfDNA fragments; determining a sequence associated with at least a portion of the plurality of cfDNA fragments; determining a genomic location within a reference genome for at least some cfDNA fragment endpoints of the plurality of cfDNA fragments as a function of the cfDNA fragment sequences; and determining at least some of the tissues and/or cell types giving rise to the cfDNA fragments as a function of the genomic locations of at least some of the cfDNA fragment endpoints.

In other embodiments, the present disclosure provides a method of identifying a disease or disorder in a subject, the method comprising isolating cell-free DNA (cfDNA) from a biological sample from the subject, the isolated cfDNA comprising a plurality of cfDNA fragments; determining a sequence associated with at least a portion of the plurality of cfDNA fragments; determining a genomic location within a reference genome for at least some cfDNA fragment endpoints of the plurality of cfDNA fragments as a function of the cfDNA fragment sequences; determining at least some of the tissues and/or cell types giving rise to the cfDNA as a function of the genomic locations of at least some of the cfDNA fragment endpoints; and identifying the disease or disorder as a function of the determined tissues and/or cell types giving rise to the cfDNA.

In other embodiments, the present disclosure provides a method for determining tissues and/or cell types giving rise to cell-free DNA (cfDNA) in a subject, the method comprising: (i) generating a nucleosome map by obtaining a biological sample from the subject, isolating the cfDNA from the biological sample, and measuring distributions (a), (b) and/or (c) by library construction and massively parallel sequencing of cfDNA; (ii) generating a reference set of nucleosome maps by obtaining a biological sample from control subjects or subjects with known disease, isolating the cfDNA from the biological sample, measuring distributions (a), (b) and/or (c) by library construction and massively parallel sequencing of cfDNA; and (iii) determining tissues and/or cell types giving rise to the cfDNA from the biological sample by comparing the nucleosome map derived from the cfDNA from the biological sample to the reference set of nucleosome maps; wherein (a), (b) and (c) are: (a) the distribution of likelihoods any specific base-pair in a human genome will appear at a terminus of a cfDNA fragment; (b) the distribution of likelihoods that any pair of base-pairs of a human genome will appear as a pair of termini of a cfDNA fragment; and (c) the distribution of likelihoods that any specific base-pair in a human genome will appear in a cfDNA fragment as a consequence of differential nucleosome occupancy.

In yet other embodiments, the present disclosure provides a method for determining tissues and/or cell types giving rise to cfDNA in a subject, the method comprising: (i) generating a nucleosome map by obtaining a biological sample from the subject, isolating the cfDNA from the biological sample, and measuring distributions (a), (b) and/or (c) by library construction and massively parallel sequencing of cfDNA; (ii) generating a reference set of nucleosome maps by obtaining a biological sample from control subjects or subjects with known disease, isolating the cfDNA from the biological sample, measuring distributions (a), (b) and/or (c) by library construction and massively parallel sequencing of DNA derived from fragmentation of chromatin with an enzyme such as micrococcal nuclease, DNase, or transposase; and (iii) determining tissues and/or cell types giving rise to the cfDNA from the biological sample by comparing the nucleosome map derived from the cfDNA from the biological sample to the reference set of nucleosome maps; wherein (a), (b) and (c) are: (a) the distribution of likelihoods any specific base-pair in a human genome will appear at a terminus of a sequenced fragment; (b) the distribution of likelihoods that any pair of base-pairs of a human genome will appear as a pair of termini of a sequenced fragment; and (c) the distribution of likelihoods that any specific base-pair in a human genome will appear in a sequenced fragment as a consequence of differential nucleosome occupancy.

In other embodiments, the present disclosure provides a method for diagnosing a clinical condition in a subject, the method comprising: (i) generating a nucleosome map by obtaining a biological sample from the subject, isolating cfDNA from the biological sample, and measuring distributions (a), (b) and/or (c) by library construction and massively parallel sequencing of cfDNA; (ii) generating a reference set of nucleosome maps by obtaining a biological sample from control subjects or subjects with known disease, isolating the cfDNA from the biological sample, measuring distributions (a), (b) and/or (c) by library construction and massively parallel sequencing of cfDNA; and (iii) determining the clinical condition by comparing the nucleosome map derived from the cfDNA from the biological sample to the reference set of nucleosome maps; wherein (a), (b) and (c) are: (a) the distribution of likelihoods any specific base-pair in a human genome will appear at a terminus of a cfDNA fragment; (b) the distribution of likelihoods that any pair of base-pairs of a human genome will appear as a pair of termini of a cfDNA fragment; and (c) the distribution of likelihoods that any specific base-pair in a human genome will appear in a cfDNA fragment as a consequence of differential nucleosome occupancy.

In other embodiments, the present disclosure provides a method for diagnosing a clinical condition in a subject, the method comprising (i) generating a nucleosome map by obtaining a biological sample from the subject, isolating cfDNA from the biological sample, and measuring distributions (a), (b) and/or (c) by library construction and massively parallel sequencing of cfDNA; (ii) generating a reference set of nucleosome maps by obtaining a biological sample from control subjects or subjects with known disease, isolating the cfDNA from the biological sample, measuring distributions (a), (b) and/or (c) by library construction and massively parallel sequencing of DNA derived from fragmentation of chromatin with an enzyme such as micrococcal nuclease (MNase), DNase, or transposase; and (iii) determining the tissue-of-origin composition of the cfDNA from the biological sample by comparing the nucleosome map derived from the cfDNA from the biological sample to the reference set of nucleosome maps; wherein (a), (b) and (c) are: (a) the distribution of likelihoods any specific base-pair in a human genome will appear at a terminus of a sequenced fragment; (b) the distribution of likelihoods that any pair of base-pairs of a human genome will appear as a pair of termini of a sequenced fragment; and (c) the distribution of likelihoods that any specific base-pair in a human genome will appear in a sequenced fragment as a consequence of differential nucleosome occupancy.

These and other embodiments are described in greater detail below.

BRIEF DESCRIPTION OF THE DRAWINGS

This application contains at least one drawing executed in color. Copies of this application with color drawing(s) will be provided by the Office upon request and payment of the necessary fees.

FIG. 1A shows the distribution of likelihoods any specific base-pair in a human genome will appear at a terminus of a sequenced fragment (i.e. points of fragmentation); FIG. 1B shows the distribution of likelihoods that any pair of base-pairs of a human genome will appear as a pair of termini of a sequenced fragment (i.e. consecutive pairs of fragmentation points that give rise to an individual molecule); and FIG. 1C shows the distribution of likelihoods that any specific base-pair in a human genome will appear within a sequenced fragment (i.e. relative coverage) as a consequence of differential nucleosome occupancy.

FIG. 4A shows PC 2 vs. PC 1; FIG. 4B shows PC 3 vs. PC 2.

FIG. 6A shows PC 2 vs. PC 1; FIG. 6B shows PC3 vs. PC 2.

FIG. 8A shows PC 2 vs. PC 1; FIG. 8B shows PC 3 vs. PC 2; FIG. 8C shows PC 4 vs. PC 3; FIG. 8D shows PC 5 vs. PC 4; FIG. 8E shows PC 6 vs. PC 5; FIG. 8F shows PC 7 vs. PC 6.

FIGS. 9A-E show principal component analysis of intensities at 181 bp to 202 bp periodicity in 10 kbp blocks across all autosomes for the MNase data sets: FIG. 9A shows PC 2 vs. PC 1; FIG. 9B shows PC 3 vs. PC 2; FIG. 9C shows PC 4 vs. PC 3; FIG. 9D shows PC 5 vs. PC 4; FIG. 9E shows PC 6 vs. PC 5.

FIG. 32A shows IH01 vs. BH01; FIG. 32B shows IH02 vs. BH01; FIG. 32C shows IH02 vs. IH01.

FIG. 34A shows BH01 simulation vs. BH01 actual; FIG. 34B shows IH01 simulation vs. IH01 actual; FIG. 34C shows IH02 simulation vs. IH01 actual.

FIG. 46 shows inter-peak distances for the three closest upstream and three closest downstream peak calls for 518,632 CTCF binding sites predicted by FIMO. FIG. 47 shows inter-peak distances for the three closest upstream and three closest downstream peak calls for 518,632 CTCF binding sites predicted by FIMO as in FIG. 46, but where the same set of CTCF sites has been filtered based on overlap with ENCODE ChIP-seq peaks, leaving 93,530 sites. FIG. 48 shows inter-peak distances for the three closest upstream and three closest downstream peak calls for 93,530 CTCF binding sites predicted by FIMO as in FIG. 47, but where the set of CTCF sites has been filtered based on overlap with the set of active CTCF sites experimentally observed across 19 cell lines, leaving 23,732 sites.

FIG. 50 shows mean short fraction WPS (top panel) and mean long fraction WPS (bottom panel) for the 518,632 sites, partitioned into distance bins denoting the number of base-pairs separating the flanking+1 and −1 nucleosome calls for each site. FIG. 51 shows mean short fraction WPS (top panel) and mean long fraction WPS (bottom panel) for the 518,632 sites of FIG. 50, but where the same set of CTCF sites has been filtered based on overlap with ENCODE ChIP-seq peaks. FIG. 52 shows mean short fraction WPS (top panel) and mean long fraction WPS (bottom panel) for the sites of FIG. 51, but where the same set of sites has been further filtered based on overlap with the set of active CTCF sites experimentally observed across 19 cell lines. Key defining colored lines for FIG. 50 is the same as in FIG. 51 and FIG. 52.

FIG. 53A: AP-2; FIG. 53B: E2F-2;

FIG. 53C: EBOX-TF; FIG. 53D: IRF; FIG. 53E: MYC-MAX; FIG. 53F: PAX5-2; FIG. 53G: RUNX-AML; FIG. 53H: YY1.

FIG. 62A shows the sums of Z scores for each chromosome calculated based on observed vs. expected numbers of sequencing reads for each sample (black dots) compared to simulated samples that assume no aneuploidy (red dots). FIG. 62B shows the allele balance at each of 48,800 common SNPs, evaluated per chromosome, for a subset of samples that were selected for additional sequencing.

FIG. 63A shows the distance between nucleosome peak calls across three published data sets (Gaffney et al. 2012, J S Pedersen et al. 2014, and A Schep et al. 2015) as well as the calls generated here, including the matched simulation of CA01. Previously published data sets do not show one defined mode at the canonical ~185 bp nucleosome distance, probably due to their sparse sampling or wide call ranges. In contrast, all the nucleosome calls from cfDNA show one well-defined mode. The matched simulated data set has shorter mode (166 bp) and a wider distribution. Further, the higher the coverage of the cfDNA data set used to generate calls, the higher the proportion of calls represented by the mode of the distribution. FIG. 63B shows the number of nucleosomes for each of the same list of sets as FIG. 63A. The cfDNA nucleosome calls present the most comprehensive call set with nearly 13 M nucleosome peak calls. FIG. 63C shows the distances between each peak call in the IH01 cfDNA sample and the nearest peak call from three previously published data sets. FIG. 63D shows the distances between each peak call in the IH02 cfDNA sample and the nearest peak call from three previously published data sets. FIG. 63E shows the distances between each peak call in the BH01 cfDNA sample and the nearest peak call from three previously published data sets. FIG. 63F shows the distances between each peak call in the CH01 cfDNA sample and the nearest peak call from three previously published data sets. FIG. 63G shows the distances between each peak call in the CA01 cfDNA sample and the nearest peak call from three previously published data sets. Negative numbers indicate the nearest peak is upstream; positive numbers indicate the nearest peak is downstream. With increased cfDNA coverage, a higher proportion of previously published calls are found in closer proximity to the determined nucleosome call. Highest concordance was found with calls generated by Gaffney et al., *PLoS Genet.*, vol. 8, e1003036 (2012) and A Schep et al. (2015). FIG. 63H shows the distances between each peak call and the nearest peak call from three previously published data sets, but this time for the matched simulation of CA01. The closest real nucleosome positions tend to be away from the peaks called in the simulation for the Gaffney et al., *PLoS Genet.*, vol. 8, e1003036 (2012) and J S Pedersen et al., *Genome Research*, vol. 24, pp. 454-466 (2014) calls. Calls generated by A Schep et al. (2015) seem to show some overlap with the simulated calls.

DETAILED DESCRIPTION

The present disclosure provides methods of determining one or more tissues and/or cell-types giving rise to cell-free DNA in a subject's biological sample. In some embodiments, the present disclosure provides a method of identifying a disease or disorder in a subject as a function of one or more determined tissues and/or cell-types associated with cfDNA in a biological sample from the subject.

Figure 1A:
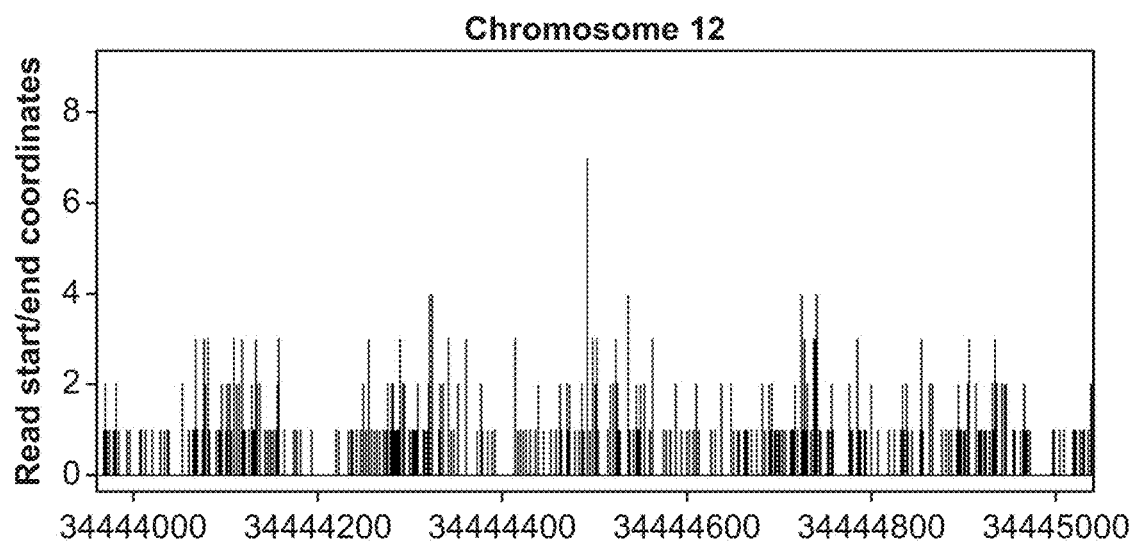
FIGS. 1A-C show three types of information that relate cfDNA fragmentation patterns to nucleosome occupancy, exemplified for a small genomic region. These same types of information might also arise through fragmentation of chromatin with an enzyme such as micrococcal nuclease (MNase), DNase, or transposase.
Figure 1B:
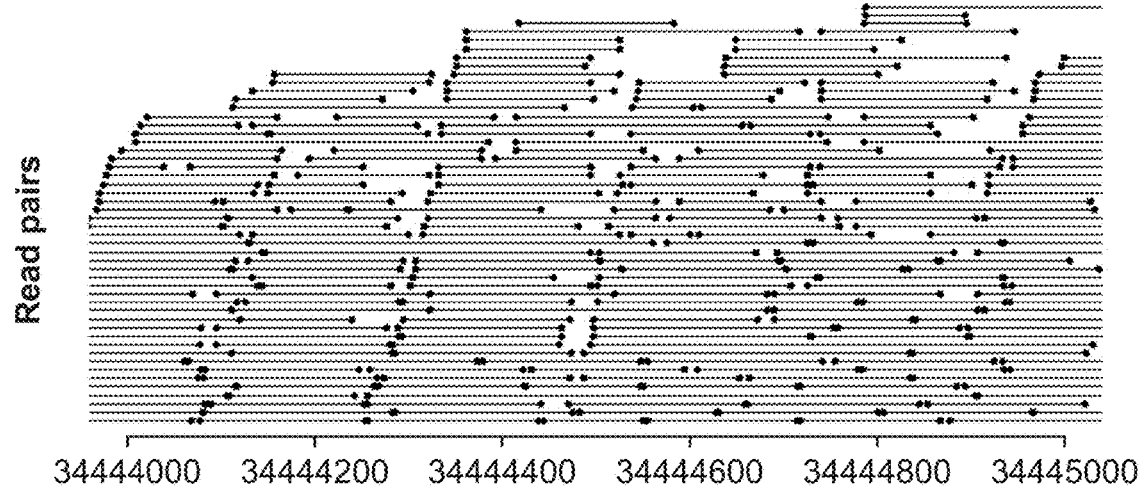
Figure 1C:
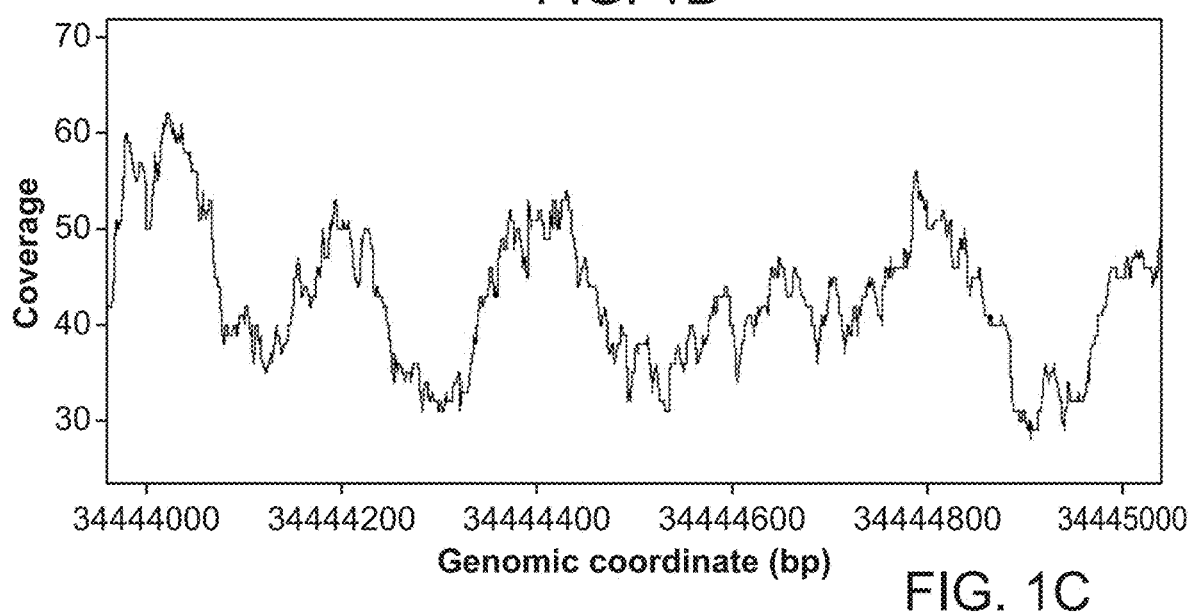

The present disclosure is based on a prediction that cfDNA molecules originating from different cell types or tissues differ with respect to: (a) the distribution of likelihoods any specific base-pair in a human genome will appear at a terminus of a cfDNA fragment (i.e. points of fragmentation); (b) the distribution of likelihoods that any pair of base-pairs of a human genome will appear as a pair of termini of a cfDNA fragment (i.e. consecutive pairs of fragmentation points that give rise to an individual cfDNA molecule); and (c) the distribution of likelihoods that any specific base-pair in a human genome will appear in a cfDNA fragment (i.e. relative coverage) as a consequence of differential nucleosome occupancy. These are referred to below as distributions (a), (b) and (c), or collectively referred to as "nucleosome dependent cleavage probability maps", "cleavage accessibility maps" or "nucleosome maps" (FIG. 1). Of note, nucleosome maps might also be measured through the sequencing of fragments derived from the fragmentation of chromatin with an enzyme such as micrococcal nuclease (MNase), DNase, or transposase, or equivalent procedures that preferentially fragment genomic DNA between or at the boundaries of nucleosomes or chromatosomes.

Figure 2:
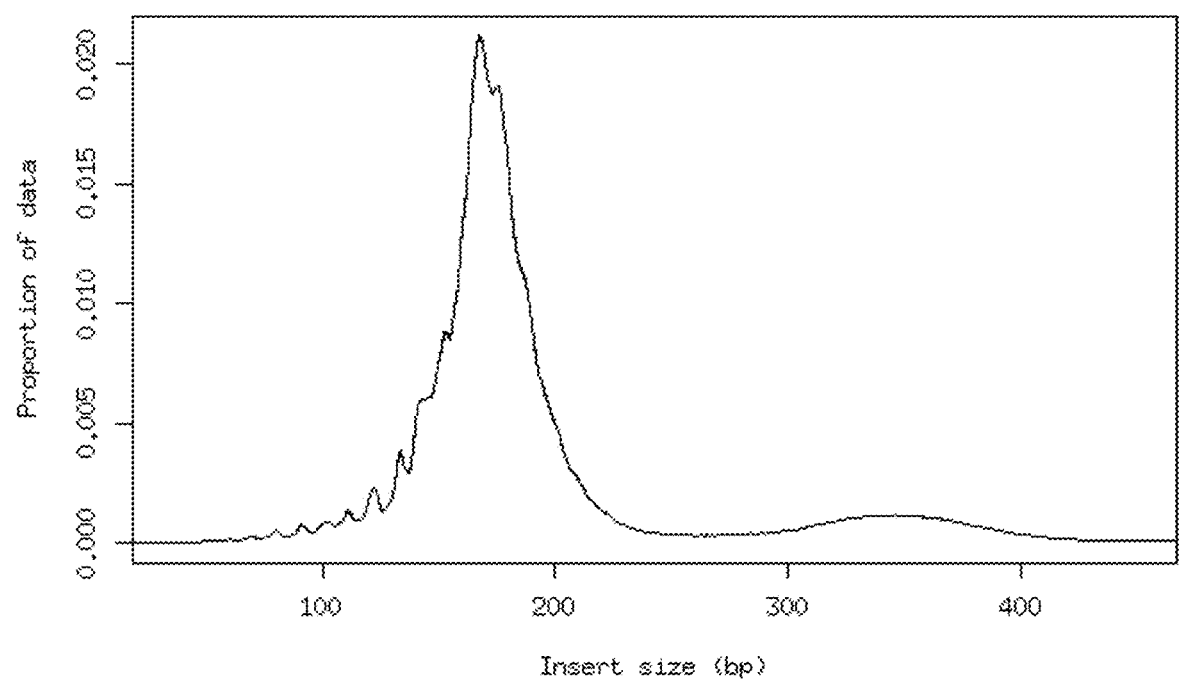
FIG. 2 shows insert size distribution of a typical cfDNA sequencing library; here shown for the pooled cfDNA sample derived from human plasma containing contributions from an unknown number of healthy individuals (bulk.cfDNA).

In healthy individuals, cfDNA overwhelmingly derives from apoptosis of blood cells, i.e. cells of the hematopoietic lineage. As these cells undergo programmed cell death, their genomic DNA is cleaved and released into circulation, where it continues to be degraded by nucleases. The length distribution of cfDNA oscillates with a period of approximately 10.5 base-pairs (bp), corresponding to the helical pitch of DNA coiled around the nucleosome, and has a marked peak around 167 bp, corresponding to the length of DNA associated with a linker-associated mononucleosome (FIG. 2). This evidence has led to the hypothesis that cfDNA's association with the nucleosome is what protects it from complete, rapid degradation in the circulation. An alternative possibility is that the length distribution arises simply from the pattern of DNA cleavage during apoptosis itself, which is influenced directly by nucleosome positioning. Regardless, the length distribution of cfDNA provides clear evidence that the fragmentation processes that give rise to cfDNA are influenced by nucleosome positioning.

In some embodiments, the present disclosure defines a nucleosome map as the measurement of distributions (a), (b) and/or (c) by library construction and massively parallel sequencing of either cfDNA from a bodily fluid or DNA derived from the fragmentation of chromatin with an enzyme such as micrococcal nuclease (MNase), DNase, or transposase, or equivalent procedures that preferentially fragment genomic DNA between or at the boundaries of nucleosomes or chromatosomes. As described below, these distributions may be 'transformed' in order to aggregate or summarize the periodic signal of nucleosome positioning within various subsets of the genome, e.g. quantifying periodicity in contiguous windows or, alternatively, in discontiguous subsets of the genome defined by transcription factor binding sites, gene model features (e.g. transcription start sites or gene bodies), topologically associated domains, tissue expression data or other correlates of nucleosome positioning. Furthermore, these might be defined by tissue-specific data. For example, one could aggregate or summarize signal in the vicinity of tissue-specific DNase I hypersensitive sites.

Figure 33A:
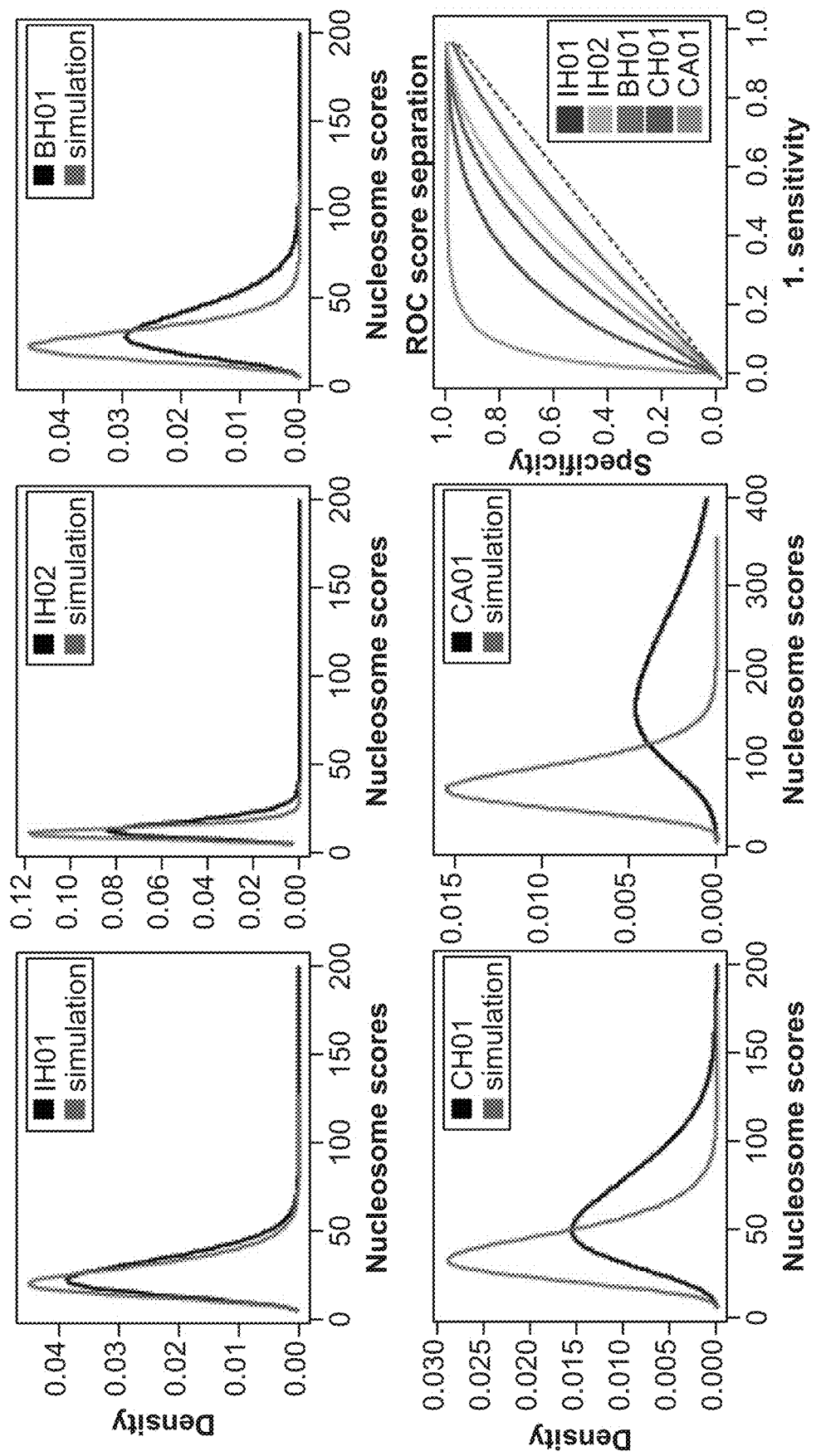
FIG. 33A shows nucleosome scores for real vs. simulated peaks.
Figure 33B:
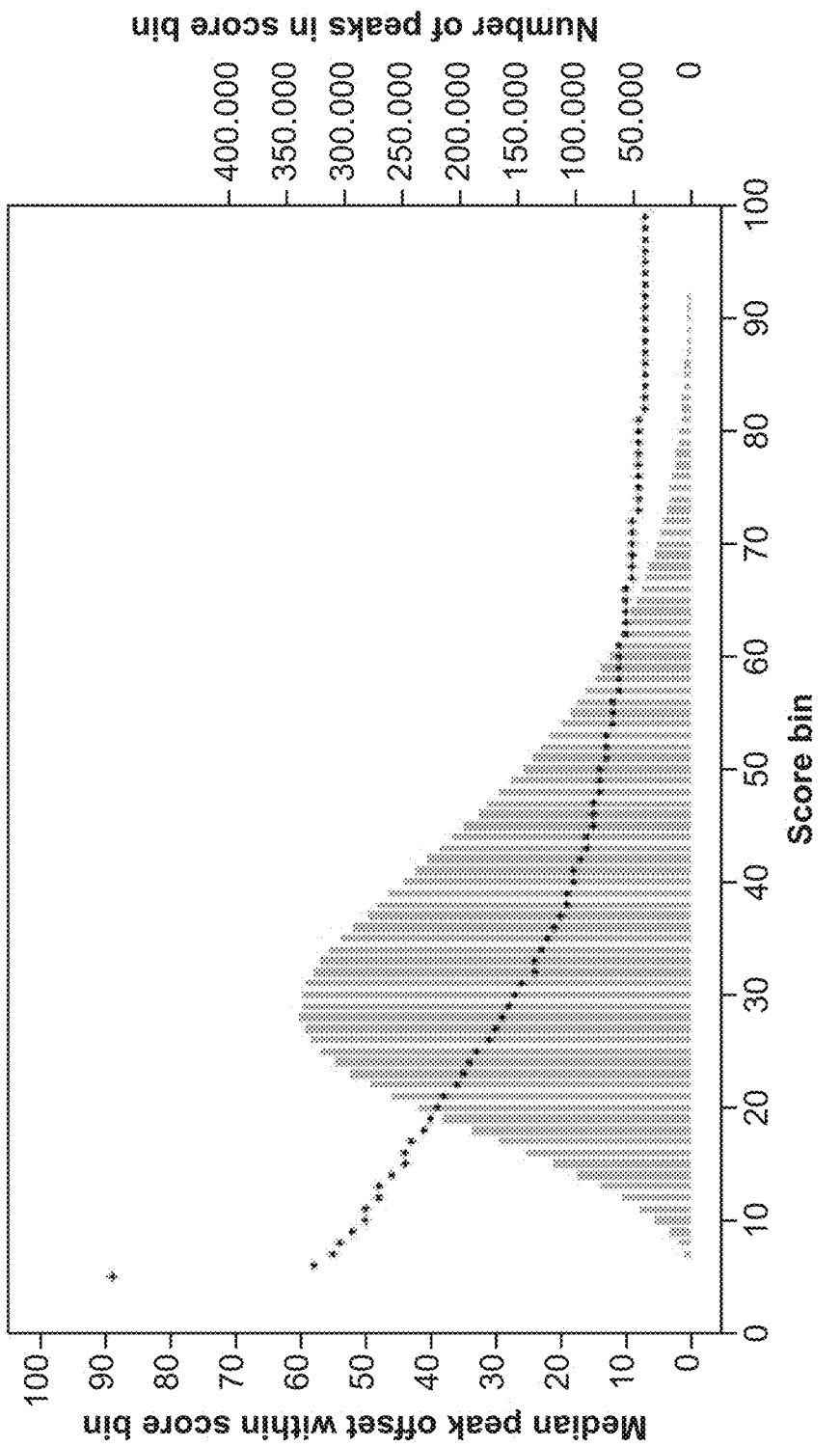
FIG. 33B shows median peak offset within a score bin as a function of the score bin (left y-axis), and the number of peaks in each score bin (right y-axis).

The present disclosure provides a dense, genome-wide map of in vivo nucleosome protection inferred from plasma-borne cfDNA fragments. The CH01 map, derived from cfDNA of healthy individuals, comprises nearly 13 M uniformly spaced local maxima of nucleosome protection that span the vast majority of the mappable human reference genome. Although the number of peaks is essentially saturated in CH01, other metrics of quality continued to be a function of sequencing depth (FIGS. 33A-B). An additional genome-wide nucleosome map was therefore constructed—by identical methods—that is based on nearly all of the cfDNA sequencing that the inventors have performed to date, for this study and other work ('CA01', 14.5 billion (G) fragments; 700-fold coverage; 13.0 M peaks). Although this map exhibits even more uniform spacing and more highly supported peak calls (FIGS. 33A-B, 63A-H), we caution that it is based on cfDNA from both healthy and non-healthy individuals (Tables 1, 5).

The dense, genome-wide map of nucleosome protection disclosed herein approaches saturation of the mappable portion of the human reference genome, with peak-to-peak spacing that is considerably more uniform and consistent with the expected nucleosome repeat length than previous efforts to generate human genome-wide maps of nucleosome positioning or protection (FIGS. 63A-H). In contrast with nearly all previous efforts, the fragments that observed herein are generated by endogenous physiological processes, and are therefore less likely to be subject to the technical variation associated with in vitro micrococcal nuclease digestion. The cell types that give rise to cfDNA considered in this reference map are inevitably heterogeneous (e.g. a mixture of lymphoid and myeloid cell types in healthy individuals). Nonetheless, the map's relative completeness may facilitate a deeper understanding of the processes that dictate nucleosome positioning and spacing in human cells, as well as the interplay of nucleosomes with epigenetic regulation, transcriptional output, and nuclear architecture.

Methods of Determining the Source(s) of cfDNA in a Subject's Biological Sample

As discussed generally above, and as demonstrated more specifically in the Examples which follow, the present technology may be used to determine (e.g., predict) the tissue(s) and/or cell type(s) which contribute to the cfDNA in a subject's biological sample.

Accordingly, in some embodiments, the present disclosure provides a method of determining tissues and/or cell-types giving rise to cell-free DNA (cfDNA) in a subject, the method comprising isolating cfDNA from a biological sample from the subject, the isolated cfDNA comprising a plurality of cfDNA fragments; determining a sequence associated with at least a portion of the plurality of cfDNA fragments; determining a genomic location within a reference genome for at least some cfDNA fragment endpoints of the plurality of cfDNA fragments as a function of the cfDNA fragment sequences; and determining at least some of the tissues and/or cell types giving rise to the cfDNA fragments as a function of the genomic locations of at least some of the cfDNA fragment endpoints.

In some embodiments, the biological sample comprises, consists essentially of, or consists of whole blood, peripheral blood plasma, urine, or cerebral spinal fluid.

In some embodiments, the step of determining at least some of the tissues and/or cell-types giving rise to the cfDNA fragments comprises comparing the genomic locations of at least some of the cfDNA fragment endpoints, or mathematical transformations of their distribution, to one or more reference maps. As used herein, the term "reference map" refers to any type or form of data which can be correlated or compared to an attribute of the cfDNA in the subject's biological sample as a function of the coordinate within the genome to which cfDNA sequences are aligned (e.g., the reference genome). The reference map may be correlated or compared to an attribute of the cfDNA in the subject's biological sample by any suitable means. For example and without limitation, the correlation or comparison may be accomplished by analyzing frequencies of cfDNA endpoints, either directly or after performing a mathematical transformation on their distribution across windows within the reference genome, in the subject's biological sample in view of numerical values or any other states defined for equivalent coordinates of the reference genome by the reference map. In another non-limiting example, the correlation or comparison may be accomplished by analyzing the determined nucleosome spacing(s) based on the cfDNA of the subject's biological sample in view of the determined nucleosome spacing(s), or another property that correlates with nucleosome spacing(s), in the reference map.

The reference map(s) may be sourced or derived from any suitable data source including, for example, public databases of genomic information, published data, or data generated for a specific population of reference subjects which may each have a common attribute (e.g., disease status). In some embodiments, the reference map comprises a DNase I hypersensitivity dataset. In some embodiments, the reference map comprises an RNA expression dataset. In some embodiments, the reference map comprises a chromosome conformation map. In some embodiments, the reference map comprises a chromatin accessibility map. In some embodiments, the reference map comprises data that is generated from at least one tissue or cell-type that is associated with a disease or a disorder. In some embodiments, the reference map comprises positions of nucleosomes and/or chromatosomes in a tissue or cell type. In some embodiments, the reference map is generated by a procedure that includes digesting chromatin with an exogenous nuclease (e.g., micrococcal nuclease). In some embodiments, the reference map comprises chromatin accessibility data determined by a transposition-based method (e.g., ATAC-seq). In some embodiments, the reference map comprises data associated with positions of a DNA binding and/or DNA occupying protein for a tissue or cell type. In some embodiments, the DNA binding and/or DNA occupying protein is a transcription factor. In some embodiments, the positions are determined by a procedure that includes chromatin immunoprecipitation of a crosslinked DNA-protein complex. In some embodiments, the positions are determined by a procedure that includes treating DNA associated with the tissue or cell type with a nuclease (e.g., DNase-I). In some embodiments, the reference map is generated by sequencing of cfDNA fragments from a biological sample from one or more individuals with a known disease. In some embodiments, this biological sample from which the reference map is generated is collected from an animal to which human cells or tissues have been xenografted.

In some embodiments, the reference map comprises a biological feature corresponding to positions of a DNA binding or DNA occupying protein for a tissue or cell type. In some embodiments, the reference map comprises a biological feature corresponding to quantitative RNA expression of one or more genes. In some embodiments, the reference map comprises a biological feature corresponding to the presence or absence of one or more histone marks. In some embodiments, the reference map comprises a biological feature corresponding to hypersensitivity to nuclease cleavage.

The step of comparing the genomic locations of at least some of the cfDNA fragment endpoints to one or more reference maps may be accomplished in a variety of ways. In some embodiments, the cfDNA data generated from the biological sample (e.g., the genomic locations of the cfDNA fragments, their endpoints, the frequencies of their endpoints, and/or nucleosome spacing(s) inferred from their distribution) is compared to more than one reference map. In such embodiments, the tissues or cell-types associated with the reference maps which correlate most highly with the cfDNA data in the biological sample are deemed to be contributing. For example and without limitation, if the cfDNA data includes a list of likely cfDNA endpoints and their locations within the reference genome, the reference map(s) having the most similar list of cfDNA endpoints and their locations within the reference genome may be deemed to be contributing. As another non-limiting example, the reference map(s) having the most correlation (or increased correlation, relative to cfDNA from a healthy subject) with a mathematical transformation of the distribution of cfDNA fragment endpoints from the biological sample may be deemed to be contributing. The tissue types and/or cell types which correspond to those reference maps deemed to be contributing are then considered as potential sources of the cfDNA isolated from the biological sample.

In some embodiments, the step of determining at least some of the tissues and/or cell types giving rise to the cfDNA fragments comprises performing a mathematical transformation on a distribution of the genomic locations of at least some of the cfDNA fragment endpoints. One non-limiting example of a mathematical transformation suitable for use in connection with the present technology is a Fourier transformation, such as a fast Fourier transformation ("FFT").

In some embodiments, the method further comprises determining a score for each of at least some coordinates of the reference genome, wherein the score is determined as a function of at least the plurality of cfDNA fragment endpoints and their genomic locations, and wherein the step of determining at least some of the tissues and/or cell types giving rise to the observed cfDNA fragments comprises comparing the scores to one or more reference map. The score may be any metric (e.g., a numerical ranking or probability) which may be used to assign relative or absolute values to a coordinate of the reference genome. For example, the score may consist of, or be related to a probability, such as a probability that the coordinate represents a location of a cfDNA fragment endpoint, or a probability that the coordinate represents a location of the genome that is preferentially protected from nuclease cleavage by nucleosome or protein binding. As another example, the score may relate to nucleosome spacing in particular regions of the genome, as determined by a mathematical transformation of the distribution of cfDNA fragment endpoints within that region. Such scores may be assigned to the coordinate by any suitable means including, for example, by counting absolute or relative events (e.g., the number of cfDNA fragment endpoints) associated with that particular coordinate, or performing a mathematical transformation on the values of such counts in the region or a genomic coordinate. In some embodiments, the score for a coordinate is related to the probability that the coordinate is a location of a cfDNA fragment endpoint. In other embodiments, the score for a coordinate is related to the probability that the coordinate represents a location of the genome that is preferentially protected from nuclease cleavage by nucleosome or protein binding. In some embodiments, the score is related to nucleosome spacing in the genomic region of the coordinate.

The tissue(s) and/or cell-type(s) referred to in the methods described herein may be any tissue or cell-type which gives rise to cfDNA. In some embodiments, the tissue or cell-type is a primary tissue from a subject having a disease or disorder. In some embodiments, the disease or disorder is selected from the group consisting of: cancer, normal pregnancy, a complication of pregnancy (e.g., aneuploid pregnancy), myocardial infarction, inflammatory bowel disease, systemic autoimmune disease, localized autoimmune disease, allotransplantation with rejection, allotransplantation without rejection, stroke, and localized tissue damage.

In some embodiments, the tissue or cell type is a primary tissue from a healthy subject.

In some embodiments, the tissue or cell type is an immortalized cell line.

In some embodiments, the tissue or cell type is a biopsy from a tumor.

In some embodiments, the reference map is based on sequence data obtained from samples obtained from at least one reference subject. In some embodiments, this sequence data defines positions of cfDNA fragment endpoints within a reference genome—for example, if the reference map is generated by sequencing of cfDNA from subject(s) with known disease. In other embodiments, this sequence data on which the reference map is based may comprise any one or more of: a DNase I hypersensitive site dataset, an RNA expression dataset, a chromosome conformation map, or a chromatin accessibility map, or nucleosome positioning map generated by digestion of chromatin with micrococcal nuclease.

In some embodiments, the reference subject is healthy. In some embodiments, the reference subject has a disease or disorder, optionally selected from the group consisting of: cancer, normal pregnancy, a complication of pregnancy (e.g., aneuploid pregnancy), myocardial infarction, inflammatory bowel disease, systemic autoimmune disease, localized autoimmune disease, allotransplantation with rejection, allotransplantation without rejection, stroke, and localized tissue damage.

In some embodiments, the reference map comprises scores for at least a portion of coordinates of the reference genome associated with the tissue or cell type. In some embodiments, the reference map comprises a mathematical transformation of the scores, such as a Fourier transformation of the scores. In some embodiments, the scores are based on annotations of reference genomic coordinates for the tissue or cell type. In some embodiments, the scores are based on positions of nucleosomes and/or chromatosomes. In some embodiments, the scores are based on transcription start sites and/or transcription end sites. In some embodiments, the scores are based on predicted binding sites of at least one transcription factor. In some embodiments, the scores are based on predicted nuclease hypersensitive sites. In some embodiments, the scores are based on predicted nucleosome spacing.

In some embodiments, the scores are associated with at least one orthogonal biological feature. In some embodiments, the orthogonal biological feature is associated with highly expressed genes. In some embodiments, the orthogonal biological feature is associated with lowly expression genes.

In some embodiments, at least some of the plurality of the scores has a value above a threshold (minimum) value. In such embodiments, scores falling below the threshold (minimum) value are excluded from the step of comparing the scores to a reference map. In some embodiments, the threshold value is determined before determining the tissue(s) and/or the cell type(s) giving rise to the cfDNA. In other embodiments, the threshold value is determined after determining the tissue(s) and/or the cell type(s) giving rise to the cfDNA.

In some embodiments, the step of determining the tissues and/or cell types giving rise to the cfDNA as a function of a plurality of the genomic locations of at least some of the cfDNA fragment endpoints comprises comparing a mathematical transformation of the distribution of the genomic locations of at least some of the cfDNA fragment endpoints of the sample with one or more features of one or more reference maps. One non-limiting example of a mathematical transformation suitable for this purpose is a Fourier transformation, such as a fast Fourier transformation ("FFT").

In any embodiment described herein, the method may further comprise generating a report comprising a list of the determined tissues and/or cell-types giving rise to the isolated cfDNA. The report may optionally further include any other information about the sample and/or the subject, the type of biological sample, the date the biological sample was obtained from the subject, the date the cfDNA isolation step was performed and/or tissue(s) and/or cell-type(s) which likely did not give rise to any cfDNA isolated from the biological sample.

In some embodiments, the report further includes a recommended treatment protocol including, for example and without limitation, a suggestion to obtain an additional diagnostic test from the subject, a suggestion to begin a therapeutic regimen, a suggestion to modify an existing therapeutic regimen with the subject, and/or a suggestion to suspend or stop an existing therapeutic regiment.

Methods of Identifying a Disease or Disorder in a Subject

As discussed generally above, and as demonstrated more specifically in the Examples which follow, the present technology may be used to determine (e.g., predict) a disease or disorder, or the absence of a disease or a disorder, based at least in part on the tissue(s) and/or cell type(s) which contribute to cfDNA in a subject's biological sample.

Accordingly, in some embodiments, the present disclosure provides a method of identifying a disease or disorder in a subject, the method comprising isolating cell free DNA (cfDNA) from a biological sample from the subject, the isolated cfDNA comprising a plurality of cfDNA fragments; determining a sequence associated with at least a portion of the plurality of cfDNA fragments; determining a genomic location within a reference genome for at least some cfDNA fragment endpoints of the plurality of cfDNA fragments as a function of the cfDNA fragment sequences; determining at least some of the tissues and/or cell types giving rise to the cfDNA as a function of the genomic locations of at least some of the cfDNA fragment endpoints; and identifying the disease or disorder as a function of the determined tissues and/or cell types giving rise to the cfDNA.

In some embodiments, the biological sample comprises, consists essentially of, or consists of whole blood, peripheral blood plasma, urine, or cerebral spinal fluid.

In some embodiments, the step of determining the tissues and/or cell-types giving rise to the cfDNA comprises comparing the genomic locations of at least some of the cfDNA fragment endpoints, or mathematical transformations of their distribution, to one or more reference maps. The term "reference map" as used in connection with these embodiments may have the same meaning described above with respect to methods of determining tissue(s) and/or cell type(s) giving rise to cfDNA in a subject's biological sample. In some embodiments, the reference map may comprise any one or more of: a DNase I hypersensitive site dataset, an RNA expression dataset, a chromosome conformation map, a chromatin accessibility map, sequence data that is generated from samples obtained from at least one reference subject, enzyme-mediated fragmentation data corresponding to at least one tissue that is associated with a disease or a disorder, and/or positions of nucleosomes and/or chromatosomes in a tissue or cell type. In some embodiments, the reference map is generated by sequencing of cfDNA fragments from a biological sample from one or more individuals with a known disease. In some embodiments, this biological sample from which the reference map is generated is collected from an animal to which human cells or tissues have been xenografted.

In some embodiments, the reference map is generated by digesting chromatin with an exogenous nuclease (e.g., micrococcal nuclease). In some embodiments, the reference maps comprise chromatin accessibility data determined by a transposition-based method (e.g., ATAC-seq). In some embodiments, the reference maps comprise data associated with positions of a DNA binding and/or DNA occupying protein for a tissue or cell type. In some embodiments, the DNA binding and/or DNA occupying protein is a transcription factor. In some embodiments, the positions are determined chromatin immunoprecipitation of a crosslinked DNA-protein complex. In some embodiments, the positions are determined by treating DNA associated with the tissue or cell type with a nuclease (e.g., DNase-I).

In some embodiments, the reference map comprises a biological feature corresponding to positions of a DNA binding or DNA occupying protein for a tissue or cell type. In some embodiments, the reference map comprises a biological feature corresponding to quantitative expression of one or more genes. In some embodiments, the reference map comprises a biological feature corresponding to the presence or absence of one or more histone marks. In some embodiments, the reference map comprises a biological feature corresponding to hypersensitivity to nuclease cleavage.

In some embodiments, the step of determining the tissues and/or cell types giving rise to the cfDNA comprises performing a mathematical transformation on a distribution of the genomic locations of at least some of the plurality of the cfDNA fragment endpoints. In some embodiments, the mathematical transformation includes a Fourier transformation.

In some embodiments, the method further comprises determining a score for each of at least some coordinates of the reference genome, wherein the score is determined as a function of at least the plurality of cfDNA fragment endpoints and their genomic locations, and wherein the step of determining at least some of the tissues and/or cell types giving rise to the observed cfDNA fragments comprises comparing the scores to one or more reference maps. The score may be any metric (e.g., a numerical ranking or probability) which may be used to assign relative or absolute values to a coordinate of the reference genome. For example, the score may consist of, or be related to a probability, such as a probability that the coordinate represents a location of a cfDNA fragment endpoint, or a probability that the coordinate represents a location of the genome that is preferentially protected from nuclease cleavage by nucleosome or protein binding. As another example, the score may relate to nucleosome spacing in particular regions of the genome, as determined by a mathematical transformation of the distribution of cfDNA fragment endpoints within that region. Such scores may be assigned to the coordinate by any suitable means including, for example, by counting absolute or relative events (e.g., the number of cfDNA fragment endpoints) associated with that particular coordinate, or performing a mathematical transformation on the values of such counts in the region or a genomic coordinate. In some embodiments, the score for a coordinate is related to the probability that the coordinate is a location of a cfDNA fragment endpoint. In other embodiments, the score for a coordinate is related to the probability that the coordinate represents a location of the genome that is preferentially protected from nuclease cleavage by nucleosome or protein binding. In some embodiments, the score is related to nucleosome spacing in the genomic region of the coordinate.

The term "score" as used in connection with these embodiments may have the same meaning described above with respect to methods of determining tissue(s) and/or cell type(s) giving rise to cfDNA in a subject's biological sample. In some embodiments, the score for a coordinate is related to the probability that the coordinate is a location of a cfDNA fragment endpoint. In other embodiments, the score for a coordinate is related to the probability that the coordinate represents a location of the genome that is preferentially protected from nuclease cleavage by nucleosome or protein binding. In some embodiments, the score is related to nucleosome spacing in the genomic region of the coordinate.

In some embodiments, the tissue or cell-type used for generating a reference map is a primary tissue from a subject having a disease or disorder. In some embodiments, the disease or disorder is selected from the group consisting of: cancer, normal pregnancy, a complication of pregnancy (e.g., aneuploid pregnancy), myocardial infarction, systemic autoimmune disease, localized autoimmune disease, inflammatory bowel disease, allotransplantation with rejection, allotransplantation without rejection, stroke, and localized tissue damage.

In some embodiments, the tissue or cell type is a primary tissue from a healthy subject.

In some embodiments, the tissue or cell type is an immortalized cell line.

In some embodiments, the tissue or cell type is a biopsy from a tumor.

In some embodiments, the reference map is based on sequence data obtained from samples obtained from at least one reference subject. In some embodiments, this sequence data defines positions of cfDNA fragment endpoints within a reference genome—for example, if the reference map is generated by sequencing of cfDNA from subject(s) with known disease. In other embodiments, this sequence data on which the reference map is based may comprise any one or more of: a DNase I hypersensitive site dataset, an RNA expression dataset, a chromosome conformation map, or a chromatin accessibility map, or nucleosome positioning map generated by digestion with micrococcal nuclease. In some embodiments, the reference subject is healthy. In some embodiments, the reference subject has a disease or disorder. In some embodiments, the disease or disorder is selected from the group consisting of: cancer, normal pregnancy, a complication of pregnancy (e.g., aneuploid pregnancy), myocardial infarction, systemic autoimmune disease, inflammatory bowel disease, localized autoimmune disease, allotransplantation with rejection, allotransplantation without rejection, stroke, and localized tissue damage.

In some embodiments, the reference map comprises cfDNA fragment endpoint probabilities, or a quantity that correlates with such probabilities, for at least a portion of the reference genome associated with the tissue or cell type. In some embodiments, the reference map comprises a mathematical transformation of the cfDNA fragment endpoint probabilities, or a quantity that correlates with such probabilities.

In some embodiments, the reference map comprises scores for at least a portion of coordinates of the reference genome associated with the tissue or cell type. In some embodiments, the reference map comprises a mathematical transformation of the scores, such as a Fourier transformation of the scores. In some embodiments, the scores are based on annotations of reference genomic coordinates for the tissue or cell type. In some embodiments, the scores are based on positions of nucleosomes and/or chromatosomes. In some embodiments, the scores are based on transcription start sites and/or transcription end sites. In some embodiments, the scores are based on predicted binding sites of at least one transcription factor. In some embodiments, the scores are based on predicted nuclease hypersensitive sites.

In some embodiments, the scores are associated with at least one orthogonal biological feature. In some embodiments, the orthogonal biological feature is associated with highly expressed genes. In some embodiments, the orthogonal biological feature is associated with lowly expression genes.

In some embodiments, at least some of the plurality of the scores each has a score above a threshold value. In such embodiments, scores falling below the threshold (minimum) value are excluded from the step of comparing the scores to a reference map. In some embodiments, the threshold value is determined before determining the tissue(s) and/or the cell type(s) giving rise to the cfDNA. In other embodiments, the threshold value is determined after determining the tissue(s) and/or the cell type(s) giving rise to the cfDNA.

In some embodiments, the step of determining the tissues and/or cell types giving rise to the cfDNA as a function of a plurality of the genomic locations of at least some of the cfDNA fragment endpoints comprises a mathematical transformation of the distribution of the genomic locations of at least some of the cfDNA fragment endpoints of the sample with one or more features of one or more reference maps.

In some embodiments, this mathematical transformation includes a Fourier transformation.

In some embodiments, the reference map comprises enzyme-mediated fragmentation data corresponding to at least one tissue that is associated with the disease or disorder.

In some embodiments, the reference genome is associated with a human.

In one aspect of the invention, the methods described herein are used for detection, monitoring and tissue(s) and/or cell-type(s)-of-origin assessment of malignancies from analysis of cfDNA in bodily fluids. It is now well documented that in patients with malignancies, a portion of cfDNA in bodily fluids such as circulating plasma can be derived from the tumor. The methods described here can potentially be used to detect and quantify this tumor derived portion. Furthermore, as nucleosome occupancy maps are cell-type specific, the methods described here can potentially be used to determine the tissue(s) and/or cell-type(s)-of-origin of a malignancy. Also, as noted above, it has been observed that there is a major increase in the concentration of circulating plasma cfDNA in cancer, potentially disproportionate to the contribution from the tumor itself. This suggests that other tissues (e.g. stromal, immune system) may possibly be contributing to circulating plasma cfDNA during cancer. To the extent that contributions from such other tissues to cfDNA are consistent between patients for a given type of cancer, the methods described above may enable cancer detection, monitoring, and/or tissue(s) and/or cell-type(s)-of-origin assignment based on signal from these other tissues rather than the cancer cells per se.

In another aspect of the invention, the methods described herein are used for detection, monitoring and tissue(s) and/or cell-type(s)-of-origin assessment of tissue damage from analysis of cfDNA in bodily fluids. It is to be expected that many pathological processes will result in a portion of cfDNA in bodily fluids such as circulating plasma deriving from damaged tissues. The methods described here can potentially be used to detect and quantify cfDNA derived from tissue damage, including identifying the relevant tissues and/or cell-types of origin. This may enable diagnosis and/or monitoring of pathological processes including myocardial infarction (acute damage of heart tissue), autoimmune disease (chronic damage of diverse tissues), and many others involving either acute or chronic tissue damage.

In another aspect of the invention, the methods described herein are used for estimating the fetal fraction of cfDNA in pregnancy and/or enhancing detection of chromosomal or other genetic abnormalities. Relatively shallow sequencing of the maternal plasma-borne DNA fragments, coupled with nucleosome maps described above, may allow a cost-effective and rapid estimation of fetal fraction in both male and female fetus pregnancies. Furthermore, by enabling non-uniform probabilities to be assigned to individual sequencing reads with respect to their likelihood of having originated from the maternal or fetal genome, these methods may also enhance the performance of tests directed at detecting chromosomal aberrations (e.g. trisomies) through analysis of cfDNA in maternal bodily fluids.

In another aspect of the invention, the methods described herein are used for quantifying the contribution of a transplant (autologous or allograft) to cfDNA—Current methods for early and noninvasive detection of acute allograft rejection involve sequencing plasma-borne DNA and identifying increased concentrations of fragments derived from the donor genome. This approach relies on relatively deep sequencing of this pool of fragments to detect, for example, 5-10% donor fractions. An approach based instead on nucleosome maps of the donated organ may enable similar estimates with shallower sequencing, or more sensitive estimates with an equivalent amount of sequencing. Analogous to cancer, it is also possible that cell types other than the transplant itself contribute to cfDNA composition during transplant rejection. To the extent that contributions from such other tissues to cfDNA are consistent between patients during transplant rejection, the methods described above may enable monitoring of transplant rejection based on signal from these other tissues rather than the transplant donor cells per se.

Additional Embodiments of the Present Disclosure.

The present disclosure also provides methods of diagnosing a disease or disorder using nucleosome reference map(s) generated from subjects having a known disease or disorder. In some such embodiments, the method comprises: (1) generating a reference set of nucleosome maps, wherein each nucleosome map is derived from either cfDNA from bodily fluids of individual(s) with defined clinical conditions (e.g. normal, pregnancy, cancer type A, cancer type B, etc.) and/or DNA derived from digestion of chromatin of specific tissues and/or cell types; (2) predicting the clinical condition and/or tissue/cell-type-of-origin composition of cfDNA from bodily fluids of individual(s) by comparing a nucleosome map derived from their cfDNA to the reference set of nucleosome maps.

STEP 1: Generating a reference set of nucleosome maps, and aggregating or summarizing signal from nucleosome positioning.

A preferred method for generating a nucleosome map includes DNA purification, library construction (by adaptor ligation and possibly PCR amplification) and massively parallel sequencing of cfDNA from a bodily fluid. An alternative source for nucleosome maps, which are useful in the context of this invention as reference points or for identifying principal components of variation, is DNA derived from digestion of chromatin with micrococcal nuclease (MNase), DNase treatment, ATAC-Seq or other related methods wherein information about nucleosome positioning is captured in distributions (a), (b) or (c). Descriptions of these distributions (a), (b) and (c) are provided above in [0078] and are shown graphically in FIG. 1.

In principle, very deep sequencing of such libraries can be used to quantify nucleosome occupancy in the aggregate cell types contributing to cfDNA at specific coordinates in the genome, but this is very expensive today. However, the signal associated with nucleosome occupancy patterns can be summarized or aggregated across continuous or discontinuous regions of the genome. For example, in Examples 1 and 2 provided herein, the distribution of sites in the reference human genome to which sequencing read start sites map, i.e. distribution (a), is subjected to Fourier transformation in 10 kilobase-pair (kbp) contiguous windows, followed by quantitation of intensities for frequency ranges that are associated with nucleosome occupancy. This effectively summarizes the extent to which nucleosomes exhibit structured positioning within each 10 kbp window. In Example 3 provided herein, we quantify the distribution of sites in the reference human genome to which sequencing read start sites map, i.e. distribution (a), in the immediate vicinity of transcription factor binding sites (TFBS) of specific transcription factor (TF), which are often immediately flanked by nucleosomes when the TFBS is bound by the TF. This effectively summarizes nucleosome positioning as a consequence of TF activity in the cell type(s) contributing to cfDNA. Importantly, there are many related ways in which nucleosome occupancy signals can be meaningfully summarized. These include aggregating signal from distributions (a), (b), and/or (c) around other genomic landmarks such as DNaseI hypersensitive sites, transcription start sites, topological domains, other epigenetic marks or subsets of all such sites defined by correlated behavior in other datasets (e.g. gene expression, etc.). As sequencing costs continue to fall, it will also be possible to directly use maps of nucleosome occupancy, including those generated from cfDNA samples associated with a known disease, as reference maps, i.e. without aggregating signal, for the purposes of comparison to an unknown cfDNA sample. In some embodiments, this biological sample from which the reference map of nucleosome occupancy is generated is collected from an animal to which human cells or tissues have been xenografted. The advantage of this is that sequenced cfDNA fragments mapping to the human genome will exclusively derive from the xenografted cells or tissues, as opposed to representing a mixture of cfDNA derived from the cells/tissues of interest along with hematopoietic lineages.

STEP 2: Predicting pathology(s), clinical condition(s) and/or tissue/cell-types-of-origin composition on the basis of comparing the cfDNA-derived nucleosome map of one or more new individuals/samples to the reference set of nucleosome maps either directly or after mathematical transformation of each map.

Once one has generated a reference set of nucleosome maps, there are a variety of statistical signal processing methods for comparing additional nucleosome map(s) to the reference set. In Examples 1 & 2, we first summarize long-range nucleosome ordering within 10 kbp windows along the genome in a diverse set of samples, and then perform principal components analysis (PCA) to cluster samples (Example 1) or to estimate mixture proportions (Example 2). Although we know the clinical condition of all cfDNA samples and the tissue/cell-type-of-origin of all cell line samples used in these Examples, any one of the samples could in principle have been the "unknown", and its behavior in the PCA analysis used to predict the presence/absence of a clinical condition or its tissue/cell-type-of-origin based on its behavior in the PCA analysis relative to all other nucleosome maps.

The unknown sample does not necessarily need to be precisely matched to 1+ members of the reference set in a 1:1 manner. Rather, its similarities to each can be quantified (Example 1), or its nucleosome map can be modeled as a non-uniform mixture of 2+ samples from the reference set (Example 2).

The tissue/cell-type-of-origin composition of cfDNA in each sample need not be predicted or ultimately known for the method of the present invention to be successful. Rather, the method described herein relies on the consistency of tissue/cell-type-of-origin composition of cfDNA in the context of a particular pathology or clinical condition. However, by surveying the nucleosome maps of a large number of tissues and/or cell types directly by analysis of DNA derived from digestion of chromatin and adding these to the nucleosome map, it would be possible to estimate the tissue(s) and/or cell-type(s) contributing to an unknown cfDNA-derived sample.

In any embodiment described herein, the method may further comprise generating a report comprising a statement identifying the disease or disorder. In some embodiments, the report may further comprise a list of the determined tissues and/or cell types giving rise to the isolated cfDNA. In some embodiments, the report further comprises a list of diseases and/or disorders which are unlikely to be associated with the subject. The report may optionally further include any other information about the sample and/or the subject, the type of biological sample, the date the biological sample was obtained from the subject, the date the cfDNA isolation step was performed and/or tissue(s) and/or cell type(s) which likely did not give rise to any cfDNA isolated from the biological sample.

In some embodiments, the report further includes a recommended treatment protocol including, for example and without limitation, a suggestion to obtain an additional diagnostic test from the subject, a suggestion to begin a therapeutic regimen, a suggestion to modify an existing therapeutic regimen with the subject, and/or a suggestion to suspend or stop an existing therapeutic regiment.

EXAMPLES

Example 1. Principal Components Analysis of Cell Free DNA Nucleosome Maps

The distribution of read start positions in sequencing data derived from cfDNA extractions and MNase digestion experiments were examined to assess the presence of signals related to nucleosome positioning. For this purpose, a pooled cfDNA sample (human plasma containing contributions from an unknown number of healthy individuals; bulk.cfDNA), a cfDNA sample from single healthy male control individual (MC2.cfDNA), four cfDNA samples from patients with intracranial tumors (tumor.2349, tumor.2350, tumor.2351, tumor.2353), six MNase digestion experiments from five different human cell lines (Hap1.MNase, HeLa.MNase, HEK.MNase, NA12878.MNase, HeLaS3, MCF.7) and seven cfDNA samples from different pregnant female individuals (gm1matplas, gm2matplas, im1matplas, fgs002, fgs003, fgs004, fgs005) were analyzed and contrasted with regular shotgun sequencing data set of DNA extracted from a female lymphoblastoid cell line (NA12878). A subset of the pooled cfDNA sample (26%, bulk.cfDNA part) and of the single healthy male control individual (18%, MC2.cfDNA_part) were also included, as separate samples, to explore the effect of sequencing depth.

Figure 3A:
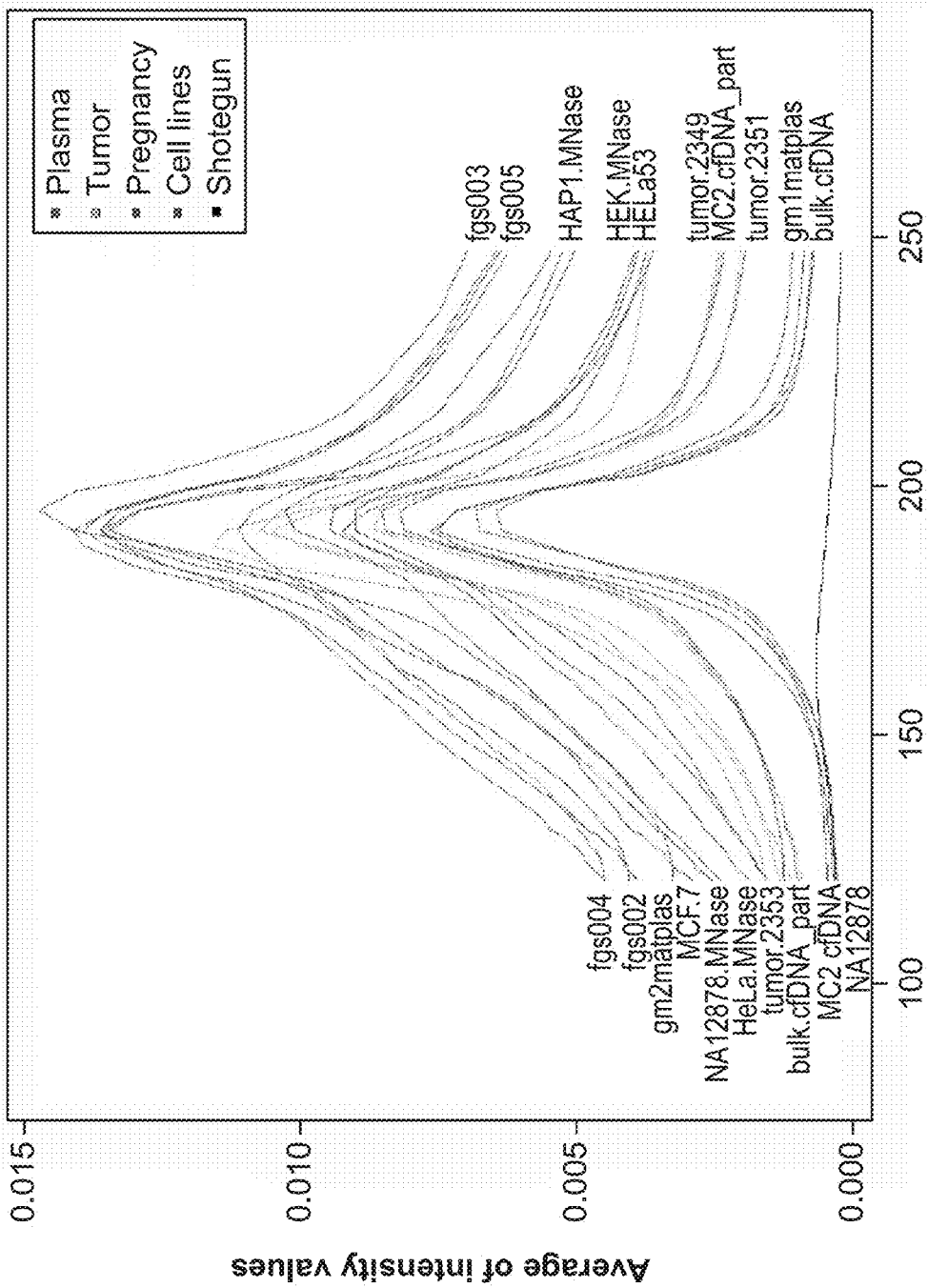
FIG. 3A shows average periodogram intensities from Fast Fourier Transformation (FFT) of read start coordinates mapping to the first (chr1) human autosome across all cfDNA samples (Plasma), cfDNA from tumor patient samples (Tumor), cfDNA from pregnant female individuals (Pregnancy), MNase of human different human cell lines (Cell lines) and a human DNA shotgun sequencing library (Shotgun).
Figure 3B:
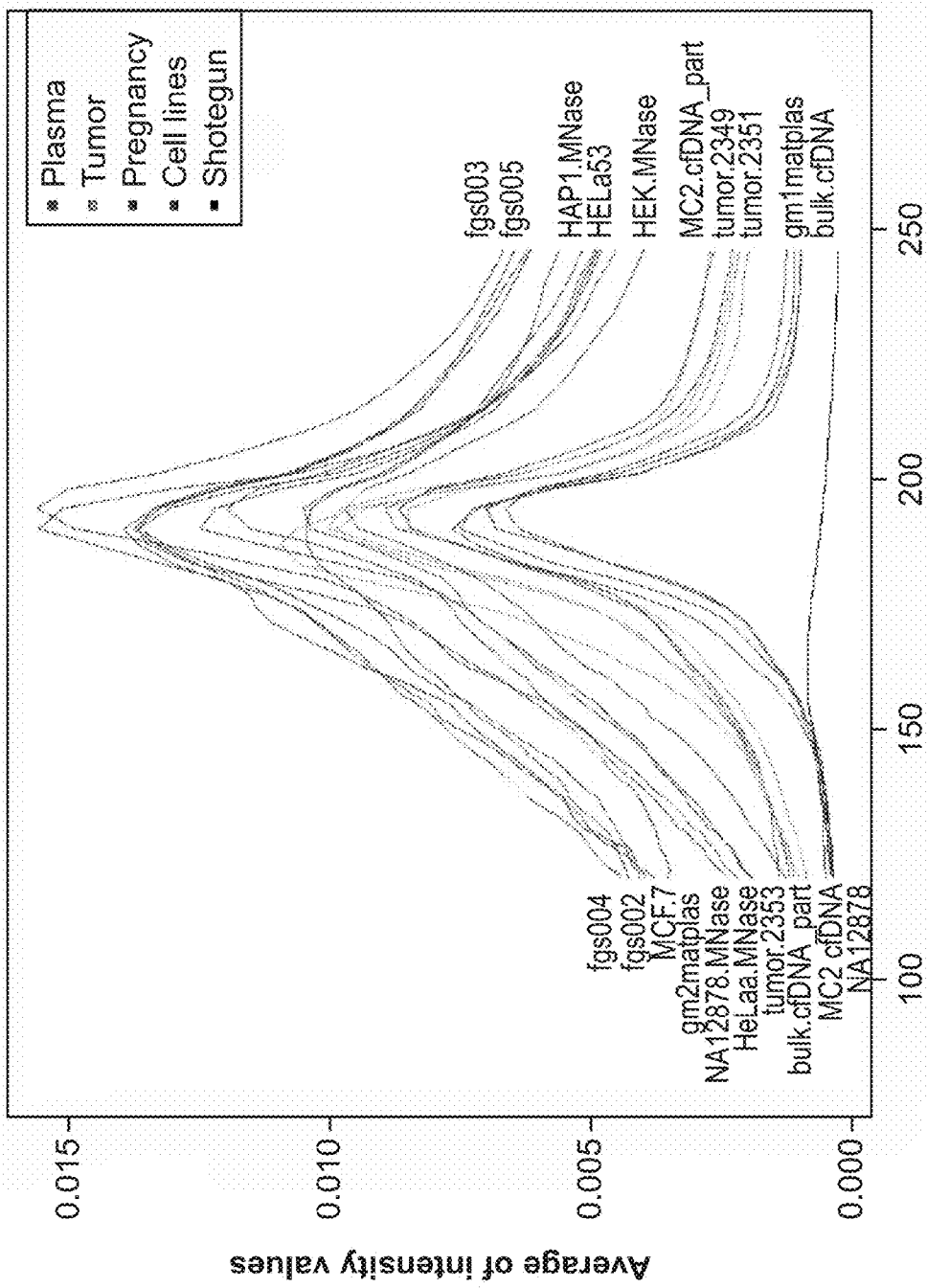
FIG. 3B shows average periodogram intensities from Fast Fourier Transformation (FFT) of read start coordinates mapping to the last (chr22) human autosome across all cfDNA samples (Plasma), cfDNA from tumor patient samples (Tumor), cfDNA from pregnant female individuals (Pregnancy), MNase of human different human cell lines (Cell lines) and a human DNA shotgun sequencing library (Shotgun).

Read start coordinates were extracted and periodograms were created using Fast Fourier Transformation (FFT) as described in the Methods section. This analysis determines how much of the non-uniformity in the distribution of read start sites can be explained by signals of specific frequencies/periodicities. We focused on a range of 120-250 bp, which comprises the length range of DNA wrapped around a single nucleosome (147 bp) as well as additional sequence of the nucleosome linker sequence (10-80 bp). FIG. 3 shows the average intensities for each frequency across all blocks of human chromosome 1 and human chromosome 22. It can be seen that MNase digestion experiments as well cfDNA samples show clear peaks below 200 bp periodicity. Such a peak is not observed in the human shotgun data. These analyses are consistent with a major effect of nucleosome positioning on the distribution of fragment boundaries in cfDNA.

Variation in the exact peak frequency between samples was also observed. This is possibly a consequence of different distributions of linker sequence lengths in each cell type. That the peak derives from patterns of nucleosome bound DNA plus linker sequence is supported by the observations that the flanks around the peaks are not symmetrical and that the intensities for frequencies higher than the peak compared to frequencies lower than the peak are lower. This suggests that plots similar to those presented in FIG. 3 can be used to perform quality control of cfDNA and MNase sequencing data. Random fragmentation or contamination of cfDNA and MNase with regular (shotgun) DNA will cause dilution or, in extreme cases, total absence of these characteristic intensity patterns in periodograms.

Figure 4A:
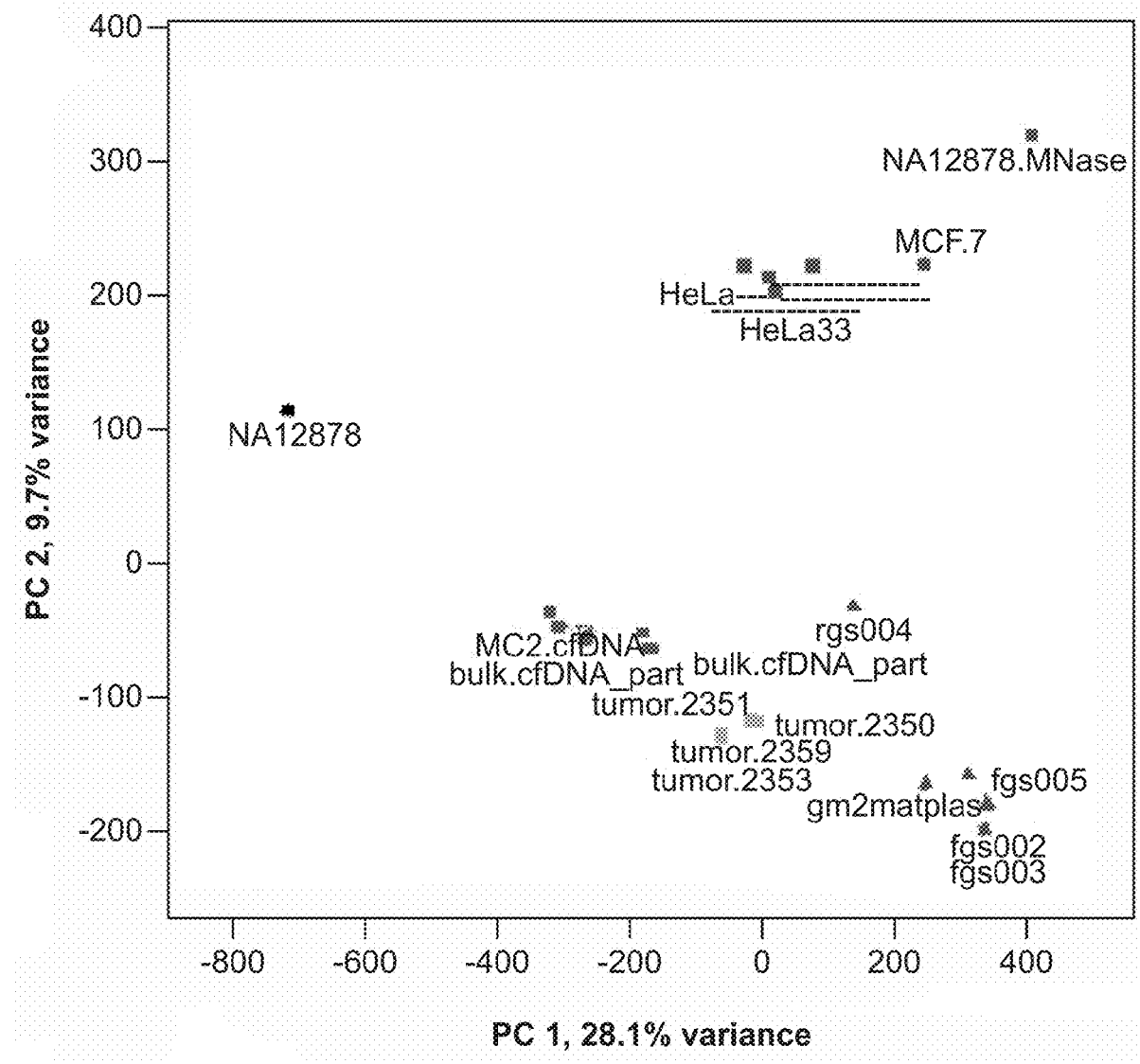
FIGS. 4A-B show first three principal components (PC) of intensities at 196 base-pairs (bp) periodicity in 10 kilo-base-pair (kbp) blocks across all autosomes.
Figure 4B:
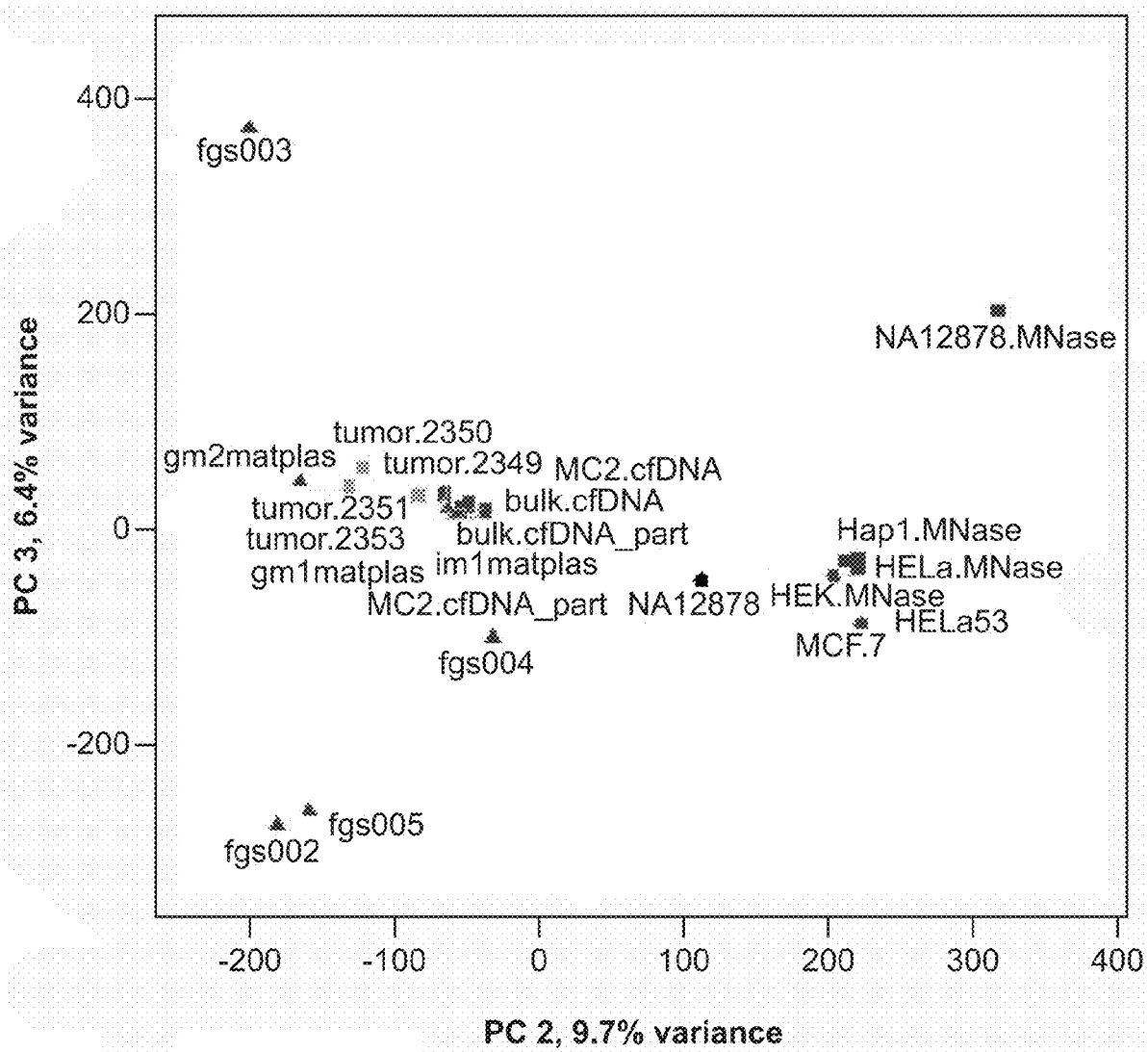
Figure 5:
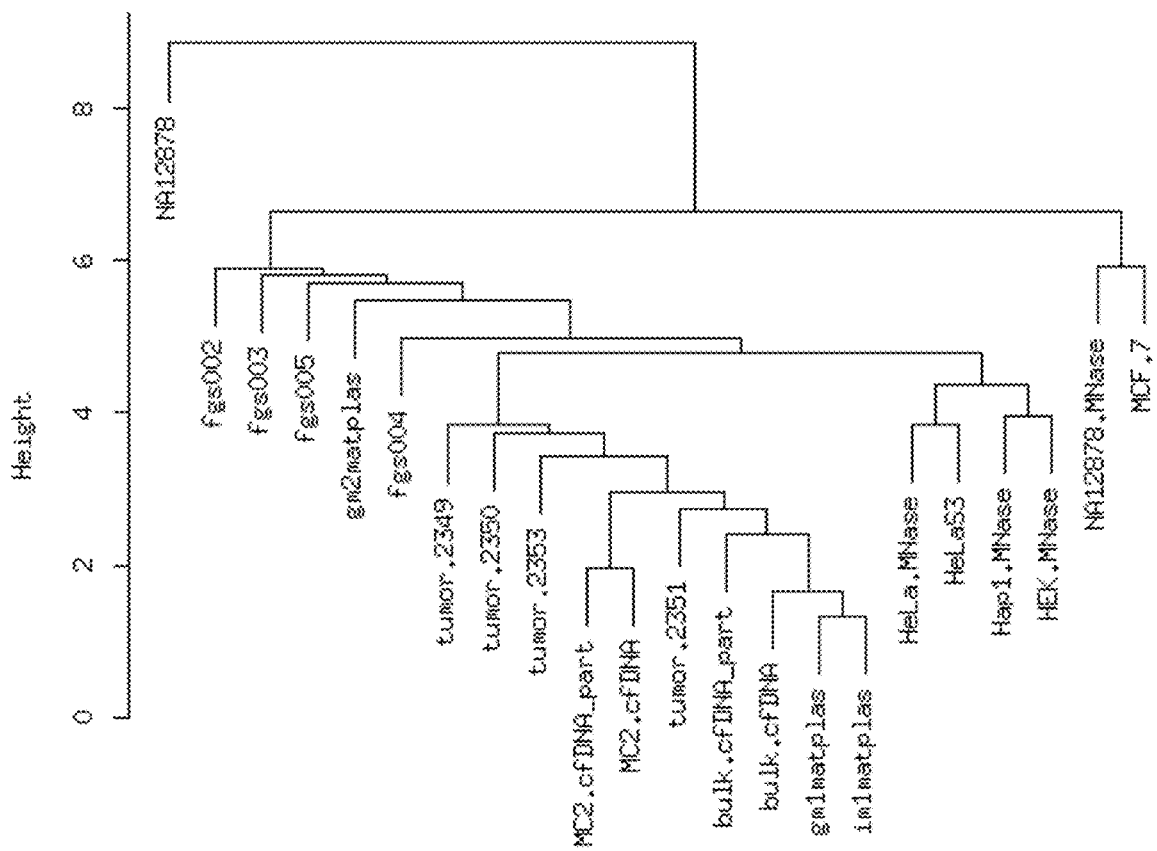
FIG. 5 shows hierarchical clustering dendogram of Euclidean distances of intensities measured at 196 bp periodicity in 10 kbp blocks across all autosomes.

In the following, data were analyzed based on measured intensities at a periodicity of 196 bp as well as all intensities determined for the frequency range of 181 bp to 202 bp. A wider frequency range was chosen in order to provide higher resolution because a wider range of linker lengths are being captured. These intensities were chosen as the focus purely for computational reasons here; different frequency ranges may be used in related embodiments. FIGS. 4 and 5, explore visualizations of the periodogram intensities at 196 bp across contiguous, non-overlapping 10 kbp blocks tiling the full length of human autosomes (see Methods for details). FIG. 4 presents a Principal Component Analysis (PCA) of the data and the projections across the first three components. Principal component 1 (PC1) (28.1% of variance) captures the differences in intensity strength seen in FIG. 3 and thereby separates MNase and cfDNA samples from genomic shotgun data. In contrast, PC2 (9.7% of variance) captures the differences between MNase and cfDNA samples. PC3 (6.4% variance) captures differences between individual samples. FIG. 5 shows the hierarchical clustering dendogram of this data based on Euclidean distances of the intensity vectors. We note that the two HeLa S3 experiments tightly cluster in the PCA and dendogram, even though data was generated in different labs and following different experimental protocols. "Normal" cfDNA samples, tumor cfDNA samples and groups of cell line MNase samples also clustered. Specifically, the three tumor samples originating from the same tumor type (glioblastoma multiforme) appear to cluster, separately from tumor.2351 sample which originates from a different tumor type (see Table 1). The GM1 and IM1 samples cluster separately from the other cfDNA samples obtained from pregnant women. This coincides with higher intensities observed for frequencies below the peak in these samples (i.e., a more pronounced left shoulder in FIG. 3). This might indicate subtle differences in the preparation of the cfDNA between the two sets of samples, or biological differences which were not controlled for (e.g., gestational age).

Figure 6A:
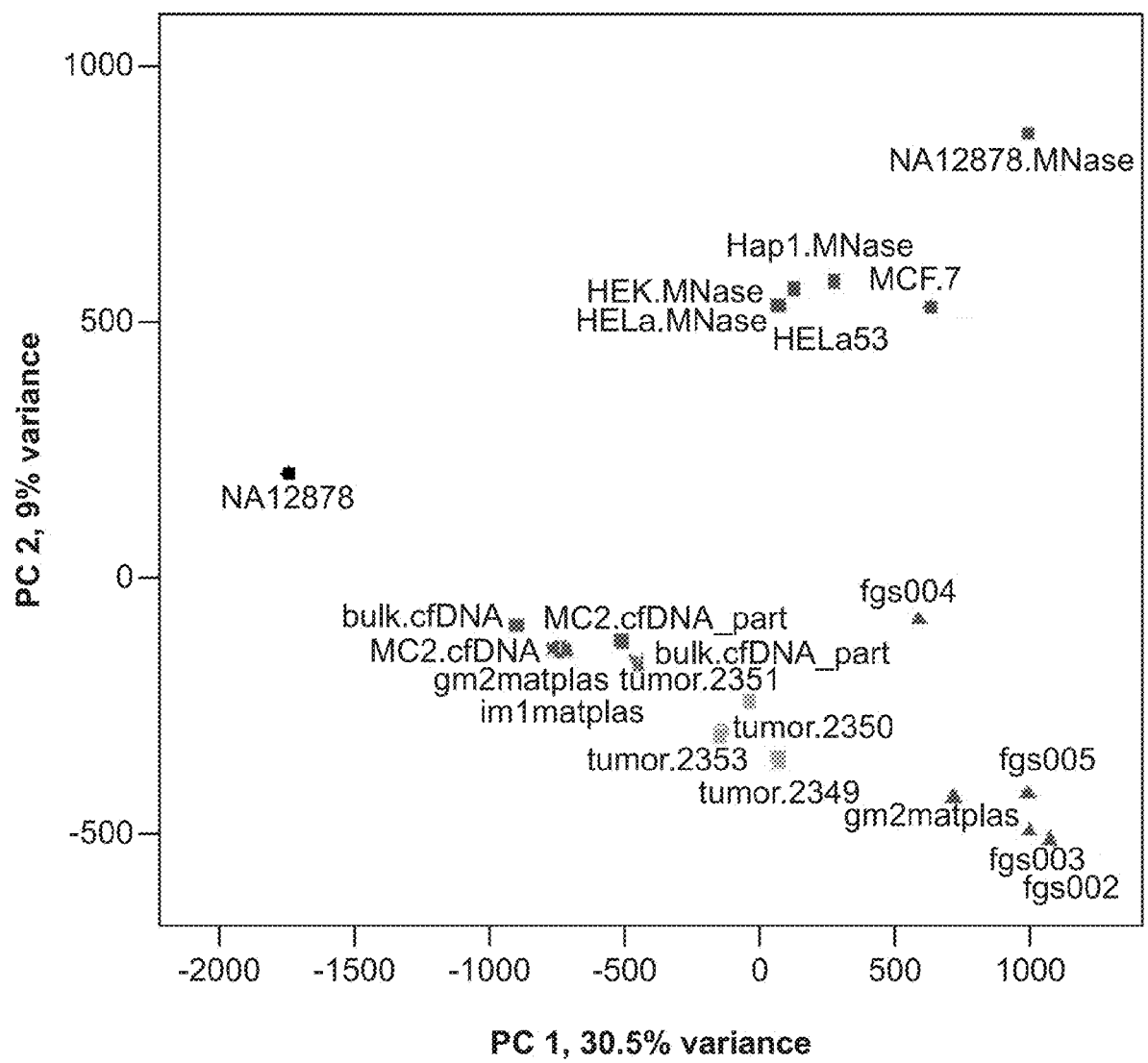
FIGS. 6A-B show first three principal components of intensities at 181 bp to 202 bp periodicity in 10 kbp blocks across all autosomes.
Figure 6B:
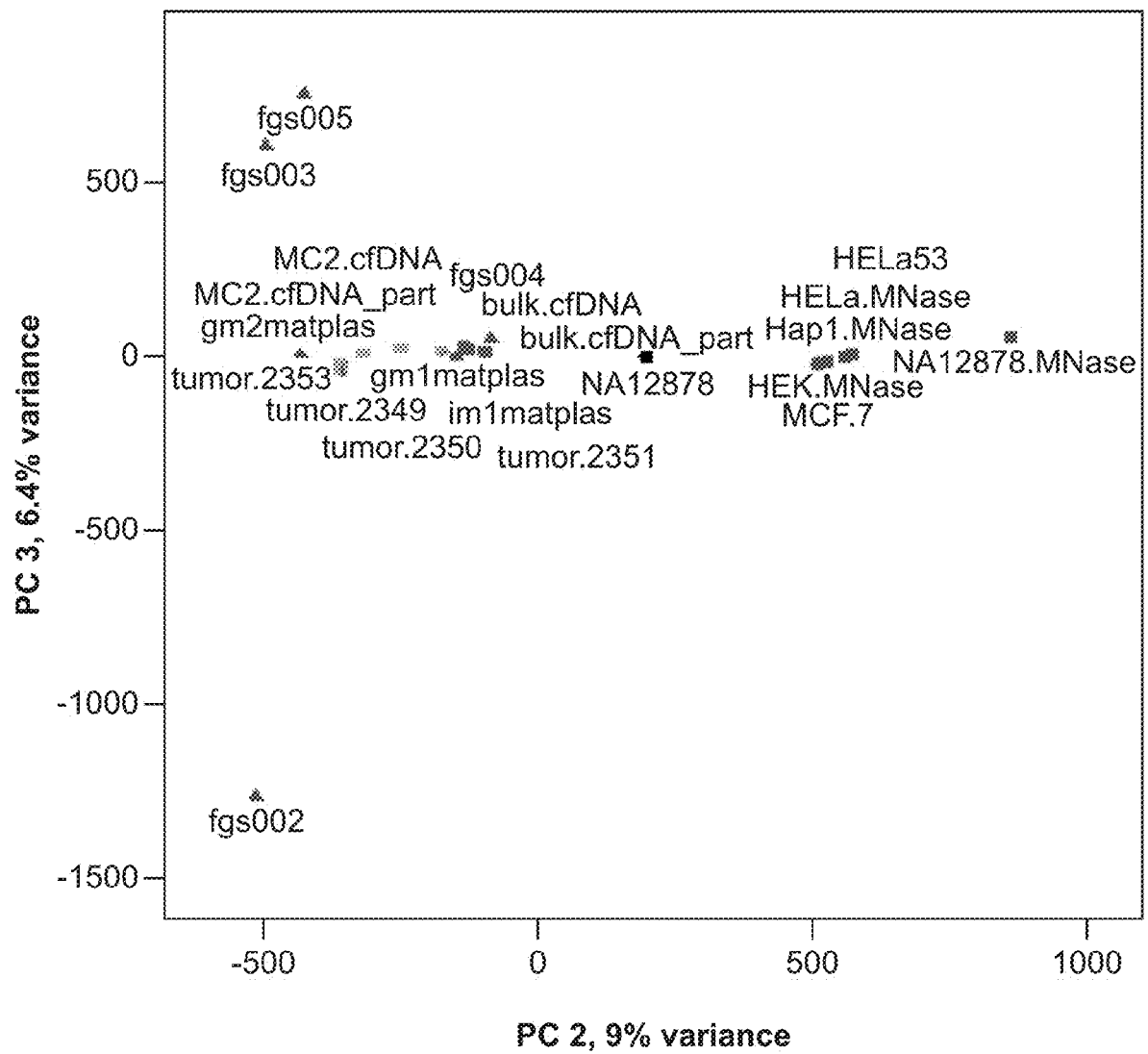
Figure 7:
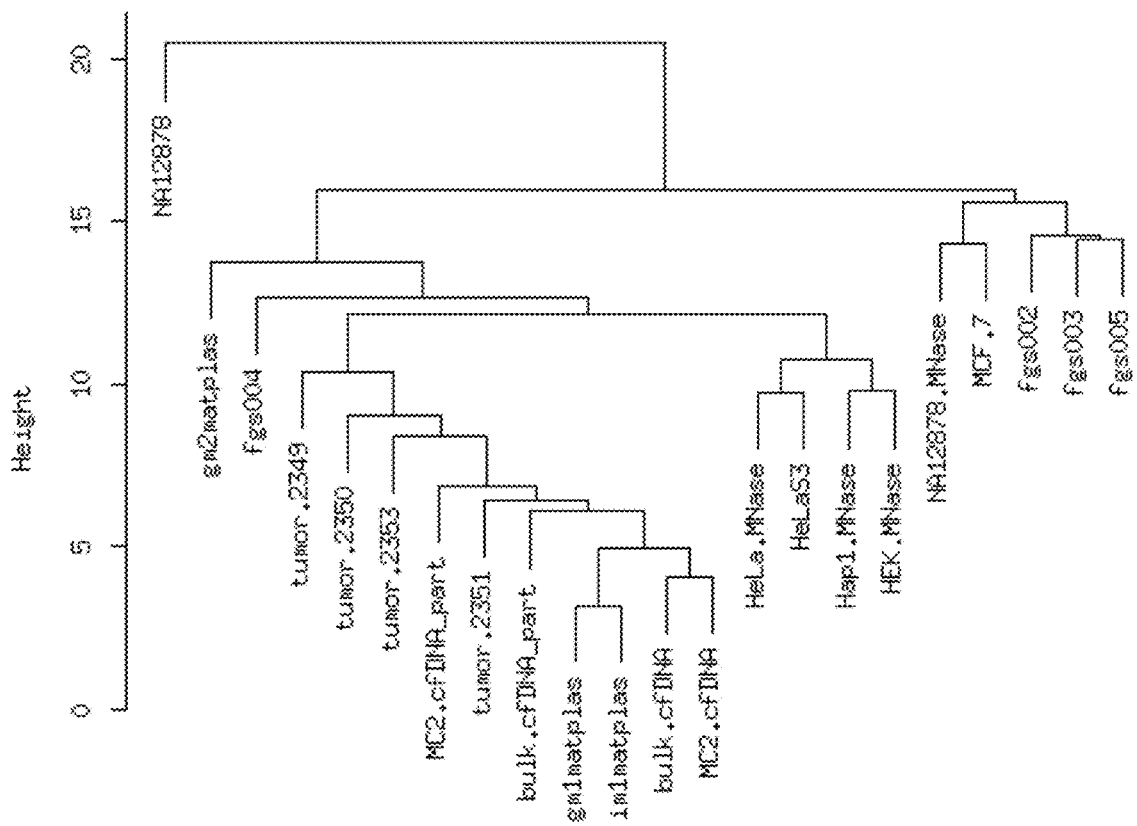
FIG. 7 shows hierarchical clustering dendogram of Euclidean distances of intensities measured at 181 bp to 202 bp periodicity in 10 kbp blocks across all autosomes.
Figure 8B:
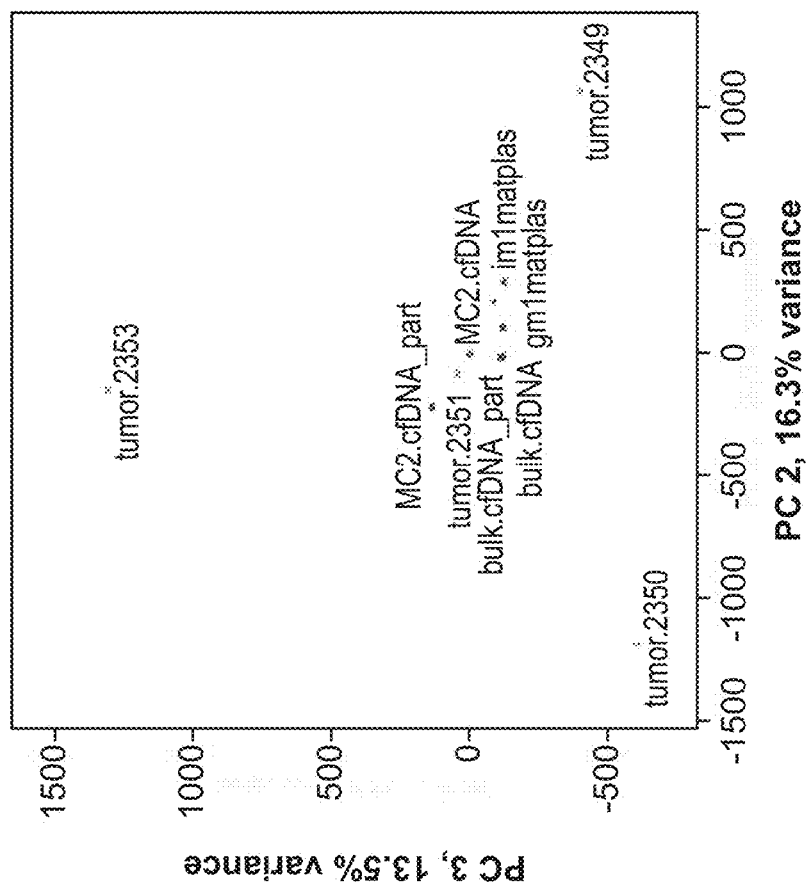
FIGS. 8A-F show principal component analysis (first 7 of 10 PCs) of intensities at 181 bp to 202 bp periodicity in 10 kbp blocks across all autosomes for the cfDNA data sets.
Figure 8A:
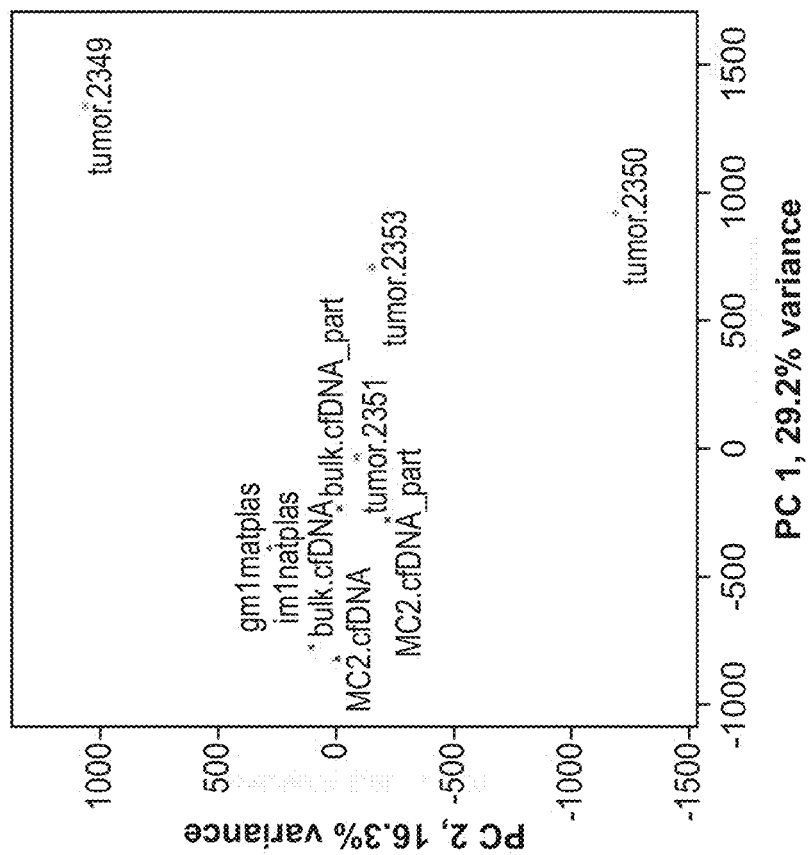
Figure 8D:
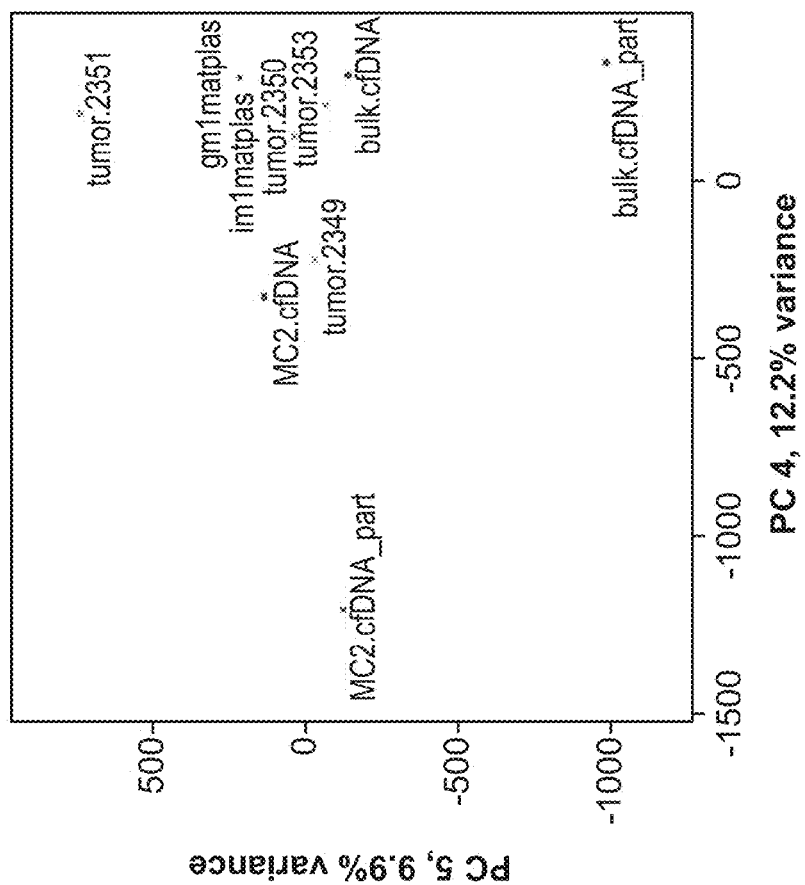
Figure 8C:
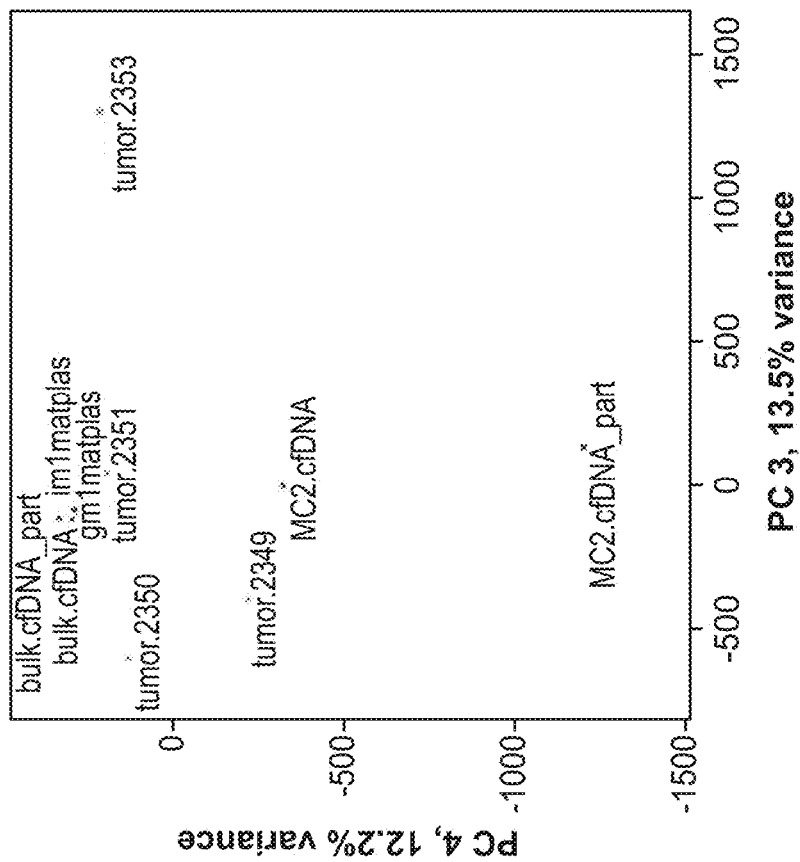
Figure 8F:
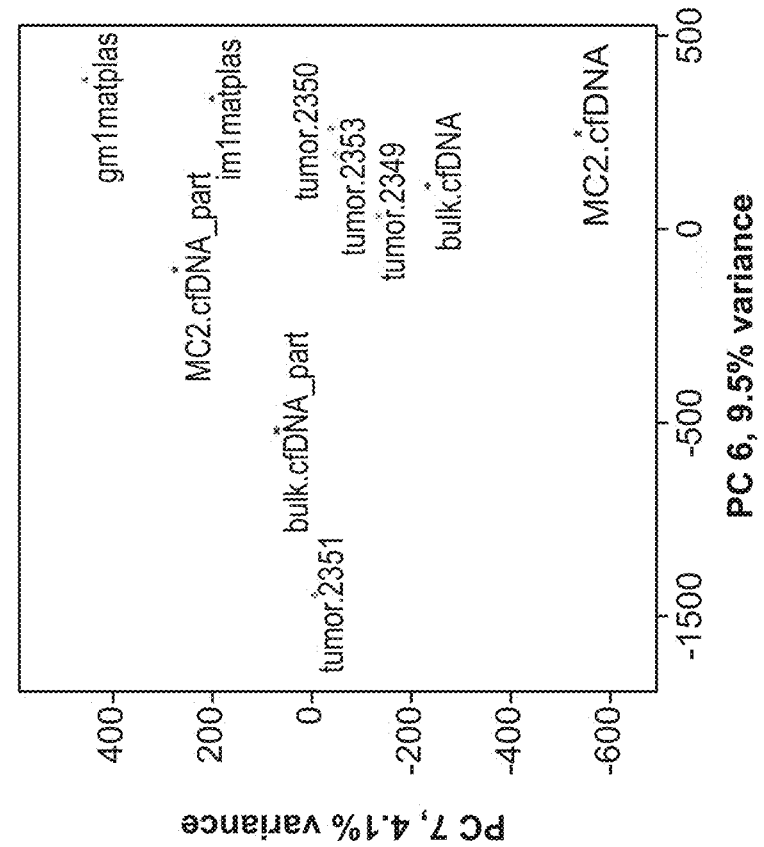
Figure 8E:
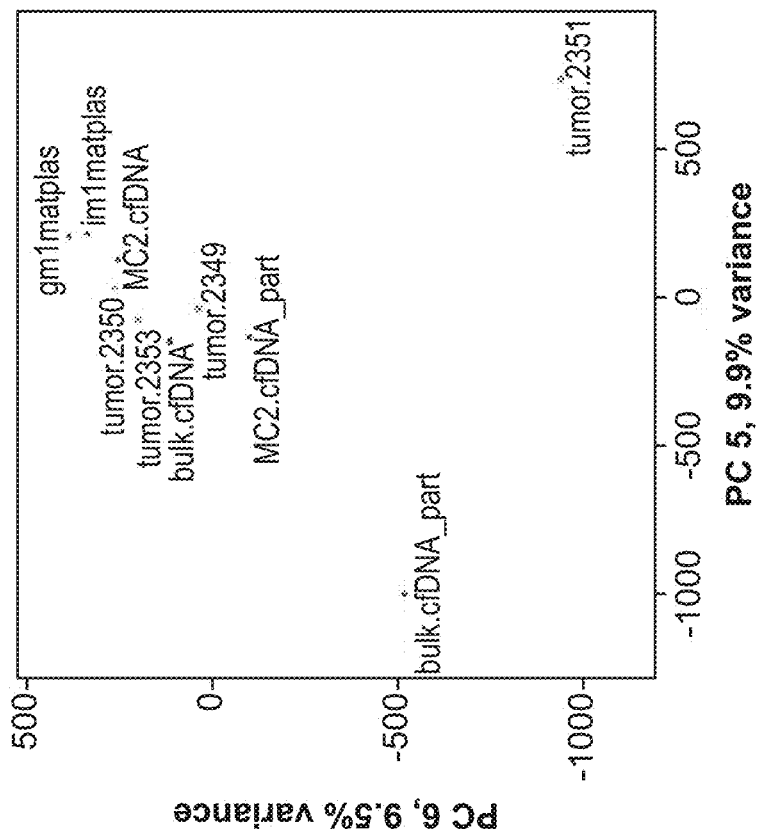
Figures 9A, 9B:
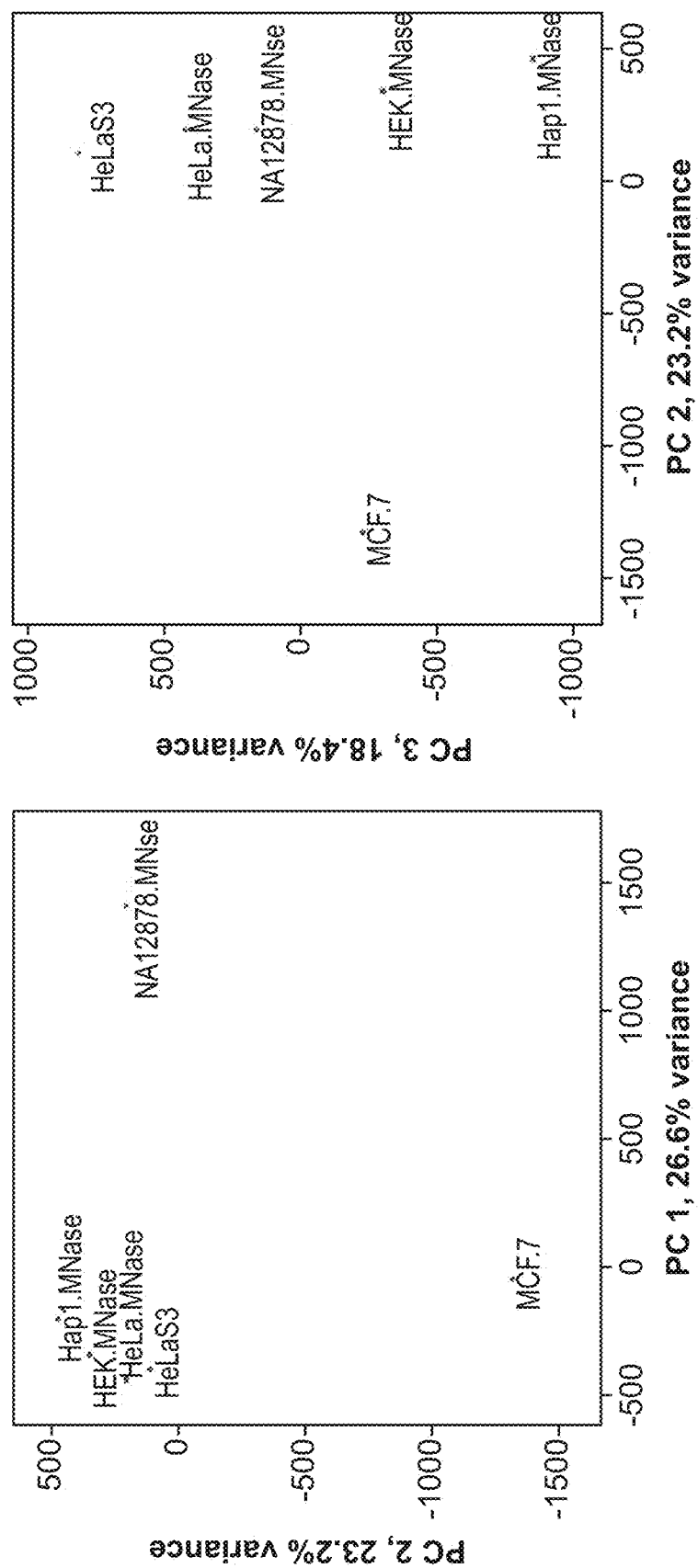

FIGS. 6 and 7 show the results of equivalent analyses but based on the frequency range of 181 bp to 202 bp. Comparing these plots, the results are largely stable to a wider frequency range; however additional frequencies may improve sensitivity in more fine-scaled analyses. To further explore cell-type origin specific patterns, the cfDNA and MNase data sets were analyzed separately using PCA of intensities for this frequency range. In the following set of analyses, the five cfDNA samples from pregnant women, which show the pronounced left shoulder in FIG. 3, were excluded. FIG. 8 shows the first 7 principal components of the cfDNA data and FIG. 9 all six principal components for the six MNase data sets. While there is a clustering of related samples, there is also considerable variation (biological and technical variation) to separate each sample from the rest. For example, an effect of sequencing depth was observable, as can be seen from the separation of bulk.cfDNA and bulk.cfDNA_part as well as MC2.cfDNA and MC2.cfDNA_part. Read sampling may be used to correct for this technical confounder.

Some key observations of this example include:

1) Read start coordinates in cfDNA sequencing data capture a strong signal of nucleosome positioning.

2) Differences in the signal of nucleosome positioning, aggregated across subsets of the genome such as contiguous 10 kbp windows, correlate with sample origin.

Example 2—Mixture Proportion Estimation of Nucleosome Maps

In Example 1, basic clustering of samples that were generated or downloaded from public databases was studied. The analyses showed that read start coordinates in these data sets capture a strong signal of nucleosome positioning (across a range of sequencing depths obtained from 20 million sequences to more than a 1,000 million sequences) and that sample origin correlates with this signal. For the goals of this method, it would also be useful to be able to identify mixtures of known cell types and to some extent quantify the contributions of each cell type from this signal. For this purpose, this example explored synthetic mixtures (i.e., based on sequence reads) of two samples. We mixed sequencing reads in ratios of 5:95, 10:90, 15:85, 20:80, 30:70, 40:60, 50:50, 60:40, 30:70, 80:20, 90:10 and 95:5 for two MNase data sets (MCF.7 and NA12878.MNase) and two cfDNA data sets (tumor.2349 and bulk.cfDNA). The synthetic MNase mixture datasets were drawn from two sets of 196.9 million aligned reads (each from one of the original samples) and the synthetic cfDNA mixture datasets were drawn from two sets of 181.1 million aligned reads (each from one of the original samples).

Figure 10:
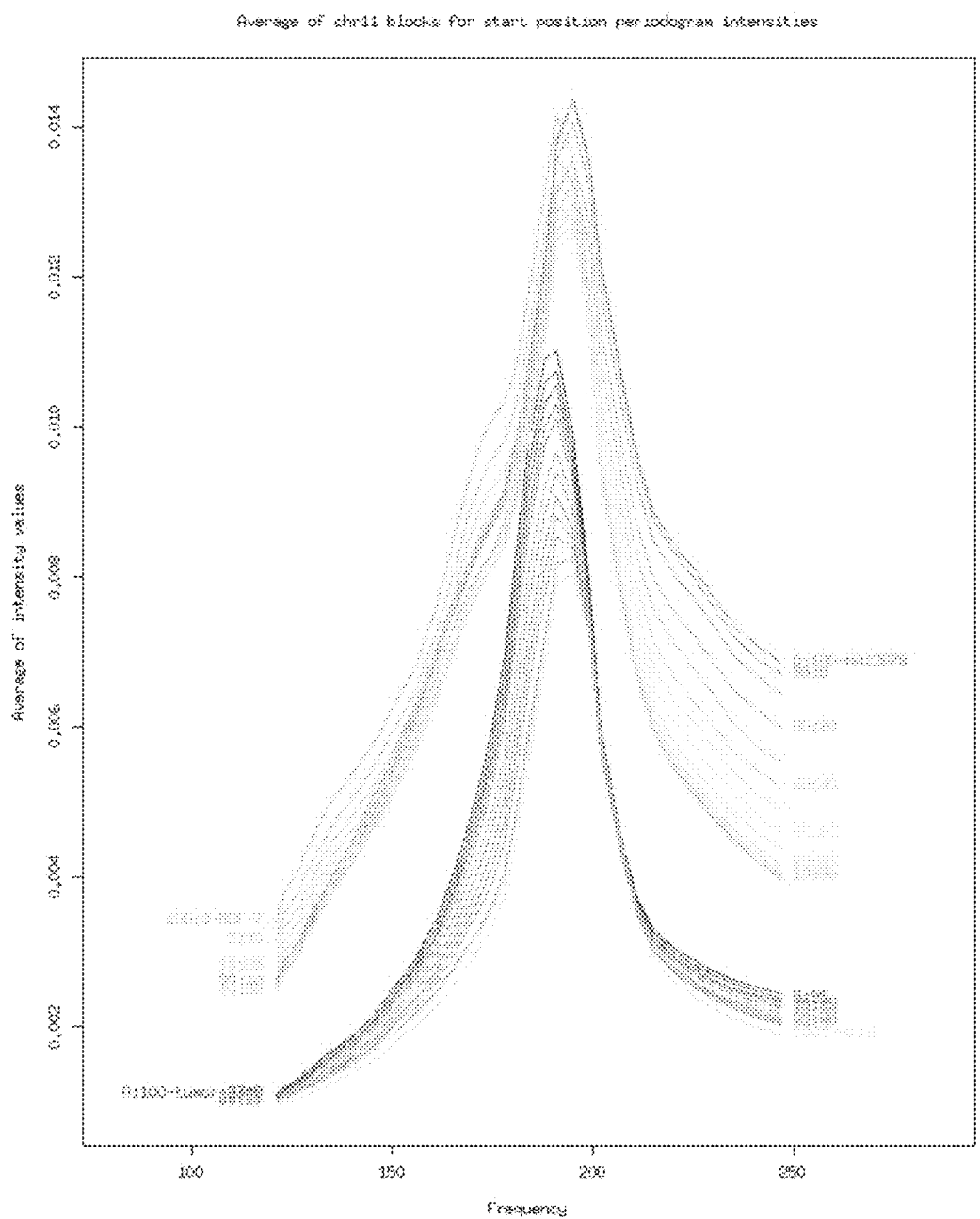
FIG. 10 shows average periodogram intensities for a representative human autosome (chr11) across all synthetic cfDNA and MNase data set mixtures.
Figure 11:
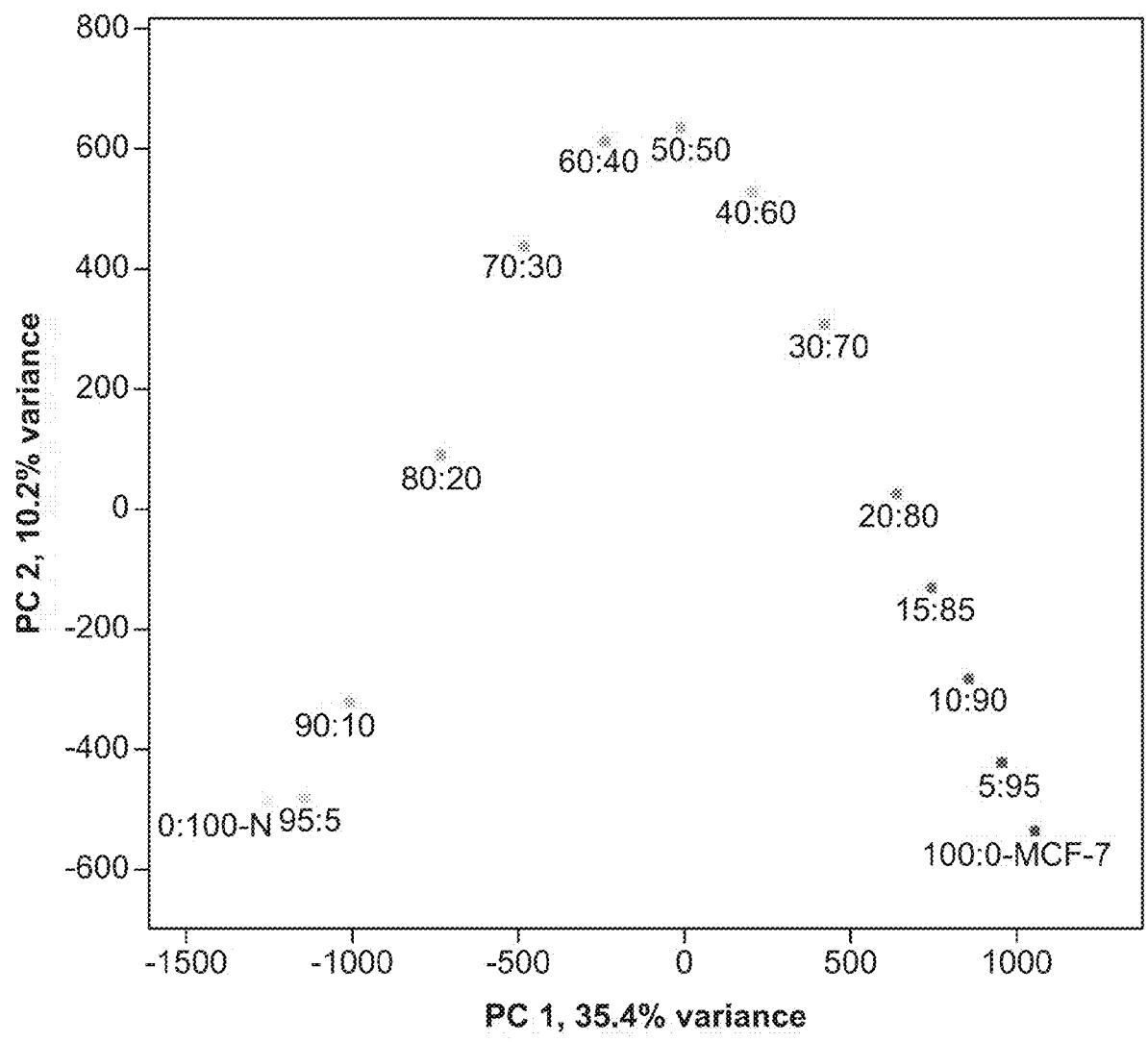
FIG. 11 shows first two principal components of intensities at 181 bp to 202 bp periodicity in 10 kbp blocks across all autosomes for the synthetic MNase data set mixtures.
Figure 12:
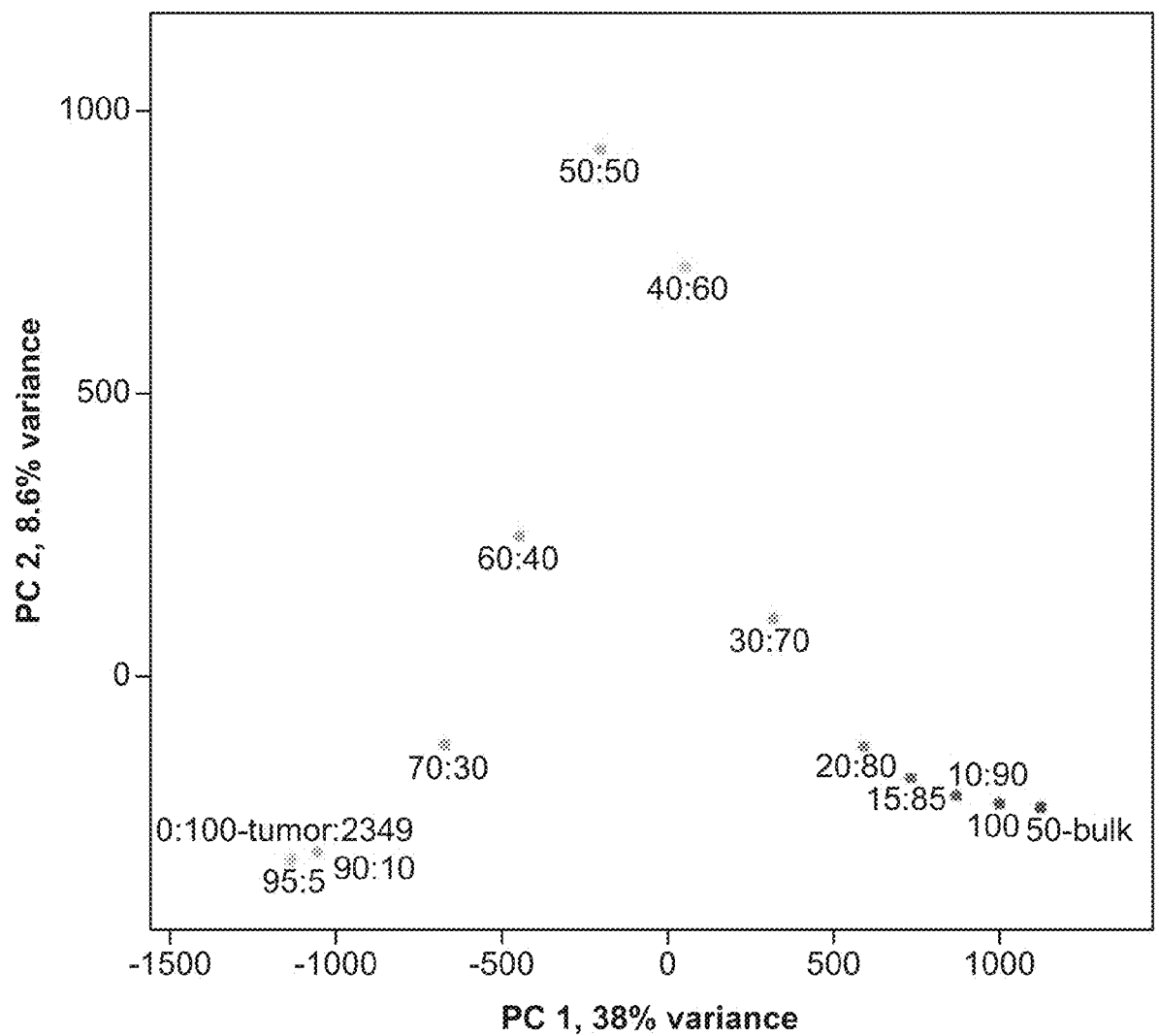
FIG. 12 shows first two principal components of intensities at 181 bp to 202 bp periodicity in 10 kbp blocks across all autosomes for the synthetic cfDNA data set mixtures.
Figure 13:
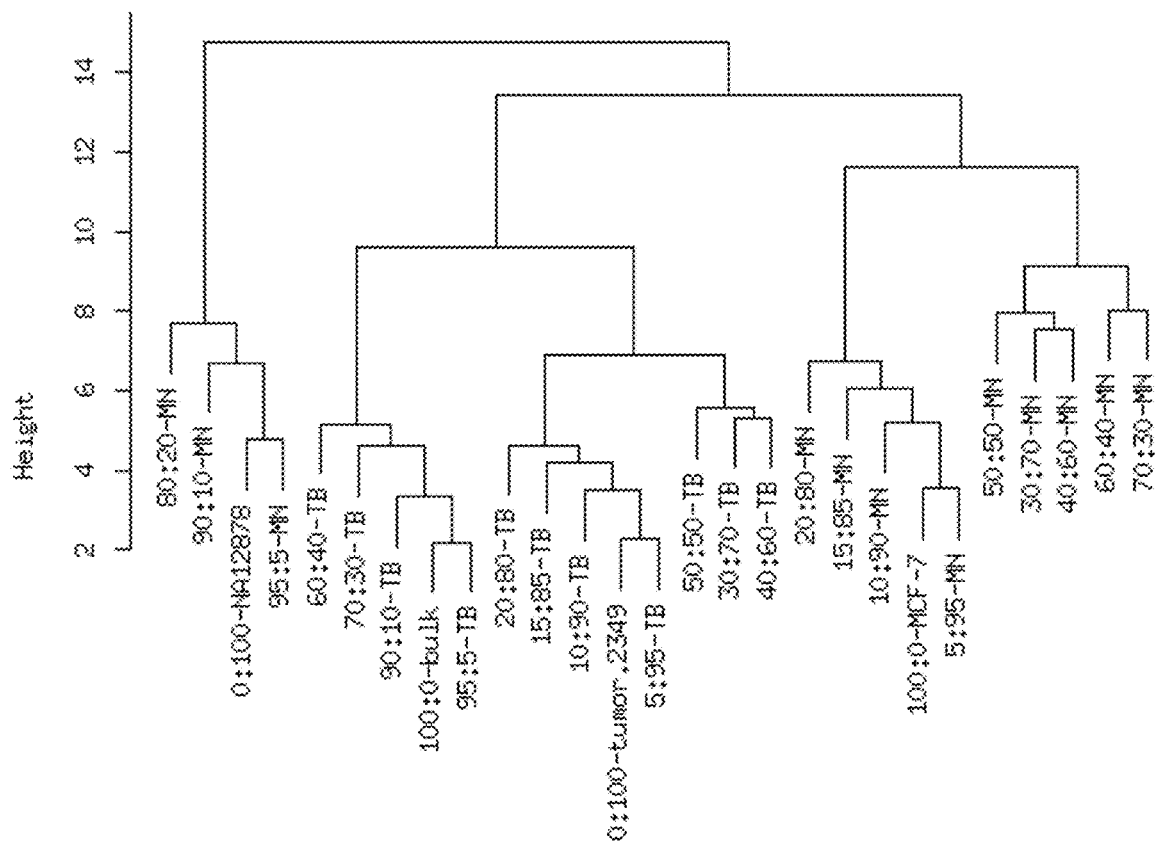
FIG. 13 shows hierarchical clustering dendogram of Euclidean distances of intensities at 181 bp to 202 bp periodicity in 10 kbp blocks across all autosomes for the synthetic MNase and cfDNA mixture data sets.

FIG. 10 shows the average intensities for chromosome 11, equivalent to FIG. 3 but for these synthetic mixtures. It can be seen from FIG. 10 how the different sample contributions cause shifts in the global frequency intensity patterns. This signal can be exploited to infer the synthetic mixture proportions. FIG. 11 shows the first two principal components for the MNase data set mixtures and FIG. 12 shows the first two principal components for the cfDNA data set mixtures. In both cases, the first PC directly captures the composition of the mixed data set. It is therefore directly conceivable how mixture proportions for two and possibly more cell types could be estimated from transformation of the frequency intensity data given the appropriate reference sets and using for example regression models. FIG. 13 shows the dendogram of both data sets, confirming the overall similarities of mixture samples deriving from similar sample proportions as well as the separation of the cfDNA and MNase samples.

One of the key observations of this example is that the mixture proportions of various sample types (cfDNA or cell/tissue types) to an unknown sample can be estimated by modeling of nucleosome occupancy patterns.

Example 3: Measuring Nucleosome Occupancy Relative to Transcription Factor Binding Sites with cfDNA Sequencing Data While previous examples demonstrate that signals of nucleosome positioning can be obtained by partitioning the genome into contiguous, non-overlapping 10 kbp windows, orthogonal methods can also be used to generate cleavage accessibility maps and may be less prone to artifacts based on window size and boundaries. One such method, explored in some detail in this Example, is the inference of nucleosome positioning through observed periodicity of read-starts around transcription factor (TF) binding sites.

It is well established that local nucleosome positioning is influenced by nearby TF occupancy. The effect on local remodeling of chromatin, and thus on the stable positioning of nearby nucleosomes, is not uniform across the set of TFs; occupancy of a given TF may have local effects on nucleosome positioning that are preferentially 5' or 3' of the binding site and stretch for greater or lesser genomic distance in specific cell types. Furthermore, and importantly for the purposes of this disclosure, the set of TF binding sites occupied in vivo in a particular cell varies between tissues and cell types, such that if one were able to identify TF binding site occupancy maps for tissues or cell types of interest, and repeated this process for one or more TFs, one could identify components of the mixture of cell types and tissues contributing to a population of cfDNA by identifying enrichment or depletion of one or more cell type- or tissue-specific TF binding site occupancy profiles.

To demonstrate this idea, read-starts in the neighborhood of TF binding sites were used to visually confirm cleavage biases reflective of preferential local nucleosome positioning. ChIP-seq transcription factor (TF) peaks were obtained from the Encyclopedia of DNA Elements ("ENCODE") project (National Human Genome Research Institute, National Institutes of Health, Bethesda, Md.). Because the genomic intervals of these peaks are broad (200 to 400 bp on average), the active binding sites within these intervals were discerned by informatically scanning the genome for respective binding motifs with a conservative p-value cutoff ($1 \times 10^{-5}$, see Methods for details). The intersection of these two independently derived sets of predicted TF binding sites were then carried forward into downstream analysis.

The number of read-starts at each position within 500 bp of each candidate TF binding site was calculated in samples with at least 100 million sequences. Within each sample, all read-starts were summed at each position, yielding a total of 1,014 to 1,019 positions per sample per TF, depending on the length of the TF recognition sequence.

Figure 14:
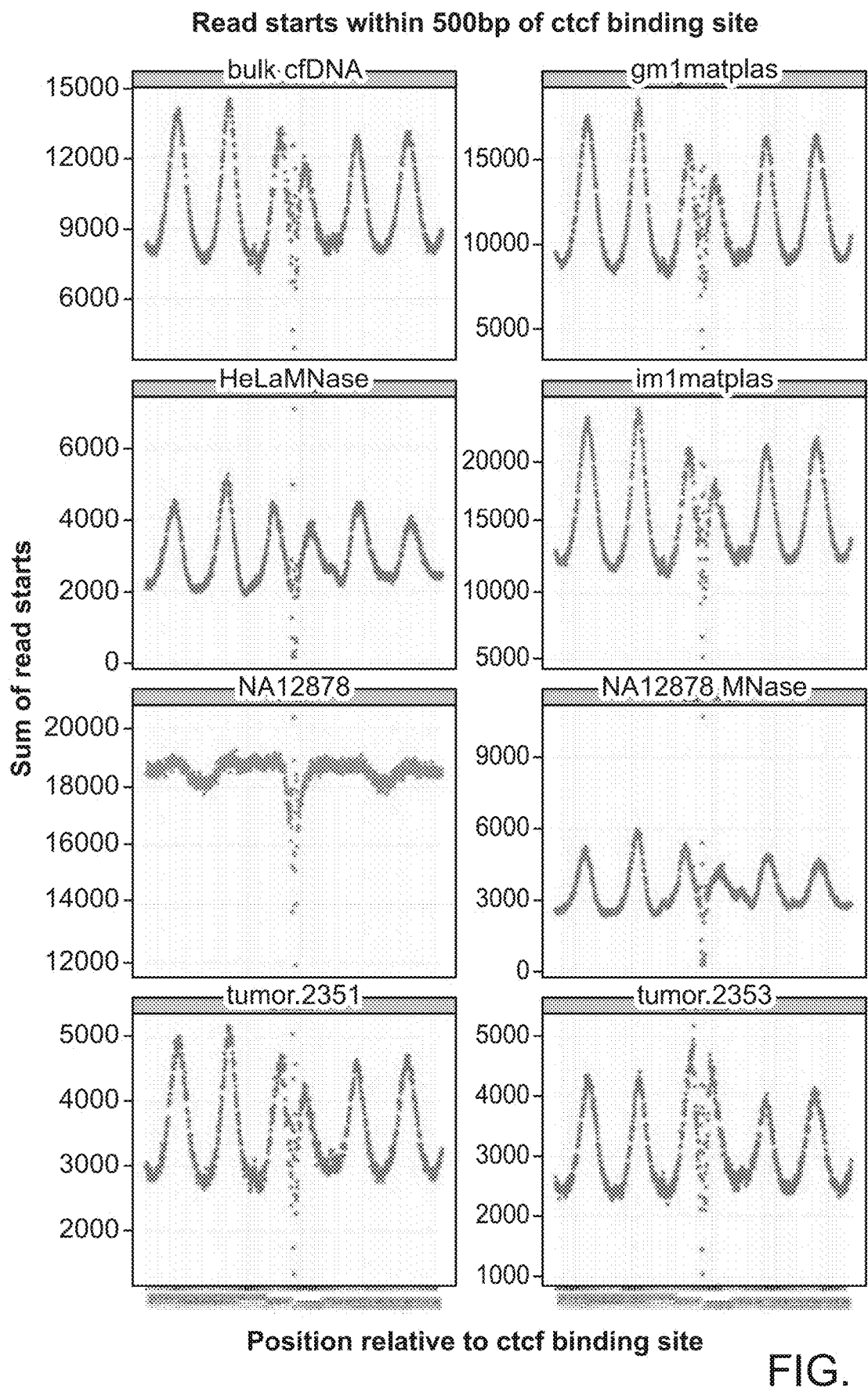
FIG. 14 shows read-start density in 1 kbp window around 23,666 CTCF binding sites for a set of samples with at least 100 M reads.
Figure 14:
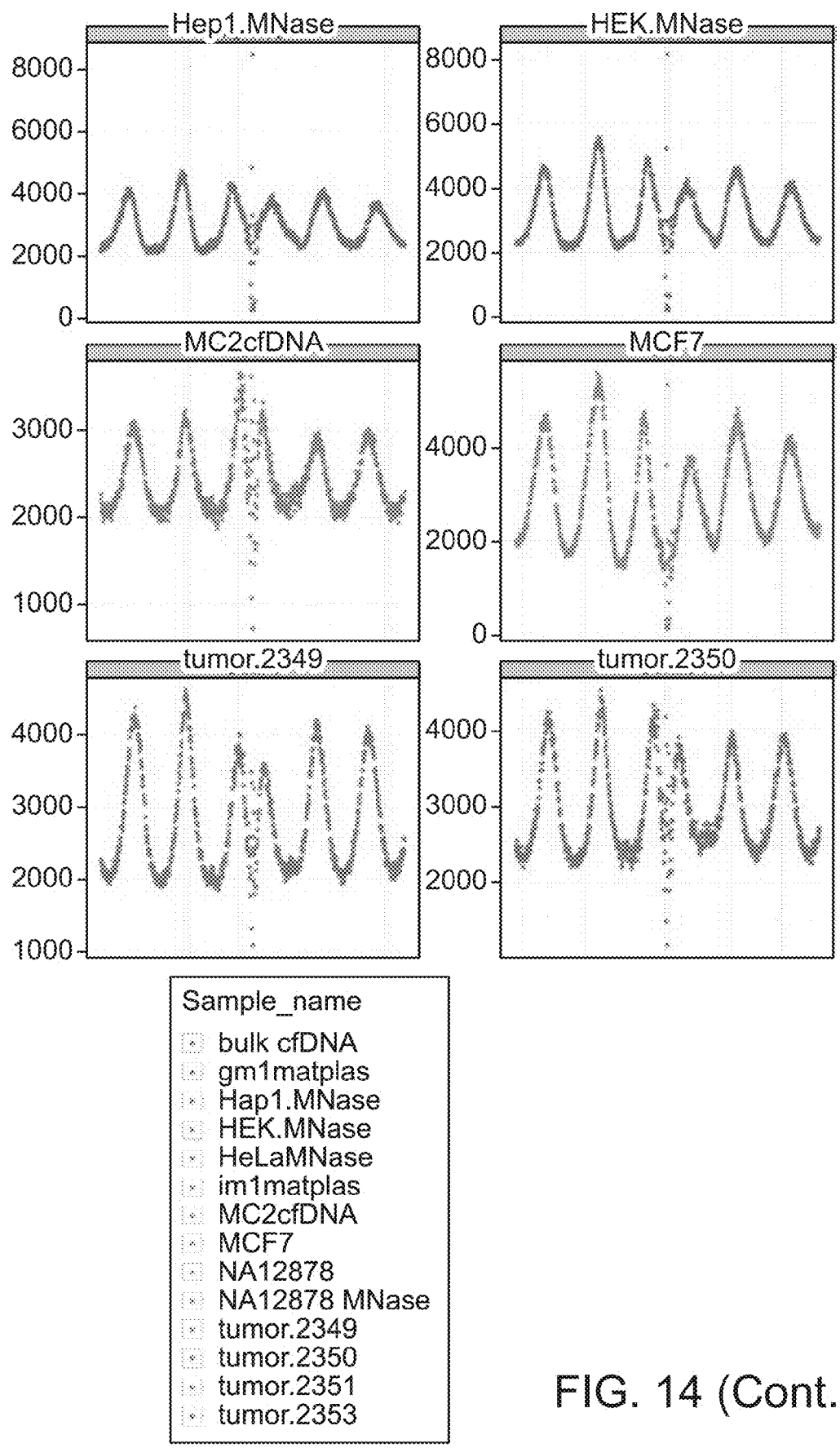

FIG. 14 shows the distribution of read-starts around 24,666 CTCF binding sites in the human genome in a variety of different samples, centered around the binding site itself. CTCF is an insulator binding protein and plays a major role in transcriptional repression. Previous studies suggest that CTCF binding sites anchor local nucleosome positioning such that at least 20 nucleosomes are symmetrically and regularly spaced around a given binding site, with an approximate period of 185 bp. One striking feature common to nearly all of the samples in FIG. 14 is the clear periodicity of nucleosome positioning both upstream and downstream of the binding site, suggesting that the local and largely symmetrical effects of CTCF binding in vivo are recapitulated in a variety of cfDNA and MNase-digested samples. Intriguingly, the periodicity of the upstream and downstream peaks is not uniform across the set of samples; the MNase-digested samples display slightly wider spacing of the peaks relative to the binding site, suggesting the utility of not only the intensity of the peaks, but also their period.

Figure 15:
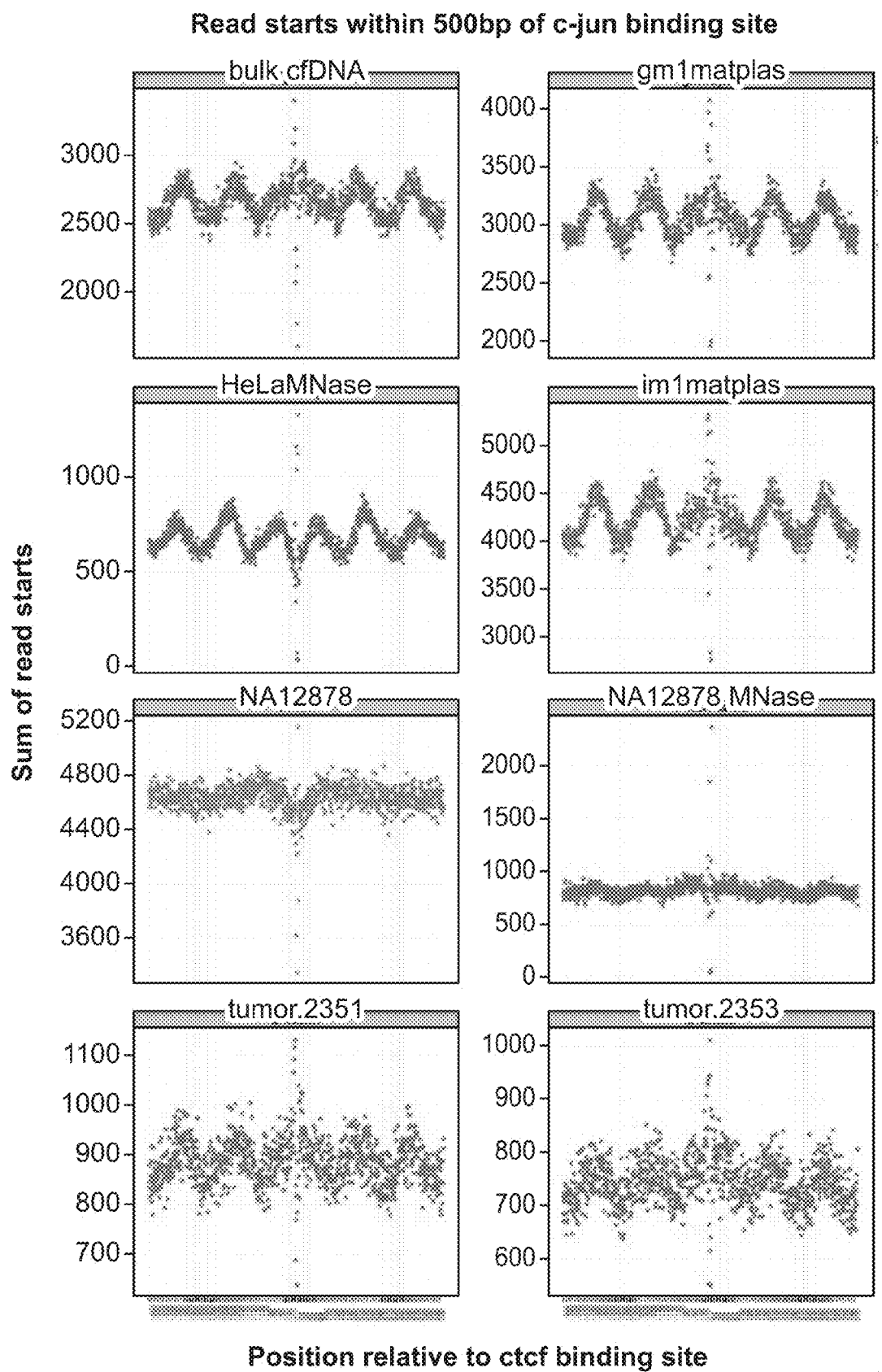
FIG. 15 shows read-start density in 1 kbp window around 5,644 c-Jun binding sites for a set of samples with at least 100 M reads.
Figure 15:
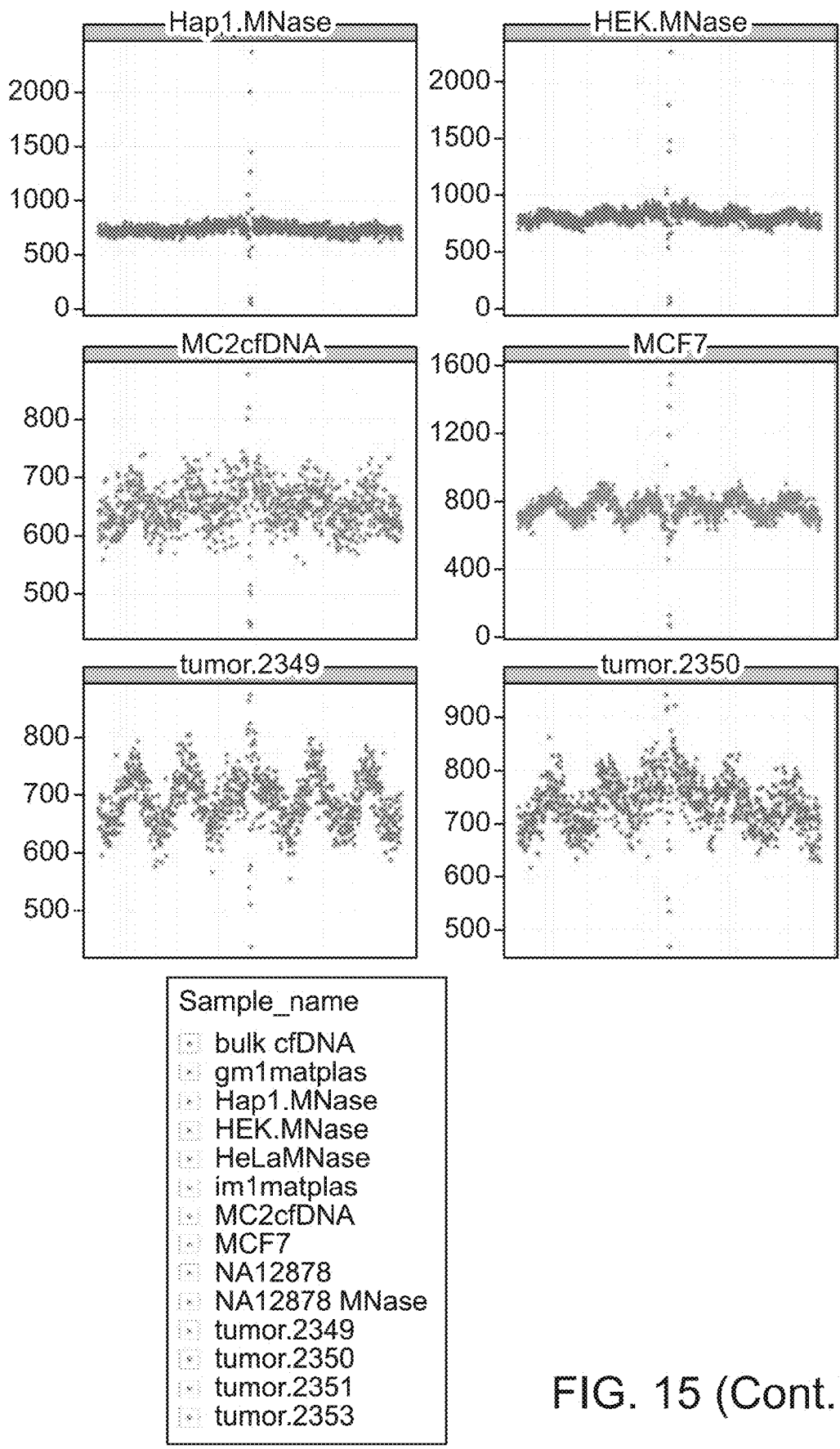

FIG. 15 shows the distribution of read-starts around 5,644 c-Jun binding sites. While the familiar periodicity is again visually identifiable for several samples in this figure, the effect is not uniform. Of note, three of the MNase-digested samples (Hap1.MNase, HEK.MNase, and NA12878.MNase) have much flatter distributions, which may indicate that c-Jun binding sites are not heavily occupied in these cells, or that the effect of c-Jun binding on local chromatin remodeling is less pronounced in these cell types. Regardless of the underlying mechanism, the observation that bias in the local neighborhood of read-starts varies from TF to TF and between sample types reinforces the potential role for read start-based inference of nucleosome occupancy for correlating or deconvoluting tissue-of-origin composition in cfDNA samples.

Figure 16:
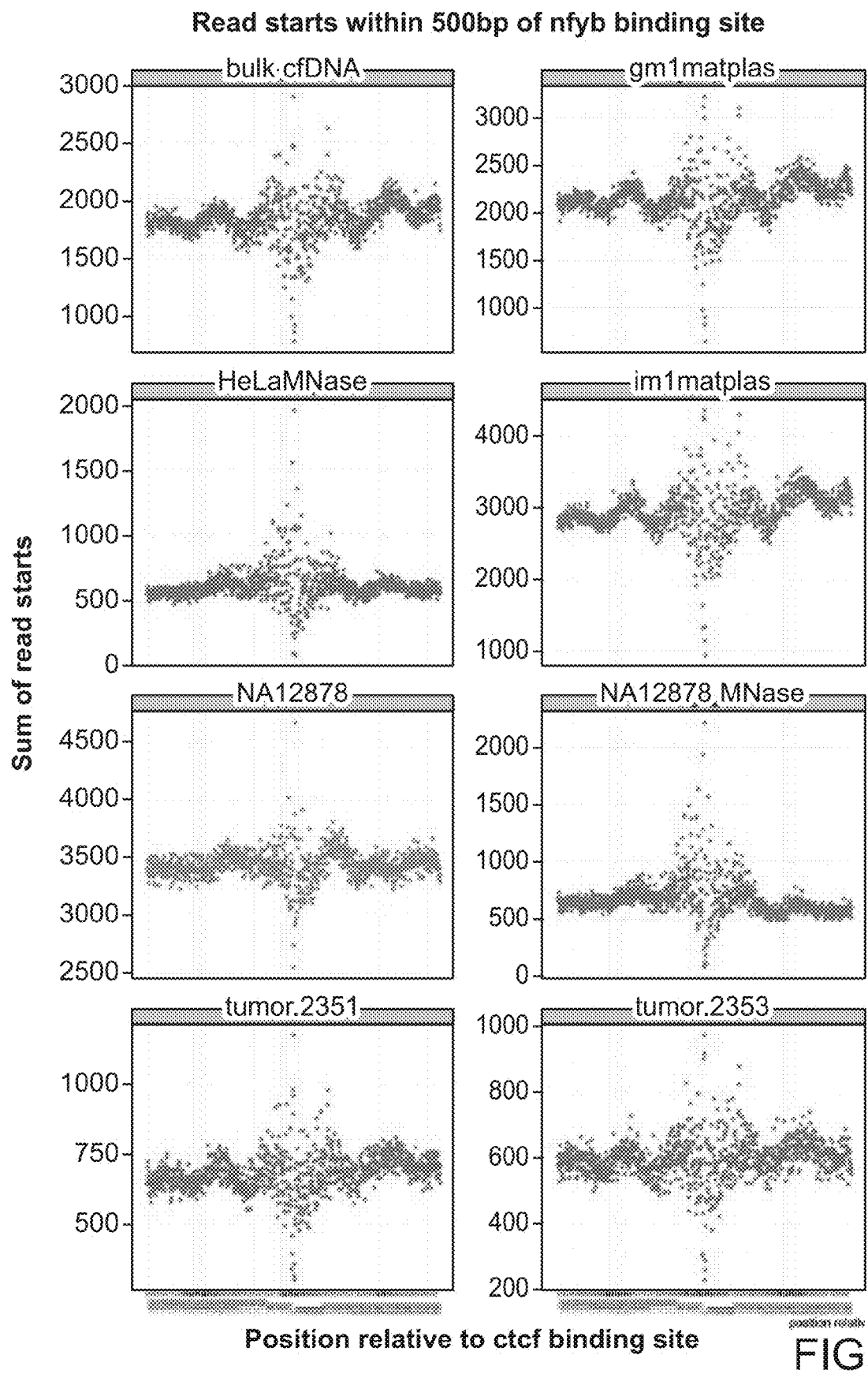
FIG. 16 shows read-start density for 1 kbp window around 4,417 NF-YB binding sites for a set of samples with at least 100 M reads.
Figure 16:
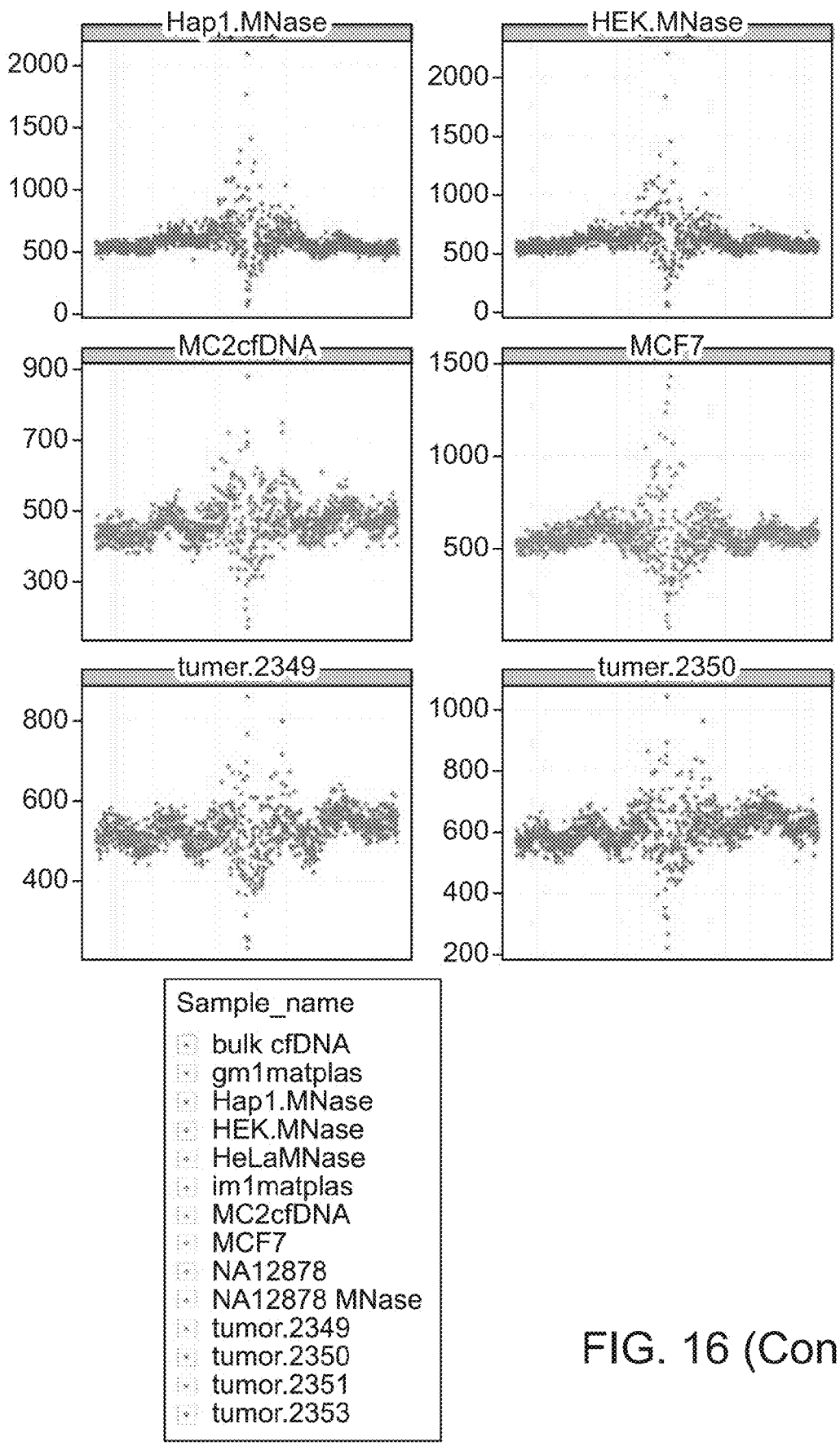

FIG. 16 shows the distribution of read-starts around 4,417 NF-YB binding sites. The start site distributions in the neighborhood of these TF binding sites demonstrate a departure from symmetry: here, the downstream effects (to the right within each plot) appear to be stronger than the upstream effects, as evidenced by the slight upward trajectory in the cfDNA samples. Also of note is the difference between the MNase-digested samples and the cfDNA samples: the former show, on average, a flatter profile in which peaks are difficult to discern, whereas the latter have both more clearly discernable periodicity and more identifiable peaks.

Methods for Examples 1-3

Clinical and Control Samples

Whole blood was drawn from pregnant women fgs002, fgs003, fgs004, and fgs005 during routine third-trimester prenatal care and stored briefly in Vacutainer tubes containing EDTA (BD). Whole blood from pregnant women IM1, GM1, and GM2 was obtained at 18, 13, and 10 weeks gestation, respectively, and stored briefly in Vacutainer tubes containing EDTA (BD). Whole blood from glioma patients 2349, 2350, 2351, and 2353 was collected as part of brain surgical procedures and stored for less than three hours in Vacutainer tubes containing EDTA (BD). Whole blood from Male Control 2 (MC2), a healthy adult male, was collected in Vacutainer tubes containing EDTA (BD). Four to ten ml of blood was available for each individual. Plasma was separated from whole blood by centrifugation at 1,000×g for 10 minutes at 4° C., after which the supernatant was collected and centrifuged again at 2,000×g for 15 minutes at 4° C. Purified plasma was stored in 1 ml aliquots at −80° C. until use.

Bulk human plasma, containing contributions from an unknown number of healthy individuals, was obtained from STEMCELL Technologies (Vancouver, British Columbia, Canada) and stored in 2 ml aliquots at −80° C. until use.

Processing of Plasma Samples

Frozen plasma aliquots were thawed on the bench-top immediately before use. Circulating cfDNA was purified from 2 ml of each plasma sample with the QiaAMP Circulating Nucleic Acids kit (Qiagen, Venlo, Netherlands) as per the manufacturers protocol. DNA was quantified with a Qubit fluorometer (Invitrogen, Carlsbad, Calif.) and a custom qPCR assay targeting a human Alu sequence.

MNase Digestions

Approximately 50 million cells of each line (GM12878, HeLa S3, HEK, Hap1) were grown using standard methods. Growth media was aspirated and cells were washed with PBS. Cells were trypsinized and neutralized with 2× volume of CSS media, then pelleted in conical tubes by centrifugation for at 1,300 rpm for 5 minutes at 4° C. Cell pellets were resuspended in 12 ml ice-cold PBS with 1× protease inhibitor cocktail added, counted, and then pelleted by centrifugation for at 1,300 rpm for 5 minutes at 4° C. Cell pellets were resuspended in RSB buffer (10 mM Tris-HCl, 10 mM NaCl, 3 mM $MgCl_2$, 0.5 mM spermidine, 0.02% NP-40, 1× protease inhibitor cocktail) to a concentration of 3 million cells per ml and incubated on ice for 10 minutes with gentle inversion. Nuclei were pelleted by centrifugation at 1,300 rpm for five minutes at 4° C. Pelleted nuclei were resuspended in NSB buffer (25% glycerol, 5 mM $MgAc_2$, 5 mM HEPES, 0.08 mM EDTA, 0.5 mM spermidine, 1 mM DTT, 1× protease inhibitor cocktail) to a final concentration of 15 M per ml. Nuclei were again pelleted by centrifugation at 1,300 rpm for 5 minutes at 4° C., and resuspended in MN buffer (500 mM Tris-HCl, 10 mM NaCl, 3 mM $MgCl_2$, 1 mM $CaCl$, 1× protease inhibitor cocktail) to a final concentration of 30 M per ml. Nuclei were split into 200 µl aliquots and digested with 4 U of micrococcal nuclease (Worthington Biochemical Corp., Lakewood, N.J., USA) for five minutes at 37° C. The reaction was quenched on ice with the addition of 85 µl of MNSTOP buffer (500 mM NaCl, 50 mM EDTA, 0.07% NP-40, 1× protease inhibitor), followed by a 90 minute incubation at 4° C. with gentle inversion. DNA was purified using phenol:chloroform:isoamyl alcohol extraction. Mononucleosomal fragments were size selected with 2% agarose gel electrophoresis using standard methods and quantified with a Nanodrop spectrophotometer (Thermo Fisher Scientific Inc., Waltham, Mass., USA).

Preparation of Sequencing Libraries

Barcoded sequencing libraries for all samples were prepared with the ThruPLEX-FD or ThruPLEX DNA-seq 48D kits (Rubicon Genomics, Ann Arbor, Mich.), comprising a proprietary series of end-repair, ligation, and amplification reactions. Between 3.0 and 10.0 ng of DNA were used as input for all clinical sample libraries. Two bulk plasma cfDNA libraries were constructed with 30 ng of input to each library; each library was separately barcoded. Two libraries from MC2 were constructed with 2 ng of input to each library; each library was separately barcoded. Libraries for each of the MNase-digested cell lines were constructed with 20 ng of size-selected input DNA. Library amplification for all samples was monitored by real-time PCR to avoid over-amplification.

Sequencing

All libraries were sequenced on HiSeq 2000 instruments (Illumina, Inc., San Diego, Calif., USA) using paired-end 101 bp reads with an index read of 9 bp. One lane of sequencing was performed for pooled samples fgs002, fgs003, fgs004, and fgs005, yielding a total of approximately $4.5 \times 10^7$ read-pairs per sample. Samples IM1, GM1, and GM2 were sequenced across several lanes to generate $1.2 \times 10^9$, $8.4 \times 10^8$, and $7.6 \times 10^7$ read-pairs, respectively. One lane of sequencing was performed for each of samples 2349, 2350, 2351, and 2353, yielding approximately $2.0 \times 10^8$ read-pairs per sample. One lane of sequencing was performed for each of the four cell line MNase-digested libraries, yielding approximately $2.0 \times 10^8$ read-pairs per library. Four lanes of sequencing were performed for one of the two replicate MC2 libraries and three lanes for one of the two replicate bulk plasma libraries, yielding a total of $10.6 \times 10^9$ and $7.8 \times 10^8$ read-pairs per library, respectively.

Processing of cfDNA Sequencing Data

DNA insert sizes for both cfDNA and MNase libraries tend be short (majority of data between 80 bp and 240 bp); adapter sequence at the read ends of some molecules were therefore expected. Adapter sequences starting at read ends were trimmed, and forward and reverse read of paired end ("PE") data for short original molecules were collapsed into single reads ("SRs"); PE reads that overlap with at least 11 bp reads were collapsed to SRs. The SRs shorter than 30 bp or showing more than 5 bases with a quality score below 10 were discarded. The remaining PE and SR data were aligned to the human reference genome (GRCh37, 1000G release v2) using fast alignment tools (BWA-ALN or BWA-MEM). The resulting SAM (Sequence Alignment/Map) format was converted to sorted BAM (Binary Sequence Alignment/Map format) using SAMtools.

Additional Publically Available Data

Publically available PE data of Hela-S3 MNase (accessions SRR633612, SRR633613) and MCF-7 MNase experiments (accessions SRR999659-SRR999662) were downloaded and processed as described above.

Publicly available genomic shotgun sequencing data of the CEPH pedigree 146 individual NA12878 generated by Illumina Cambridge Ltd. (Essex, UK) was obtained from the European Nucleotide Archive (ENA, accessions ERR174324-ERR174329). This data was PE sequenced with 2×101 bp reads on the Illumina HiSeq platform and the libraries were selected for longer insert sizes prior to sequencing. Thus, adapter sequence at the read ends were not expected; this data was therefore directly aligned using BWA-MEM.

Extracting Read End Information

PE data provides information about the two physical ends of DNA molecules used in sequencing library preparation. This information was extracted using the SAMtools application programming interface (API) from BAM files. Both outer alignment coordinates of PE data for which both reads aligned to the same chromosome and where reads have opposite orientations were used. For non-trimmed SR data, only one read end provides information about the physical end of the original DNA molecule. If a read was aligned to the plus strand of the reference genome, the left-most coordinate was used. If a read was aligned to the reverse strand, its right-most coordinate was used instead. In cases where PE data was converted to single read data by adapter trimming, both end coordinates were considered. Both end coordinates were also considered if at least five adapter bases were trimmed from a SR sequencing experiment.

For all autosomes in the human reference sequence (chromosomes 1 to 22), the number of read ends and the coverage at all positions were extracted in windows of 10,000 bases (blocks). If there were no reads aligning in a block, the block was considered empty for that specific sample.

Smooth Periodograms

The ratio of read-starts and coverage was calculated for each non-empty block of each sample. If the coverage was 0, the ratio was set to 0. These ratios were used to calculate a periodogram of each block using Fast Fourier Transform (FFT, spec.pgram in the R statistical programming environment) with frequencies between 1/500 bases and 1/100 bases. Optionally, parameters to smooth (3 bp Daniell smoother; moving average giving half weight to the end values) and detrend the data (e.g., subtract the mean of the series and remove a linear trend) were used. Intensities for the frequency range 120-250 bp for each block were saved.

Average Chromosome Intensities

For a set of samples, blocks that were non-empty across all samples were identified. The intensities for a specific frequency were averaged across all blocks of each sample for each autosome.

Principal Component Analysis and Dendograms

Blocks that were non-empty across samples were collected. Principal component analysis (PCA; prcomp in the R statistical programming environment) was used to reduce the dimensionality of the data and to plot it in two-dimensional space. PCA identifies the dimension that captures most variation of the data and constructs orthogonal dimensions, explaining decreasing amounts of variation in the data.

Pair-wise Euclidean distances between sample intensities were calculated and visualized as dendograms (stats library in the R statistical programming environment).

Transcription Factor Binding Site Predictions

Putative transcription factor binding sites, obtained through analysis of ChIP-seq data generated across a number of cell types, was obtained from the ENCODE project.

An independent set of candidate transcription factor binding sites was obtained by scanning the human reference genome (GRCh37, 1000G release v2) with the program fimo from the MEME software package (version 4.10.0_1). Scans were performed using positional weight matrices obtained from the JASPAR_CORE_2014_vertebrates database, using options "--verbosity 1 --thresh 1 e-5". Transcription factor motif identifiers used were MA0139.1, MA0502.1, and MA0489.1.

Chromosomal coordinates from both sets of predicted sites were intersected with bedtools v2.17.0. To preserve any asymmetry in the plots, only predicted binding sites on the "+" strand were used. Read-starts were tallied for each sample if they fell within 500 bp of either end of the predicted binding site, and summed within samples by position across all such sites. Only samples with at least 100 million total reads were used for this analysis.

Example 4: Determining Normal/Healthy Tissue(s)-of-Origin from cfDNA

To evaluate whether fragmentation patterns observed in a single individual's cfDNA might contain evidence of the genomic organization of the cells giving rise to these fragments—and thus, of the tissue(s)-of-origin of the population of cfDNA molecules—even when there are no genotypic differences between contributing cell types, cfDNA was deeply sequenced to better understand the processes that give rise to it. The resulting data was used to build a genome-wide map of nucleosome occupancy that built on previous work by others, but is substantially more comprehensive. By optimizing library preparation protocols to recover short fragments, it was discovered that the in vivo occupancies of transcription factors (TFs) such as CTCF are also directly footprinted by cfDNA. Finally, it was discovered that nucleosome spacing in regulatory elements and gene bodies, as revealed by cfDNA sequencing in healthy individuals, correlates most strongly with DNase hypersensitivity and gene expression in lymphoid and myeloid cell lines.

cfDNA Fragments Correspond to Chromatosomes and Contain Substantial DNA Damage

Figure 17:
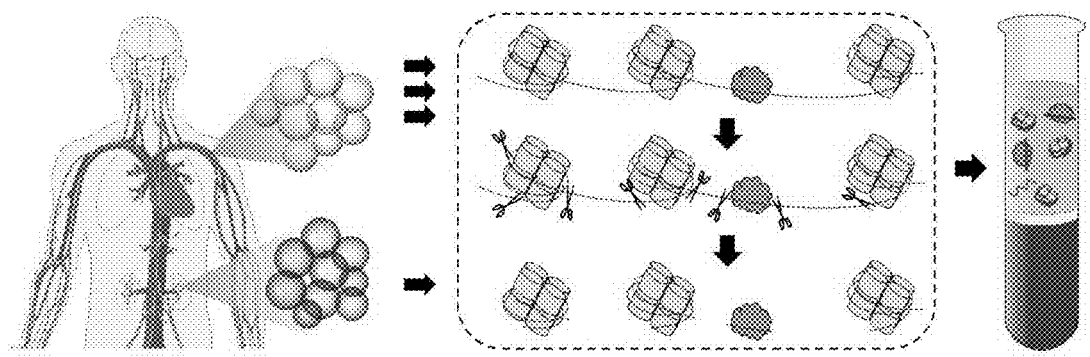
FIG. 17 shows a schematic overview of the processes giving rise to cfDNA fragments. Apoptotic and/or necrotic cell death results in near-complete digestion of native chromatin. Protein-bound DNA fragments, typically associated with histones or transcription factors, preferentially survive digestion and are released into the circulation, while naked DNA is lost. Fragments can be recovered from peripheral blood plasma following proteinase treatment. In healthy individuals, cfDNA is primarily derived from myeloid and lymphoid cell lineages, but contributions from one or more additional tissues may be present in certain medical conditions.

Conventional sequencing libraries were prepared by end-repair and adaptor ligation to cfDNA fragments purified from plasma pooled from an unknown number of healthy individuals ("BH01") or plasma from a single individual ("IH01") (FIG. 17; Table 1):

TABLE 1

Sequencing Statistics for Plasma Samples.

| Sample name | Library type | Reads | Fragments sequenced | Aligned | Aligned Q30 | Coverage | Est. % duplicates | 35-80 bp | 120-180 bp |
|---|---|---|---|---|---|---|---|---|---|
| BH01 | DSP | 2x101 | 1489569204 | 97.20% | 88.85% | 96.32 | 6.00% | 0.65% | 57.64% |
| IH01 | DSP | 2x101 | 1572050374 | 98.58% | 90.60% | 104.92 | 21.00% | 0.77% | 47.83% |
| IH02 | SSP | 2x50, 43/42 | 779794090 | 93.19% | 75.27% | 30.08 | 20.05% | 21.83% | 44.00% |
| CH01 | — | — | 3841413668 | 96.95% | 86.81% | 231.32 | 14.99% | 5.00% | 50.85% |

SSP, single-stranded library preparation protocol. DSP, double-stranded library preparation protocol.

For each sample, sequencing-related statistics, including the total number of fragments sequenced, read lengths, the percentage of such fragments aligning to the reference with and without a mapping quality threshold, mean coverage, duplication rate, and the proportion of sequenced fragments in two length bins, were tabulated. Fragment length was inferred from alignment of paired-end reads. Due to the short read lengths, coverage was calculated by assuming the entire fragment had been read. The estimated number of duplicate fragments was based on fragment endpoints, which may overestimate the true duplication rate in the presence of highly stereotyped cleavage. SSP, single-stranded library preparation protocol. DSP, double-stranded library preparation protocol.

Figure 18:
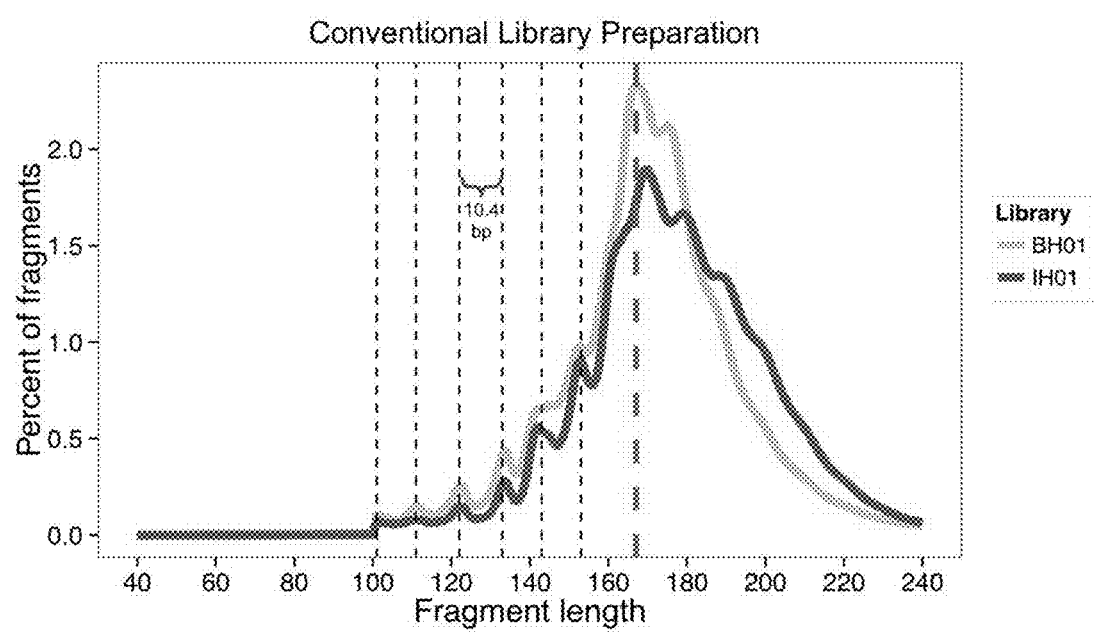
FIG. 18 shows fragment length of cfDNA observed with conventional sequencing library preparation. Length is inferred from alignment of paired-end sequencing reads. A reproducible peak in fragment length at 167 base-pairs (bp) (green dashed line) is consistent with association with chromatosomes. Additional peaks evidence ~10.4 bp periodicity, corresponding to the helical pitch of DNA on the nucleosome core. Enzymatic end-repair during library preparation removes 5' and 3' overhangs and may obscure true cleavage sites.
Figure 19:
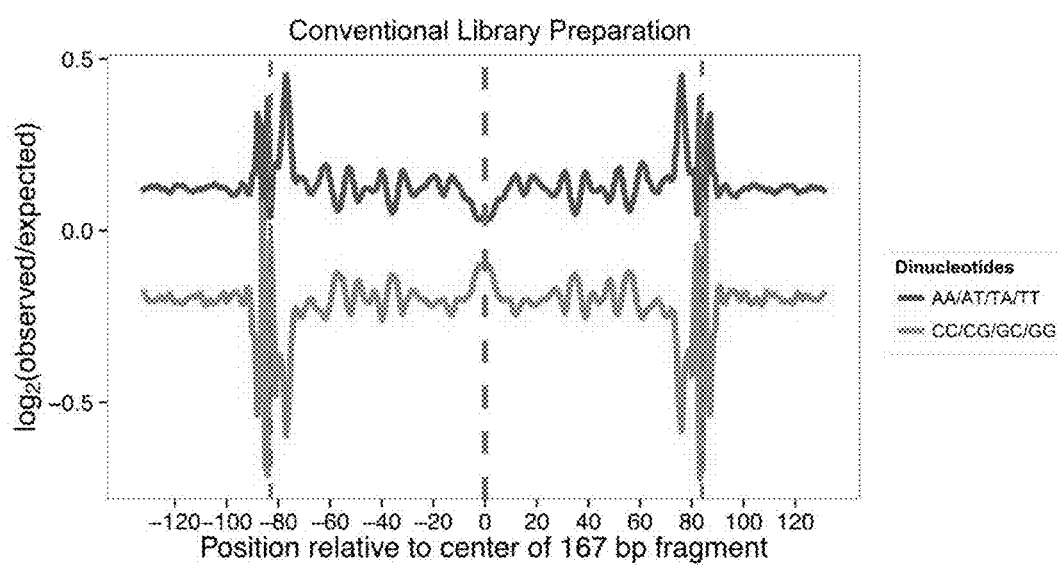
FIG. 19 shows a dinucleotide composition of 167 bp fragments and flanking genomic sequence in conventional libraries. Observed dinucleotide frequencies in the BH01 library were compared to expected frequencies from simulated fragments (matching for endpoint biases resulting from both cleavage and adapter ligation preferences).

Libraries BH01 and IH01 were sequenced to 96- and 105-fold coverage, respectively (1.5G and 1.6G fragments). The fragment length distributions, inferred from alignment of paired-end reads, have a dominant peak at ~167 bp (coincident with the length of DNA associated with a chromatosome), and ~10.4 bp periodicity in the 100-160 bp length range (FIG. 18). These distributions are consistent with a model in which cfDNA fragments are preferentially protected from nuclease cleavage both pre- and post-cell death by association with proteins—in this case, by the nucleosome core particle and linker histone—but where some degree of additional nicking or cleavage occurs in relation to the helical pitch of nucleosome-bound DNA. Further supporting this model is the dinucleotide composition of these 167 bp fragments, which recapitulate key features of earlier studies of MNase-derived, nucleosome-associated fragments (e.g. bias against NT dinucleotides at the dyad) and support the notion that the nucleosome core particle is symmetrically positioned with respect to the chromatosome (FIG. 19).

Figure 20:
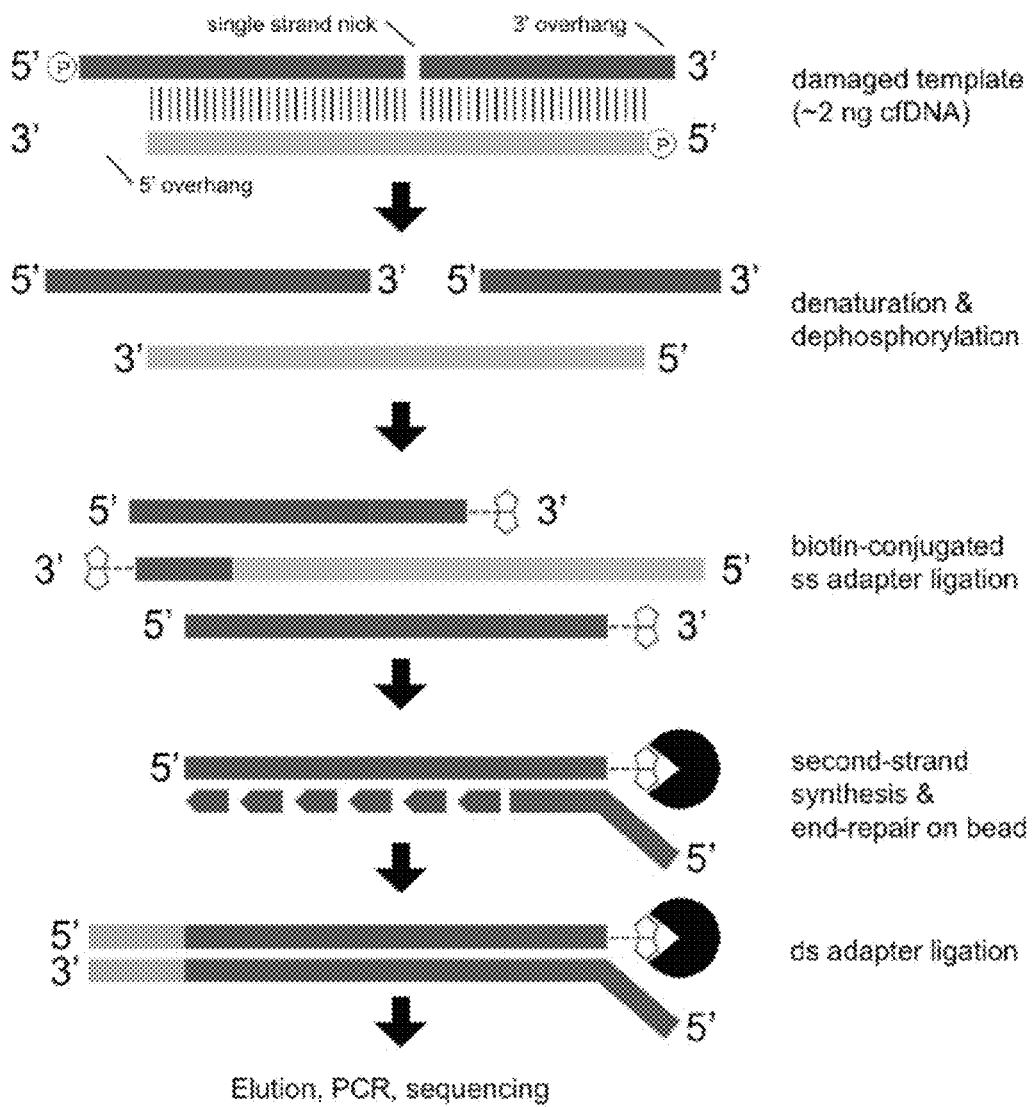
FIG. 20 shows a schematic of a single-stranded library preparation protocol for cfDNA fragments.
Figure 21:
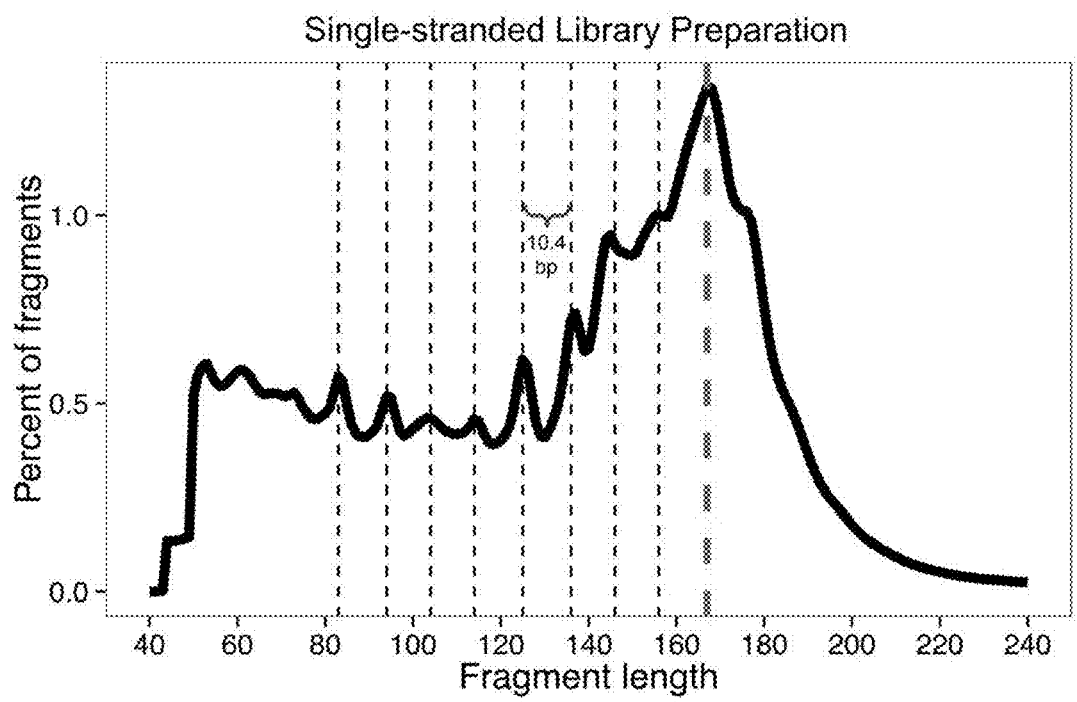
FIG. 21 shows fragment length of cfDNA observed with single-stranded sequencing library preparation. No enzymatic end-repair is performed to template molecules during library preparation. Short fragments of 50-120 bp are highly enriched compared to conventional libraries. While ~10.4 bp periodicity remains, its phase is shifted by ~3 bp.
Figure 22:
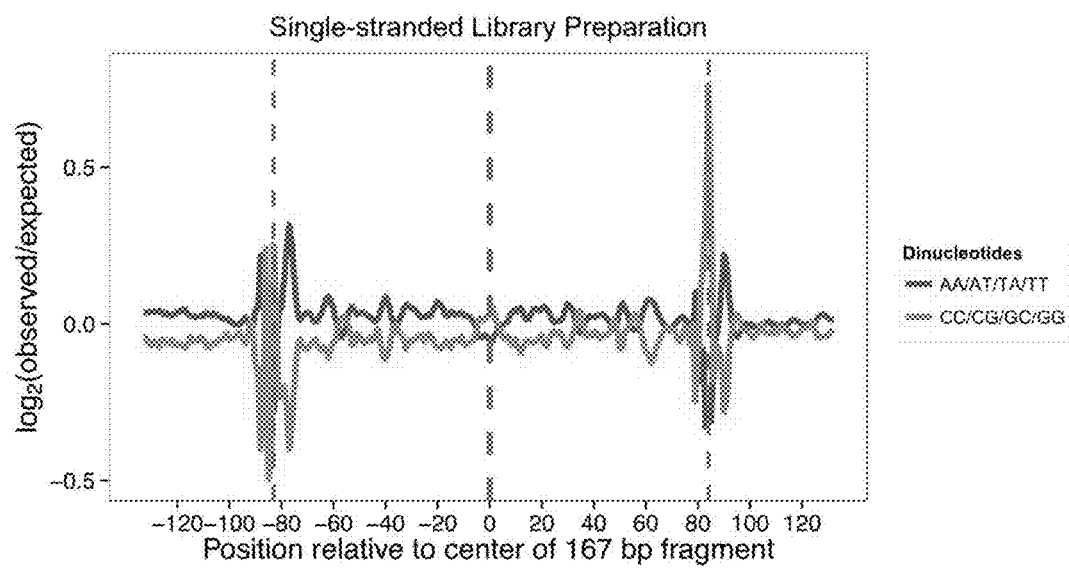
FIG. 22 shows a dinucleotide composition of 167 bp fragments and flanking genomic sequence in single-stranded libraries. Observed dinucleotide frequencies in the IH02 library were compared to expected frequencies derived from simulated fragments, again matching for endpoint biases. The apparent difference in the background level of bias between BH01 and IH02 relate to differences between the simulations, rather than the real libraries (data not shown).
Figure 23A:
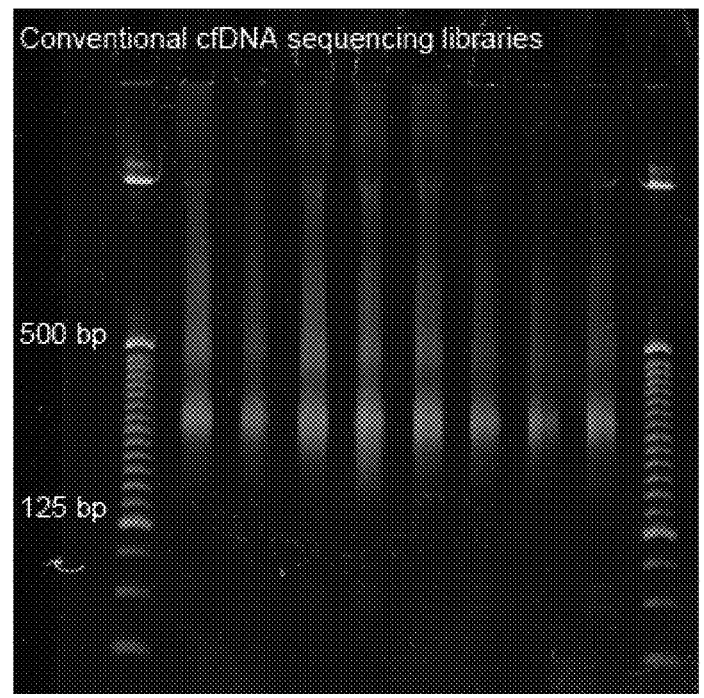
FIG. 23A shows a gel image of representative cfDNA sequencing library prepared with the conventional protocol.
Figure 23B:
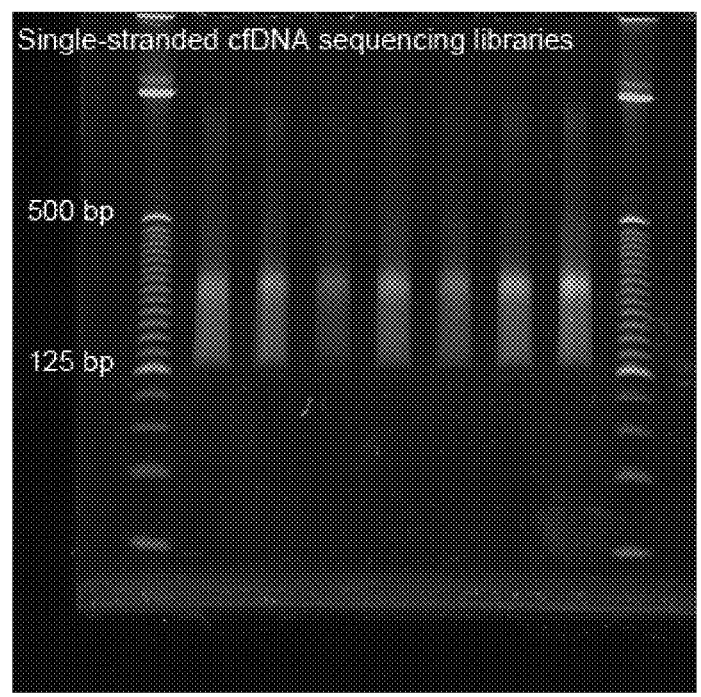
FIG. 23B shows a gel image of a representative cfDNA sequencing library prepared with the single-stranded protocol.
Figure 24A:
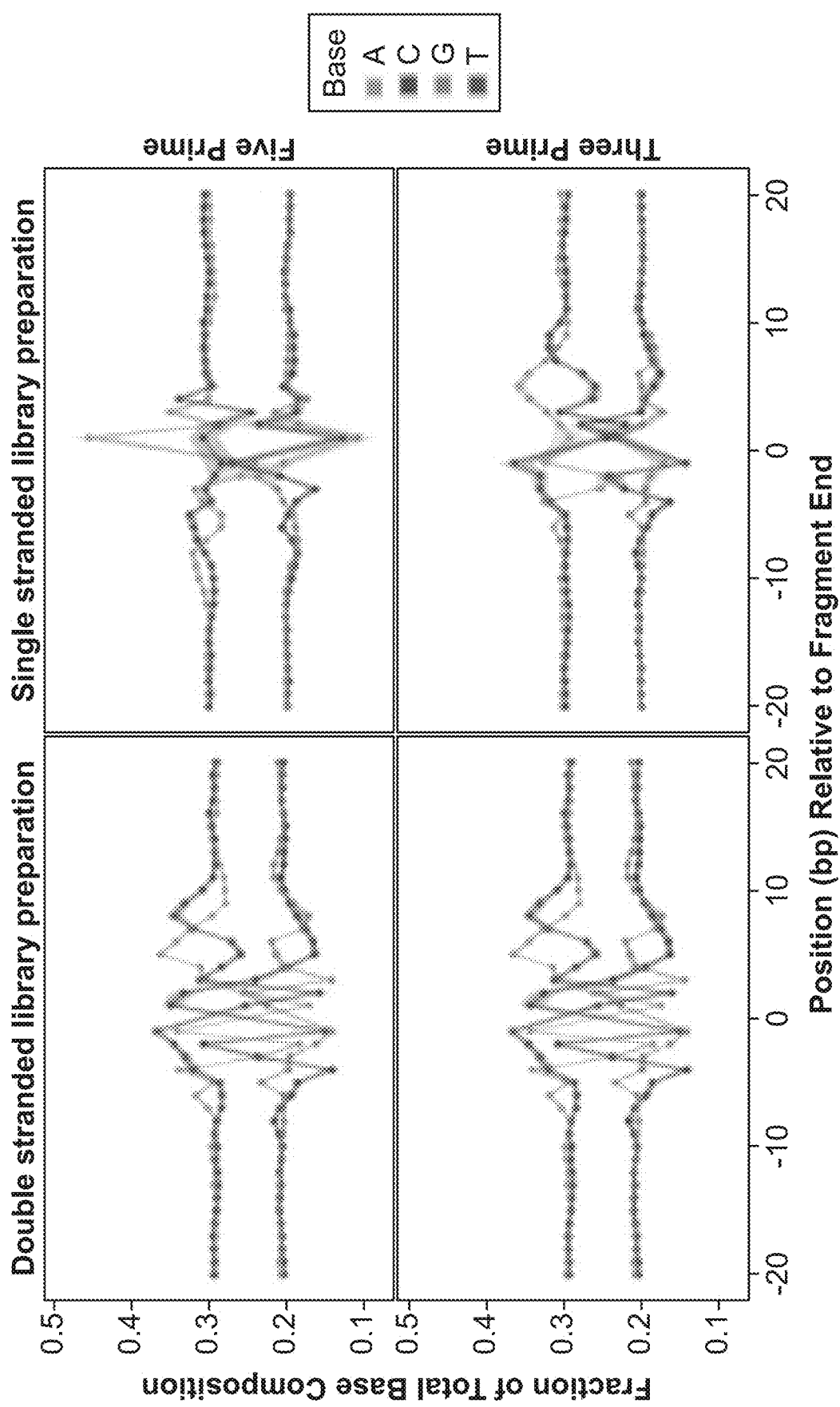
FIG. 24A shows mononucleotide cleavage biases of cfDNA fragments.
Figure 24B:
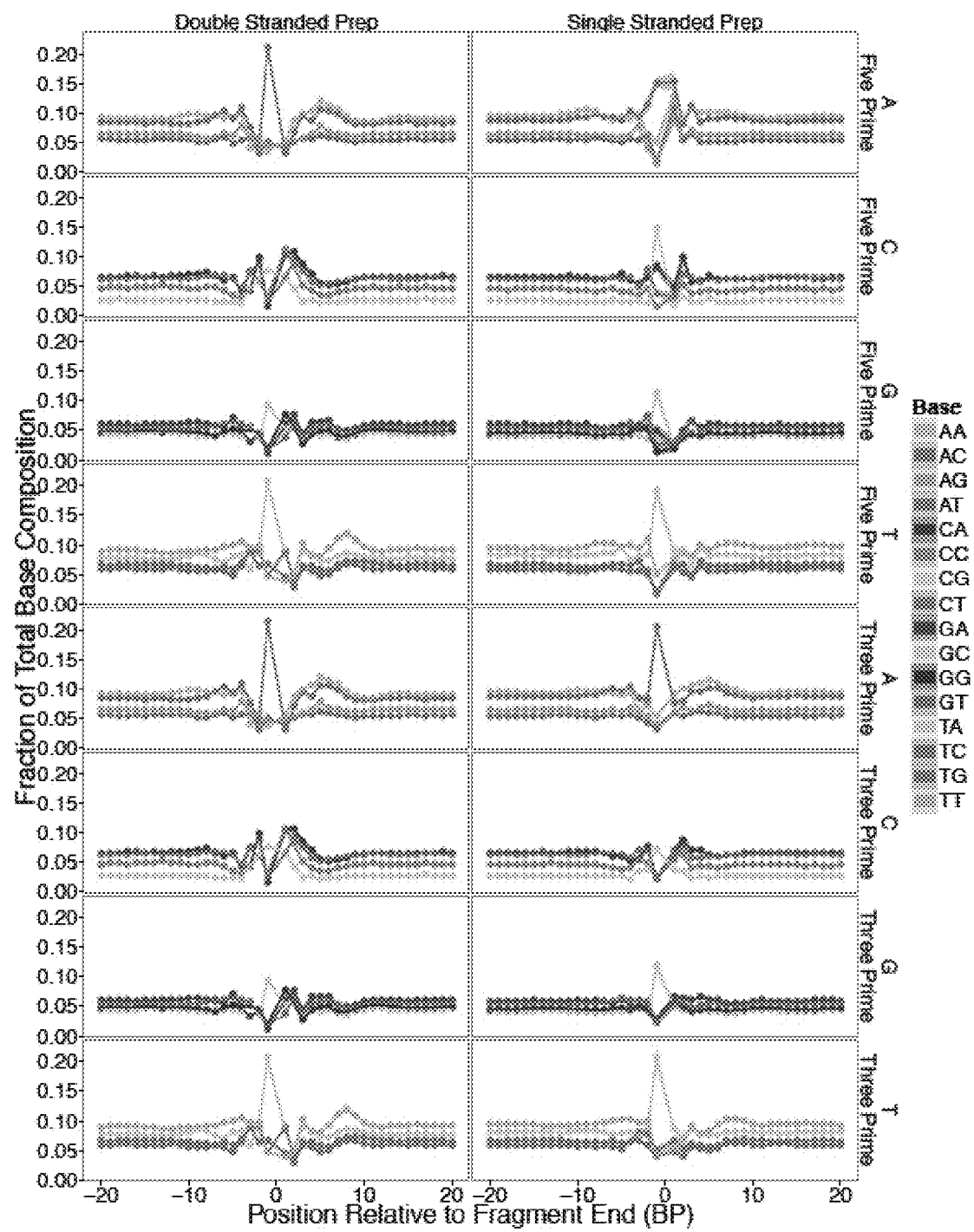
FIG. 24B shows dinucleotide cleavage biases of cfDNA fragments.

A prediction of this model of cfDNA ontology is widespread DNA damage, e.g. single-strand nicks as well as 5' and 3' overhangs. During conventional library preparation, nicked strands are not amplified, overhangs are blunted by end-repair, and short double stranded DNA ("dsDNA") molecules, which may represent a substantial proportion of total cfDNA, may simply be poorly recovered. To address this, a single-stranded sequencing library from plasma-borne cfDNA derived from an additional healthy individual ('IH02') was prepared using a protocol adapted from studies of ancient DNA by Gansauge, et al., where widespread DNA damage and nuclease cleavage around nucleosomes have been reported. Briefly, cfDNA was denatured and a biotin-conjugated, single-stranded adaptor was ligated to the resulting fragments. The ligated fragments were then subjected to second-strand synthesis, end-repair and ligation of a second adaptor while the fragments were immobilized to streptavidin beads. Finally, minimal PCR amplification was performed to enrich for adaptor-bearing molecules while also appending a sample index (FIG. 20; Table 2).

TABLE 2

Synthetic oligos used in preparation of single stranded sequencing libraries.

| Oligo Name | SEQ ID NO | Sequence (5'-3') | Notes |
|---|---|---|---|
| CL9 | 1 | GTGACTGGAGTTCAGACG TGTGCTCTTCCGATCT | HPLC purification |
| Adapter2.1 | 2 | CGACGCTCTTCCGATC/ ddT/ | HPLC purification |
| Adapter2.2 | 3 | /5Phos/AGATCGGAAGA GCGTCGTGTAGGGAAAGA G*T*G*T*A | HPLC purification |
| CL78 | 4 | /5Phos/AGATCGGAAG/ iSpC3/iSpC3/iSpC3/ iSpC3/iSpC3/iSpC3/ iSpC3/iSpC3/iSpC3/ 3BioTEG/ | Dual HPLC purification |

For IH02, the resulting library was sequenced to 30-fold coverage (779M fragments). The fragment length distribution again exhibited a dominant peak at ~167 bp corresponding to the chromatosome, but was considerably enriched for shorter fragments relative to conventional library preparation (FIGS. 21, 22, 23A-B, 24A-B). Although all libraries exhibit ~10.4 bp periodicity, the fragment sizes are offset by 3 bp for the two methods, consistent with damaged or non-flush input molecules whose true endpoints are more faithfully represented in single-stranded libraries.

Figure 25:
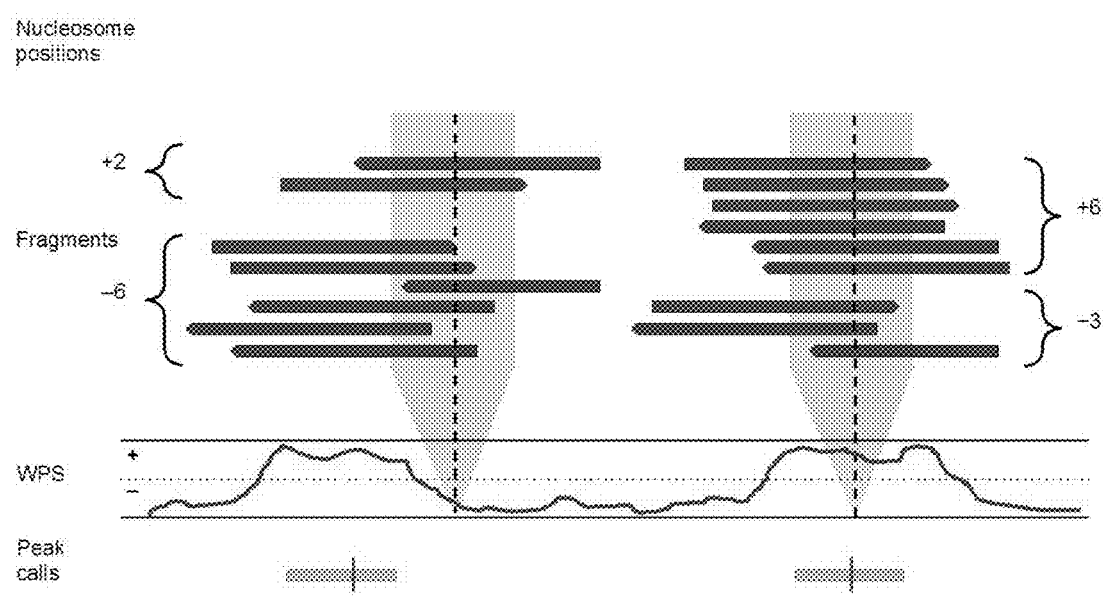
FIG. 25 shows a schematic overview of inference of nucleosome positioning. A per-base windowed protection score (WPS) is calculated by subtracting the number of fragment endpoints within a 120 bp window from the number of fragments completely spanning the window. High WPS values indicate increased protection of DNA from digestion; low values indicate that DNA is unprotected. Peak calls identify contiguous regions of elevated WPS.
Figure 26:
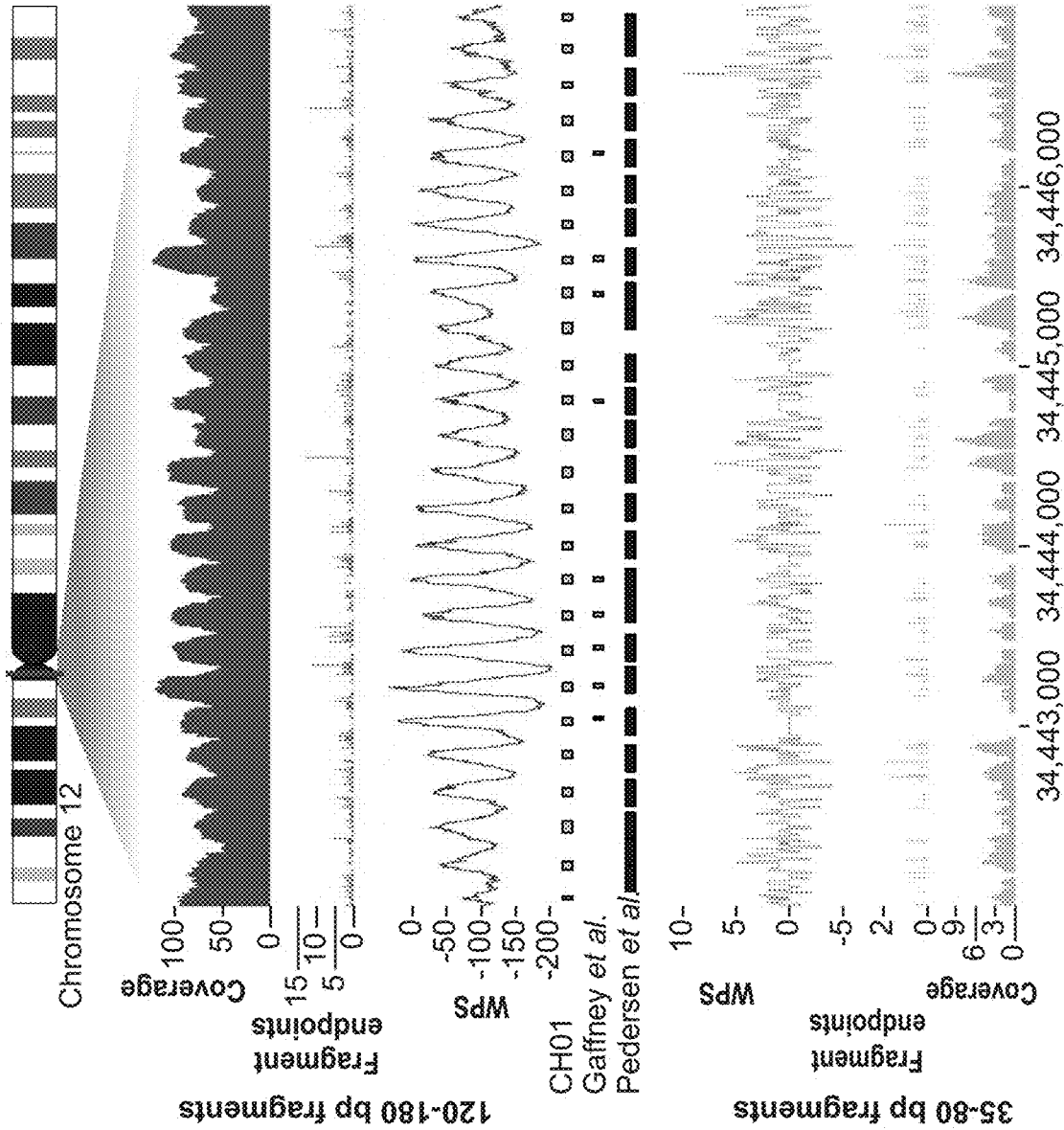
FIG. 26 shows strongly positioned nucleosomes at a well-studied alpha-satellite array. Coverage, fragment endpoints, and WPS values from sample CH01 are shown for long fragment (120 bp window; 120-180 bp reads) or short fragment (16 bp window; 35-80 bp reads) bins at a pericentromeric locus on chromosome 12. Nucleosome calls from CH01 (middle, blue boxes) are regularly spaced across the locus. Nucleosome calls based on MNase digestion from two published studies (middle, purple and black boxes) are also displayed. The locus overlaps with an annotated alpha-satellite array.
Figure 27:
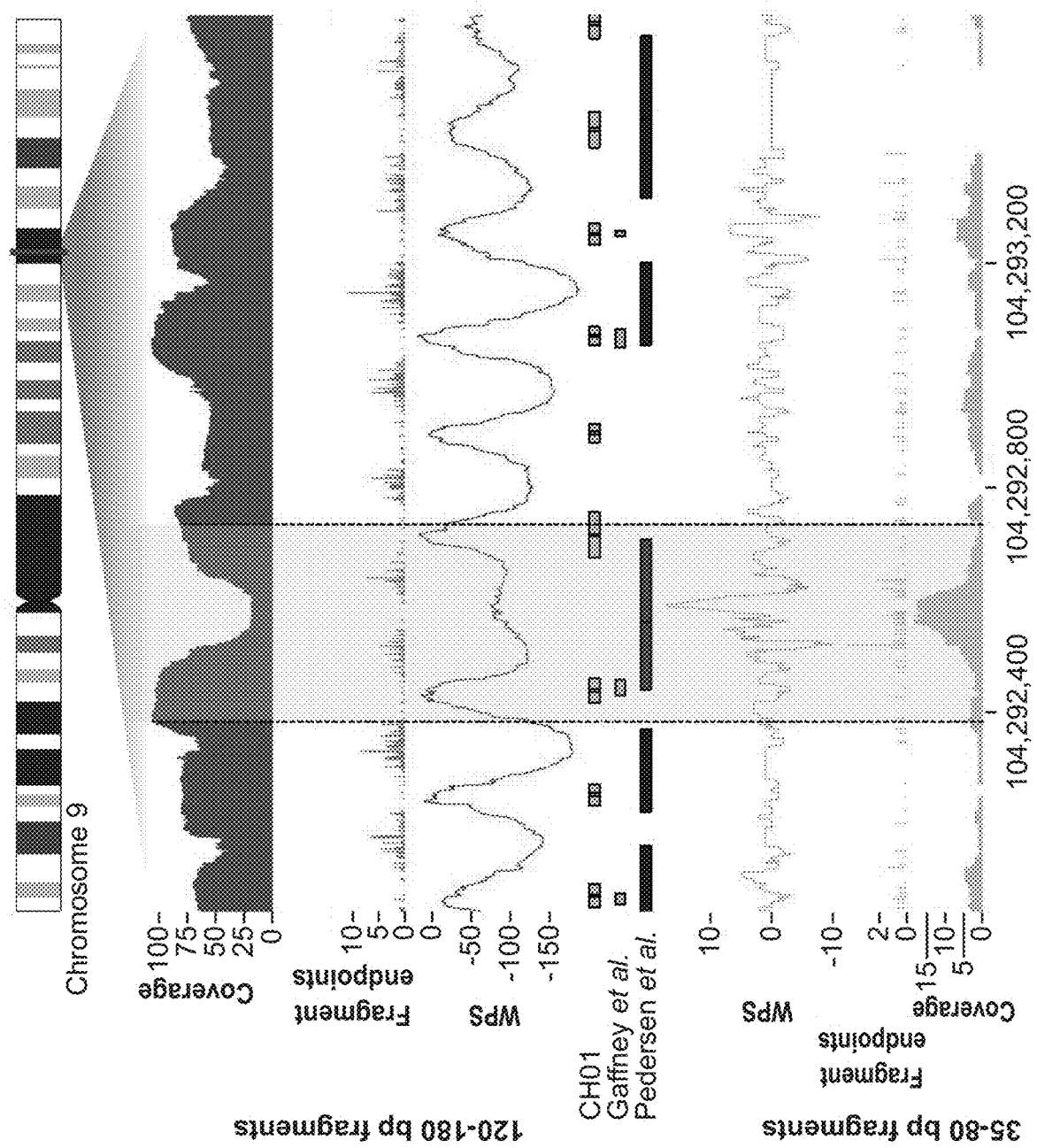
FIG. 27 shows inferred nucleosome positioning around a DNase I hypersensitive site (DHS) on chromosome 9. Coverage, fragment endpoints, and WPS values from sample CH01 are shown for long and short fragment bins. The hypersensitive region, highlighted in gray, is marked by reduced coverage in the long fragment bin. Nucleosome calls from CH01 (middle, blue boxes) adjacent to the DHS are spaced more widely than typical adjacent pairs, consistent with accessibility of the intervening sequence to regulatory proteins including transcription factors. Coverage of shorter fragments, which may be associated with such proteins, is increased at the DHS, which overlaps with several annotated transcription factor binding sites (not shown). Nucleosome calls based on MNase digestion from two published studies are shown as in FIG. 26.
Figure 28:
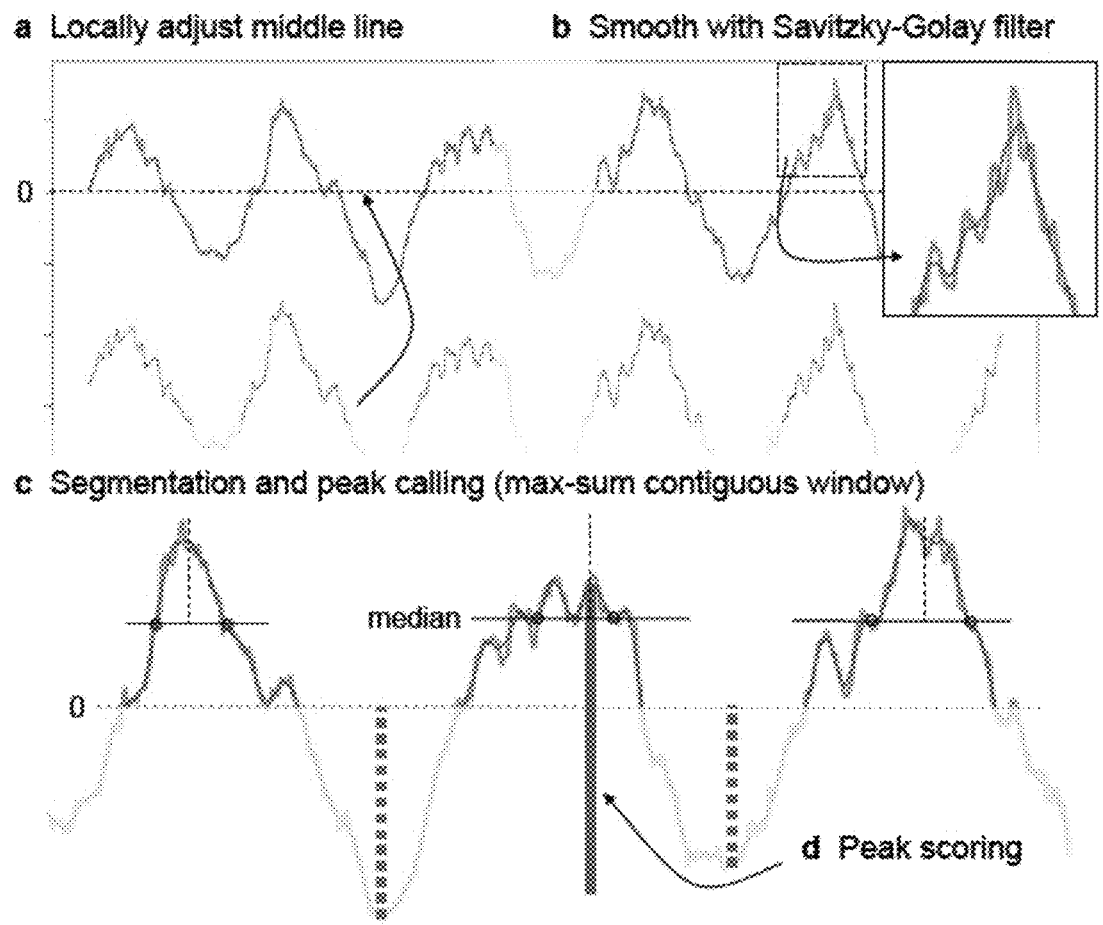
FIG. 28 shows a schematic of peak calling and scoring according to one embodiment of the present disclosure.
Figure 29:
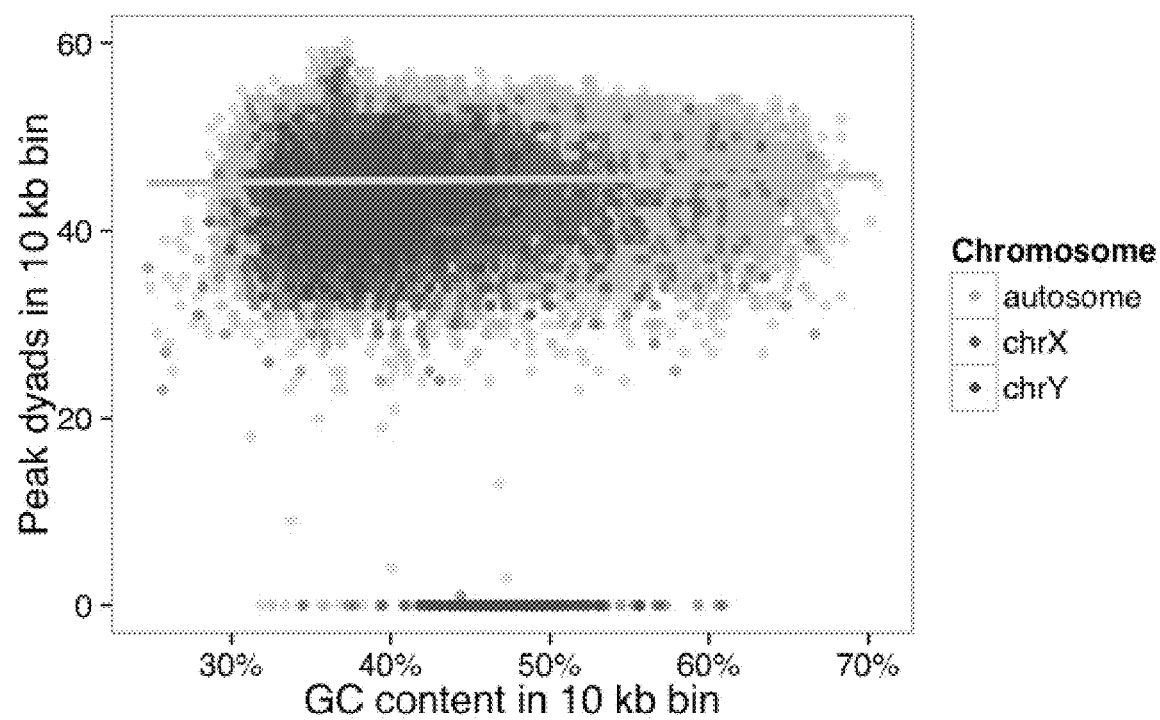
FIG. 29 shows CH01 peak density by GC content.
Figure 30:
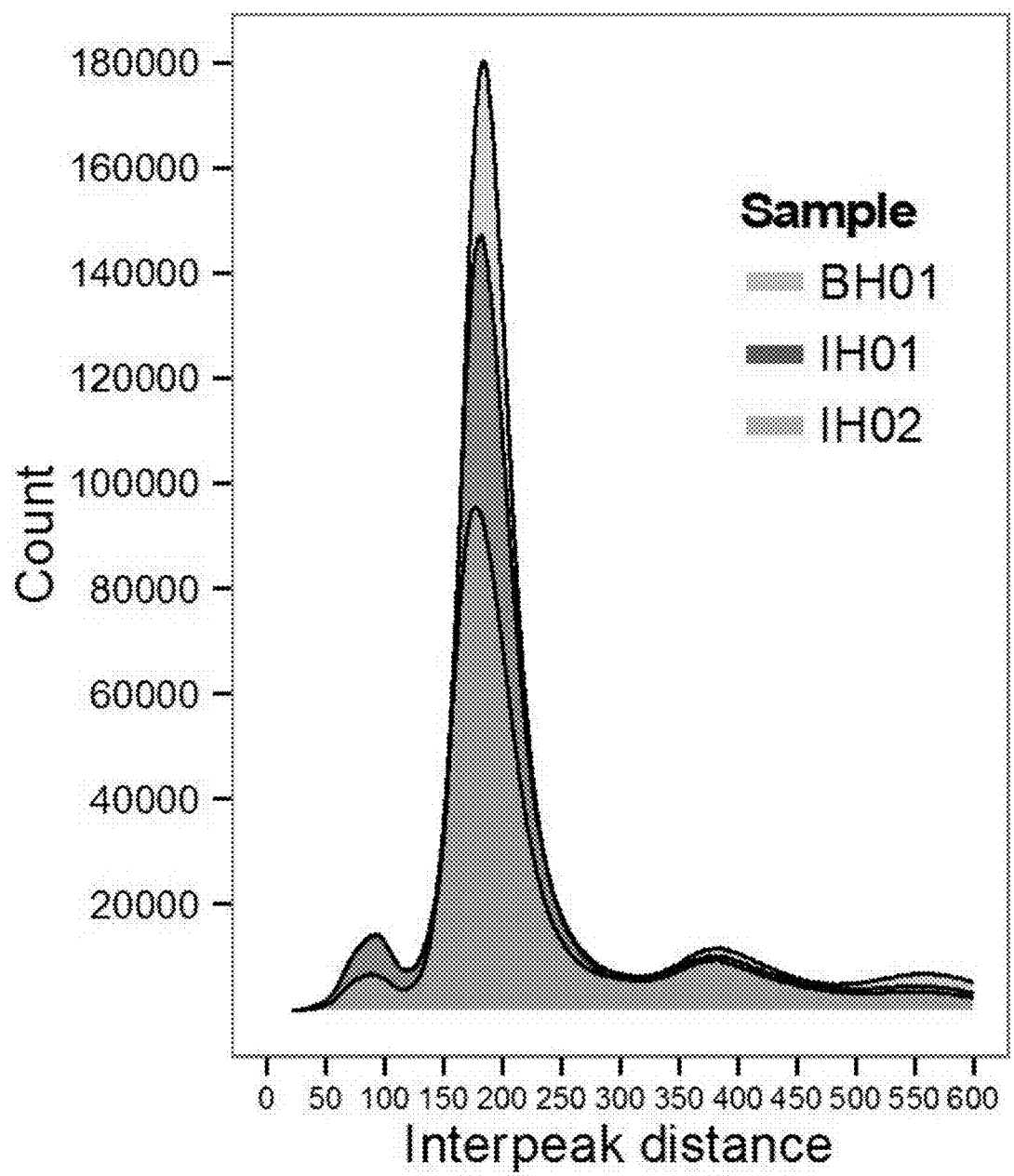
FIG. 30 shows a histogram of distances between adjacent peaks by sample. Distances are measured from peak call to adjacent call.
Figure 31:
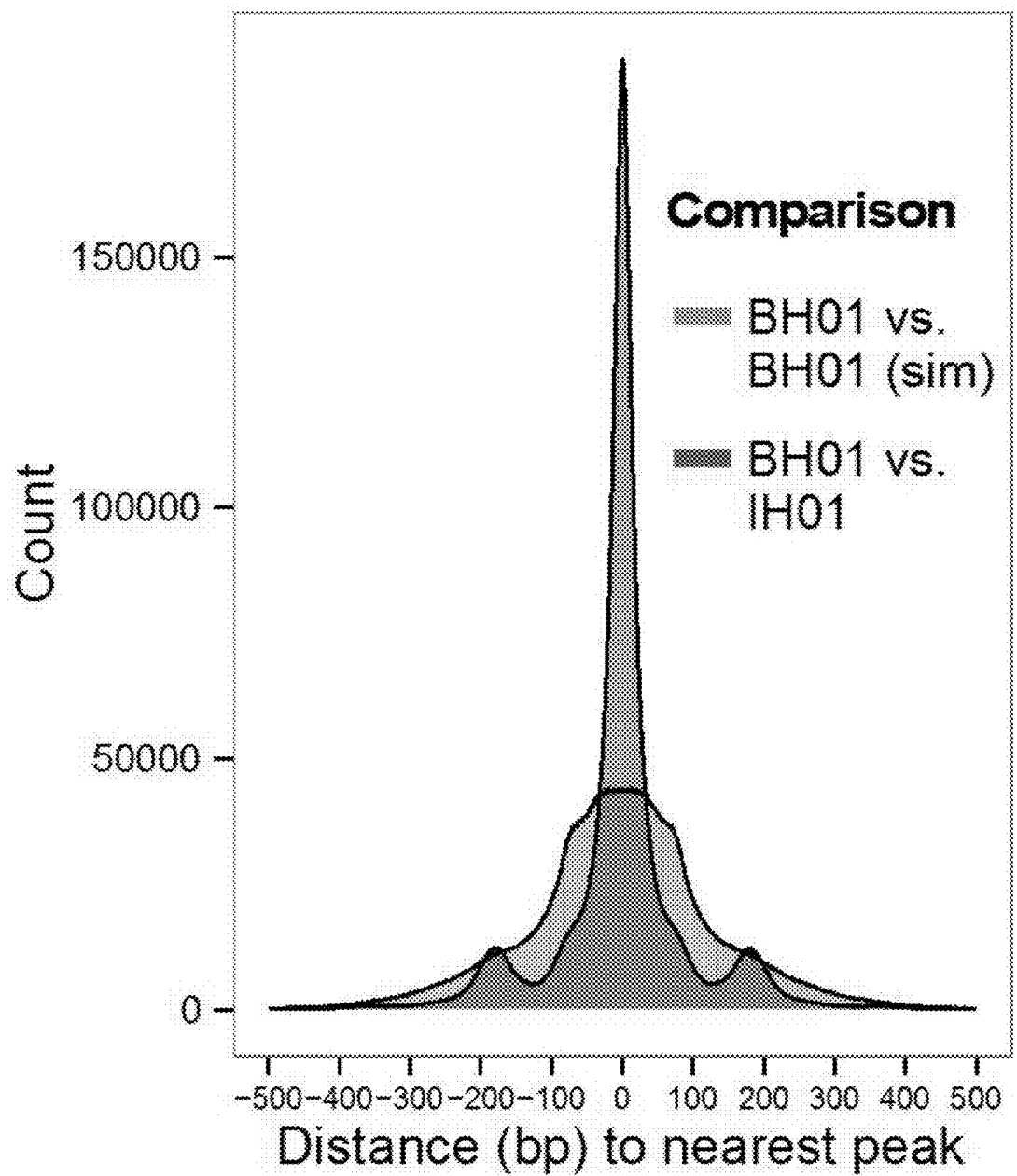
FIG. 31 shows a comparison of peak calls between samples. For each pair of samples, the distances between each peak call in the sample with fewer peaks and the nearest peak call in the other sample are calculated and visualized as a histogram with bin size of 1. Negative numbers indicate the nearest peak is upstream; positive numbers indicate the nearest peak is downstream.

A Genome-Wide Map of In Vivo Nucleosome Protection Based on Deep cfDNA Sequencing To assess whether the predominant local positions of nucleosomes across the human genome in tissue(s) contributing to cfDNA could be inferred by comparing the distribution of aligned fragment endpoints, or a mathematical transformation thereof, to one or more reference maps, a Windowed Protection Score ("WPS") was developed. Specifically, it was expected that cfDNA fragment endpoints should cluster adjacent to nucleosome boundaries, while also being depleted on the nucleosome itself. To quantify this, the WPS was developed, which represents the number of DNA fragments completely spanning a 120 bp window centered at a given genomic coordinate, minus the number of fragments with an endpoint within that same window (FIG. 25). As intended, the value of the WPS correlates with the locations of nucleosomes within strongly positioned arrays, as mapped by other groups with in vitro methods or ancient DNA (FIG. 26). At other sites, the WPS correlates with genomic features such as DNase I hypersensitive (DHS) sites (e.g., consistent with the repositioning of nucleosomes flanking a distal regulatory element) (FIG. 27).

A heuristic algorithm was applied to the genome-wide WPS of the BH01, IH01 and IH02 datasets to identify 12.6M, 11.9M, and 9.7M local maxima of nucleosome protection, respectively (FIGS. 25-31). In each sample, the mode of the distribution of distances between adjacent peaks was 185 bp with low variance (FIG. 30), generally consistent with previous analyses of the nucleosome repeat length in human or mouse cells.

Figure 32A:
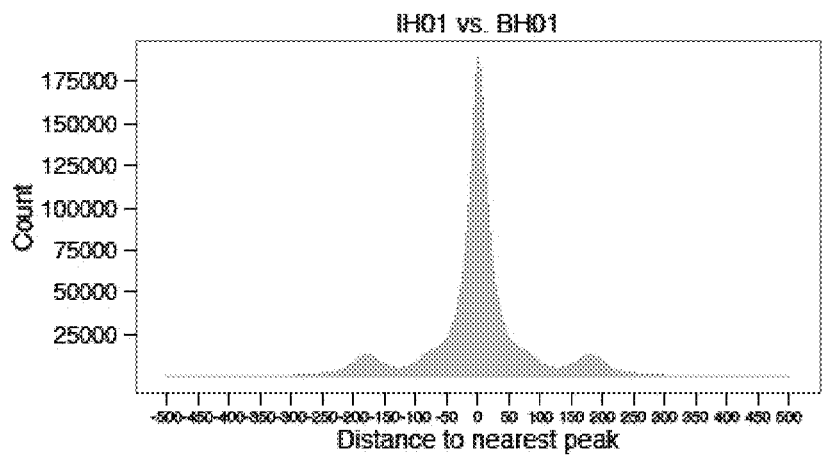
FIGS. 32A-C show a comparison of peak calls between samples.
Figure 32B:
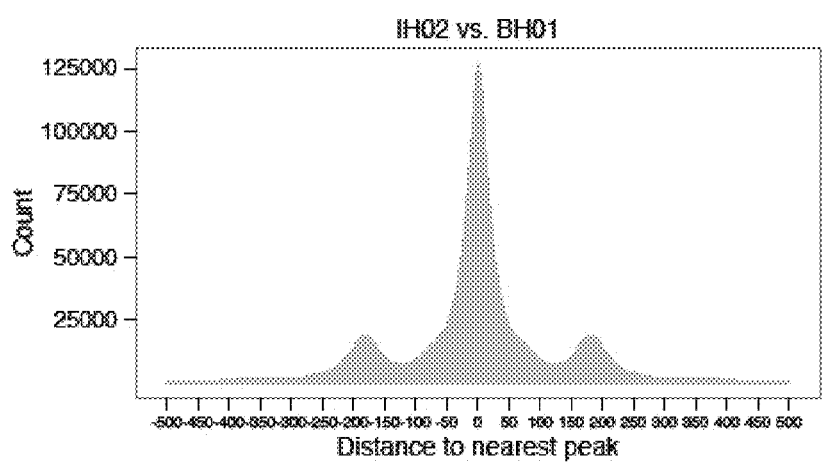
Figure 32C:
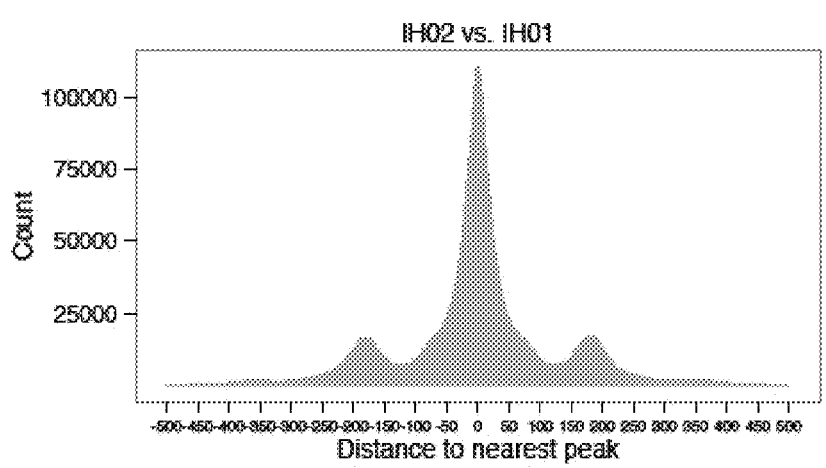

To determine whether the positions of peak calls were similar across samples, the genomic distance for each peak in a sample to the nearest peak in each of the other samples was calculated. High concordance was observed (FIG. 31; FIGS. 32A-C). The median (absolute) distance from a BH01 peak call to a nearest-neighbor IH01 peak call was 23 bp overall, but was less than 10 bp for the most highly scored peaks (FIGS. 33A-B).

Figure 34A:
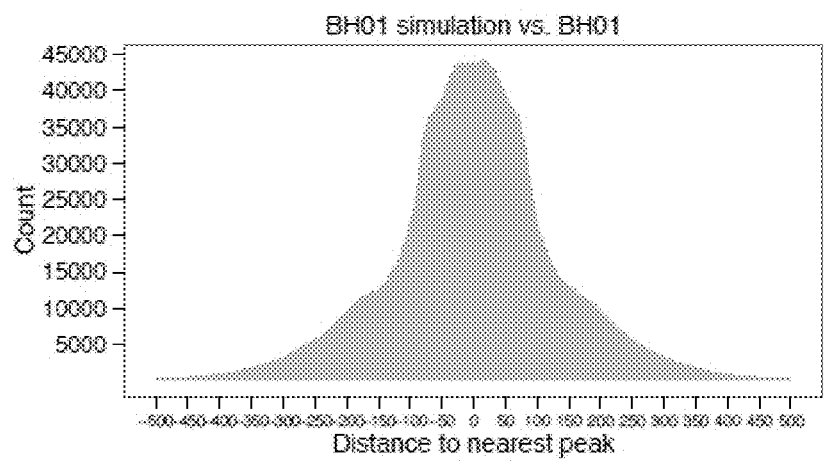
FIGS. 34A-C show a comparison of peak calls between samples and matched simulations.
Figure 34B:
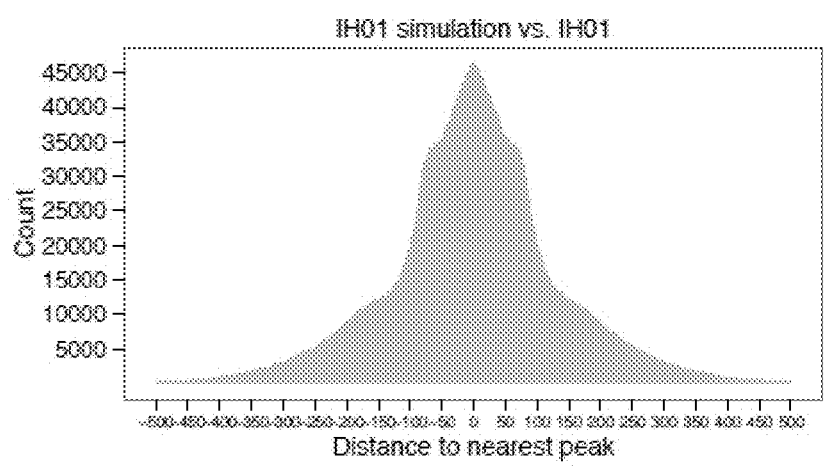
Figure 34C:
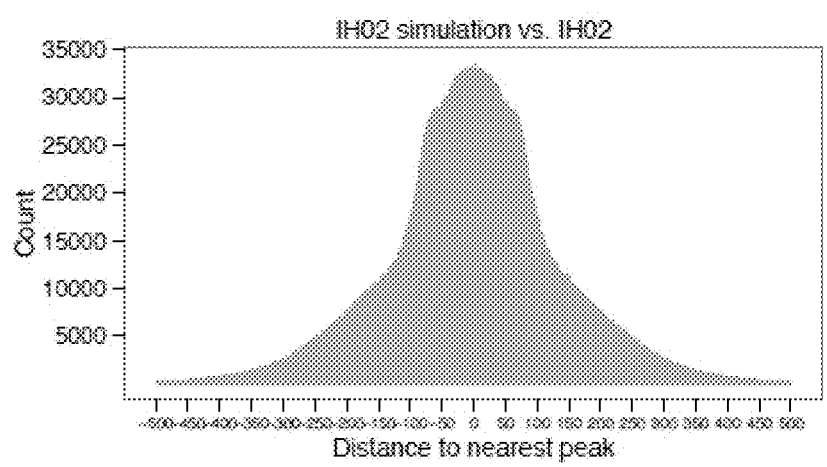

Because biases introduced either by nuclease specificity or during library preparation might artifactually contribute to the signal of nucleosome protection, fragment endpoints were also simulated, matching for the depth, size distribution and terminal dinucleotide frequencies of each sample. Genome-wide WPS were then calculated, and 10.3M, 10.2M, and 8.0M were called local maxima by the same heuristic, for simulated datasets matched to BH01, IH01 and IH02, respectively. Peaks from simulated datasets were associated with lower scores than peaks from real datasets (FIGS. 33A-B). Furthermore, the relatively reproducible locations of peaks called from real datasets (FIG. 31; FIGS. 32A-C) did not align well with the locations of peaks called from simulated datasets (FIG. 31; FIGS. 34A-C).

Figure 35:
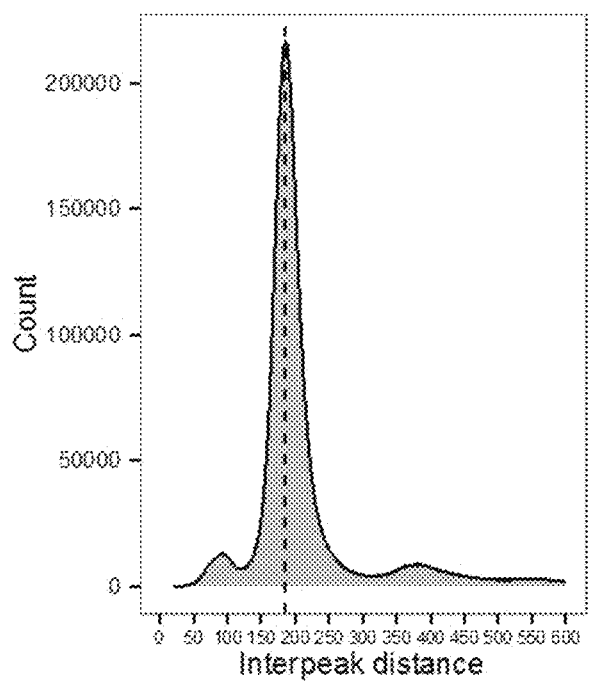
FIG. 35 shows distances between adjacent peaks, sample CH01. The dotted black line indicates the mode of the distribution (185 bp).

To improve the precision and completeness of the genome-wide nucleosome map, the cfDNA sequencing data from BH01, IH01, and IH02 were pooled and reanalyzed for a combined 231 fold-coverage ('CH01'; 3.8B fragments; Table 1). The WPS was calculated and 12.9M peaks were called for this combined sample. This set of peak calls was associated with higher scores and approached saturation in terms of the number of peaks (FIGS. 33A-B). Considering all peak-to-peak distances that were less than 500 bp (FIG. 35), the CH01 peak set spans 2.53 gigabases (Gb) of the human reference genome.

Figure 41:
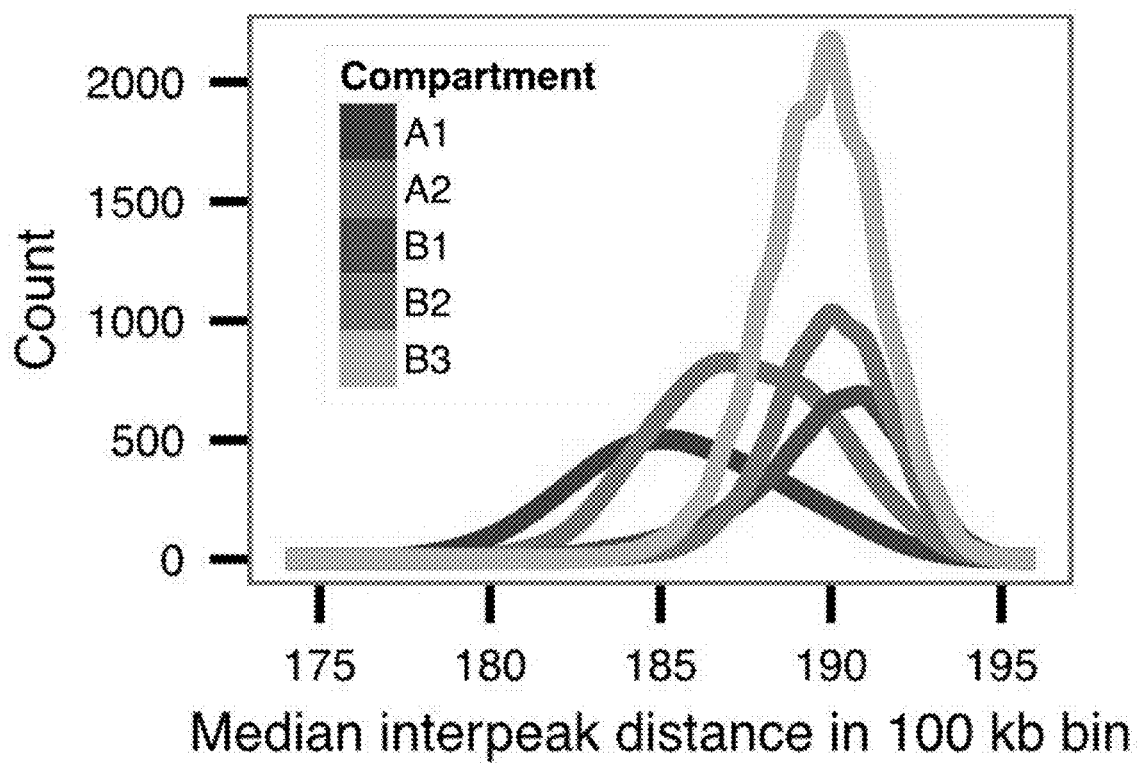
FIG. 41 shows nucleosome spacing in A/B compartments. Median nucleosome spacing in non-overlapping 100 kilobase (kb) bins, each containing ~500 nucleosome calls, is calculated genome-wide. A/B compartment predictions for GM12878, also with 100 kb resolution, are from published sources. Compartment A is associated with open chromatin and compartment B with closed chromatin.
Figure 42:
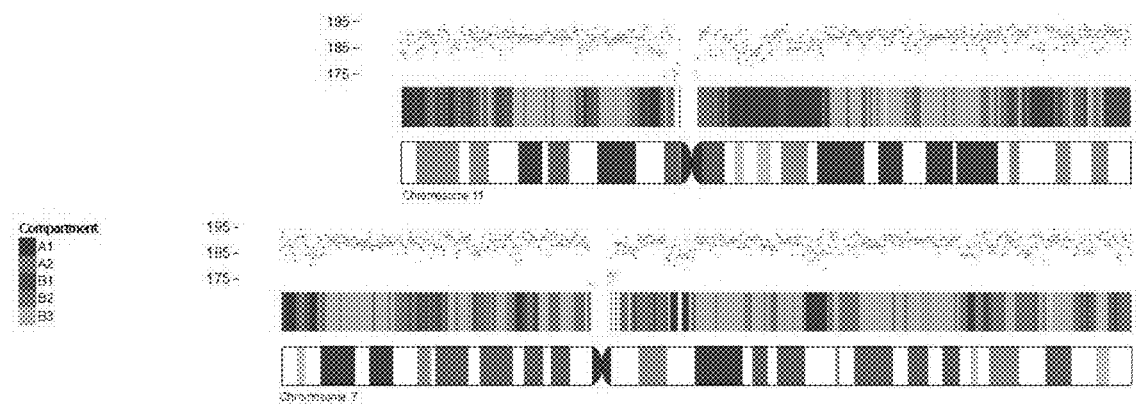
FIG. 42 shows nucleosome spacing and A/B compartments on chromosomes 7 and 11. A/B segmentation (red and blue bars) largely recapitulates chromosomal G-banding (ideograms, gray bars). Median nucleosome spacing (black dots) is calculated in 100 kb bins and plotted above the A/B segmentation.

Nucleosomes are known to be well-positioned in relation to landmarks of gene regulation, for example transcriptional start sites and exon-intron boundaries. Consistent with that understanding, similar positioning was observed in this data as well, in relation to landmarks of transcription, translation and splicing (FIGS. 36-40). Building on past observations of correlations between nucleosome spacing with transcriptional activity and chromatin marks, the median peak-to-peak spacing within 100 kilobase (kb) windows that had been assigned to compartment A (enriched for open chromatin) or compartment B (enriched for closed chromatin) on the basis of long-range interactions (in situ Hi-C) in a lymphoblastoid cell line was examined. Nucleosomes in compartment A exhibited tighter spacing than nucleosomes in compartment B (median 187 bp (A) vs. 190 bp (B)), with further differences between certain subcompartments (FIG. 41). Along the length of chromosomes, no general pattern was seen, except that median nucleosome spacing dropped sharply in pericentromeric regions, driven by strong positioning across arrays of alpha satellites (171 bp monomer length; FIG. 42; FIG. 26).

Short cfDNA Fragments Directly Footprint CTCF and Other Transcription Factors

Previous studies of DNase I cleavage patterns identified two dominant classes of fragments: longer fragments associated with cleavage between nucleosomes, and shorter fragments associated with cleavage adjacent to transcription factor binding sites (TFBS). To assess whether in vivo-derived cfDNA fragments also resulted from two classes of sensitivity to nuclease cleavage, sequence reads (CH01) were partitioned on the basis of inferred fragment length, and the WPS was recalculated using long fragments (120-180 bp; 120 bp window; effectively the same as the WPS described above for nucleosome calling) or short fragments (35-80 bp; 16 bp window) separately (FIGS. 26-27). To obtain a set of well-defined TFBSs enriched for actively bound sites in our data, clustered FIMO predictions were intersected with a unified set of ChIP-seq peaks from ENCODE (TfbsClusteredV3) for each TF.

Figure 43:
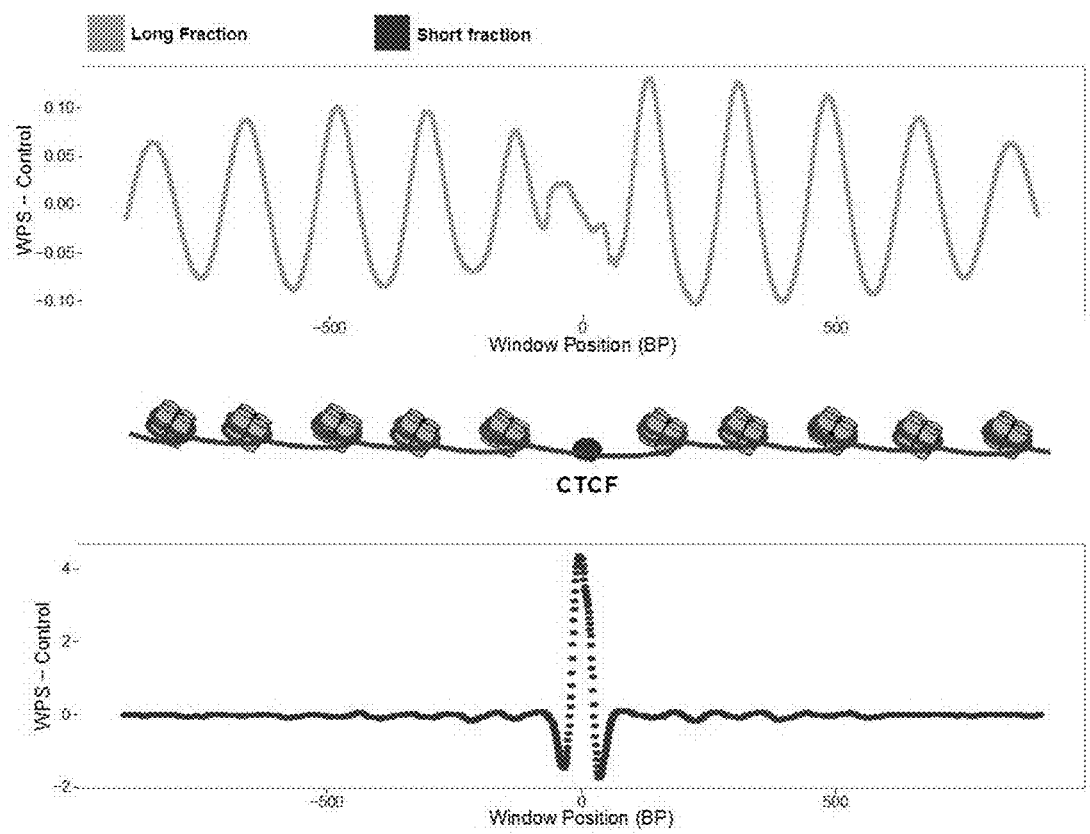
FIG. 43 shows aggregate, adjusted WPS for 93,550 CTCF sites for the long (top) and short (bottom) fractions.
Figure 44:
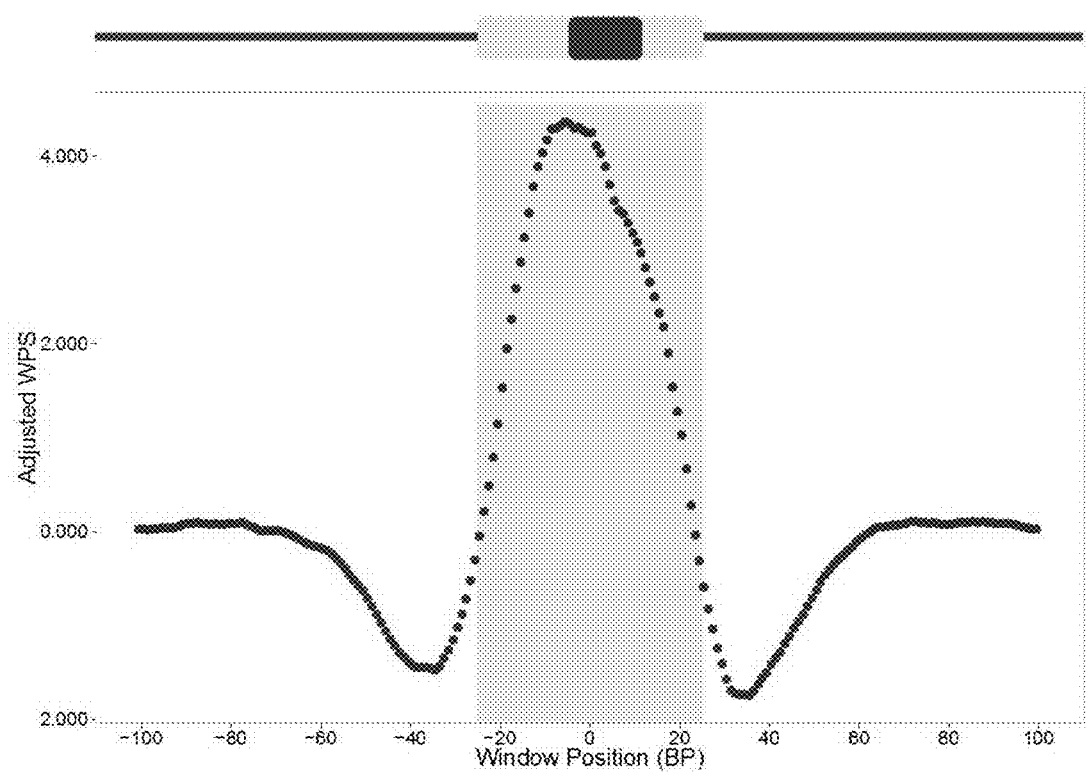
FIG. 44 shows a zoomed-in view of the aggregate, adjusted WPS for short fraction cfDNA at CTCF sites. The light red bar (and corresponding shading within the plot) indicate the position of the known 52 bp CTCF binding motif. The dark red subsection of this bar indicates the location of the 17 bp motif used for the FIMO motif search.
Figure 45:
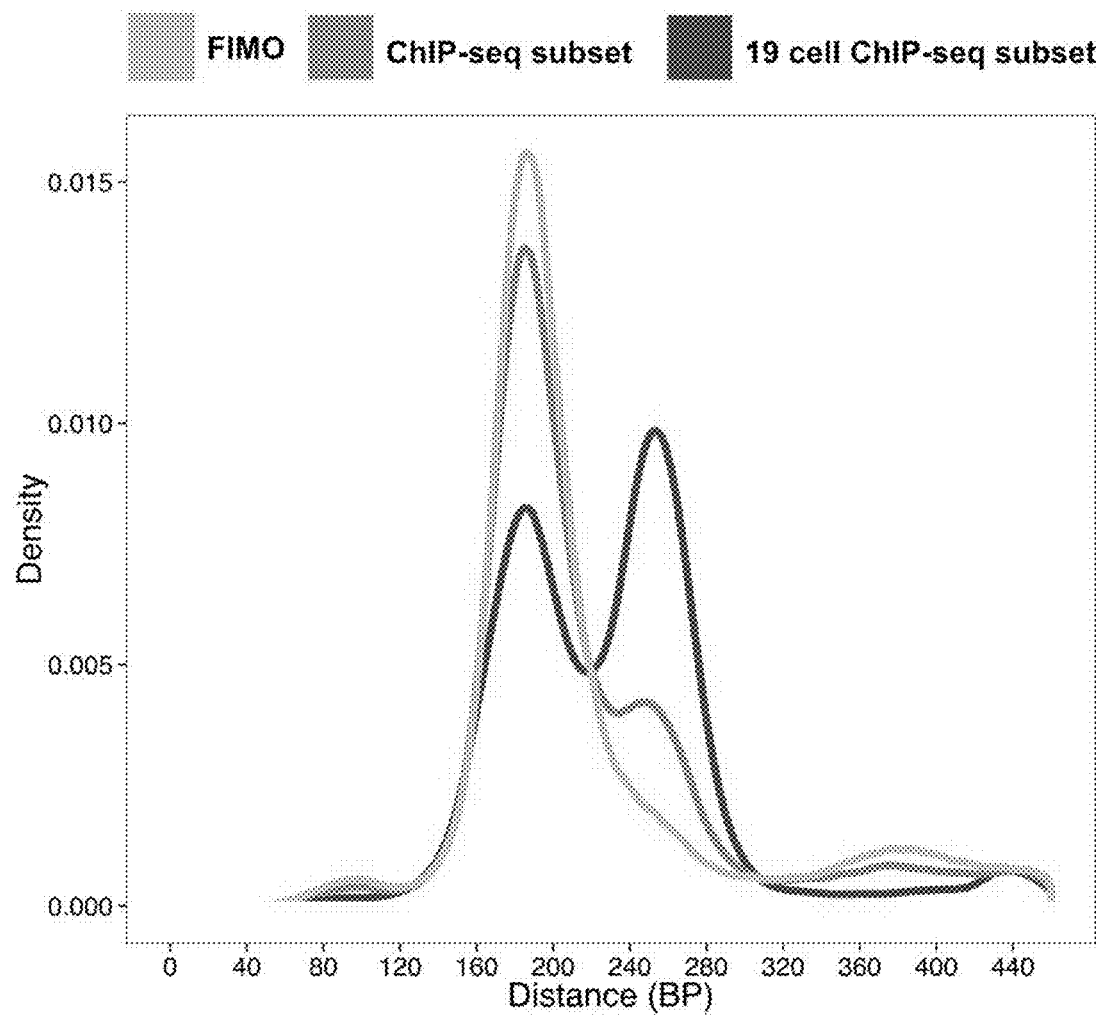
FIG. 45 shows −1 to +1 nucleosome spacing calculated around CTCF sites derived from clustered FIMO predicted CTCF sites (purely motif-based: 518,632 sites), a subset of these predictions overlapping with ENCODE ChIP-seq peaks (93,530 sites), and a further subset that have been experimentally observed to be active across 19 cell lines (23,723 sites). The least stringent set of CTCF sites are predominantly separated by distances that are approximately the same as the genome-wide average (~190 bp). However, at the highest stringency, most CTCF sites are separated by a much wider distance (~260 bp), consistent with active CTCF binding and repositioning of adjacent nucleosomes.
Figure 46:
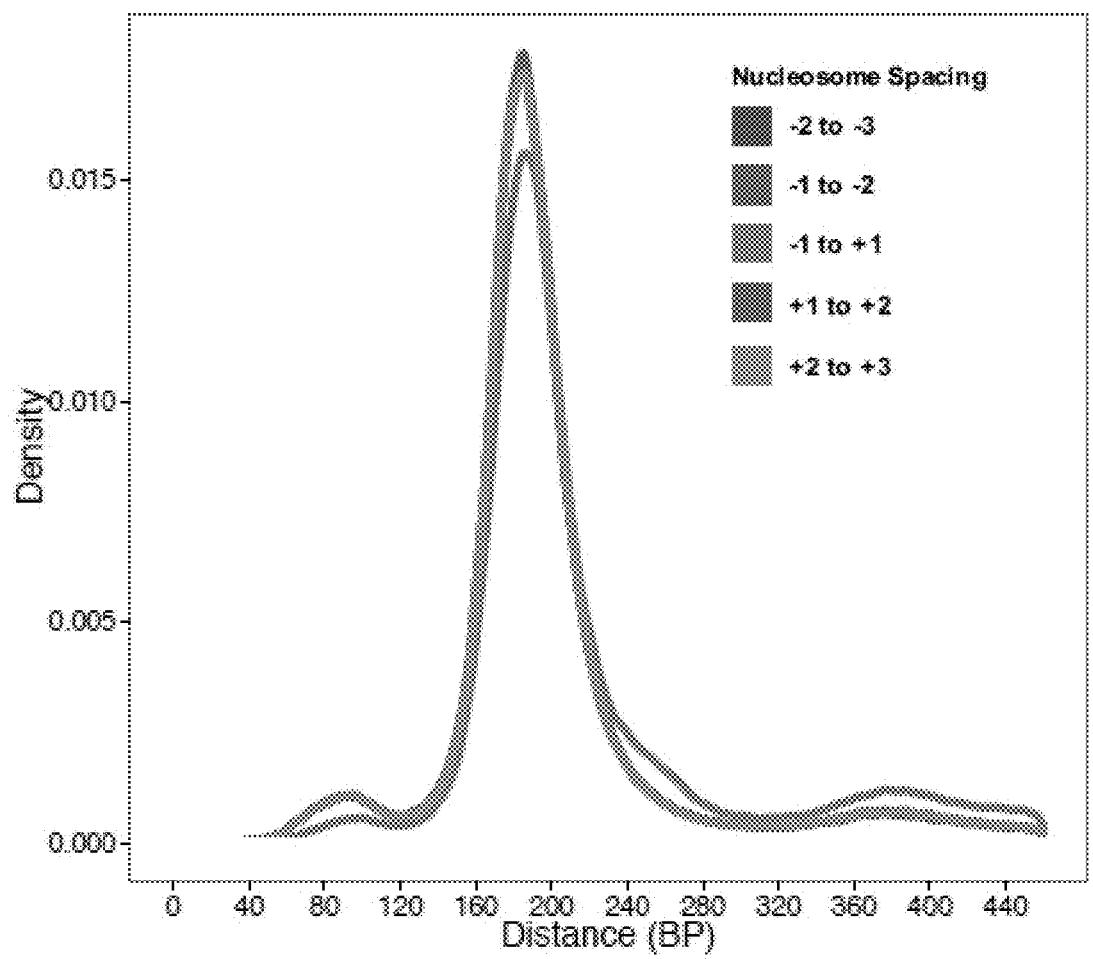
FIGS. 46-48 show CTCF occupancy repositions flanking nucleosomes.
Figure 47:
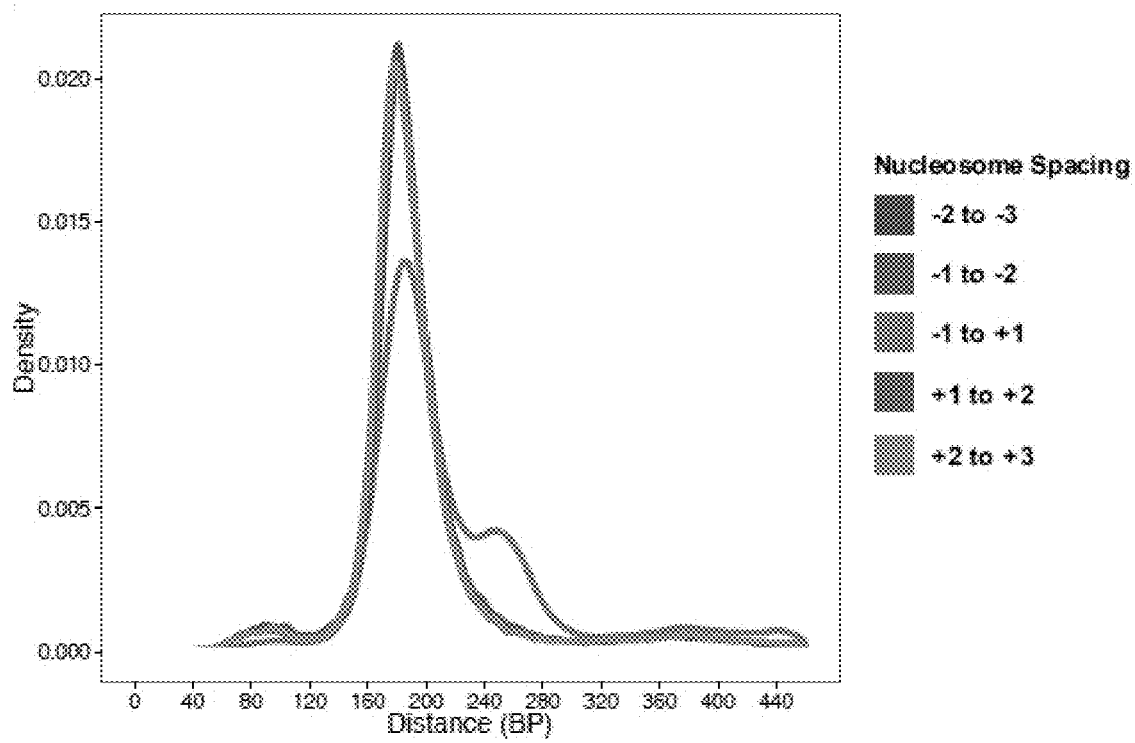
Figure 48:
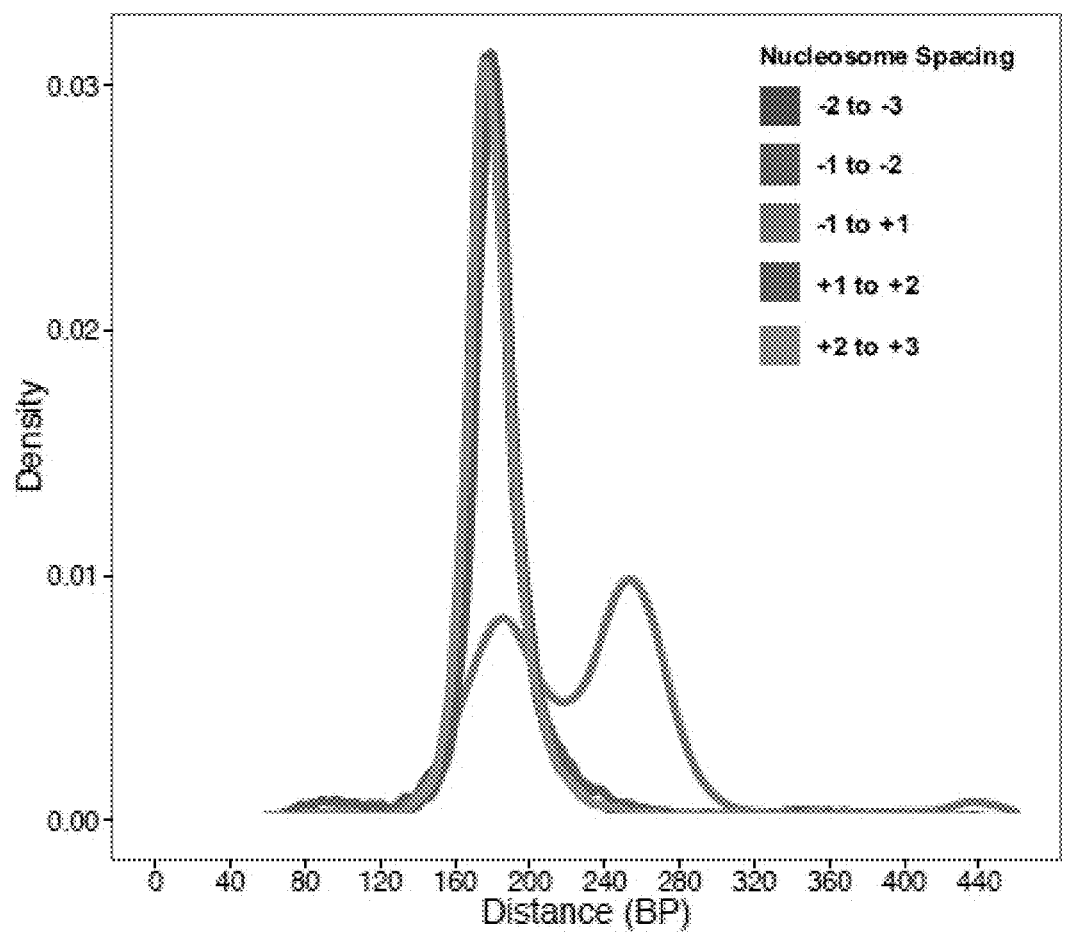
Figure 49:
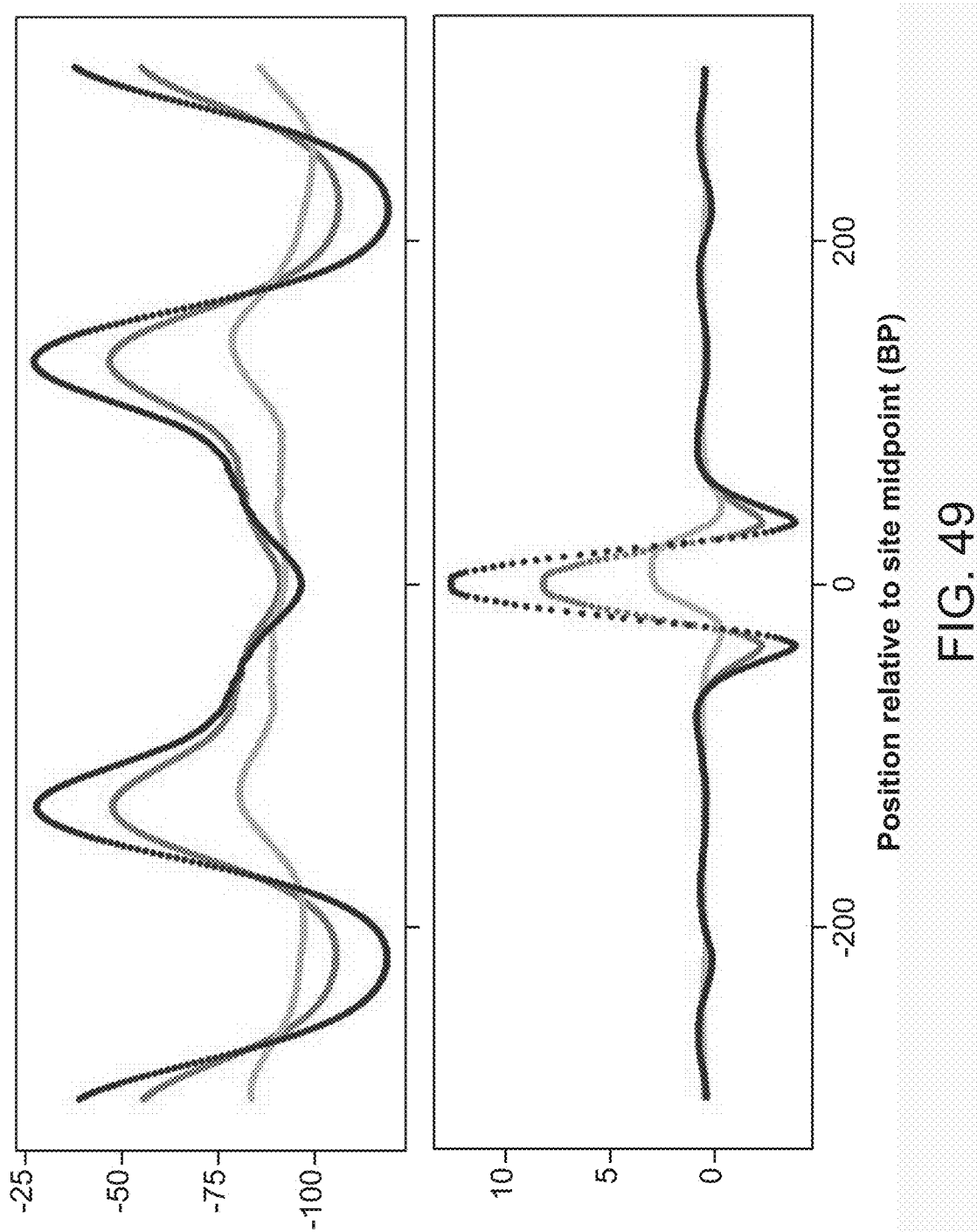
FIG. 49 shows, for the subset of putative CTCF sites with flanking nucleosomes spaced widely (230-270 bp), that both the long (top) and short (bottom) fractions exhibit a stronger signal of positioning with increasingly stringent subsets of CTCF sites. See FIG. 45 for key defining colored lines.
Figure 50:
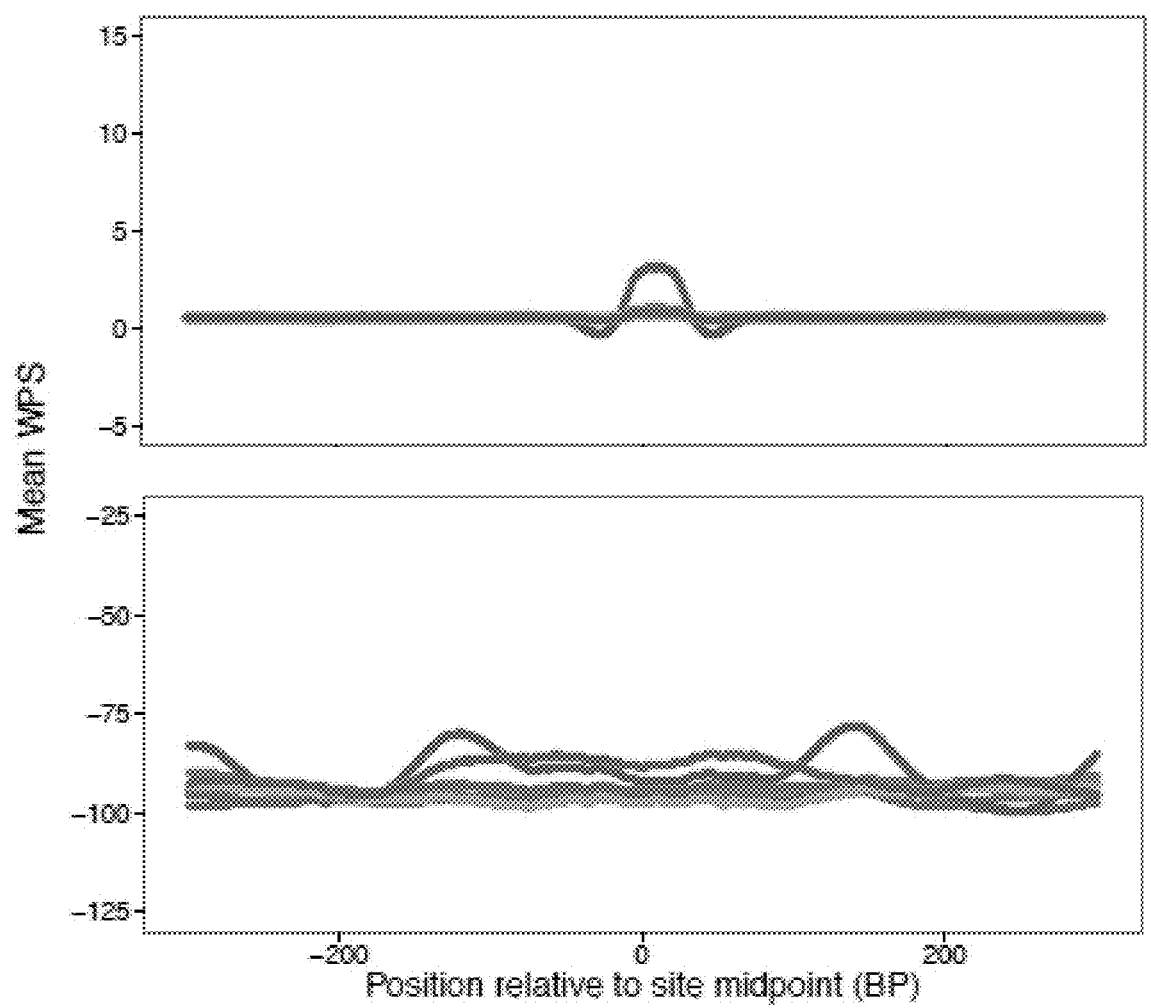
FIGS. 50-52 show CTCF occupancy repositions flanking nucleosomes.
Figure 51:
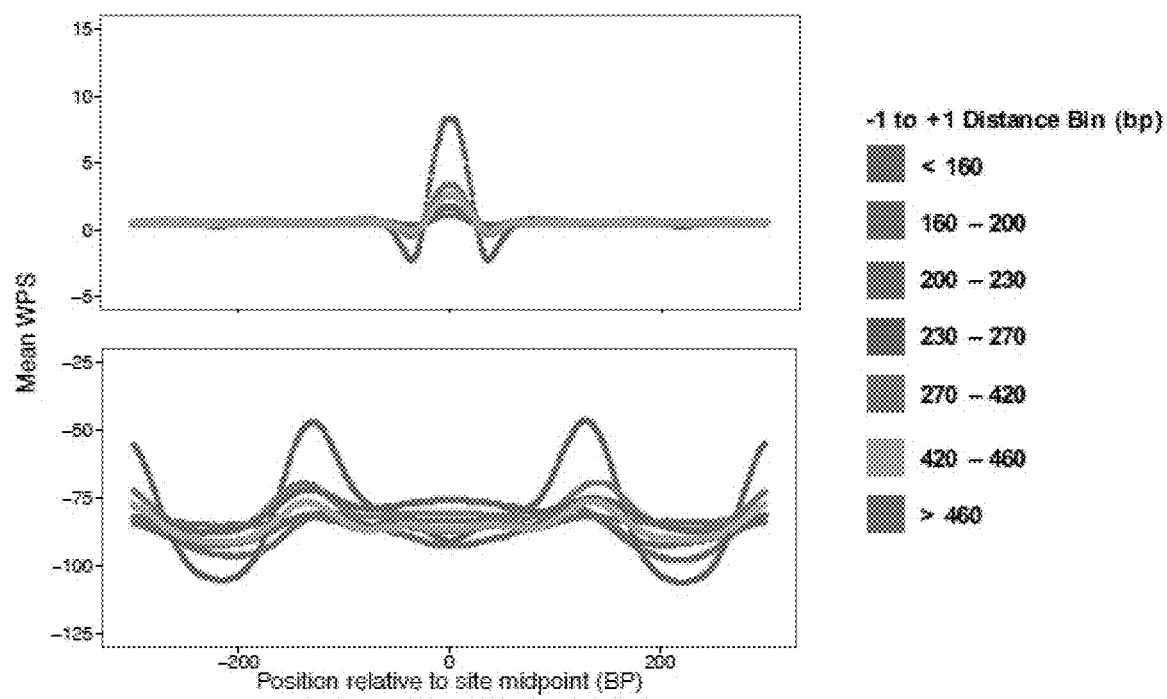
Figure 52:
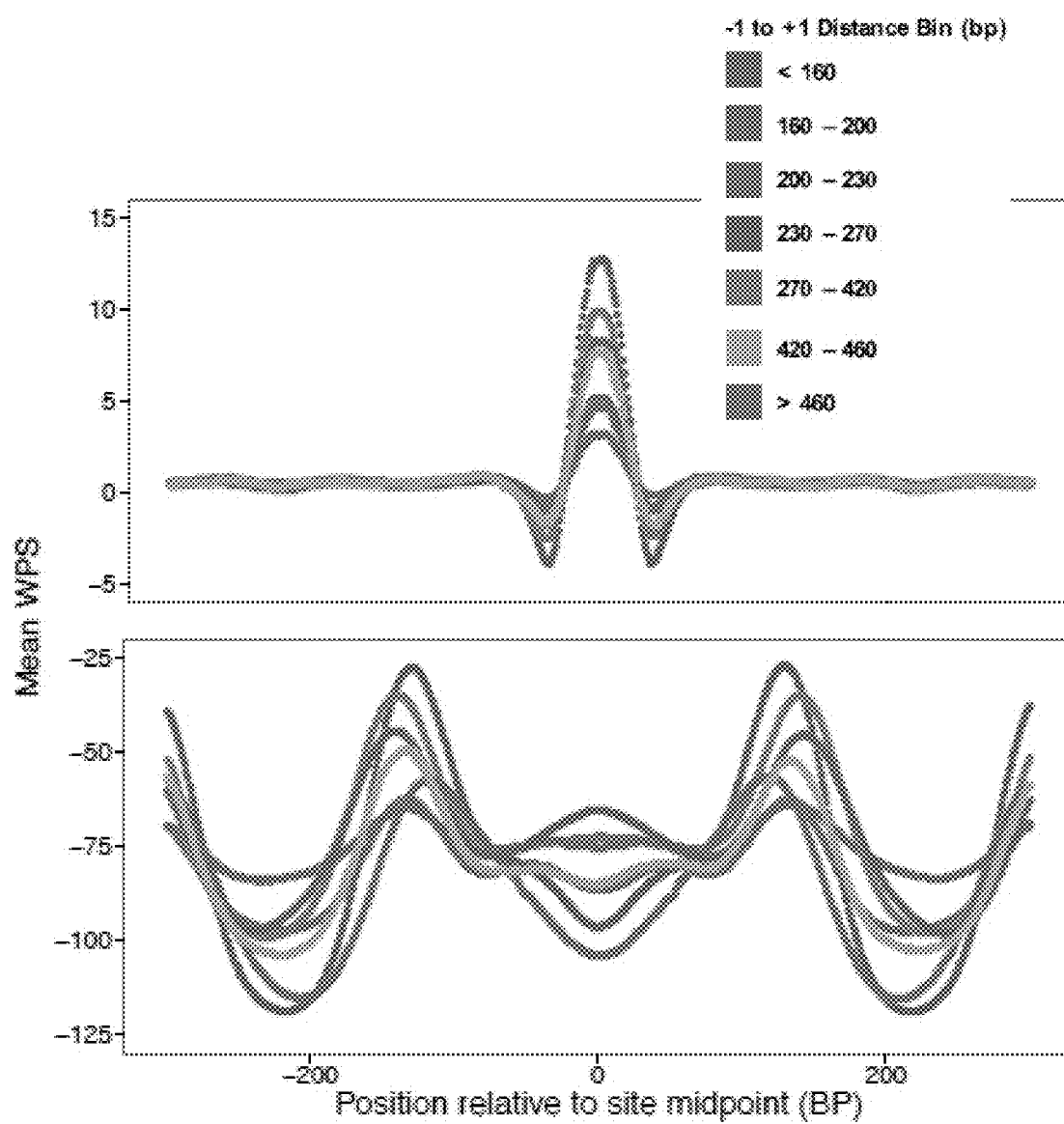
Figure 53A:
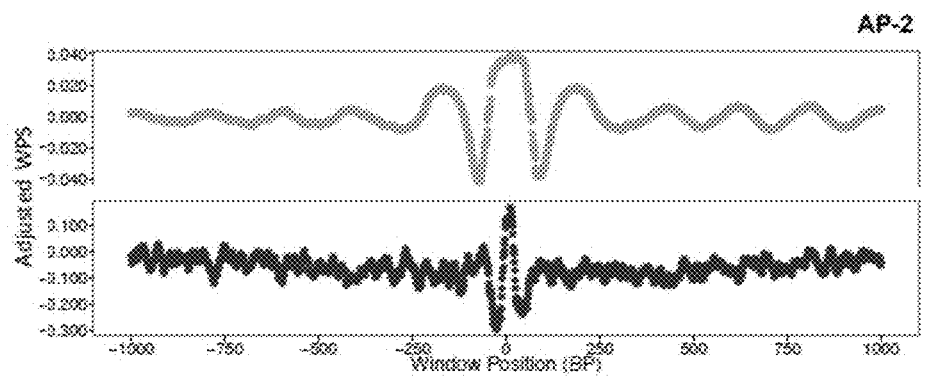
FIGS. 53A-H show footprints of transcription factor binding sites from short and long cfDNA fragments. Clustered FIMO binding sites predictions were intersected with ENCODE ChIP-seq data to obtain a confident set of transcription factor (TF) binding sites for a set of additional factors. Aggregate, adjusted WPS for regions flanking the resulting sets of TF binding sites is displayed for both the long and short fractions of cfDNA fragments. Higher WPS values indicate higher likelihood of nucleosome or TF occupancy, respectively.
Figure 53B:
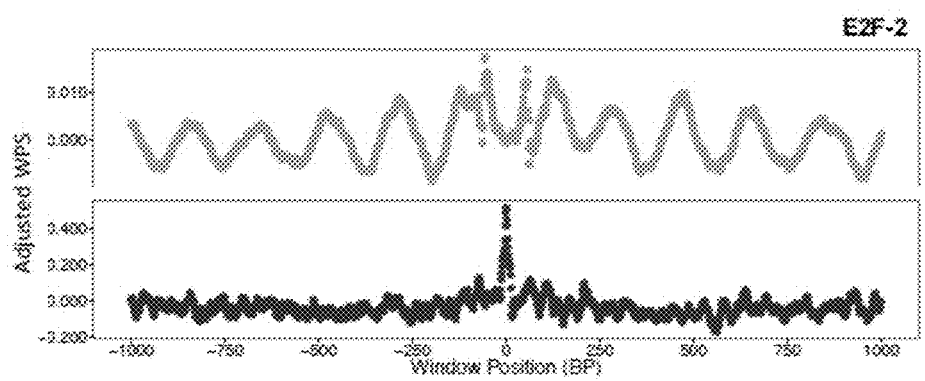
Figure 53C:
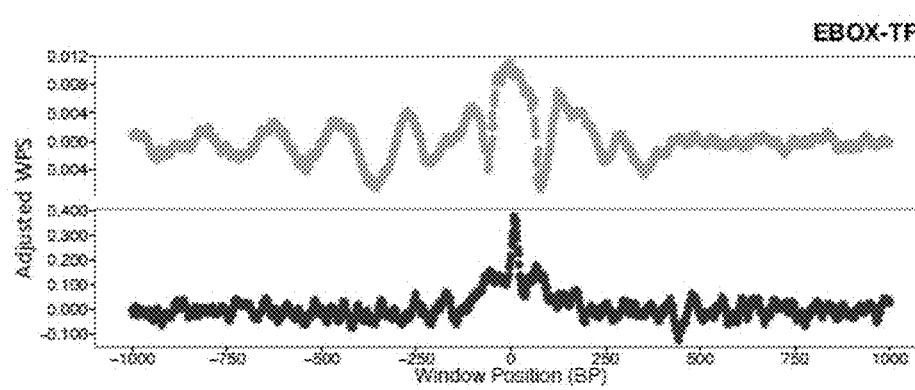
Figure 53D:
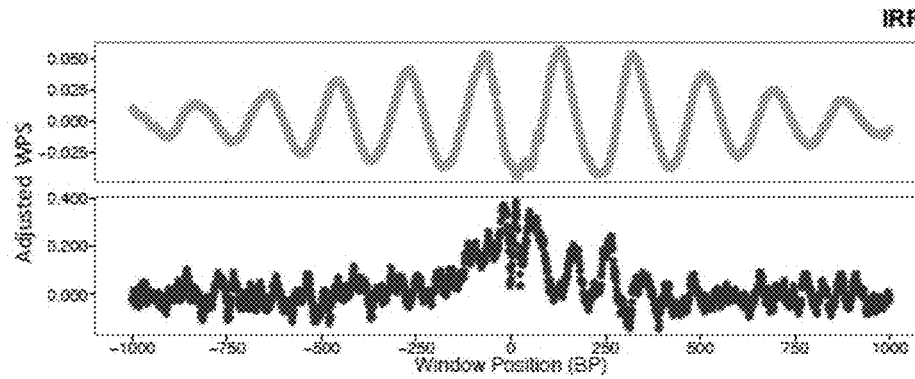
Figure 53E:
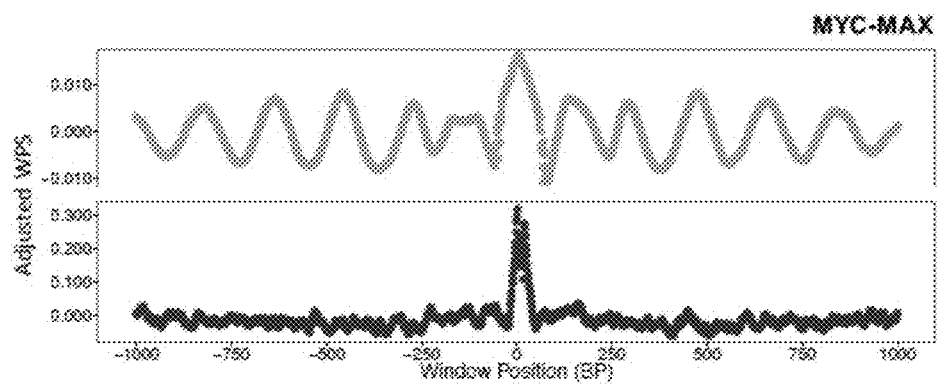
Figure 53F:
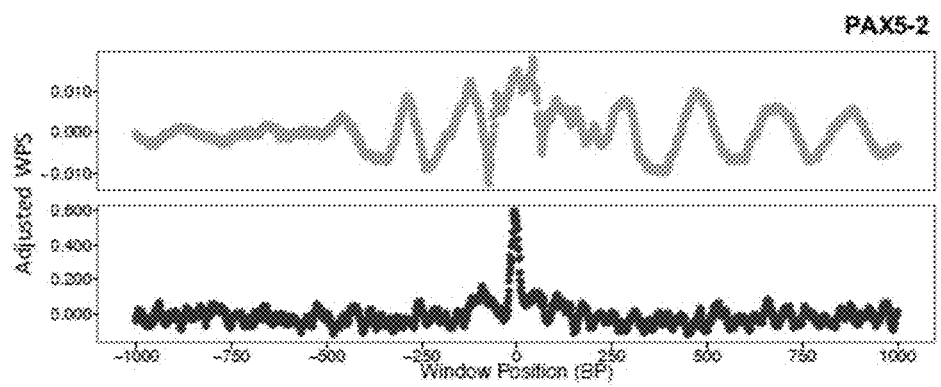
Figure 53G:
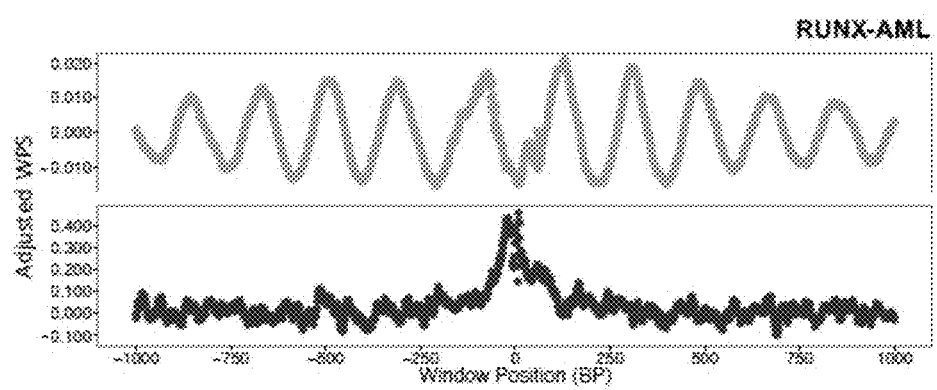
Figure 53H:
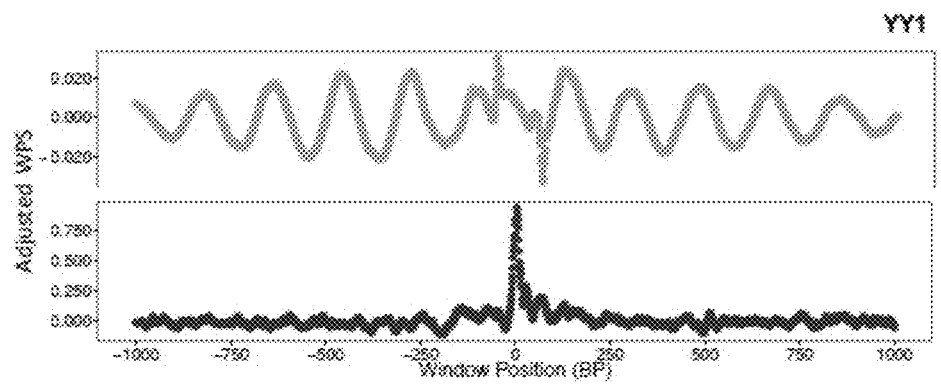

The long fraction WPS supports strong organization of nucleosomes in the vicinity of CTCF binding sites (FIG. 43). However, a strong signal in the short fraction WPS is also observed that is coincident with the CTCF binding site itself (FIGS. 44-45). CTCF binding sites were stratified based on a presumption that they are bound in vivo (all FIMO predictions vs. the subset intersecting with ENCODE ChIP-seq vs. the further subset intersecting with those that appear to be utilized across 19 cell lines). Experimentally well-supported CTCF sites exhibit a substantially broader spacing between the flanking −1 and +1 nucleosomes based on the long fraction WPS, consistent with their repositioning upon CTCF binding (~190 bp →~260 bp; FIGS. 45-48). Furthermore, experimentally well-supported CTCF sites exhibit a much stronger signal for the short fraction WPS over the CTCF binding site itself (FIGS. 49-52).

Figure 54:
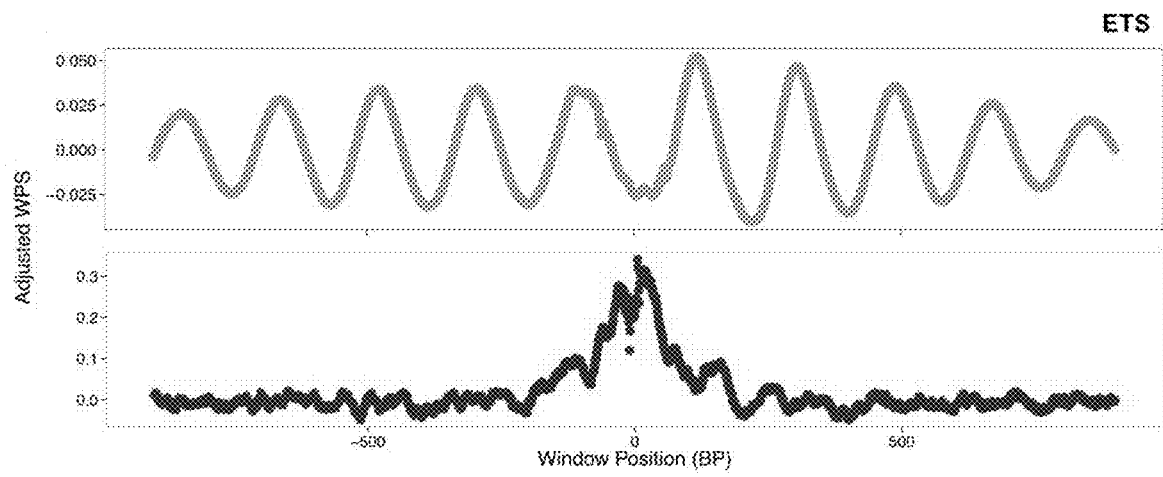
FIG. 54 shows aggregate, adjusted WPS for transcription factor ETS (210,798 sites). WPS calculated from both long (top) and short (bottom) cfDNA fractions are shown. Signal consistent with TF protection at the binding site itself (short fraction) with organization of the surrounding nucleosomes (long fraction) is observed. Similar analyses for additional TFs are shown in FIGS. 53A-H.
Figure 55:
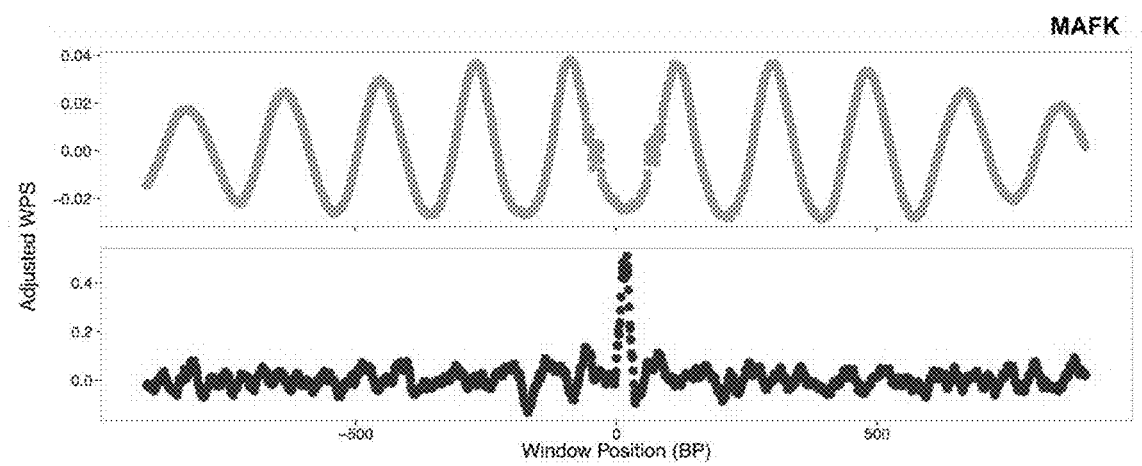
FIG. 55 shows aggregate, adjusted WPS for transcription factor MAFK (32,159 sites). WPS calculated from both long (top) and short (bottom) cfDNA fractions are shown. Signal consistent with TF protection at the binding site itself (short fraction) with organization of the surrounding nucleosomes (long fraction) is observed. Similar analyses for additional TFs are shown in FIGS. 53A-H.

Similar analyses were performed for additional TFs for which both FIMO predictions and ENCODE CHiP-seq data were available (FIGS. 53A-H). For many of these TFs, such as ETS and MAFK (FIGS. 54-55), a short fraction footprint was observed, accompanied by periodic signal in the long fraction WPS. This is consistent with strong positioning of nucleosomes surrounding bound TFBS. Overall, these data support the view that short cfDNA fragments, which are recovered markedly better by the single-stranded protocol (FIG. 18, FIG. 21), directly footprint the in vivo occupancy of DNA-bound transcription factors, including CTCF and others.

Nucleosome Spacing Patterns Inform cfDNA Tissues-of-Origin

Figure 56:
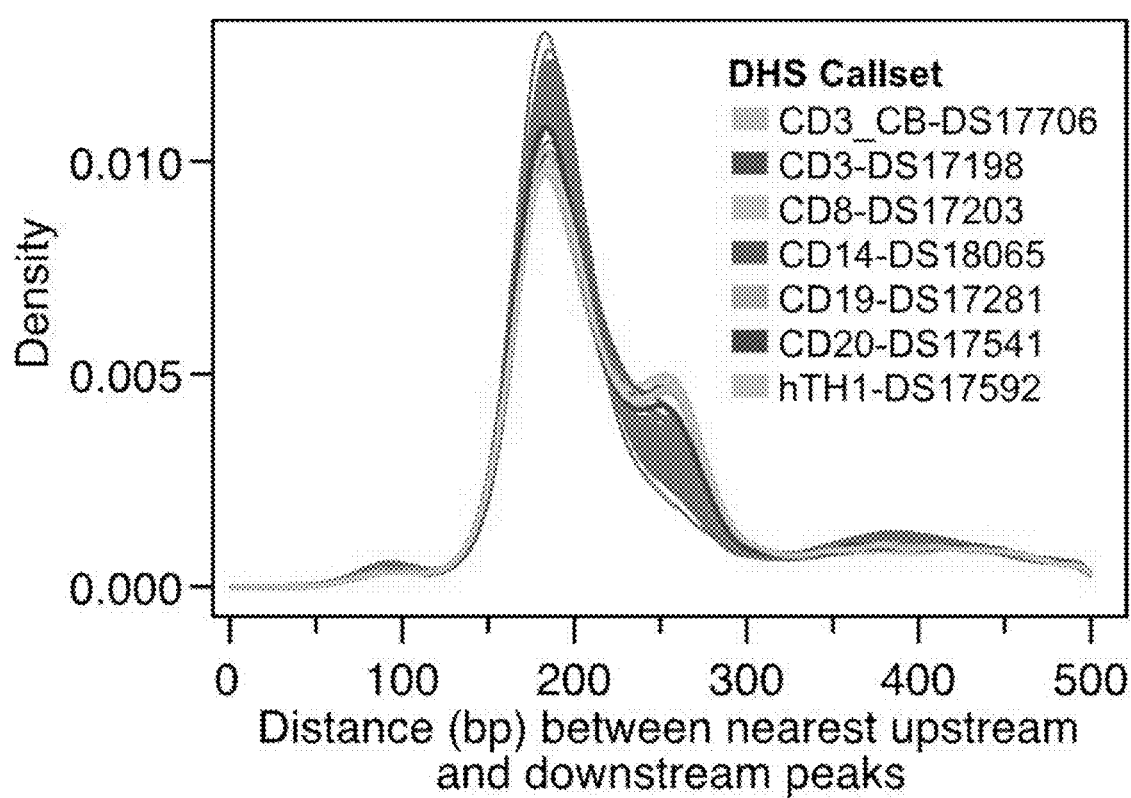
FIG. 56 shows the inference of mixtures of cell-types contributing to cell-free DNA based on DNase hypersensitivity (DHS) sites. The frequency distribution of peak-to-peak spacing of nucleosome calls at DHS sites from 116 diverse biological samples shows a bimodal distribution, with the second mode plausibly corresponding to widened nucleosome spacing at active DHS sites due to intervening transcription factor binding (~190 bp→260 bp). DHS sites identified in lymphoid or myeloid samples have the largest proportions of DHS sites with widened nucleosome spacing, consistent with hematopoietic cell death as the dominant source of cfDNA in healthy individuals.

To determine whether in vivo nucleosome protection, as measured through cfDNA sequencing, could be used to infer the cell types contributing to cfDNA in healthy individuals, the peak-to-peak spacing of nucleosome calls within DHS sites defined in 116 diverse biological samples was examined. Widened spacing was previously observed between the −1 and +1 nucleosomes at regulatory elements (e.g., anecdotally at DHS sites (FIG. 27) or globally at bound CTCF sites (FIG. 45)). Similar to bound CTCF sites, substantially broader spacing was observed for nucleosome pairs within a subset of DHS sites, plausibly corresponding to sites at which the nucleosomes are repositioned by intervening transcription factor binding in the cell type(s) giving rise to cfDNA (~190 bp →~260 bp; FIG. 56). Indeed, the proportion of widened nucleosome spacing (~260 bp) varies considerably depending on which cell type's DHS sites are used. However, all of the cell types for which this proportion is highest are lymphoid or myeloid in origin (e.g., CD3_CB-DS17706, etc. in FIG. 56). This is consistent with hematopoietic cell death as the dominant source of cfDNA in healthy individuals.

Figure 36:
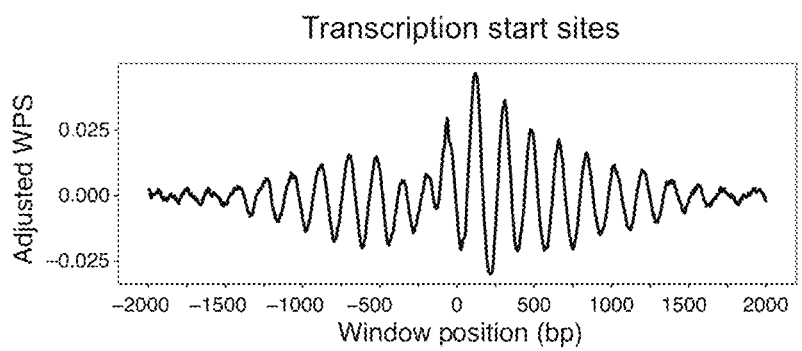
FIG. 36 shows aggregate, adjusted windowed protection scores (WPS; 120 bp window) around 22,626 transcription start sites (TSS). TSS are aligned at the 0 position after adjusting for strand and direction of transcription. Aggregate WPS is tabulated for both real data and simulated data by summing per-TSS WPS at each position relative to the centered TSS. The values plotted represent the difference between the real and simulated aggregate WPS, further adjusted to local background as described in greater detail below. Higher WPS values indicate preferential protection from cleavage.
Figure 37:
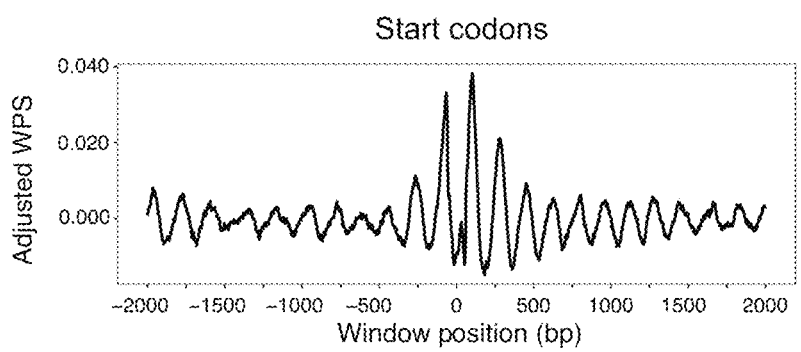
FIG. 37 shows aggregate, adjusted WPS around 22,626 start codons.
Figure 38:
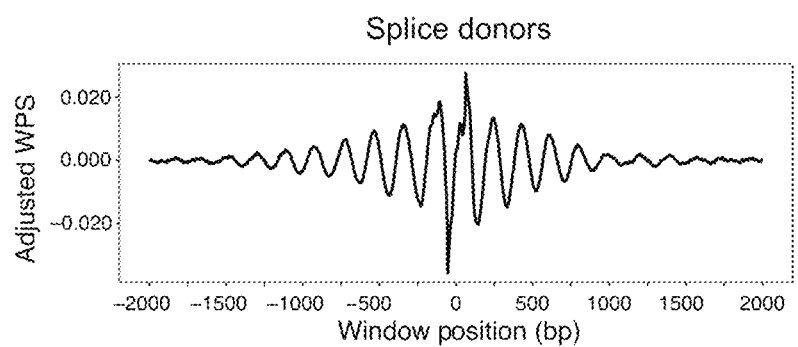
FIG. 38 shows aggregate, adjusted WPS around 224,910 splice donor sites.
Figure 39:
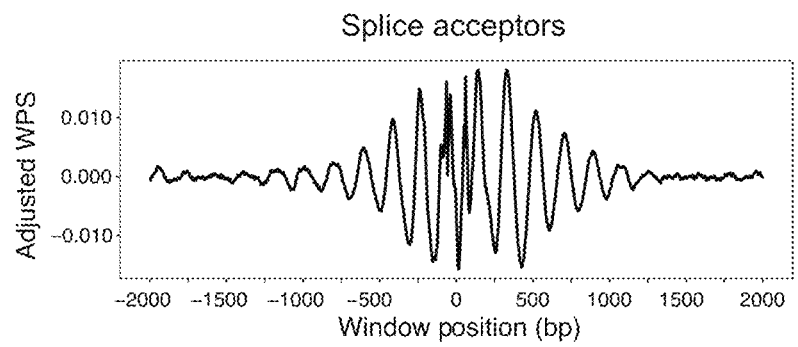
FIG. 39 shows aggregate, adjusted WPS around 224,910 splice acceptor sites.
Figure 40:
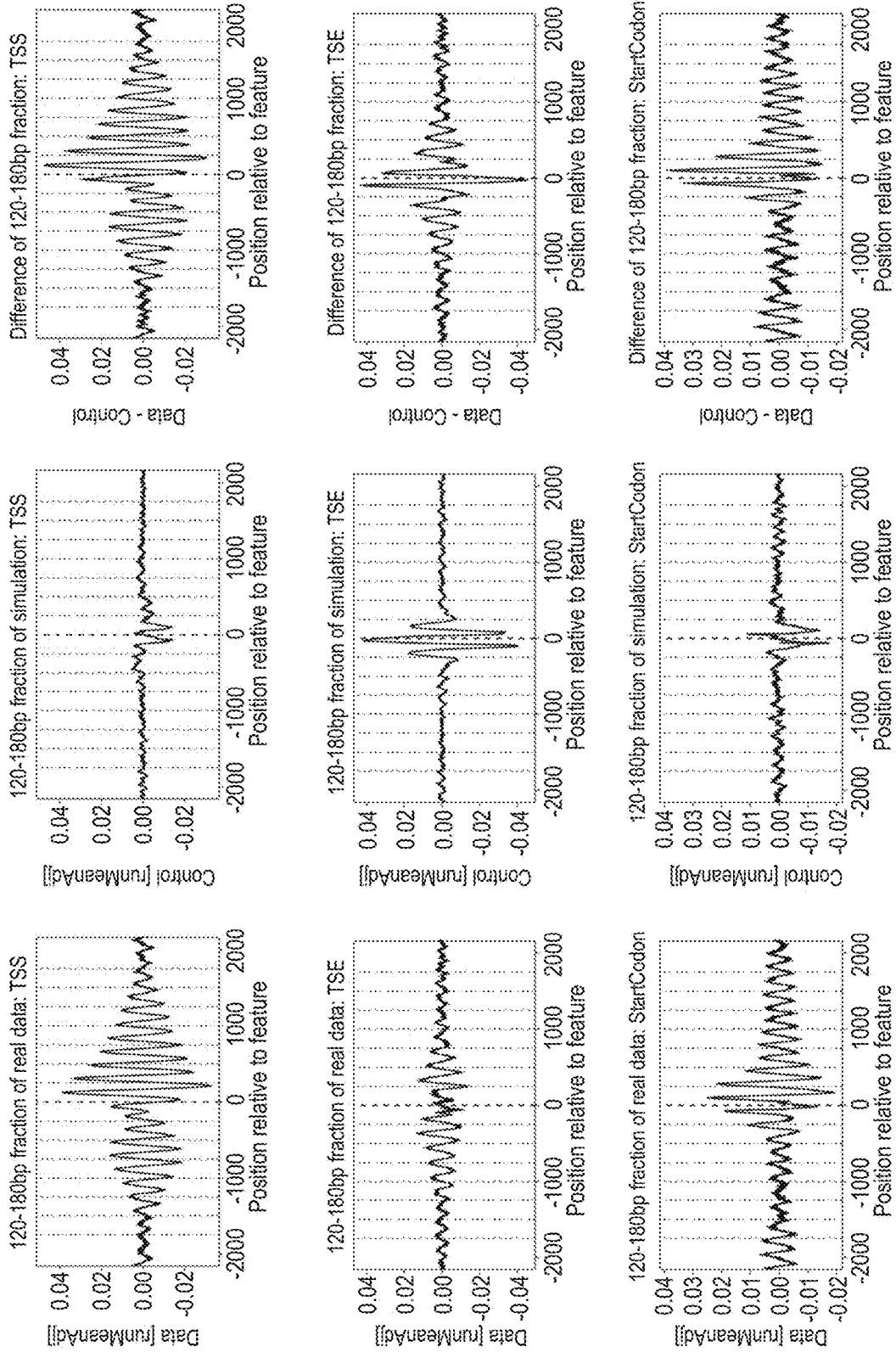
FIG. 40 shows aggregate, adjusted WPS around various genic features with data from CH01, including for real data, matched simulation, and their difference.
Figure 40:
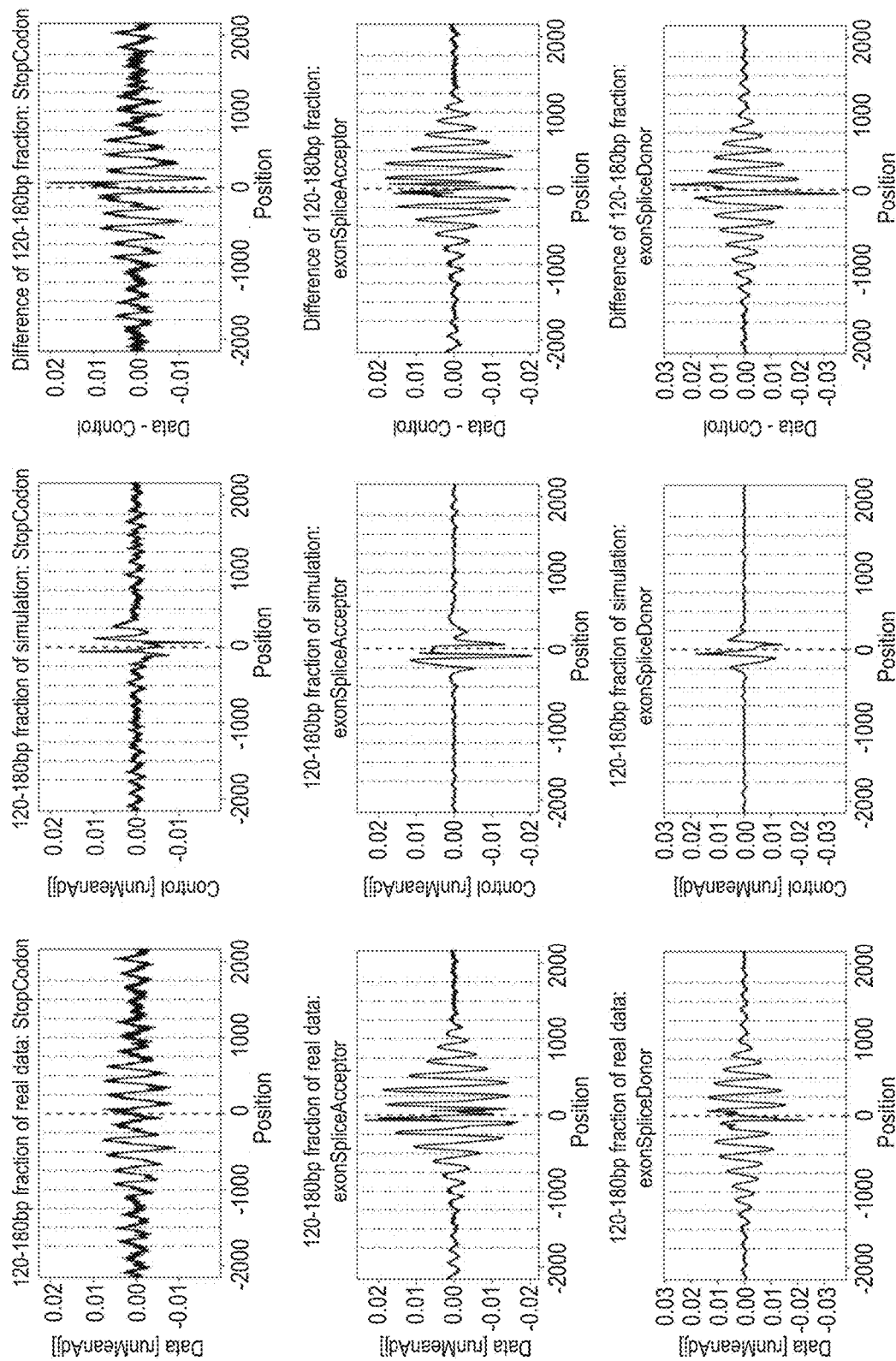
Figure 57:
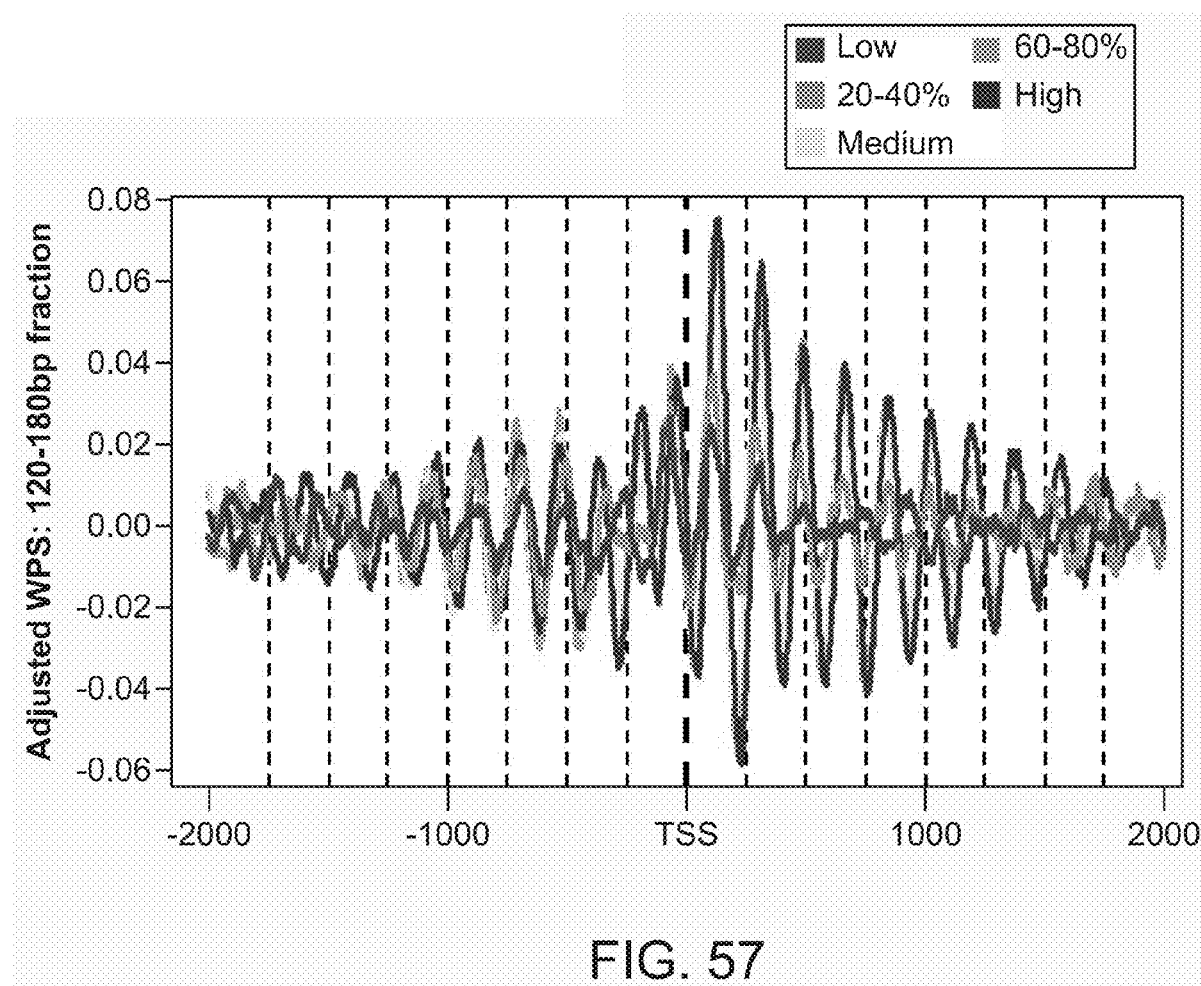
FIG. 57 shows how partitioning of adjusted WPS scores around transcriptional start sites (TSS) into five gene expression bins (quintiles) defined for NB-4 (an acute promyelocytic leukemia cell line) reveals differences in the spacing and placement of nucleosomes. Highly expressed genes show a strong phasing of nucleosomes within the transcript body. Upstream of the TSS, -1 nucleosomes are well-positioned across expression bins, but -2 and -3 nucleosomes are only well-positioned for medium to highly expressed genes.
Figure 58:
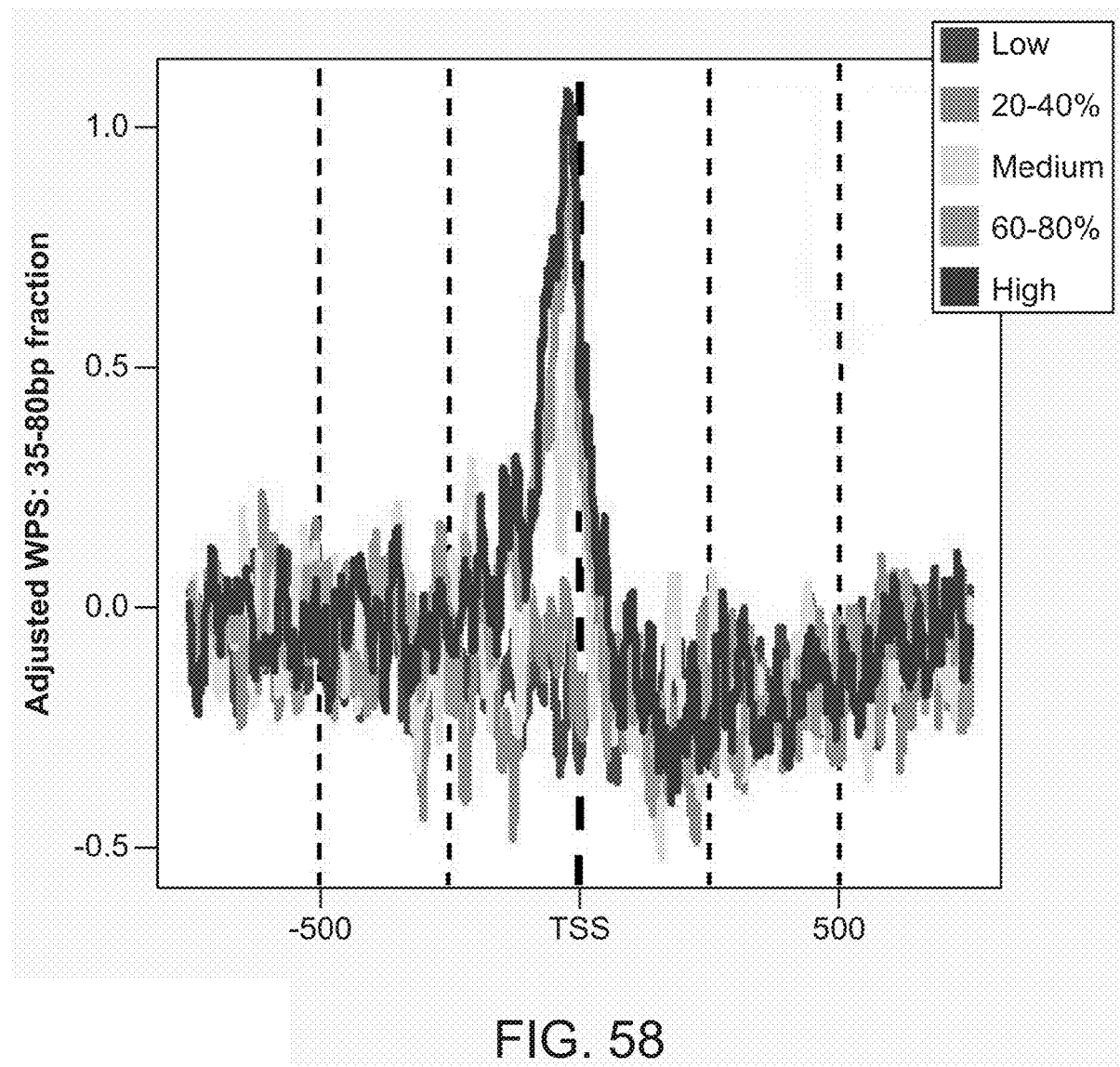
FIG. 58 shows that, for medium to highly expressed genes, a short fragment peak is observed between the TSS and the -1 nucleosome, consistent with footprinting of the transcription preinitiation complex, or some component thereof, at transcriptionally active genes.

Next the signal of nucleosome protection in the vicinity of transcriptional start sites was re-examined (FIG. 36). When the signal was stratified based on gene expression in a lymphoid lineage cell line, NB-4, strong differences in the locations or intensity of nucleosome protection in relation to the TSS were observed, in highly vs. lowly expressed genes (FIG. 57). Furthermore, the short fraction WPS exhibits a clear footprint immediately upstream of the TSS whose intensity also strongly correlates with expression level (FIG. 58). This plausibly reflects footprinting of the transcription preinitiation complex, or some component thereof, at transcriptionally active genes.

These data demonstrate that cfDNA fragmentation patterns do indeed contain signal that might be used to infer the tissue(s) or cell-type(s) giving rise to cfDNA.

However, a challenge is that relatively few reads in a genome-wide cfDNA library directly overlap DHS sites and transcriptional start sites.

Figure 59:
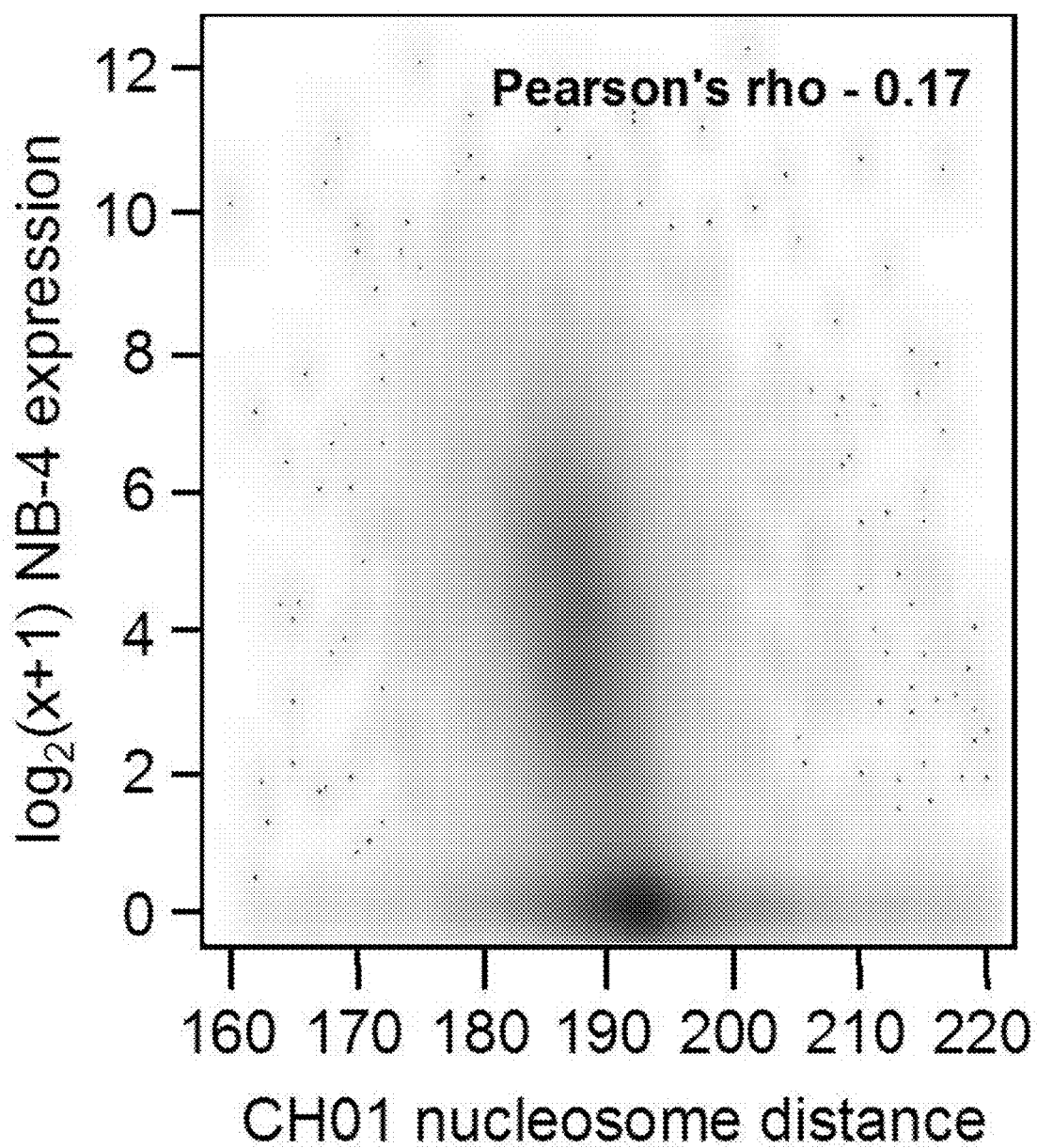
FIG. 59 shows that median nucleosome distance in the transcript body is negatively correlated with gene expression as measured for the NB-4 cell line ($\rho=-0.17$, n=19,677 genes). Genes with little-to-no expression show a median nucleosome distance of 193 bp, while for expressed genes, this ranges between 186-193 bp. This negative correlation is stronger when more nucleosome calls are used to determine a more precise median distance (e.g. requiring at least 60 nucleosomes, $\rho=-0.50$; n=12,344 genes).

Nucleosome spacing varies between cell types, and as a function of chromatin state and gene expression. In general, open chromatin and transcription are associated with a shorter nucleosome repeat length, consistent with this Example's analyses of compartment A vs. B (FIG. 41). This Example's peak call data also exhibits a correlation between nucleosome spacing across gene bodies and their expression levels, with tighter spacing associated with higher expression (FIG. 59; $\rho=-0.17$; n=19,677 genes). The correlation is highest for the gene body itself, relative to adjacent regions (upstream 10 kb $\rho=-0.08$; downstream 10 kb $\rho=-0.01$). If the analysis is limited to gene bodies that span at least 60 nucleosome calls, tighter nucleosome spacing is even more strongly correlated with gene expression ($\rho=-0.50$; n=12, 344 genes).

Figure 60:
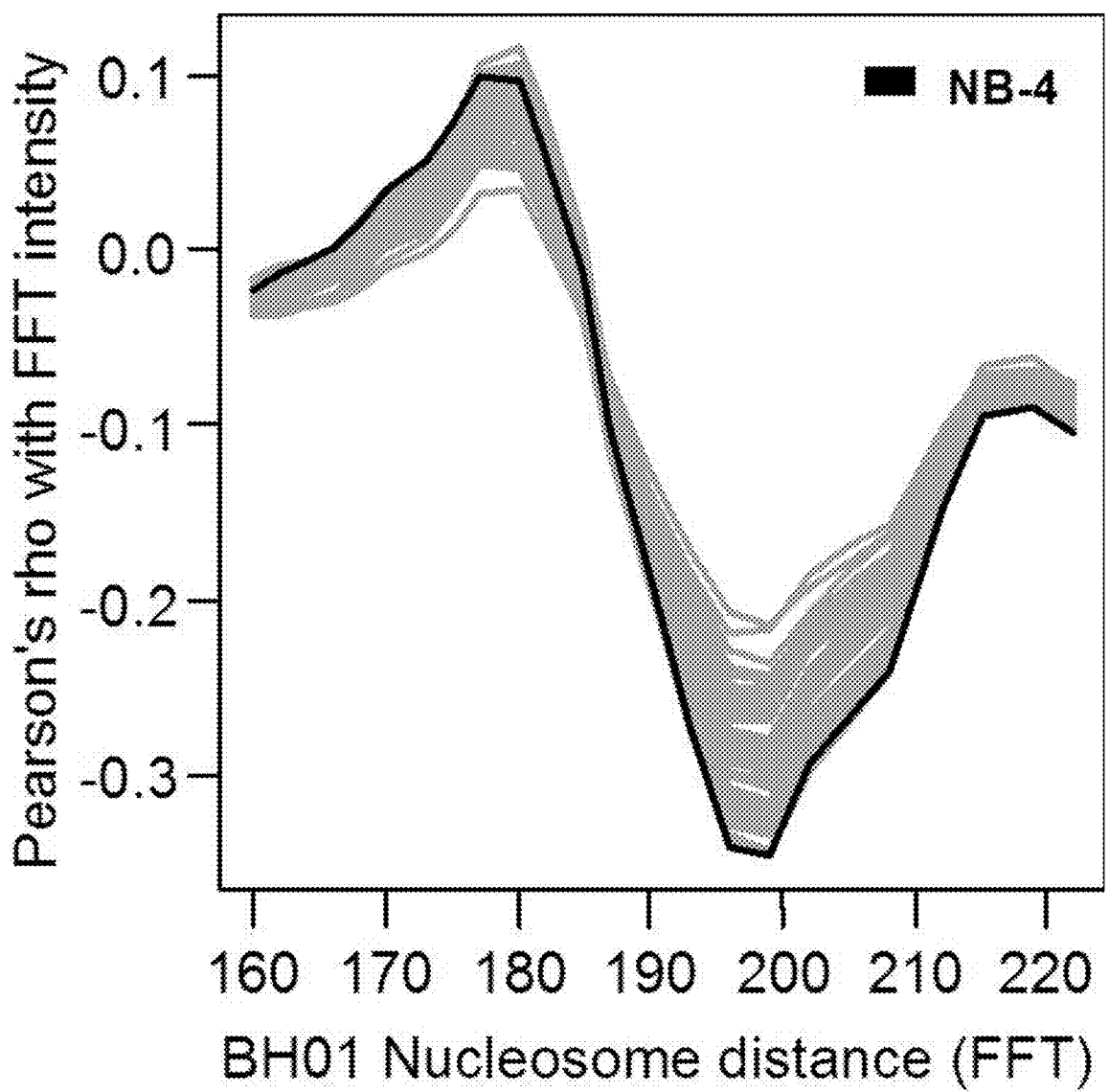
FIG. 60 shows how, to deconvolve multiple contributions, fast Fourier transformation (FFT) was used to quantify the abundance of specific frequency contributions (intensities) in the long fragment WPS for the first 10 kb of gene bodies starting at each TSS. Shown are trajectories of correlation between RNA expression in 76 cell lines and primary tissues with these intensities at different frequencies. Marked with a bold black line is the NB-4 cell line. Correlations are strongest in magnitude for intensities in the 193-199 bp frequency range.
Figure 61:
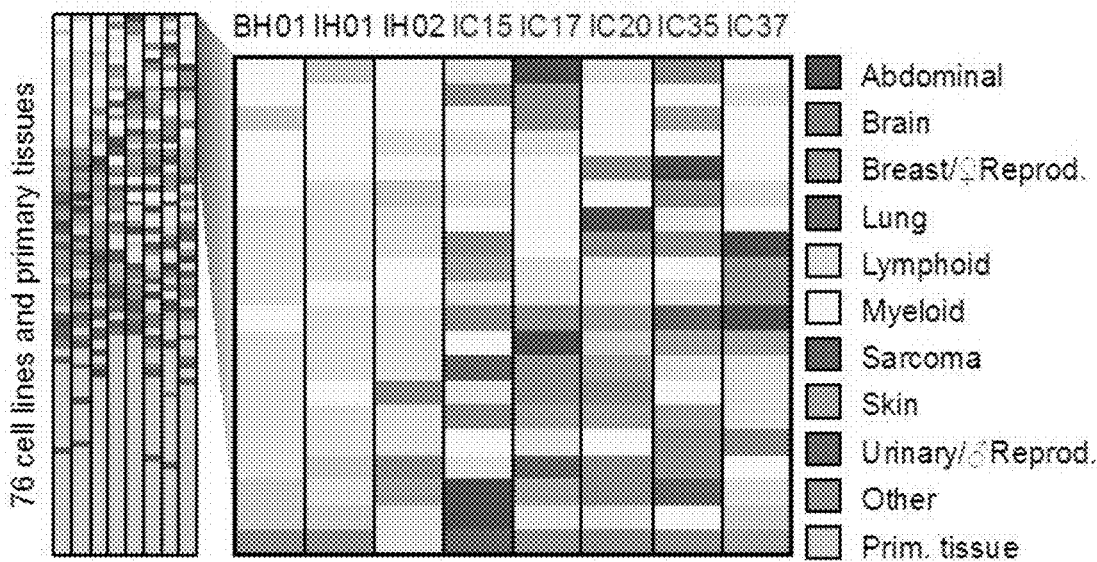
FIG. 61 shows the inference of cell-types contributing to cell-free DNA in healthy states and cancer. The top panel shows the ranks of correlation for 76 RNA expression datasets with average intensity in the 193-199 bp frequency range for various cfDNA libraries, categorized by type and listed from highest rank (top rows) to lowest rank (bottom rows). Correlation values and full cell line or tissue names are provided in Table 3. All of the strongest correlations for all three healthy samples (BH01, IH01 and IH02; first three columns) are with lymphoid and myeloid cell lines as well as bone marrow. In contrast, cfDNA samples obtained from stage IV cancer patients (IC15, IC17, IC20, IC35, IC37; last five columns) show top correlations with various cancer cell lines, e.g. IC17 (hepatocellular carcinoma, HCC) showing highest correlations with HepG2 (hepatocellular carcinoma cell line), and IC35 (breast ductal carcinoma, DC) with MCF7 (metastatic breast adenocarcinoma cell line). When comparing cell line/tissue ranks observed for the cancer samples to each of the three healthy samples and averaging the rank changes (bottom panel), maximum rank changes are more than 2× higher than those observed from comparing the three healthy samples with each other and averaging rank changes ('Control'). For example, for IC15 (small cell lung carcinoma, SCLC) the rank of SCLC-21H (small cell lung carcinoma cell line) increased by an average of 31 positions, for IC20 (squamous cell lung carcinoma, SCC) SK-BR-3 (metastatic breast adenocarcinoma cell line) increased by an average rank of 21, and for IC37 (colorectal adenocarcinoma, AC) HepG2 increased by 24 ranks.

One advantage of exploiting signals such as nucleosome spacing across gene bodies or other domains is that a much larger proportion of cfDNA fragments will be informative. Another potential advantage is that mixtures of signals resulting from multiple cell types contributing to cfDNA might be detectable. To test this, a further mathematical transformation, fast Fourier transformation (FFT), was performed on the long fragment WPS across the first 10 kb of gene bodies and on a gene-by-gene basis. The intensity of the FFT signal correlated with gene expression at specific frequency ranges, with a maximum at 177-180 bp for positive correlation and a minimum at -199 bp for negative correlation (FIG. 60). In performing this analysis against a dataset of 76 expression datasets for human cell lines and primary tissues, the strongest correlations were with hematopoietic lineages (FIG. 60). For example, the most highly ranked negative correlations with average intensity in the 193-199 bp frequency range for each of three healthy samples (BH01, IH01, IH02) were all to lymphoid cell lines, myeloid cell lines, or bone marrow tissue (FIG. 61; Table 3):

TABLE 3

Correlation of WPS FFT intensities with gene expression datasets.

| RName | Category | Type | Description | BH01 | IH01 | IH02 | IC15 |
|---|---|---|---|---|---|---|---|
| A.431 | Skin | Skin cancer (Squamous cells) | Epidermoid carcinoma cell line | −0.298 | −0.188 | −0.149 | −0.200 |
| A549 | Lung | Lung carcinoma | Lung carcinoma cell line | −0.289 | −0.185 | −0.144 | −0.202 |
| adipose_tissue | Primary Tissue | Adipose tissue | Primary tissue | −0.270 | −0.169 | −0.137 | −0.169 |
| adrenal_gland | Primary Tissue | Adrenal gland | Primary tissue | −0.257 | −0.158 | −0.131 | −0.173 |
| AN3.CA | Breast/Female Reproductive | Uterine cancer | Metastatic endometrial adenocarcinoma cell line | −0.303 | −0.194 | −0.157 | −0.213 |
| appendix | Primary Tissue | Appendix | Primary tissue | −0.287 | −0.185 | −0.137 | −0.168 |
| BEWO | Other | Uterine cancer | Metastatic choriocarcinoma cell line | −0.284 | −0.184 | −0.147 | −0.193 |
| bone_marrow | Primary Tissue | Bone marrow | Primary tissue | −0.343 | −0.230 | −0.165 | −0.192 |
| CACO.2 | Abdominal | Colon adenocarcinoma | Colon adenocarcinoma cell line | −0.281 | −0.177 | −0.137 | −0.192 |
| CAPAN.2 | Abdominal | Pancreas adenocarcinoma | Pancreas adenocarcinoma cell line | −0.291 | −0.187 | −0.145 | −0.202 |
| cerebral_cortex | Primary Tissue | Cerebral cortex | Primary tissue | −0.225 | −0.136 | −0.120 | −0.168 |
| colon | Primary Tissue | Colon | Primary tissue | −0.261 | −0.162 | −0.124 | −0.164 |
| Daudi | Lymphoid | Human Burkitt lymphoma | Human Burkitt lymphoma cell line | −0.321 | −0.206 | −0.153 | −0.195 |
| duodenum | Primary Tissue | Duodenum | Primary tissue | −0.261 | −0.164 | −0.122 | −0.159 |
| EFO.21 | Breast/Female Reproductive | Ovarian cancer | Metastatic ovarian serous cystadenocarcinoma cell line | −0.287 | −0.186 | −0.149 | −0.201 |
| endometrium | Primary Tissue | Endometrium | Primary tissue | −0.257 | −0.158 | −0.132 | −0.178 |
| esophagus | Primary Tissue | Esophagus | Primary tissue | −0.237 | −0.147 | −0.124 | −0.156 |
| fallopian_tube | Primary Tissue | Fallopian tube | Primary tissue | −0.247 | −0.157 | −0.129 | −0.171 |
| gallbladder | Primary Tissue | Gallbladder | Primary tissue | −0.249 | −0.156 | −0.119 | −0.153 |
| HaCaT | Skin | Keratinocyte cell line | Keratinocyte cell line | −0.290 | −0.186 | −0.149 | −0.194 |
| HDLM.2 | Lymphoid | Hodgkin lymphoma | Hodgkin lymphoma cell line | −0.316 | −0.200 | −0.154 | −0.201 |

TABLE 3-continued

Correlation of WPS FFT intensities with gene expression datasets.

| | | | | | | | |
|---|---|---|---|---|---|---|---|
| heart_muscle | Primary Tissue | Heart muscle | Primary tissue | −0.246 | −0.149 | −0.126 | −0.166 |
| HEK_293 | Other | Kidney adrenal precursor cell line | Embryonal kidney cell line, transformed by adenovirus type 5 | −0.292 | −0.187 | −0.150 | −0.209 |
| HEL | Myeloid | Erythroleukemia | Erythroleukemia cell line (AML M6 in relapse after treatment for Hodgkin's disease) | −0.324 | −0.205 | −0.161 | −0.210 |
| HeLa | Breast/Female Reproductive | Cervical cancer | Cervical epithelial adenocarcinoma cell line | −0.296 | −0.186 | −0.149 | −0.203 |
| Hep_G2 | Abdominal | Hepatocellular carcinoma | Hepatocellular carcinoma cell line | −0.294 | −0.186 | −0.152 | −0.202 |
| HL.60 | Myeloid | Promyelocytic leukemia | Acute promyelocytic leukemia (APL) cell line | −0.332 | −0.208 | −0.161 | −0.202 |
| HMC.1 | Myeloid | Mastcell leukemia | Mastcell leukemia cell line | −0.337 | −0.228 | −0.165 | −0.212 |
| K.562 | Lymphoid | Leukemia | Chronic myeloid leukemia (CML) cell line | −0.317 | −0.202 | −0.158 | −0.211 |
| Karpas.707 | Lymphoid | Multiple myeloma | Multiple myeloma cell line | −0.325 | −0.210 | −0.155 | −0.195 |
| kidney | Primary Tissue | Kidney | Primary tissue | −0.245 | −0.150 | −0.130 | −0.168 |
| liver | Primary Tissue | Liver | Primary tissue | −0.248 | −0.148 | −0.122 | −0.150 |
| lung | Primary Tissue | Lung | Primary tissue | −0.264 | −0.170 | −0.133 | −0.170 |
| lymph_node | Primary Tissue | Lymph node | Primary tissue | −0.308 | −0.195 | −0.148 | −0.182 |
| MCF7 | Breast/Female Reproductive | Breast cancer | Metastatic breast adenocarcinoma cell line | −0.298 | −0.195 | −0.154 | −0.207 |
| MOLT.4 | Lymphoid | Leukemia (ALL) | Acute lymphoblastic leukemia (T-ALL) cell line | −0.323 | −0.204 | −0.163 | −0.212 |
| NB.4 | Myeloid | Promyelocytic leukemia | Acute promyelocytic leukemia (APL) cell line | −0.348 | −0.228 | −0.172 | −0.211 |
| NTERA.2 | Urinary/Male Reproductive | Urinary cancer | Metastatic embryonal carcinoma cell line, cloned from TERA-2 | −0.269 | −0.170 | −0.137 | −0.193 |
| ovary | Primary Tissue | Ovary | Primary tissue | −0.266 | −0.162 | −0.135 | −0.181 |
| pancreas | Primary Tissue | Pancreas | Primary tissue | −0.250 | −0.159 | −0.132 | −0.170 |
| PC.3 | Urinary/Male Reproductive | Prostate cancer | Metastatic poorly differentiated prostate adenocarcinoma cell line | −0.295 | −0.190 | −0.151 | −0.204 |
| placenta | Primary Tissue | Placenta | Primary tissue | −0.266 | −0.166 | −0.134 | −0.168 |
| prostate | Primary Tissue | Prostate | Primary tissue | −0.248 | −0.161 | −0.133 | −0.175 |
| rectum | Primary Tissue | Rectum | Primary tissue | −0.255 | −0.154 | −0.117 | −0.159 |
| REH | Lymphoid | Leukemia (ALL) | Pre-B cell leukemia cell line (ALL, first relapse) | −0.330 | −0.216 | −0.165 | −0.214 |
| RH.30 | Sarcoma | Rhabdomyosarcoma | Metastatic rhabdomyosarcoma cell line | −0.280 | −0.165 | −0.137 | −0.194 |
| RPMI.8226 | Lymphoid | Multiple Myeloma | Multiple myeloma cell line | −0.322 | −0.207 | −0.155 | −0.198 |
| RT4 | Urinary/Male Reproductive | Bladder cancer | Urinary bladder transitional cell carcinoma cell line | −0.282 | −0.168 | −0.145 | −0.192 |
| salivary_gland | Primary Tissue | Salivary gland | Primary tissue | −0.262 | −0.166 | −0.138 | −0.177 |
| SCLC.21H | Lung | Small cell lung carcinoma | Small cell lung carcinoma cell line | −0.259 | −0.160 | −0.138 | −0.201 |

TABLE 3-continued

Correlation of WPS FFT intensities with gene expression datasets.

| | | | | | | | |
|---|---|---|---|---|---|---|---|
| SH.SY5Y | Brain | Neuroblastoma | Metastatic neuroblastoma, clonal subline of neuroepithelioma cell line SK-N-SH | −0.271 | −0.170 | −0.137 | −0.201 |
| SiHa | Breast/Female Reproductive | Cervical cancer | Cervical squamous cell carcinoma cell line, integrated 1-2 copies of HPV16 | −0.288 | −0.180 | −0.148 | −0.201 |
| SK.BR.3 | Breast/Female Reproductive | Breast cancer | Metastatic breast adenocarcinoma cell line | −0.288 | −0.176 | −0.148 | −0.195 |
| SK.MEL.30 | Primary Tissue | Melanoma | Metastatic malignant melanoma cell line | −0.301 | −0.187 | −0.154 | −0.208 |
| skeletal_muscle | Primary Tissue | Skeletal muscle | Primary tissue | −0.261 | −0.166 | −0.134 | −0.179 |
| skin | Skin | Skin | Primary tissue | −0.259 | −0.166 | −0.134 | −0.168 |
| small_intestine | Primary Tissue | Small intestine | Primary tissue | −0.260 | −0.164 | −0.121 | −0.158 |
| smooth_muscle | Primary Tissue | Smooth muscle | Primary tissue | −0.259 | −0.158 | −0.127 | −0.169 |
| spleen | Primary Tissue | Spleen | Primary tissue | −0.308 | −0.202 | −0.148 | −0.180 |
| stomach | Primary Tissue | Stomach | Primary tissue | −0.264 | −0.170 | −0.131 | −0.170 |
| testis | Primary Tissue | Testis | Primary tissue | −0.215 | −0.142 | −0.109 | −0.147 |
| THP.1 | Myeloid | Monocytic leukemia | Acute monocytic leukemia (AML) cell line | −0.338 | −0.218 | −0.168 | −0.206 |
| thyroid_gland | Primary Tissue | Thyroid gland | Primary tissue | −0.261 | −0.158 | −0.136 | −0.178 |
| TIME | Other | Microvascular endothelial cell line | Telomerase-immortalized human microvascular endothelial cells (pooled) | −0.296 | −0.180 | −0.147 | −0.198 |
| tonsil | Primary Tissue | Tonsil | Primary tissue | −0.282 | −0.179 | −0.141 | −0.169 |
| U.138_MG | Brain | Glioblastoma | Glioblastoma cell line | −0.288 | −0.177 | −0.144 | −0.191 |
| U.2_OS | Sarcoma | Osteosarcoma | Osteosarcoma cell line | −0.275 | −0.175 | −0.139 | −0.192 |
| U.2197 | Sarcoma | Sarcoma | Malignant fibrous histiocytoma cell line | −0.290 | −0.181 | −0.146 | −0.195 |
| U.251_MG | Brain | Glioblastoma | Glioblastoma cell line | −0.292 | −0.178 | −0.140 | −0.197 |
| U.266.70 | Lymphoid | Multiple Myeloma | Multiple myeloma cell line (1970, IL-6-dependent) | −0.320 | −0.207 | −0.157 | −0.202 |
| U.266.84 | Lymphoid | Multiple Myeloma | Multiple myeloma cell line (1984, in vitro differentiated) | −0.326 | −0.212 | −0.162 | −0.207 |
| U.698 | Lymphoid | B-cell lymphoma | B-cell lymphoma cell line (lymphoblastic lymphosarcoma) | −0.328 | −0.212 | −0.159 | −0.203 |
| U.87_MG | Brain | Glioblastoma, astrocytoma | Glioblastoma, astrocytoma cell line | −0.285 | −0.175 | −0.143 | −0.192 |
| U.937 | Myeloid | Myelomonocytic histiocytic lymphoma | Myelomonocytic histiocytic lymphoma cell line | −0.346 | −0.224 | −0.167 | −0.201 |
| urinary_bladder | Primary Tissue | Urinary bladder | Primary tissue | −0.260 | −0.158 | −0.130 | −0.165 |
| WM.115 | Skin | Melanoma | Malignant melanoma cell line | −0.284 | −0.175 | −0.144 | −0.193 |

| | Correlations | | | | Rank Differences | | | | |
|---|---|---|---|---|---|---|---|---|---|
| RName | IC20 | IC17 | IC37 | IC35 | healthy | IC15 | IC20 | IC17 | IC37 | IC35 |
| A.431 | −0.140 | −0.176 | −0.195 | −0.178 | 2 | 3 | −9 | −9 | −12 | −21 |
| A549 | −0.139 | −0.172 | −0.188 | −0.170 | 3 | −14 | −12 | −9 | −2 | −13 |
| adipose_tissue | −0.121 | −0.153 | −0.166 | −0.148 | 1 | 12 | 5 | 0 | 14 | 12 |
| adrenal_gland | −0.118 | −0.145 | −0.161 | −0.138 | −2 | −11 | −5 | 1 | 5 | 8 |
| AN3.CA | −0.147 | −0.183 | −0.195 | −0.171 | −4 | −16 | −13 | −15 | −8 | −2 |
| appendix | −0.118 | −0.148 | −0.171 | −0.152 | 6 | 24 | 20 | 23 | 8 | 9 |
| BEWO | −0.139 | −0.173 | −0.194 | −0.173 | −5 | 3 | −12 | −15 | −19 | −27 |

TABLE 3-continued

Correlation of WPS FFT intensities with gene expression datasets.

| | | | | | | | | | | |
|---|---|---|---|---|---|---|---|---|---|---|
| bone_marrow | −0.142 | −0.167 | −0.193 | −0.165 | 2 | 40 | 9 | 30 | 16 | 28 |
| CACO.2 | −0.128 | −0.169 | −0.184 | −0.164 | 5 | −5 | −5 | −14 | −10 | −9 |
| CAPAN.2 | −0.136 | −0.176 | −0.195 | −0.175 | 3 | −12 | −2 | −18 | −19 | −25 |
| cerebral_cortex | −0.108 | −0.134 | −0.142 | −0.125 | −1 | −9 | −3 | 0 | 0 | 0 |
| colon | −0.111 | −0.145 | −0.168 | −0.148 | 7 | 8 | 8 | 6 | −7 | 1 |
| Daudi | −0.133 | −0.165 | −0.189 | −0.160 | 4 | 17 | 19 | 19 | 13 | 24 |
| duodenum | −0.109 | −0.144 | −0.166 | −0.144 | 10 | 10 | 10 | 7 | −4 | 7 |
| EFO.21 | −0.140 | −0.176 | −0.188 | −0.169 | −7 | −9 | −14 | −20 | −1 | −8 |
| endometrium | −0.119 | −0.151 | −0.166 | −0.151 | −3 | −11 | −4 | −8 | −3 | −12 |
| esophagus | −0.116 | −0.141 | −0.158 | −0.145 | −3 | 1 | −7 | 0 | 0 | −7 |
| fallopian_tube | −0.114 | −0.145 | −0.161 | −0.145 | −4 | −13 | −2 | −3 | 3 | −2 |
| gallbladder | −0.103 | −0.138 | −0.154 | −0.141 | 4 | 4 | 4 | 3 | 4 | 1 |
| HaCaT | −0.142 | −0.173 | −0.193 | −0.173 | −5 | 7 | −18 | −8 | −8 | −17 |
| HDLM.2 | −0.136 | −0.173 | −0.195 | −0.171 | 1 | 6 | 11 | 1 | −5 | −5 |
| heart_muscle | −0.113 | −0.141 | −0.155 | −0.140 | −3 | −3 | −3 | 0 | 3 | 2 |
| HEK_293 | −0.139 | −0.172 | −0.189 | −0.168 | −4 | −17 | −4 | −2 | 3 | 0 |
| HEL | −0.140 | −0.172 | −0.194 | −0.168 | −1 | −5 | 4 | 12 | 5 | 14 |
| HeLa | −0.139 | −0.172 | −0.190 | −0.171 | 1 | −10 | −5 | −3 | 1 | −8 |
| Hep_G2 | −0.145 | −0.186 | −0.196 | −0.167 | −4 | −6 | −18 | −24 | −17 | 2 |
| HL.60 | −0.137 | −0.171 | −0.197 | −0.170 | 2 | 8 | 18 | 18 | −1 | 11 |
| HMC.1 | −0.149 | −0.181 | −0.199 | −0.180 | 0 | −1 | −2 | 3 | 0 | −2 |
| K.562 | −0.143 | −0.178 | −0.195 | −0.166 | −3 | −9 | −5 | −6 | −1 | 13 |
| Karpas.707 | −0.136 | −0.167 | −0.188 | −0.164 | 4 | 20 | 18 | 22 | 21 | 22 |
| kidney | −0.119 | −0.153 | −0.171 | −0.147 | −7 | −4 | −12 | −19 | −21 | −6 |
| liver | −0.110 | −0.150 | −0.164 | −0.138 | 1 | 4 | −1 | −13 | −4 | 3 |
| lung | −0.121 | −0.148 | −0.167 | −0.149 | 3 | 4 | 0 | 7 | 3 | 6 |
| lymph_node | −0.128 | −0.155 | −0.181 | −0.156 | 7 | 24 | 17 | 25 | 14 | 22 |
| MCF7 | −0.145 | −0.183 | −0.196 | −0.181 | −3 | −9 | −12 | −18 | −11 | −19 |
| MOLT.4 | −0.144 | −0.177 | −0.197 | −0.173 | −3 | −7 | −2 | −1 | −5 | −1 |
| NB.4 | −0.148 | −0.182 | −0.202 | −0.171 | 0 | 4 | 3 | 5 | 2 | 13 |
| NTERA.2 | −0.117 | −0.157 | −0.169 | −0.153 | −2 | −8 | 16 | −2 | 5 | 0 |
| ovary | −0.120 | −0.152 | −0.166 | −0.151 | 1 | −7 | 2 | −2 | 6 | −1 |
| pancreas | −0.116 | −0.150 | −0.166 | −0.150 | −5 | −5 | 1 | −6 | −5 | −7 |
| PC.3 | −0.138 | −0.174 | −0.188 | −0.173 | −3 | −10 | 2 | −6 | 8 | −12 |
| placenta | −0.126 | −0.151 | −0.166 | −0.150 | 3 | 10 | −7 | 1 | 9 | 6 |
| prostate | −0.123 | −0.150 | −0.165 | −0.151 | −8 | −10 | −11 | −8 | 1 | −12 |
| rectum | −0.102 | −0.136 | −0.161 | −0.142 | 6 | 0 | 5 | 4 | −2 | 0 |
| REH | −0.150 | −0.182 | −0.204 | −0.174 | −2 | −5 | −5 | −2 | −4 | 1 |
| RH.30 | −0.125 | −0.158 | −0.175 | −0.158 | 2 | −14 | −3 | −7 | −7 | −7 |
| RPMI.8226 | −0.138 | −0.169 | −0.190 | −0.164 | 1 | 16 | 11 | 19 | 14 | 22 |
| RT4 | −0.136 | −0.170 | −0.191 | −0.171 | −5 | −1 | −12 | −16 | −19 | −25 |
| salivary_gland | −0.128 | −0.154 | −0.172 | −0.155 | −7 | 2 | −9 | −2 | −5 | −5 |
| SCLC.21H | −0.123 | −0.157 | −0.172 | −0.146 | −11 | −31 | −5 | −12 | −10 | 8 |
| SH.SY5Y | −0.124 | −0.157 | −0.170 | −0.151 | 2 | −25 | 2 | −5 | 1 | 6 |
| SiHa | −0.139 | −0.176 | −0.193 | −0.175 | −2 | −7 | −15 | −19 | −11 | −27 |
| SK.BR.3 | −0.140 | −0.176 | −0.191 | −0.169 | −3 | −4 | −21 | −22 | −12 | −11 |
| SK.MEL.30 | −0.141 | −0.174 | −0.193 | −0.171 | −2 | −12 | −8 | −3 | −1 | −6 |
| skeletal_muscle | −0.125 | −0.150 | −0.164 | −0.145 | −1 | −7 | −7 | 0 | 9 | 11 |
| skin | −0.127 | −0.148 | −0.167 | −0.151 | −4 | 8 | −14 | 5 | −1 | −4 |
| small_intestine | −0.107 | −0.141 | −0.166 | −0.142 | 9 | 10 | 11 | 9 | 0 | 7 |
| smooth_muscle | −0.113 | −0.144 | −0.161 | −0.149 | 2 | −6 | 3 | 4 | 4 | −5 |
| spleen | −0.130 | −0.155 | −0.177 | −0.154 | 7 | 27 | 15 | 25 | 20 | 25 |
| stomach | −0.117 | −0.149 | −0.169 | −0.151 | 6 | 3 | 9 | 6 | 0 | 2 |
| testis | −0.093 | −0.126 | −0.133 | −0.123 | 0 | 0 | 0 | 0 | 0 | 0 |
| THP.1 | −0.149 | −0.182 | −0.204 | −0.176 | −1 | 8 | −1 | 1 | −3 | 0 |
| thyroid_gland | −0.121 | −0.153 | −0.170 | −0.161 | −2 | −7 | −2 | −6 | −6 | −19 |
| TIME | −0.134 | −0.170 | −0.186 | −0.170 | 5 | −3 | 3 | −1 | 3 | −11 |
| tonsil | −0.125 | −0.147 | −0.173 | −0.152 | −1 | 20 | 8 | 23 | 4 | 9 |
| U.138_MG | −0.126 | −0.162 | −0.177 | −0.161 | 1 | 8 | 7 | 0 | 2 | 2 |
| U.2_OS | −0.134 | −0.159 | −0.170 | −0.160 | −2 | 0 | −11 | −3 | 6 | −3 |
| U.2197 | −0.129 | −0.164 | −0.180 | −0.165 | 2 | 1 | 5 | 3 | 4 | 0 |
| U.251_MG | −0.125 | −0.160 | −0.177 | −0.165 | 9 | −6 | 11 | 4 | 4 | −4 |
| U.266.70 | −0.135 | −0.170 | −0.191 | −0.165 | −1 | 4 | 19 | 15 | 12 | 17 |
| U.266.84 | −0.139 | −0.175 | −0.194 | −0.169 | −1 | 2 | 11 | 8 | 10 | 14 |
| U.698 | −0.137 | −0.170 | −0.194 | −0.166 | 2 | 5 | 18 | 20 | 6 | 20 |
| U.87_MG | −0.127 | −0.160 | −0.174 | −0.162 | 1 | 0 | 2 | −2 | 2 | −4 |
| U.937 | −0.146 | −0.180 | −0.199 | −0.173 | 1 | 18 | 3 | 5 | 2 | 6 |
| urinary_bladder | −0.118 | −0.146 | −0.164 | −0.150 | 3 | 5 | −2 | 1 | 3 | −6 |
| WM.115 | −0.130 | −0.160 | −0.178 | −0.157 | −1 | −4 | −4 | −3 | −3 | 2 |

Correlation values between average FFT (fast Fourier Transformation) intensities for the 193-199 bp frequencies in the first 10 kb downstream of the transcriptional start site with FPKM expression values measured for 19,378 Ensembl gene identifiers in 44 human cell lines and 32 primary tissues by the Human Protein Atlas. Table 3 also contains brief descriptions for each of the expression samples as provided by the Protein Atlas as well as rank transformations and rank differences to the IH01, IH02 and BH01 samples.

Example 5: Determining Non-Healthy Tissue(s)-of-Origin from cfDNA

To test whether additional contributing tissues in non-healthy states might be inferred, cfDNA samples obtained from five late-stage cancer patients were sequenced. The patterns of nucleosome spacing in these samples revealed additional contributions to cfDNA that correlated most strongly with non-hematopoietic tissues or cell lines, often matching the anatomical origin of the patient's cancer.

Nucleosome Spacing in Cancer Patients' cfDNA Identifies Non-Hematopoietic Contributions To determine whether signatures of non-hematopoietic lineages contributing to circulating cfDNA in non-healthy states could be detected, 44 plasma samples from individuals with clinical diagnoses of a variety of Stage IV cancers were screened with light sequencing of single-stranded libraries prepared from cfDNA (Table 4; median 2.2-fold coverage):

TABLE 4

Clinical diagnoses and cfDNA yield for cancer panel.

| Sample ID | Clinical Dx | Stage | cfDNA Yield (ng/ml) | Patient Sex |
|---|---|---|---|---|
| IC01 † | Kidney cancer (Transitional cell) | IV | 242 | F |
| IC02 | Ovarian cancer (undefined) | IV | 22.5 | F |
| IC03 | Skin cancer (Melanoma) | IV | 12.0 | M |
| IC04 | Breast cancer (Invasive/infiltrating ductal) | IV | 12.6 | F |
| IC05 | Lung cancer (Adenocarcinoma) | IV | 5.4 | M |
| IC06 | Lung cancer (Mesothelioma) | IV | 11.4 | M |
| IC07 † | Gastric cancer (undefined) | IV | 52.2 | M |
| IC08 | Uterine cancer (undefined) | IV | 15.0 | F |
| IC09 | Ovarian cancer (serous tumors) | IV | 8.4 | F |
| IC10 | Lung cancer (adenocarcinoma) | IV | 11.4 | F |
| IC11 | Colorectal cancer (undefined) | IV | 11.4 | M |
| IC12 | Breast cancer (Invasive/infiltrating lobular) | IV | 12.0 | F |
| IC13 | Prostate cancer (undefined) | IV | 12.3 | M |
| IC14 | Head and neck cancer (undefined) | IV | 27.0 | M |
| IC15 § | Lung cancer (Small cell) | IV | 22.5 | M |
| IC16 | Bladder cancer (undefined) | IV | 14.1 | M |
| IC17 § | Liver cancer (Hepatocellular carcinoma) | IV | 39.0 | M |
| IC18 | Kidney cancer (Clear cell) | IV | 10.5 | F |
| IC19 | Testicular cancer (Seminomatous) | IV | 9.6 | M |
| IC20 § | Lung cancer (Squamous cell carcinoma) | IV | 21.9 | M |
| IC21 | Pancreatic cancer (Ductal adenocarcinoma) | IV | 35.4 | M |
| IC22 | Lung cancer (Adenocarcinoma) | IV | 11.4 | F |
| IC23 | Liver cancer (Hepatocellular carcinoma) | IV | 17.1 | M |
| IC24 | Pancreatic cancer (Ductal adenocarcinoma) | IV | 37.2 | M |
| IC25 | Pancreatic cancer (Ductal adenocarcinoma) | IV | 27.9 | M |
| IC26 | Prostate cancer (Adenocarcinoma) | IV | 24.6 | M |
| IC27 | Uterine cancer (undefined) | IV | 19.2 | F |
| IC28 | Lung cancer (Squamous cell carcinoma) | IV | 33.3 | M |
| IC29 | Head and neck cancer (undefined) | IV | 14.4 | M |
| IC30 | Esophageal cancer (undefined) | IV | 10.5 | M |
| IC31 † | Ovarian cancer (undefined) | IV | 334.8 | F |
| IC32 | Lung cancer (Small cell) | IV | 9.6 | F |
| IC33 | Colorectal cancer (Adenocarcinoma) | IV | 13.8 | M |
| IC34 | Breast cancer (Invasive/infiltrating lobular) | IV | 33.6 | F |
| IC35 § | Breast cancer (Ductal carcinoma in situ) | IV | 16.2 | F |
| IC36 | Liver cancer (undefined) | IV | 26.4 | M |
| IC37 § | Colorectal cancer (Adenocarcinoma) | IV | 15.9 | F |
| IC38 | Bladder cancer (undefined) | IV | 6.6 | M |
| IC39 | Kidney cancer (undefined) | IV | 39.0 | M |
| IC40 | Prostate cancer (Adenocarcinoma) | IV | 13.8 | M |
| IC41 | Testicular cancer (Seminomatous) | IV | 16.5 | M |
| IC42 | Lung cancer (Adenocarcinoma) | IV | 11.4 | F |
| IC43 | Skin cancer (Melanoma) | IV | 21.9 | F |
| IC44 | Esophageal cancer (undefined) | IV | 25.8 | F |
| IC45 † | Colorectal cancer (Adenocarcinoma) | IV | 3.0 | M |
| IC46 ** | Breast cancer (Ductal carcinoma in situ) | IV | 36.6 | F |
| IC47 | Pancreatic cancer (Ductal adenocarcinoma) | IV | 19.2 | F |
| IC48 ** | Breast cancer (Invasive/infiltrating lobular) | IV | 13.8 | F |

§ sample was selected for additional sequencing.
** only 0.5 ml of plasma was available for this sample.
† sample failed QC and was not used for further analysis.

Table 4 shows clinical and histological diagnoses for 48 patients from whom plasma-borne cfDNA was screened for evidence of high tumor burden, along with total cfDNA yield from 1.0 ml of plasma from each individual and relevant clinical covariates. Of these 48, 44 passed QC and had sufficient material. Of these 44, five were selected for deeper sequencing. cfDNA yield was determined by Qubit Fluorometer 2.0 (Life Technologies).

These samples were prepared with the same protocol and many in the same batch as IH02 of Example 4. Human peripheral blood plasma for 52 individuals with clinical diagnosis of Stage IV cancer (Table 4) was obtained from Conversant Bio or PlasmaLab International (Everett, Wash., USA) and stored in 0.5 ml or 1 ml aliquots at −80° C. until use. Human peripheral blood plasma for four individuals with clinical diagnosis of systemic lupus erythematosus was obtained from Conversant Bio and stored in 0.5 ml aliquots at −80° C. until use. Frozen plasma aliquots were thawed on the bench-top immediately before use. Circulating cell-free DNA was purified from 2 ml of each plasma sample with the QiaAMP Circulating Nucleic Acids kit (Qiagen) as per the manufacturer's protocol. DNA was quantified with a Qubit fluorometer (Invitrogen). To verify cfDNA yield in a subset of samples, purified DNA was further quantified with a custom qPCR assay targeting a multicopy human Alu sequence; the two estimates were found to be concordant.

Figure 62A:
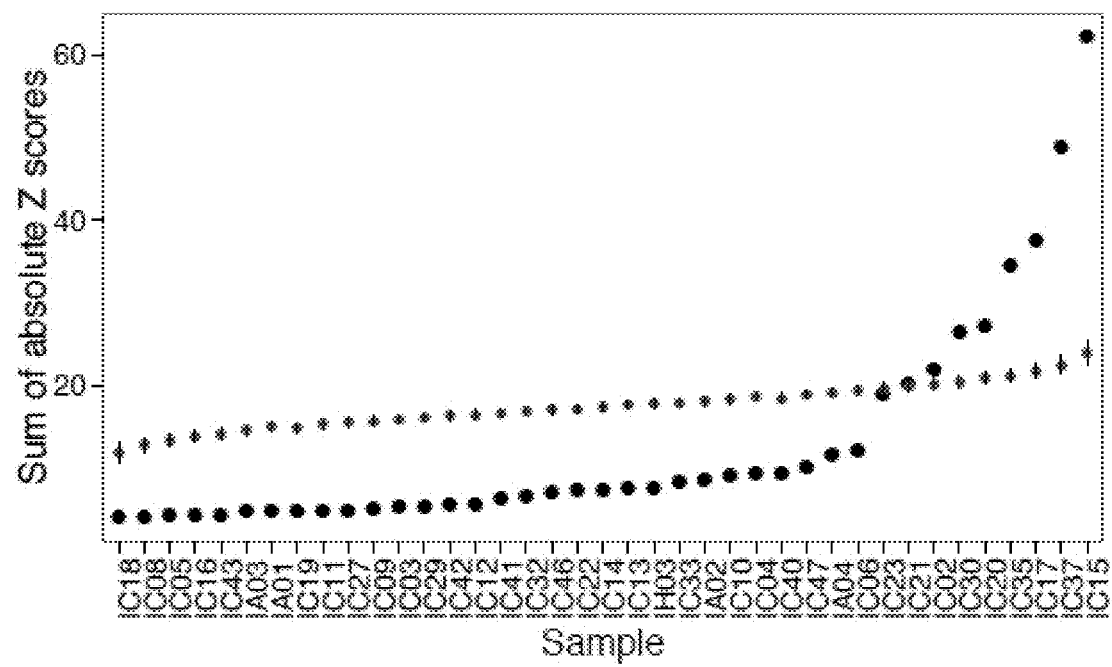
FIGS. 62A-B show quantitation of aneuploidy to select samples with high burden of circulating tumor DNA, based on coverage (FIG. 62A) or allele balance (FIG. 62B).
Figure 62B:
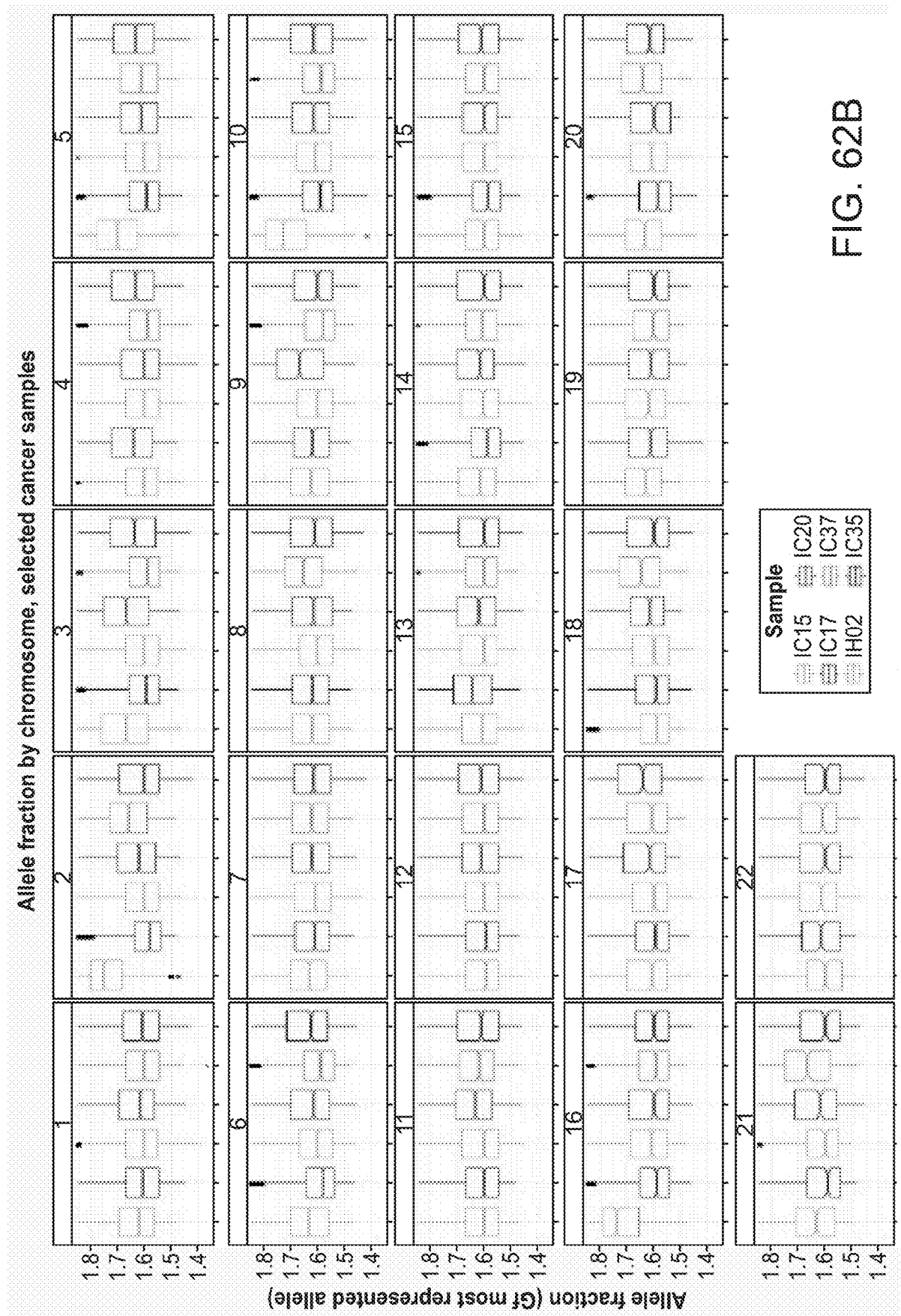
Figure 63A:
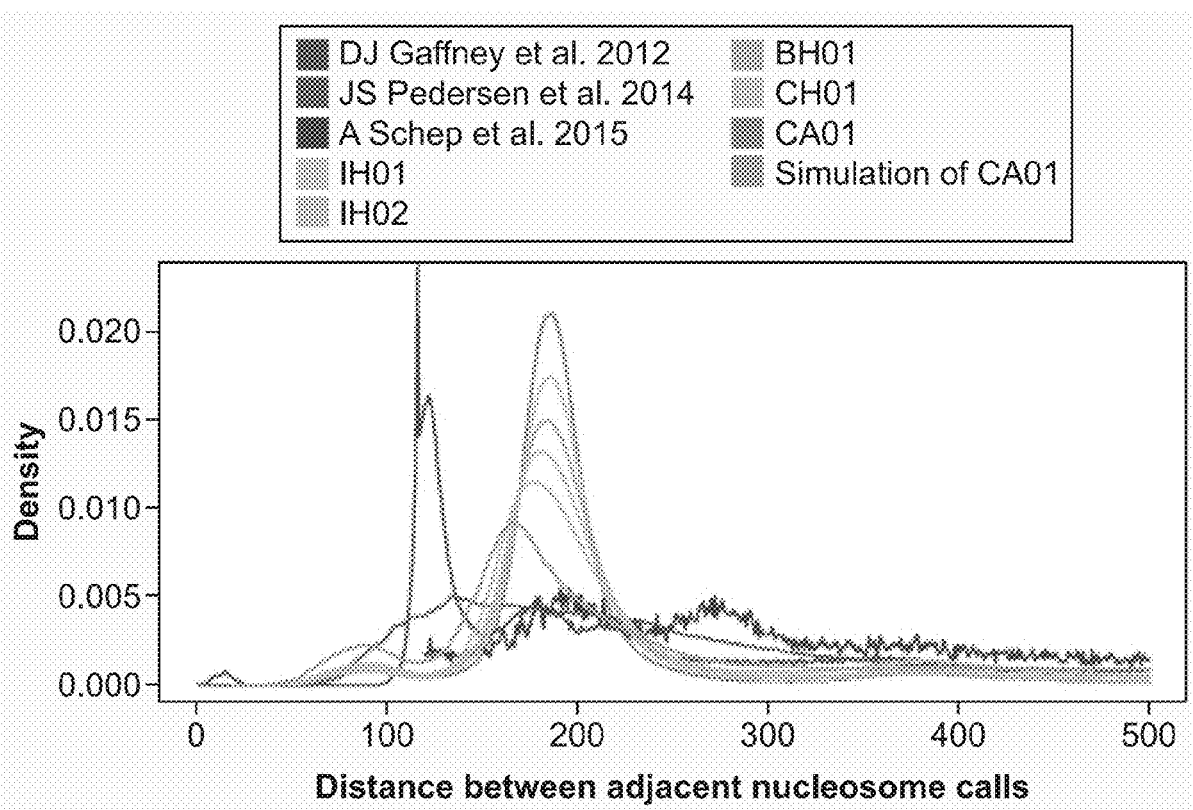
FIGS. 63A-H show a comparison of peak calls to published nucleosome call sets.
Figure 63B:
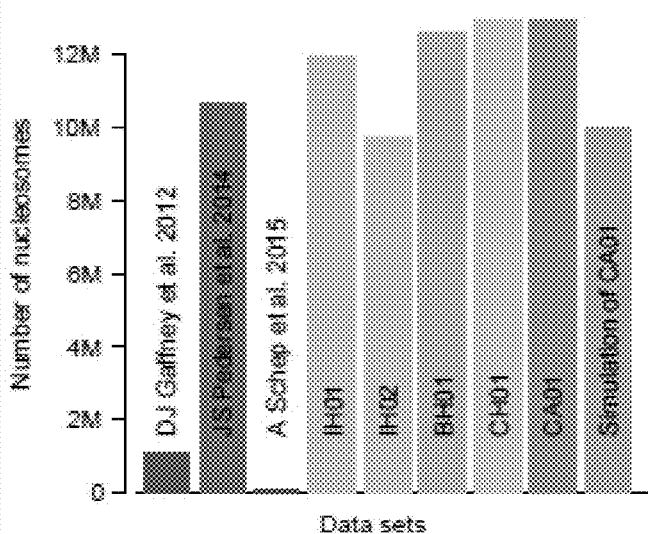
Figures 63C, 63D:
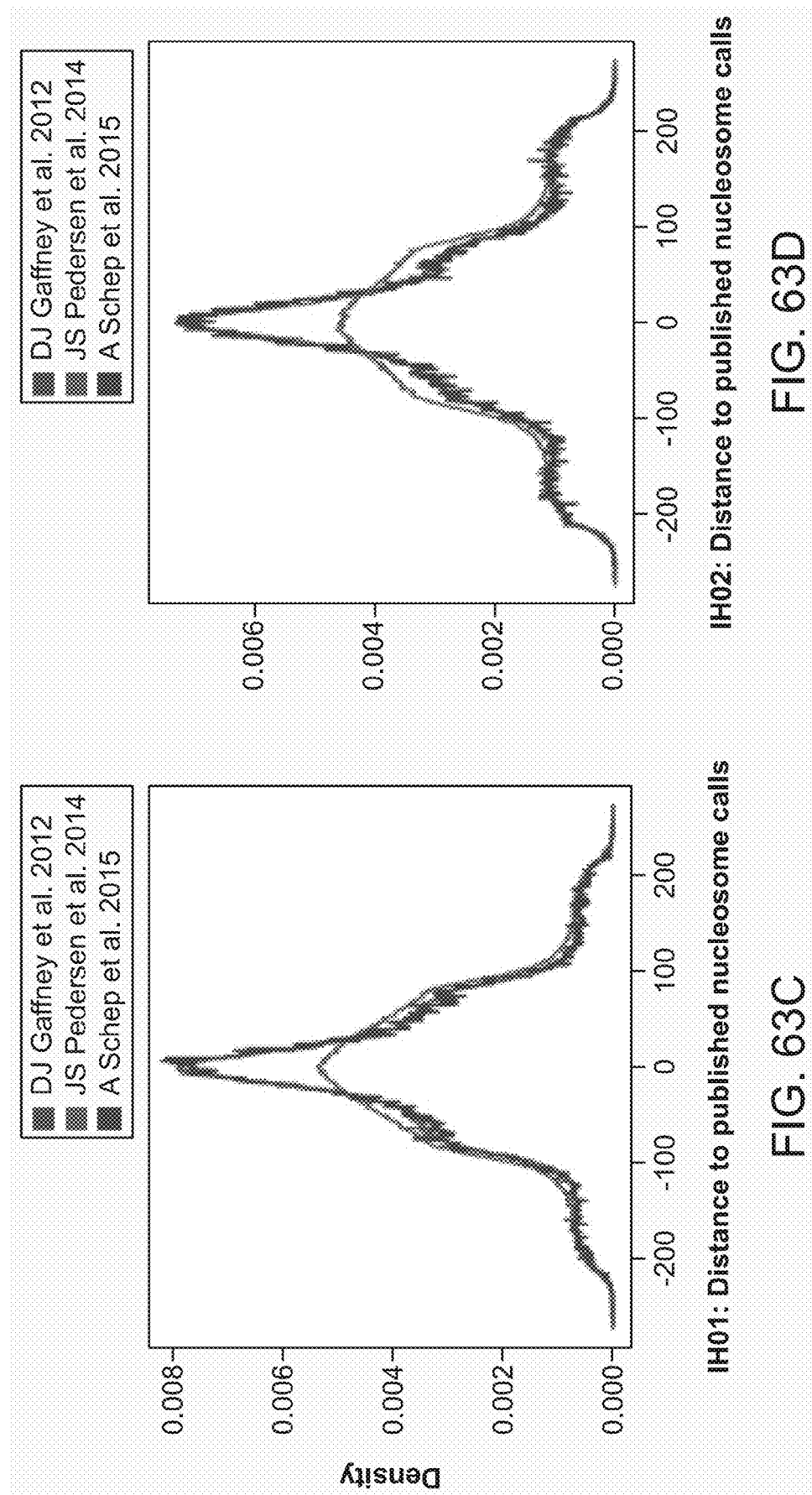
Figure 63F:
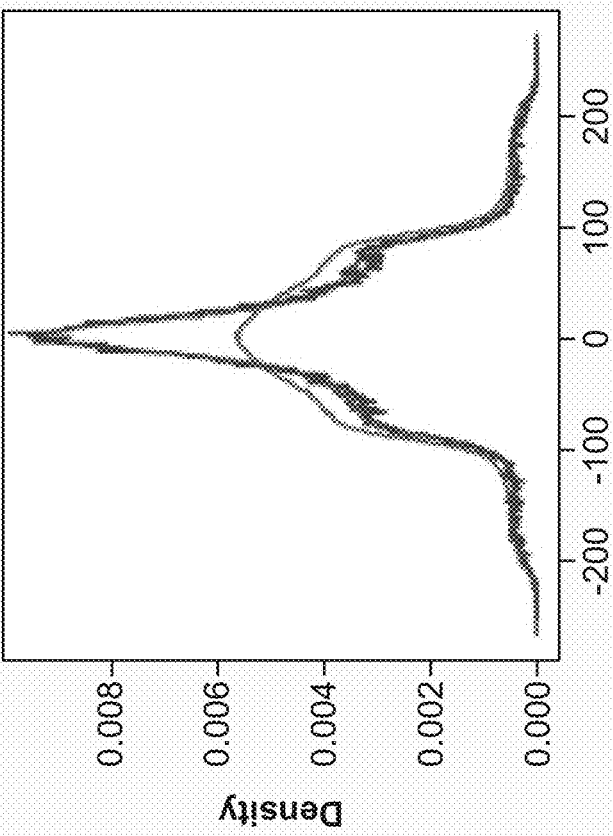
Figure 63E:
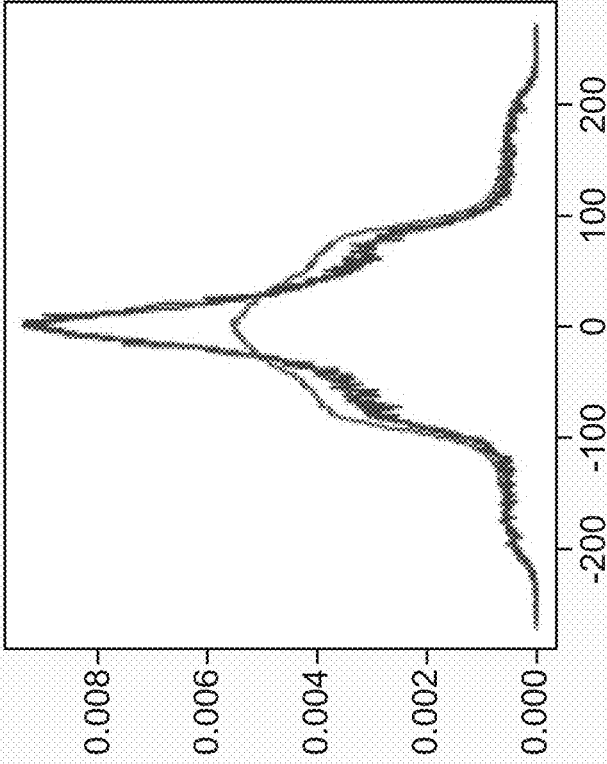
Figures 63G, 63H:
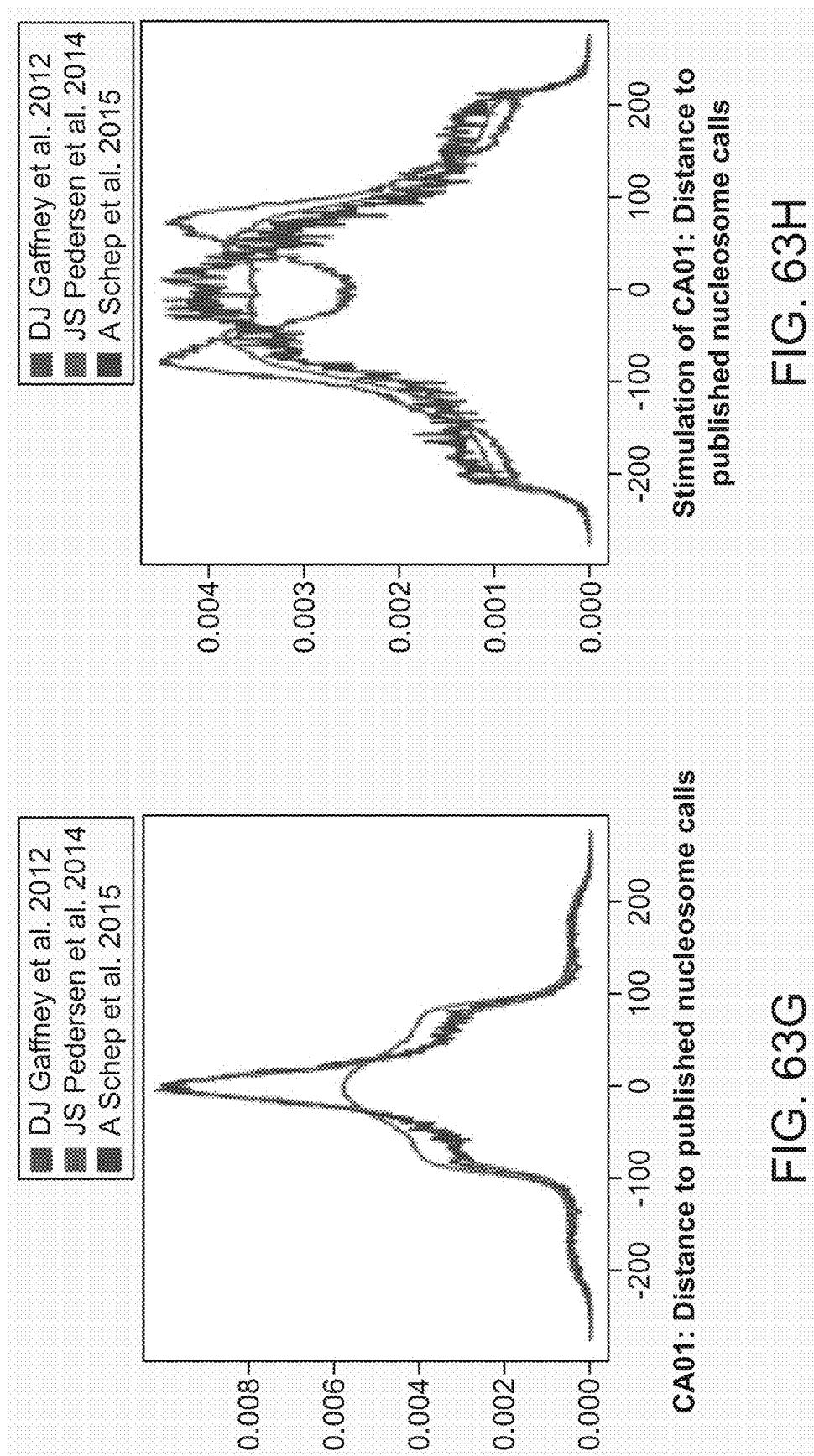

Because matched tumor genotypes were not available, each sample was scored on two metrics of aneuploidy to identify a subset likely to contain a high proportion of tumor-derived cfDNA: first, the deviation from the expected proportion of reads derived from each chromosome (FIG. 62A); and second, the per-chromosome allele balance profile for a panel of common single nucleotide polymorphisms (FIG. 62B). Based on these metrics, single-stranded libraries derived from five individuals (with a small cell lung cancer, a squamous cell lung cancer, a colorectal adenocarcinoma, a hepatocellular carcinoma, and a ductal carcinoma in situ breast cancer) were sequenced to a depth similar to that of IH02 in Example 4 (Table 5; mean 30-fold coverage):

TABLE 5

Sequencing statistics for additional samples included in CA01 set.

| Sample name | Library type | Reads | Fragments sequenced | Aligned | Aligned Q30 | Coverage | Est. % duplicates | 35–80 bp | 120–180 bp |
|---|---|---|---|---|---|---|---|---|---|
| IH03 | SSP | 2x39 | 53292855 | 92.66% | 72.37% | 2.29 | 15.46% | 11.05% | 52.34% |
| IP01 † | DSP | 2x101, 2x102 | 1214536629 | 97.22% | 86.38% | 76.11 | 0.55% | 0.08% | 62.77% |
| IP02 † | DSP | 2x101, 2x102 | 855040273 | 97.16% | 87.72% | 52.46 | 0.83% | 0.07% | 68.10% |
| IA01 | SSP | 2x39 | 53934607 | 87.42% | 68.30% | 2.02 | 22.70% | 15.20% | 49.77% |
| IA02 | SSP | 2x39 | 42496222 | 95.42% | 76.61% | 1.95 | 4.74% | 12.28% | 59.00% |
| IA03 | SSP | 2x39 | 51278489 | 93.12% | 71.33% | 2.05 | 25.68% | 14.27% | 52.57% |
| IA04 | SSP | 2x39 | 50768476 | 90.30% | 70.51% | 2.14 | 7.83% | 17.80% | 36.76% |
| IA05 | DSP | 2x101 | 194985271 | 98.80% | 90.61% | 11.09 | 12.05% | 2.24% | 71.67% |
| IA06 | DSP | 2x101 | 171670054 | 98.90% | 90.88% | 9.90 | 5.41% | 1.93% | 71.26% |
| IA07 | DSP | 2x101 | 208609489 | 98.67% | 90.34% | 11.69 | 11.45% | 2.59% | 74.84% |
| IA08 | DSP | 2x101 | 193729556 | 98.81% | 90.70% | 10.84 | 11.96% | 2.58% | 76.24% |
| IC02 | SSP | 2x39 | 57913605 | 95.07% | 75.57% | 2.59 | 5.40% | 12.98% | 60.00% |
| IC03 | SSP | 2x39 | 63862631 | 95.78% | 75.66% | 2.79 | 8.32% | 13.25% | 62.20% |
| IC04 | SSP | 2x39 | 55239248 | 95.47% | 76.26% | 2.57 | 8.28% | 10.98% | 58.48% |
| IC05 | SSP | 2x39 | 39623850 | 89.80% | 69.92% | 1.60 | 9.24% | 14.63% | 50.33% |
| IC06 | SSP | 2x39 | 59679981 | 95.57% | 74.90% | 2.11 | 3.93% | 24.30% | 41.46% |
| IC08 | SSP | 2x39 | 46933688 | 94.38% | 74.21% | 1.92 | 5.92% | 16.04% | 45.25% |
| IC09 | SSP | 2x42 | 59639583 | 91.22% | 71.15% | 2.13 | 6.69% | 21.39% | 43.50% |
| IC10 | SSP | 2x42 | 53994406 | 93.73% | 73.40% | 1.83 | 2.00% | 27.08% | 37.62% |
| IC11 | SSP | 2x42 | 59225460 | 93.25% | 72.51% | 2.15 | 5.26% | 21.30% | 43.33% |
| IC12 | SSP | 2x42 | 57884742 | 93.52% | 74.33% | 2.34 | 2.66% | 18.28% | 46.58% |
| IC13 | SSP | 2x42 | 71946779 | 92.94% | 72.47% | 2.52 | 2.18% | 23.51% | 43.97% |
| IC14 | SSP | 2x42 | 61649203 | 94.54% | 73.47% | 2.20 | 3.23% | 22.26% | 43.37% |
| IC15 | SSP | 2x50, 43/42 | 908512803 | 95.49% | 76.83% | 29.77 | 10.66% | 25.42% | 38.47% |
| IC16 | SSP | 2x42 | 62739733 | 92.81% | 72.85% | 2.47 | 2.77% | 17.71% | 48.04% |
| IC17 | SSP | 2x50, 2x39 | 1072374044 | 96.02% | 76.42% | 42.08 | 12.16% | 17.08% | 50.02% |
| IC18 | SSP | 2x39 | 59976914 | 87.91% | 68.67% | 2.24 | 4.39% | 18.85% | 44.44% |
| IC19 | SSP | 2x39 | 51447149 | 89.38% | 69.39% | 2.02 | 8.24% | 17.30% | 46.33% |
| IC20 | SSP | 2x50, 2x39 | 640838540 | 96.30% | 79.11% | 23.38 | 12.43% | 25.72% | 39.87% |
| IC21 | SSP | 2x39 | 53000679 | 94.64% | 74.57% | 1.79 | 37.39% | 29.89% | 43.81% |
| IC22 | SSP | 2x39 | 58102606 | 94.08% | 74.08% | 2.51 | 6.24% | 13.65% | 58.41% |
| IC23 | SSP | 2x39 | 65859970 | 95.67% | 75.67% | 2.94 | 5.34% | 11.09% | 60.85% |
| IC24 | SSP | 43/42 | 66344431 | 94.63% | 74.46% | 2.48 | 2.00% | 22.46% | 46.31% |
| IC25 | SSP | 43/42 | 75066833 | 93.75% | 73.66% | 2.86 | 2.24% | 21.30% | 46.19% |
| IC26 | SSP | 43/42 | 79180860 | 92.59% | 72.32% | 2.97 | 2.93% | 22.34% | 40.42% |
| IC27 | SSP | 43/42 | 78037377 | 88.81% | 67.04% | 2.20 | 1.50% | 31.31% | 30.59% |
| IC28 | SSP | 43/42 | 61402081 | 95.24% | 75.74% | 2.60 | 2.46% | 18.71% | 46.44% |
| IC29 | SSP | 2x39 | 49989522 | 94.46% | 73.36% | 1.75 | 3.03% | 25.82% | 36.23% |
| IC30 | SSP | 2x39 | 58439504 | 93.52% | 71.19% | 1.75 | 17.35% | 29.58% | 30.47% |
| IC32 | SSP | 43/42 | 78233981 | 87.86% | 66.80% | 2.25 | 1.79% | 30.12% | 31.20% |
| IC33 | SSP | 43/42 | 62196185 | 87.26% | 66.71% | 1.93 | 1.93% | 27.44% | 36.92% |
| IC34 | SSP | 43/42 | 63572169 | 95.42% | 76.74% | 2.53 | 2.35% | 19.64% | 48.55% |
| IC35 | SSP | 43/42 | 618554393 | 86.47% | 65.90% | 18.22 | 5.23% | 28.18% | 35.24% |
| IC36 | SSP | 43/42 | 54402943 | 94.62% | 74.73% | 2.21 | 3.32% | 17.02% | 52.42% |

TABLE 5-continued

Sequencing statistics for additional samples included in CA01 set.

| Sample name | Library type | Reads | Fragments sequenced | Aligned | Aligned Q30 | Coverage | Est. % duplicates | 35–80 bp | 120–180 bp |
|---|---|---|---|---|---|---|---|---|---|
| IC37 | SSP | 2x50, 43/42 | 1175553677 | 93.00% | 74.46% | 38.22 | 10.15% | 28.47% | 35.11% |
| IC38 | SSP | 43/42 | 47981963 | 89.35% | 69.45% | 1.78 | 6.47% | 18.59% | 43.03% |
| IC39 | SSP | 43/42 | 61968854 | 95.29% | 75.57% | 2.62 | 2.54% | 14.42% | 57.28% |
| IC40 | SSP | 2x39 | 53228209 | 93.54% | 71.69% | 1.81 | 8.85% | 24.88% | 34.95% |
| IC41 | SSP | 43/42 | 78081655 | 87.11% | 65.25% | 2.26 | 1.61% | 27.94% | 35.21% |
| IC42 | SSP | 2x39 | 53017317 | 93.59% | 74.33% | 2.02 | 10.74% | 19.04% | 44.12% |
| IC43 | SSP | 43/42 | 76395478 | 88.41% | 67.21% | 2.40 | 1.56% | 26.68% | 37.76% |
| IC44 | SSP | 43/42 | 61354307 | 95.15% | 74.88% | 2.45 | 4.34% | 19.10% | 46.39% |
| IC46 | SSP | 2x39 | 60123123 | 94.51% | 72.23% | 2.13 | 10.37% | 15.46% | 50.93% |
| IC47 | SSP | 2x39 | 59438172 | 95.58% | 73.84% | 2.07 | 9.33% | 21.67% | 43.34% |
| IC48 | SSP | 43/42 | 55704417 | 91.35% | 72.79% | 2.01 | 13.87% | 22.56% | 38.68% |
| IC49 | DSP | 2x101 | 170489015 | 99.02% | 90.53% | 11.19 | 5.93% | 2.41% | 59.93% |
| IC50 | DSP | 2x101 | 203828224 | 98.72% | 90.28% | 10.82 | 2.83% | 4.81% | 66.23% |
| IC51 | DSP | 2x101 | 200454421 | 98.63% | 90.53% | 11.77 | 9.50% | 2.58% | 67.04% |
| IC52 | DSP | 2x101 | 186975845 | 98.97% | 91.25% | 11.37 | 2.57% | 0.83% | 68.96% |

SSP, single-stranded library preparation protocol. DSP, double-stranded library preparation protocol.
† Sample has been previously published (J. O. Kitzman et al., *Science Translational Medicine* (2012)).

Table 5 tabulates sequencing-related statistics, including the total number of fragments sequenced, read lengths, the percentage of such fragments aligning to the reference with and without a mapping quality threshold, mean coverage, duplication rate, and the proportion of sequenced fragments in two length bins, for each sample. Fragment length was inferred from alignment of paired-end reads. Due to the short read lengths, coverage was calculated by assuming the entire fragment had been read. The estimated number of duplicate fragments is based on fragment endpoints, which may overestimate the true duplication rate in the presence of highly stereotyped cleavage.

As described above, FFT was performed on the long fragment WPS values across gene bodies and correlated the average intensity in the 193-199 bp frequency range against the same 76 expression datasets for human cell lines and primary tissues. In contrast with the three samples from healthy individuals from Example 4 (where all of the top 10, and nearly all of the top 20, correlations were to lymphoid or myeloid lineages), many of the most highly ranked cell lines or tissues represent non-hematopoietic lineages, in some cases aligning with the cancer type (FIG. 61; Table 3). For example, for IC17, where the patient had a hepatocellular carcinoma, the top-ranked correlation was with HepG2, a hepatocellular carcinoma cell line. For IC35, where the patient had a ductal carcinoma in situ breast cancer, the top-ranked correlation was with MCF7, a metastatic breast adenocarcinoma cell line. In other cases, the cell lines or primary tissues that exhibit the greatest change in correlation rank aligned with the cancer type. For example, for IC15, where the patient had small cell lung cancer, the largest change in correlation rank (−31) was for a small cell lung cancer cell line (SCLC-21H). For IC20 (a lung squamous cell carcinoma) and IC35 (a colorectal adenocarcinoma), there were many non-hematopoietic cancer cell lines displacing the lymphoid/myeloid cell lines in terms of correlation rank, but the alignment of these to the specific cancer type was less clear. It is possible that the specific molecular profile of these cancers was not well-represented amongst the 76 expression datasets (e.g., none of these are lung squamous cell carcinomas; CACO-2 is a cell line derived from a colorectal adenocarcinoma, but is known to be highly heterogeneous).

A greedy, iterative approach was used to estimate the proportions of various cell-types and/or tissues contributing to cfDNA derived from the biological sample. First, the cell-type or tissue whose reference map (here, defined by the 76 RNA expression datasets) had the highest correlation with the average FFT intensity in the 193-199 bp frequency of the WPS long fragment values across gene bodies for a given cfDNA sample was identified. Next, a series of "two tissue" linear mixture models were fitted, including the cell-type or tissue with the highest correlation as well as each of the other remaining cell-types or tissues from the full set of reference maps. Of the latter set, the cell-type or tissue with the highest coefficient was retained as contributory, unless the coefficient was below 1% in which case the procedure was terminated and this last tissue or cell-type not included. This procedure was repeated, i.e. "three-tissue", "four-tissue", and so on, until termination based on the newly added tissue being estimated by the mixture model to contribute less than 1%. The mixture model takes the form:

$$\arg\max\_\{a,b,c,\ldots\} cor(\text{Mean\_FFTintensity\_193-199}, a*\log 2 \text{ ExpTissue1} + b*\log 2\text{Tissue2} + c \log 2\text{Tissue3} + \ldots + (1-a-b-c-\ldots)*\log 2 \text{ ExpTissueN}).$$

For example, for IC17, a cfDNA sample derived from a patient with advanced hepatocellular carcinoma, this procedure predicted 9 contributory cell types, including Hep_G2 (28.6%), HMC.1 (14.3%), REH (14.0%), MCF7 (12.6%), AN3.CA (10.7%), THP.1 (7.4%), NB.4 (5.5%), U.266.84 (4.5%), and U.937 (2.4%). For BH01, a cfDNA sample corresponding to a mixture of healthy individuals, this procedure predicted 7 contributory cell types or tissues, including bone marrow (30.0%), NB.4 (19.6%), HMC.1 (13.9%), U.937 (13.4%), U.266.84 (12.5%), Karpas.707 (6.5%), and REH (4.2%). Of note, for IC17, the sample derived from a cancer patient, the highest proportion of predicted contribution corresponds to a cell line that is closely associated with the cancer type that is present in the patient from whom this cfDNA was derived (Hep_G2 and hepatocellular carcinoma). In contrast, for BH01, this approach predicts contributions corresponding only to tissues or cell types that are primarily associated with hematopoiesis, the predominant source of plasma cfDNA in healthy individuals.

Example 6: General Methods for Examples 4-5

Samples

Bulk human peripheral blood plasma, containing contributions from an unknown number of healthy individuals, was obtained from STEMCELL Technologies (Vancouver, British Columbia, Canada) and stored in 2 ml aliquots at −80° C. until use. Individual human peripheral blood plasma from anonymous, healthy donors was obtained from Conversant Bio (Huntsville, Ala., USA) and stored in 0.5 ml aliquots at −80° C. until use.

Whole blood from pregnant women IP01 and IP02 was obtained at 18 and 13 gestational weeks, respectively, and processed as previously described41.

Human peripheral blood plasma for 52 individuals with clinical diagnosis of Stage IV cancer (Supplementary Table 4) was obtained from Conversant Bio or PlasmaLab International (Everett, Wash., USA) and stored in 0.5 ml or 1 ml aliquots at −80° C. until use. Human peripheral blood plasma for four individuals with clinical diagnosis of systemic lupus erythematosus was obtained from Conversant Bio and stored in 0.5 ml aliquots at −80° C. until use.

Processing of Plasma Samples

Frozen plasma aliquots were thawed on the bench-top immediately before use. Circulating cell-free DNA was purified from 2 ml of each plasma sample with the QiaAMP Circulating Nucleic Acids kit (Qiagen) as per the manufacturers protocol. DNA was quantified with a Qubit fluorometer (Invitrogen). To verify cfDNA yield in a subset of samples, purified DNA was further quantified with a custom qPCR assay targeting a multicopy human Alu sequence; the two estimates were found to be concordant.

Preparation of Double-Stranded Sequencing Libraries

Barcoded sequencing libraries were prepared with the ThruPLEX-FD or ThruPLEX DNA-seq 48D kits (Rubicon Genomics), comprising a proprietary series of end-repair, ligation, and amplification reactions. Between 0.5 ng and 30.0 ng of cfDNA were used as input for all clinical sample libraries. Library amplification for all samples was monitored by real-time PCR to avoid over-amplification, and was typically terminated after 4-6 cycles.

Preparation of Single-Stranded Sequencing Libraries

Adapter 2 was prepared by combining 4.5 µl TE (pH 8), 0.5 µl 1M NaCl, 10 µl 500 uM oligo Adapter2.1, and 10 µl 500 µM oligo Adapter2.2, incubating at 95° C. for 10 seconds, and decreasing the temperature to 14° C. at a rate of 0.1° C./s. Purified cfDNA fragments were dephosphorylated by combining 2× CircLigase II buffer (Epicentre), 5 mM $MnCl_2$, and 1U FastAP alkaline phosphatase (Thermo Fisher) with 0.5-10 ng fragments in a 20 µl reaction volume and incubating at 37° C. for 30 minutes. Fragments were then denatured by heating to 95° C. for 3 minutes, and were immediately transferred to an ice bath. The reaction was supplemented with biotin-conjugated adapter oligo CL78 (5 pmol), 20% PEG-6000 (w/v), and 200U CircLigase II (Epicentre) for a total volume of 40 µl, and was incubated overnight with rotation at 60° C., heated to 95° C. for 3 minutes, and placed in an ice bath. For each sample, 20 µl MyOne C1 beads (Life Technologies) were twice washed in bead binding buffer (BBB) (10 mM Tris-HCl [pH 8], 1M NaCl, 1 mM EDTA [pH 8], 0.05% Tween-20, and 0.5% SDS), and resuspended in 250 µl BBB. Adapter-ligated fragments were bound to the beads by rotating for 60 minutes at room temperature. Beads were collected on a magnetic rack and the supernatant was discarded. Beads were washed once with 500 ul wash buffer A (WBA) (10 mM Tris-HCl [pH 8], 1 mM EDTA [pH 8], 0.05% Tween-20, 100 mM NaCl, 0.5% SDS) and once with 500 µl wash buffer B (WBB) (10 mM Tris-HCl [pH 8], 1 mM EDTA [pH 8], 0.05% Tween-20, 100 mM NaCl). Beads were combined with 1× Isothermal Amplification Buffer (NEB), 2.5 µM oligo CL9, 250 µM (each) dNTPs, and 24U Bst 2.0 DNA Polymerase (NEB) in a reaction volume of 50 µl, incubated with gentle shaking by ramping temperature from 15° C. to 37° C. at 1° C./minute, and held at 37° C. for 10 minutes. After collection on a magnetic rack, beads were washed once with 200 µl WBA, resuspended in 200 µl of stringency wash buffer (SWB) (0.1×SSC, 0.1% SDS), and incubated at 45° C. for 3 minutes. Beads were again collected and washed once with 200 µl WBB. Beads were then combined with 1× CutSmart Buffer (NEB), 0.025% Tween-20, 100 µM (each) dNTPs, and 5U T4 DNA Polymerase (NEB) and incubated with gentle shaking for 30 minutes at room temperature. Beads were washed once with each of WBA, SWB, and WBB as described above. Beads were then mixed with 1× CutSmart Buffer (NEB), 5% PEG-6000, 0.025% Tween-20, 2 µM double-stranded adapter 2, and 10U T4 DNA Ligase (NEB), and incubated with gentle shaking for 2 hours at room temperature. Beads were washed once with each of WBA, SWB, and WBB as described above, and resuspended in 25 µl TET buffer (10 mM Tris-HCl [pH 8], 1 mM EDTA [pH 8], 0.05% Tween-20). Second strands were eluted from beads by heating to 95° C., collecting beads on a magnetic rack, and transferring the supernatant to a new tube. Library amplification for all samples was monitored by real-time PCR to avoid over-amplification, and required an average of 4 to 6 cycles per library.

Sequencing

All libraries were sequenced on HiSeq 2000 or NextSeq 500 instruments (Illumina).

Primary Sequencing Data Processing

Barcoded paired end (PE) Illumine sequencing data was split allowing up to one substitution in the barcode sequence. Reads shorter or equal to read length were consensus called and adapter trimmed. Remaining consensus single end reads (SR) and the individual PE reads were aligned to the human reference genome sequence (GRCh37, 1000 Genomes phase 2 technical reference downloaded from ftp://ftp.1000genomes.ebi.ac.uk/vol1/ftp/technical/reference/phase2_reference_assembly_sequence/) using the ALN algorithm implemented in BWA v0.7.10. PE reads were further processed with BWA SAMPE to resolve ambiguous placement of read pairs or to rescue missing alignments by a more sensitive alignment step around the location of one placed read end. Aligned SR and PE data was directly converted to sorted BAM format using the SAMtools API. BAM files of the sample were merged across lanes and sequencing runs.

Quality control was performed using FastQC (v0.11.2), obtaining a library complexity estimate (Picard tools v1.113), determining the proportion of adapter dimers, the analysis of the inferred library insert size, the nucleotide and dinucleotide frequencies at the outer reads ends as well as checking the mapping quality distributions of each library.

Simulated Read Data Sets

Aligned sequencing data was simulated (SR if shorter than 45 bp, PE 45 bp otherwise) for all major chromosomes of the human reference (GRC37h). For this purpose, dinucleotide frequencies were determined from real data on both read ends and both strand orientations. Dinucleotide frequencies were also recorded for the reference genome on both strands. Further, the insert size distribution of the real data was extracted for the 1-500 bp range. Reads were simulated by iterating through the sequence of the major reference chromosomes. At each step (i.e., one or more times at each position depending on desired coverage), (1) the strand is randomly chosen, (2) the ratio of the dinucleotide frequency in the real data over the frequency in the reference sequence is used to randomly decide whether the initiating dinucleotide is considered, (3) an insert size is sampled from the provided insert-size distribution and (4) the frequency ratio of the terminal dinucleotide is used to randomly decide whether the generated alignment is reported. The simulated coverage was matched to that of the original data after PCR duplicate removal.

Coverage, Read Starts and Window Protection Scores

The data of the present disclosure provides information about the two physical ends of DNA molecules used in sequencing library preparation. We extract this information using the SAMtools application programming interface (API) from BAM files. As read starts, we use both outer alignment coordinates of PE data for which both reads aligned to the same chromosome and where reads have opposite orientations. In cases where PE data was converted to single read data by adapter trimming, we consider both end coordinates of the SR alignment as read starts. For coverage, we consider all positions between the two (inferred) molecule ends, including these end positions. We define windowed protection scores (WPS) of a window size k as the number of molecules spanning a window minus those starting at any bases encompassed by the window. We assign the determined WPS to the center of the window. For molecules in the 35-80 bp range (short fraction), we use a window size of 16 and, for molecules in the 120-180 bp (long fraction), we use a window size of 120.

Nucleosome Peak Calling

Local maxima of nucleosome protection are called from the long fraction WPS, which we locally adjust to a running median of zero (1 kb window) and smooth using a Savitzky-Golay filter (window size 21, 2nd order polynomial). The WPS track is then segmented into above zero regions (allowing up to 5 consecutive positions below zero). If the resulting region is between 50-150 bp long, we identify the median value of that region and search for the maximum-sum contiguous window above the median. We report the start, end and center coordinates of this window. Peak-to-peak distances, etc., are calculated from the center coordinates. The score of the call is determined as the distance between maximum value in the window and the average of the two adjacent WPS minima neighboring the region. If the identified region is 150-450 bp long, we apply the same above median contiguous window approach, but only report those windows that are between 50-150 bp in size. For score calculation of multiple windows derived from the 150-450 bp regions, we assume the neighboring minima within the region to be zero. We discard regions shorter than 50 bp and longer than 450 bp.

Dinucleotide Composition of 167 bp Fragments

Fragments with inferred lengths of exactly 167 bp, corresponding to the dominant peak of the fragment size distribution, were filtered within samples to remove duplicates. Dinucleotide frequencies were calculated in a strand-aware manner, using a sliding 2 bp window and reference alleles at each position, beginning 50 bp upstream of one fragment endpoint and ending 50 bp downstream of the other endpoint. Observed dinucleotide frequencies at each position were compared to expected dinucleotide frequencies determined from a set of simulated reads reflecting the same cleavage biases calculated in a library-specific manner (see above for details).

WPS Profiles Surrounding Transcription Factor Binding Sites and Genomic Features Analysis began with an initial set of clustered FIMO (motif-based) intervals defining a set of computationally predicted transcription factor binding sites. For a subset of clustered transcription factors (AP-2-2, AP-2, CTCF_Core-2, E2F-2, EBF1, Ebox-CACCTG, Ebox, ESR1, ETS, IRF-2, IRF-3, IRF, MAFK, MEF2A-2, MEF2A, MYC-MAX, PAX5-2, RUNX2, RUNX-AML, STAF-2, TCF-LEF, YY1), the set of sites was refined to a more confident set of actively bound transcription factor binding sites based on experimental data. For this purpose, only predicted binding sites that overlap with peaks defined by ChIP-seq experiments from publically available ENCODE data (TfbsClusteredV3 set downloaded from UCSC) were retained.

Windowed protection scores surrounding these sites were extracted for both the CH01 sample and the corresponding simulation. A protection score for each site/feature was calculated at each position relative to the start coordinate of each binding site and the aggregated. Plots of CTCF binding sites were shifted such that the zero coordinate on the x-axis at the center of the known 52 bp binding footprint of CTCF. The mean of the first and last 500 bp (which is predominantly flat and represents a mean offset) of the 5 kb extracted WPS signal was then subtracted from the original signal. For long fragment signal only, a sliding window mean was calculated using a 200 bp window and subtracted from the original signal. Finally, the corrected WPS profile for the simulation was subtracted from the corrected WPS profile for CH01 to correct for signal that was a product of fragment length and ligation bias. This final profile was plotted and termed the "Adjusted WPS".

Genomic features, such as transcription start sites, transcription end sites, start codons, splice donor, and splice acceptor sites were obtained from Ensembl Build version 75. Adjusted WPS surrounding these features was calculated and plotted as described above for transcription factor binding sites.

Analysis of Nucleosome Spacing Around CTCF Binding Sites and Corresponding WPS

CTCF sites used for this analysis first included clustered FIMO predictions of CTCF binding sites (computationally predicted via motifs). We then created two additional subsets of this set: 1) intersection with the set of CTCF ChIP-seq peaks available through the ENCODE TfbsClusteredV3 (see above), and 2) intersection with a set of CTCF sites that are experimentally observed to be active across 19 tissues.

The positions of 10 nucleosomes on either side of the binding site were extracted for each site. We calculated distances between all adjacent nucleosomes to obtain a distribution of inter-nucleosome distances for each set of sites. The distribution of −1 to +1 nucleosome spacing changed substantially, shifting to larger spacing, particularly in the 230-270 bp range. This suggested that truly active CTCF sites largely shift towards wider spacing between the −1 and +1 nucleosomes, and that a difference in WPS for both long and short read fractions might therefore be apparent. Therefore, the mean short and long fragment WPS at each position relative to the center of CTCF sites were additionally calculated. To explore the effect of nucleosome spacing, this mean was taken within bins of −1 to +1 nucleosome spacing of less than 160, 160-200, 200-230, 230-270, 270-420, 420-460, and greater than 420 bp. These intervals approximately captured spacings of interest, such as the dominant peak and the emerging peak at 230-270 bp for more confidently active sites.

Analysis of DNase I Hypersensitive Sites (DHS)

DHS peaks for 349 primary tissue and cell line samples in BED format by Maurano et al. (Science, vol. 337(6099), pp. 1190-95 (2012); "all_fdr0.05_hot" file, last modified Feb. 13, 2012) were downloaded from the University of Washington Encode database. Samples derived from fetal tissues, comprising 233 of these peak sets, were removed from the analysis as they behaved inconsistently within tissue type, possibly because of unequal representation of multiple cell types within each tissue sample. 116 samples representing a variety of cell lineages were retained for analysis. For the midpoint of each DHS peak in a particular set, the nearest upstream and downstream calls in the CH01 callset were identified, and the genomic distance between the centers of those two calls was calculated. The distribution of all such distances was visualized for each DHS peak callset using a smoothed density estimate calculated for distances between 0 and 500 bp.

Gene Expression Analysis

FPKM expression values, measured for 20,344 Ensembl gene identifiers in 44 human cell lines and 32 primary tissues by the Human Protein Atlas ("ma.csv" file) were used in this study. For analyses across tissues, genes with less than 3 non-zero expression values were excluded (19,378 genes passing this filter). The expression data set was provided with one decimal precession for the FPKM values. Thus, a zero expression value (0.0) indicates expression between 0 and a value less than 0.05. Unless otherwise noted, the minimum expression value was set to 0.04 FPKM before log 2-transformation of the expression values.

Smooth Periodograms and Smoothing of Trajectories

The long fragment WPS was used to calculate periodograms of genomic regions using Fast Fourier Transform (FFT, spec.pgram in the R statistical programming environment) with frequencies between 1/500 bases and 1/100 bases. Parameters to smooth (3 bp Daniell smoother; moving average giving half weight to the end values) and de-trend the data (i.e. subtract the mean of the series and remove a linear trend) are optionally additionally used.

Where indicated, the recursive time series filter as implemented in the R statistical programming environment was used to remove high frequency variation from trajectories. 24 filter frequencies (1/seq(5,100,4)) were used, and the first 24 values of the trajectory as initial values were used. Adjustments for the 24-value shift in the resulting trajectories were made by repeating the last 24 values of the trajectory.

Correlation of FFT Intensities and Expression Values

The intensity values as determined from smooth periodograms (FFT) in the context of gene expression for the 120-280 bp range were analyzed. An S-shaped Pearson correlation between gene expression values and FFT intensities around the major inter-nucleosome distance peak was observed. A pronounced negative correlation was observed in the 193-199 bp range. As a result, the intensities in this frequency range were averaged correlated with $\log_2$-transformed expression values.

Further Examples

Example 7. A method of determining tissues and/or cell types giving rise to cell free DNA (cfDNA) in a subject, the method comprising:

isolating cfDNA from a biological sample from the subject, the isolated cfDNA comprising a plurality of cfDNA fragments;

determining a sequence associated with at least a portion of the plurality of cfDNA fragments;

determining a genomic location within a reference genome for at least some cfDNA fragment endpoints of the plurality of cfDNA fragments as a function of the cfDNA fragment sequences; and determining at least some of the tissues and/or cell types giving rise to the cfDNA fragments as a function of the genomic locations of at least some of the cfDNA fragment endpoints.

Example 8. The method of Example 7 wherein the step of determining at least some of the tissues and/or cell types giving rise to the cfDNA fragments comprises comparing the genomic locations of at least some of the cfDNA fragment endpoints to one or more reference maps.

Example 9. The method of Example 7 or Example 8 wherein the step of determining at least some of the tissues and/or cell types giving rise to the cfDNA fragments comprises performing a mathematical transformation on a distribution of the genomic locations of at least some of the cfDNA fragment endpoints.

Example 10. The method of Example 9 wherein the mathematical transformation includes a Fourier transformation.

Example 11. The method of any preceding Example further comprising determining a score for each of at least some coordinates of the reference genome, wherein the score is determined as a function of at least the plurality of cfDNA fragment endpoints and their genomic locations, and wherein the step of determining at least some of the tissues and/or cell types giving rise to the observed cfDNA fragments comprises comparing the scores to one or more reference map.

Example 12. The method of Example 11, wherein the score for a coordinate represents or is related to the probability that the coordinate is a location of a cfDNA fragment endpoint.

Example 13. The method of any one of Examples 8 to 12 wherein the reference map comprises a DNase I hypersensitive site map generated from at least one cell-type or tissue.

Example 14. The method of any one of Examples 8 to 13 wherein the reference map comprises an RNA expression map generated from at least one cell-type or tissue.

Example 15. The method of any one of Examples 8 to 14 wherein the reference map is generated from cfDNA from an animal to which human tissues or cells that have been xenografted.

Example 16. The method of any one of Examples 8 to 15 wherein the reference map comprises a chromosome conformation map generated from at least one cell-type or tissue.

Example 17. The method of any one of Examples 8 to 16 wherein the reference map comprises a chromatin accessibility map generated from at least one cell-type or tissue.

Example 18. The method of any one of Examples 8 to 17 wherein the reference map comprises sequence data obtained from samples obtained from at least one reference subject.

Example 19. The method of any one of Examples 8 to 18 wherein the reference map corresponds to at least one cell-type or tissue that is associated with a disease or a disorder.

Example 20. The method of any one of Examples 8 to 19 wherein the reference map comprises positions or spacing of nucleosomes and/or chromatosomes in a tissue or cell type.

Example 21. The method of any one of Examples 8 to 20 wherein the reference map is generated by digesting chromatin obtained from at least one cell-type or tissue with an exogenous nuclease (e.g., micrococcal nuclease).

Example 22. The method of any one of Examples 8 to 21, wherein the reference maps comprise chromatin accessibility data determined by a transposition-based method (e.g., ATAC-seq) from at least one cell-type or tissue.

Example 23. The method of any one of Examples 8 to 22 wherein the reference maps comprise data associated with positions of a DNA binding and/or DNA occupying protein for a tissue or cell type.

Example 24. The method of Example 23 wherein the DNA binding and/or DNA occupying protein is a transcription factor.

Example 25. The method of Example 23 or Example 24 wherein the positions are determined by chromatin immunoprecipitation of a crosslinked DNA-protein complex.

Example 26. The method of Example 23 or Example 24 wherein the positions are determined by treating DNA associated with the tissue or cell type with a nuclease (e.g., DNase-I).

Example 27. The method of any one of Examples 8 to 26 wherein the reference map comprises a biological feature related to the positions or spacing of nucleosomes, chromatosomes, or other DNA binding or DNA occupying proteins within a tissue or cell type.

Example 28. The method of Example 27 wherein the biological feature is quantitative expression of one or more genes.

Example 29. The method of Example 27 or Example 28 wherein the biological feature is presence or absence of one or more histone marks.

Example 30. The method of any one of Examples 27 to 29 wherein the biological feature is hypersensitivity to nuclease cleavage.

Example 31. The method of any one of Examples 8 to 30 wherein the tissue or cell type used to generate a reference map is a primary tissue from a subject having a disease or disorder.

Example 32. The method of Example 31 wherein the disease or disorder is selected from the group consisting of: cancer, normal pregnancy, a complication of pregnancy (e.g., aneuploid pregnancy), myocardial infarction, inflammatory bowel disease, systemic autoimmune disease, localized autoimmune disease, allotransplantation with rejection, allotransplantation without rejection, stroke, and localized tissue damage.

Example 33. The method of any one of Examples 8 to 30 wherein the tissue or cell type used to generate a reference map is a primary tissue from a healthy subject.

Example 34. The method of any one of Examples 8 to 30 wherein the tissue or cell type used to generate a reference map is an immortalized cell line.

Example 35. The method of any one of Examples 8 to 30 wherein the tissue or cell type used to generate a reference map is a biopsy from a tumor.

Example 36. The method of Example 18 wherein the sequence data comprises positions of cfDNA fragment endpoints.

Example 37. The method of Example 36 wherein the reference subject is healthy.

Example 38. The method of Example 36 wherein the reference subject has a disease or disorder.

Example 39. The method of Example 38 wherein the disease or disorder is selected from the group consisting of: cancer, normal pregnancy, a complication of pregnancy (e.g., aneuploid pregnancy), myocardial infarction, inflammatory bowel disease, systemic autoimmune disease, localized autoimmune disease, allotransplantation with rejection, allotransplantation without rejection, stroke, and localized tissue damage.

Example 40. The method of any one of Examples 19 to 39 wherein the reference map comprises reference scores for at least a portion of coordinates of the reference genome associated with the tissue or cell type.

Example 41. The method of Example 40 wherein the reference map comprises a mathematical transformation of the scores.

Example 42. The method of Example 40 wherein the scores represent a subset of all reference genomic coordinates for the tissue or cell type.

Example 43. The method of Example 42 wherein the subset is associated with positions or spacing of nucleosomes and/or chromatosomes.

Example 44. The method of Example 42 or Example 43 wherein the subset is associated with transcription start sites and/or transcription end sites.

Example 45. The method of any one of Examples 42 to 44 wherein the subset is associated with binding sites of at least one transcription factor.

Example 46. The method of any one of Examples 42 to 45 wherein the subset is associated with nuclease hypersensitive sites.

Example 47. The method of any one of Examples 40 to 46 wherein the subset is additionally associated with at least one orthogonal biological feature.

Example 48. The method of Example 47 wherein the orthogonal biological feature is associated with high expression genes.

Example 49. The method of Example 47 wherein the orthogonal biological feature is associated with low expression genes.

Example 50. The method of any one of Examples 41 to 49 wherein the mathematical transformation includes a Fourier transformation.

Example 51. The method of any one of Examples 11 to 50 wherein at least a subset of the plurality of the scores has a score above a threshold value.

Example 52. The method of any one of Examples 7 to 51 wherein the step of determining the tissues and/or cell types giving rise to the cfDNA as a function of a plurality of the genomic locations of at least some of the cfDNA fragment endpoints comprises comparing a Fourier transform of the plurality of the genomic locations of at least some of the cfDNA fragment endpoints, or a mathematical transformation thereof, with a reference map.

Example 53. The method of any preceding Example further comprising generating a report comprising a list of the determined tissues and/or cell types giving rise to the isolated cfDNA.

Example 54. A method of identifying a disease or disorder in a subject, the method comprising:
isolating cell free DNA (cfDNA) from a biological sample from the subject, the isolated cfDNA comprising a plurality of cfDNA fragments;
determining a sequence associated with at least a portion of the plurality of cfDNA fragments;
determining a genomic location within a reference genome for at least some cfDNA fragment endpoints of the plurality of cfDNA fragments as a function of the cfDNA fragment sequences;
determining at least some of the tissues and/or cell types giving rise to the cfDNA as a function of the genomic locations of at least some of the cfDNA fragment endpoints; and identifying the disease or disorder as a function of the determined tissues and/or cell types giving rise to the cfDNA.

Example 55. The method of Example 54 wherein the step of determining the tissues and/or cell types giving rise to the cfDNA comprises comparing the genomic locations of at least some of the cfDNA fragment endpoints to one or more reference maps.

Example 56. The method of Example 54 or Example 55 wherein the step of determining the tissues and/or cell types giving rise to the cfDNA comprises performing a mathematical transformation on a distribution of the genomic locations of at least some of the plurality of the cfDNA fragment endpoints.

Example 57. The method of Example 56 wherein the mathematical transformation includes a Fourier transformation.

Example 58. The method of any one of Examples 54 to 57 further comprising determining a score for each of at least some coordinates of the reference genome, wherein the score is determined as a function of at least the plurality of cfDNA fragment endpoints and their genomic locations, and wherein the step of determining at least some of the tissues and/or cell types giving rise to the observed cfDNA fragments comprises comparing the scores to one or more reference map.

Example 59. The method of Example 58, wherein the score for a coordinate represents or is related to the probability that the coordinate is a location of a cfDNA fragment endpoint.

Example 60. The method of any one of Examples 55 to 59 wherein the reference map comprises a DNase I hypersensitive site map, an RNA expression map, expression data, a chromosome conformation map, a chromatin accessibility map, chromatin fragmentation map, or sequence data obtained from samples obtained from at least one reference subject, and corresponding to at least one cell type or tissue that is associated with a disease or a disorder, and/or positions or spacing of nucleosomes and/or chromatosomes in a tissue or cell type.

Example 61. The method of any one of Examples 55 to 60 wherein the reference map is generated by digesting chromatin from at least one cell-type or tissue with an exogenous nuclease (e.g., micrococcal nuclease).

Example 62. The method of Example 60 or Example 61, wherein the reference maps comprise chromatin accessibility data determined by applying a transposition-based method (e.g., ATAC-seq) to nuclei or chromatin from at least one cell-type or tissue.

Example 63. The method of any one of Examples 55 to 62 wherein the reference maps comprise data associated with positions of a DNA binding and/or DNA occupying protein for a tissue or cell type.

Example 64. The method of Example 63 wherein the DNA binding and/or DNA occupying protein is a transcription factor.

Example 65. The method of Example 63 or Example 64 wherein the positions are determined by applying chromatin immunoprecipitation of a crosslinked DNA-protein complex to at least one cell-type or tissue.

Example 66. The method of Example 63 or Example 64 wherein the positions are determined by treating DNA associated with the tissue or cell type with a nuclease (e.g., DNase-I).

Example 67. The method of any one of Examples 54 to 66 wherein the reference map comprises a biological feature related to the positions or spacing of nucleosomes, chromatosomes, or other DNA binding or DNA occupying proteins within a tissue or cell type.

Example 68. The method of Example 67 wherein the biological feature is quantitative expression of one or more genes.

Example 69. The method of Example 67 or Example 68 wherein the biological feature is presence or absence of one or more histone marks.

Example 70. The method of Example any one of Examples 67 to 69 wherein the biological feature is hypersensitivity to nuclease cleavage.

Example 71. The method of any one of Examples 55 to 70 wherein the tissue or cell type used to generate a reference map is a primary tissue from a subject having a disease or disorder.

Example 72. The method of Example 71 wherein the disease or disorder is selected from the group consisting of: cancer, normal pregnancy, a complication of pregnancy (e.g., aneuploid pregnancy), myocardial infarction, inflammatory bowel disease, systemic autoimmune disease, localized autoimmune disease, allotransplantation with rejection, allotransplantation without rejection, stroke, and localized tissue damage.

Example 73. The method of any one of Examples 55 to 70 wherein the tissue or cell type used to generate a reference map is a primary tissue from a healthy subject.

Example 74. The method of any one of Examples 55 to 70 wherein the tissue or cell type used to generate a reference map is an immortalized cell line.

Example 75. The method of any one of Examples 55 to 70 wherein the tissue or cell type used to generate a reference map is a biopsy from a tumor.

Example 76. The method of Example 60 wherein the sequence data obtained from samples obtained from at least one reference subject comprises positions of cfDNA fragment endpoint probabilities.

Example 77. The method of Example 76 wherein the reference subject is healthy.

Example 78. The method of Example 76 wherein the reference subject has a disease or disorder.

Example 79. The method of Example 78 wherein the disease or disorder is selected from the group consisting of: cancer, normal pregnancy, a complication of pregnancy (e.g., aneuploid pregnancy), myocardial infarction, inflammatory bowel disease, systemic autoimmune disease, localized autoimmune disease, allotransplantation with rejection, allotransplantation without rejection, stroke, and localized tissue damage.

Example 80. The method of any one of Examples 60 to 79 wherein the reference map comprises cfDNA fragment endpoint probabilities for at least a portion of the reference genome associated with the tissue or cell type.

Example 81. The method of Example 80 wherein the reference map comprises a mathematical transformation of the cfDNA fragment endpoint probabilities.

Example 82. The method of Example 80 wherein the cfDNA fragment endpoint probabilities represent a subset of all reference genomic coordinates for the tissue or cell type.

Example 83. The method of Example 82 wherein the subset is associated with positions or spacing of nucleosomes and/or chromatosomes.

Example 84. The method of Example 82 or Example 83 wherein the subset is associated with transcription start sites and/or transcription end sites.

Example 85. The method of any one of Examples 82 to 84 wherein the subset is associated with binding sites of at least one transcription factor.

Example 86. The method of any one of Examples 82 to 85 wherein the subset is associated with nuclease hypersensitive sites.

Example 87. The method of any one of Examples 82 to 86 wherein the subset is additionally associated with at least one orthogonal biological feature.

Example 88. The method of Example 87 wherein the orthogonal biological feature is associated with high expression genes.

Example 89. The method of Example 87 wherein the orthogonal biological feature is associated with low expression genes.

Example 90. The method of any one of Examples 81 to 89 wherein the mathematical transformation includes a Fourier transformation.

Example 91. The method of any one of Examples 58 to 90 wherein at least a subset of the plurality of the cfDNA fragment endpoint scores each has a score above a threshold value.

Example 92. The method of any one of Examples 54 to 91 wherein the step of determining the tissue(s) and/or cell type(s) of the cfDNA as a function of a plurality of the genomic locations of at least some of the cfDNA fragment endpoints comprises comparing a Fourier transform of the plurality of the genomic locations of at least some of the cfDNA fragment endpoints, or a mathematical transformation thereof, with a reference map.

Example 93. The method of any one of Examples 54 to 92 wherein the reference map comprises DNA or chromatin fragmentation data corresponding to at least one tissue that is associated with the disease or disorder.

Example 94. The method of any one of Examples 54 to 93 wherein the reference genome is associated with a human.

Example 95. The method of any one of Examples 54 to 94 further comprising generating a report comprising a statement identifying the disease or disorder.

Example 96. The method of Example 95 wherein the report further comprises a list of the determined tissue(s) and/or cell type(s) of the isolated cfDNA.

Example 97. The method of any preceding Example wherein the biological sample comprises, consists essentially of, or consists of whole blood, peripheral blood plasma, urine, or cerebral spinal fluid.

Example 98. A method for determining tissues and/or cell types giving rise to cell-free DNA (cfDNA) in a subject, comprising:
(i) generating a nucleosome map by obtaining a biological sample from the subject, isolating cfDNA from the biological sample, and measuring distributions (a), (b) and/or (c) by library construction and massively parallel sequencing of cfDNA;
(ii) generating a reference set of nucleosome maps by obtaining a biological sample from control subjects or subjects with known disease, isolating the cfDNA from the biological sample, measuring distributions (a), (b) and/or (c) by library construction and massively parallel sequencing of cfDNA; and
(iii) determining the tissues and/or cell types giving rise to the cfDNA by comparing the nucleosome map derived from the cfDNA to the reference set of nucleosome maps;
wherein (a), (b) and (c) are:
(a) the distribution of likelihoods any specific base-pair in a human genome will appear at a terminus of a cfDNA fragment;
(b) the distribution of likelihoods that any pair of basepairs of a human genome will appear as a pair of termini of a cfDNA fragment; and
(c) the distribution of likelihoods that any specific basepair in a human genome will appear in a cfDNA fragment as a consequence of differential nucleosome occupancy.

Example 99. A method for determining tissues and/or cell types giving rise to cell-free DNA in a subject, comprising:
(i) generating a nucleosome map by obtaining a biological sample from the subject, isolating the cfDNA from the biological sample, and measuring distributions (a), (b) and/or (c) by library construction and massively parallel sequencing of cfDNA;
(ii) generating a reference set of nucleosome maps by obtaining a biological sample from control subjects or subjects with known disease, isolating the cfDNA from the biological sample, measuring distributions (a), (b) and/or (c) by library construction and massively parallel sequencing of DNA derived from digestion of chromatin with micrococcal nuclease (MNase), DNase treatment, or ATAC-Seq; and
(iii) determining the tissues and/or cell types giving rise to the cfDNA by comparing the nucleosome map derived from the cfDNA to the reference set of nucleosome maps;
wherein (a), (b) and (c) are:
(a) the distribution of likelihoods any specific base-pair in a human genome will appear at a terminus of a sequenced fragment;
(b) the distribution of likelihoods that any pair of basepairs of a human genome will appear as a pair of termini of a sequenced fragment; and
(c) the distribution of likelihoods that any specific basepair in a human genome will appear in a sequenced fragment as a consequence of differential nucleosome occupancy.

Example 100. A method for diagnosing a clinical condition in a subject, comprising:
(i) generating a nucleosome map by obtaining a biological sample from the subject, isolating cfDNA from the biological sample, and measuring distributions (a), (b) and/or (c) by library construction and massively parallel sequencing of cfDNA;
(ii) generating a reference set of nucleosome maps by obtaining a biological sample from control subjects or subjects with known disease, isolating the cfDNA from the biological sample, measuring distributions (a), (b) and/or (c) by library construction and massively parallel sequencing of cfDNA; and
(iii) determining the clinical condition by comparing the nucleosome map derived from the cfDNA to the reference set of nucleosome maps;
wherein (a), (b) and (c) are:
(a) the distribution of likelihoods any specific base-pair in a human genome will appear at a terminus of a cfDNA fragment;
(b) the distribution of likelihoods that any pair of basepairs of a human genome will appear as a pair of termini of a cfDNA fragment; and
(c) the distribution of likelihoods that any specific basepair in a human genome will appear in a cfDNA fragment as a consequence of differential nucleosome occupancy.

Example 101. A method for diagnosing a clinical condition in a subject, comprising
(i) generating a nucleosome map by obtaining a biological sample from the subject, isolating cfDNA from the biological sample, and measuring distributions (a), (b) and/or (c) by library construction and massively parallel sequencing of cfDNA;

(ii) generating a reference set of nucleosome maps by obtaining a biological sample from control subjects or subjects with known disease, isolating the cfDNA from the biological sample, measuring distributions (a), (b) and/or (c) by library construction and massively parallel sequencing of DNA derived from digestion of chromatin with micrococcal nuclease (MNase), DNase treatment, or ATAC-Seq; and (iii) determining the tissue-of-origin composition of the cfDNA by comparing the nucleosome map derived from the cfDNA to the reference set of nucleosome maps;

wherein (a), (b) and (c) are:

(a) the distribution of likelihoods any specific base-pair in a human genome will appear at a terminus of a sequenced fragment;

(b) the distribution of likelihoods that any pair of base-pairs of a human genome will appear as a pair of termini of a sequenced fragment; and (c) the distribution of likelihoods that any specific base-pair in a human genome will appear in a sequenced fragment as a consequence of differential nucleosome occupancy.

Example 102. The method of any one of Examples 98-101, wherein the nucleosome map is generated by:
purifying the cfDNA isolated from the biological sample;
constructing a library by adaptor ligation and optionally PCR amplification; and
sequencing the resulting library.

Example 103. The method of any one of Examples 98-101, wherein the reference set of nucleosome maps are generated by:
purifying cfDNA isolated from the biological sample from control subjects;
constructing a library by adaptor ligation and optionally PCR amplification; and
sequencing the resulting library.

Example 104. The method of any one of Examples 98-101, wherein distribution (a), (b) or (c), or a mathematical transformation of one of these distributions, is subjected to Fourier transformation in contiguous windows, followed by quantitation of intensities for frequency ranges that are associated with nucleosome occupancy, in order to summarize the extent to which nucleosomes exhibit structured positioning within each contiguous window.

Example 105. The method of any one of Examples 98-101, wherein in distribution (a), (b) or (c), or a mathematical transformation of one of these distributions, we quantify the distribution of sites in the reference human genome to which sequencing read start sites map in the immediate vicinity of transcription factor binding sites (TFBS) of specific transcription factor (TF), which are often immediately flanked by nucleosomes when the TFBS is bound by the TF, in order to summarize nucleosome positioning as a consequence of TF activity in the cell type(s) contributing to cfDNA.

Example 106. The method of any one of Examples 98-101, wherein the nucleosome occupancy signals are summarized in accordance with any one of aggregating signal from distributions (a), (b), and/or (c), or a mathematical transformation of one of these distributions, around other genomic landmarks such as DNaseI hypersensitive sites, transcription start sites, topological domains, other epigenetic marks or subsets of all such sites defined by correlated behavior in other datasets (e.g. gene expression, etc.).

Example 107. The method of any one of Examples 98-101, wherein the distributions are transformed in order to aggregate or summarize the periodic signal of nucleosome positioning within various subsets of the genome, e.g. quantifying periodicity in contiguous windows or, alternatively, in discontiguous subsets of the genome defined by transcription factor binding sites, gene model features (e.g. transcription start sites), tissue expression data or other correlates of nucleosome positioning.

Example 108. The method of any one of Examples 98-101, wherein the distributions are defined by tissue-specific data, i.e. aggregate signal in the vicinity of tissue-specific DNase I hypersensitive sites.

Example 109. The method of any one of Examples 98-101, further comprising step of statistical signal processing for comparing additional nucleosome map(s) to the reference set.

Example 110. The method of Example 109, wherein we first summarize long-range nucleosome ordering within contiguous windows along the genome in a diverse set of samples, and then perform principal components analysis (PCA) to cluster samples or to estimate mixture proportions.

Example 111. The method of Example 100 or Example 101, wherein the clinical condition is cancer, i.e. malignancies.

Example 112. The method of Example 111, wherein the biological sample is circulating plasma containing cfDNA, some portion of which is derived from a tumor.

Example 113. The method of Example 100 or Example 101, wherein the clinical condition is selected from tissue damage, myocardial infarction (acute damage of heart tissue), autoimmune disease (chronic damage of diverse tissues), pregnancy, chromosomal aberrations (e.g. trisomies), and transplant rejection.

Example 114. The method of any preceding Example further comprising assigning a proportion to each of the one or more tissues or cell types determined to be contributing to cfDNA.

Example 115. The method of Example 114 wherein the proportion assigned to each of the one or more determined tissues or cell types is based at least in part on a degree of correlation or of increased correlation, relative to cfDNA from a healthy subject or subjects.

Example 116. The method of Example 114 or Example 115, wherein the degree of correlation is based at least in part on a comparison of a mathematical transformation of the distribution of cfDNA fragment endpoints from the biological sample with the reference map associated with the determined tissue or cell type.

Example 117 The method of Example 114 to 116, wherein the proportion assigned to each of the one or more determined tissues or cell types is based on a mixture model.

From the foregoing, it will be appreciated that specific embodiments of the invention have been described herein for purposes of illustration, but that various modifications may be made without deviating from the scope of the invention. Accordingly, the invention is not limited except as by the appended claims.

The invention claimed is:

1. A method of classifying a test subject sample as containing tumor DNA, the method comprising:
   (a) obtaining sequences of at least a portion of cfDNA molecules present in a test sample from the test subject, wherein the sequences have endpoints and the sequences are mappable to genomic locations;
   (b) calculating a set of test sample values indicative of the frequency of cfDNA endpoints mapping to single base genomic locations in a defined genome region comprising a plurality of single base genomic locations, wherein the test sample values are calculated using a mathematical transformation of a count of cfDNA endpoints mapping to the single base genomic locations in the genomic region and representing the distribution of the number of cfDNA endpoints occurring at multiple single base locations in the genome region;
   (c) determining a likelihood that the test sample contains tumor DNA by comparing the test sample values calculated from the frequency of cfDNA endpoints in step (b), with a plurality of reference values, wherein the reference values are calculated as in step (b), and the genome region used in the calculation are the same as the genome region in step (a), wherein the reference values are determined from cfDNA in a plurality of reference samples obtained from individuals known to not have cancer or known to have cancer; and
   (d) classifying the sample as (i) containing tumor DNA or (ii) not containing tumor DNA using the likelihood determined in step (c), wherein the classification is dependent upon meeting a classification threshold.

2. The method of claim 1, wherein the plurality of reference samples is obtained from individuals known to not have cancer and from individuals known to have cancer.

3. The method of claim 1, wherein steps (b) and (c) are performed for a plurality of genome regions.

4. The method of claim 1, wherein at least one genome region comprises a transcription factor binding site.

5. The method of claim 1, wherein at least one genome region comprises a CTCF binding site.

6. The method of claim 1, wherein the cfDNA sequenced comprises DNA derived from hematopoietic cells and non-hematopoietic cells, and wherein at least a portion of the non-hematopoietic cells are tumor cells.

7. The method of claim 1, wherein test values and reference values are calculated for a plurality of genomic locations.

8. The method of claim 1, wherein the cfDNA is sequenced on a massively parallel DNA sequencer.

9. The method of claim 1, wherein the sample is a blood sample.

10. The method of claim 9 wherein the reference samples are blood samples.

* * * * *